US007544791B2

(12) United States Patent
Fu

(10) Patent No.: US 7,544,791 B2
(45) Date of Patent: *Jun. 9, 2009

(54) ATTENUATED RABIES VIRUS WITH NUCLEOPROTEIN MUTATION AT THE PHOSPHORYLATION SITE FOR VACCINATION AGAINST RABIES AND GENE THERAPY IN THE CNS

(75) Inventor: Zhen Fang Fu, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 258 days.

This patent is subject to a terminal disclaimer.

(21) Appl. No.: 11/700,899

(22) Filed: Feb. 1, 2007

(65) Prior Publication Data

US 2007/0178555 A1 Aug. 2, 2007

Related U.S. Application Data

(62) Division of application No. 10/730,029, filed on Dec. 9, 2003, now Pat. No. 7,419,816, which is a division of application No. 10/199,024, filed on Jul. 22, 2002, now Pat. No. 6,706,523.

(60) Provisional application No. 60/331,354, filed on Jul. 20, 2001.

(51) Int. Cl.

| | |
|---|---|
| ***C12N 15/47*** | (2006.01) |
| ***C12N 15/86*** | (2006.01) |
| *C12N 7/01* | (2006.01) |
| *A61K 39/205* | (2006.01) |

(52) U.S. Cl. ................. 536/23.72; 435/235.1; 435/236; 424/224.1

(58) Field of Classification Search ....................... None
See application file for complete search history.

(56) References Cited

U.S. PATENT DOCUMENTS

| | | | | |
|---|---|---|---|---|
| 4,342,566 | A | 8/1982 | Theofilopoulos et al. | |
| 4,816,397 | A | 3/1989 | Boss et al. | |
| 4,816,567 | A | 3/1989 | Cabilly et al. | |
| 5,583,735 | A | 12/1996 | Pease et al. | |
| 6,033,886 | A | 3/2000 | Conzelmann | |
| 6,706,523 | B2 * | 3/2004 | Fu | 435/320.1 |
| 6,719,881 | B1 | 4/2004 | Hunter et al. | |
| 7,419,816 | B2 * | 9/2008 | Fu | 435/235.1 |

FOREIGN PATENT DOCUMENTS

| | | |
|---|---|---|
| EP | 0583998 | 2/1994 |
| WO | 99/18214 | 4/1999 |
| WO | 00/32755 | 6/2000 |

OTHER PUBLICATIONS

Wagner et al, in Fields Virology, Third edition, ed. Fields et al, Lippincott-Raven, Philadelphia, 1996, pp. 1121-1135.*

Dietzchold et al (Expert Rev. Vaccines 2:399-406, 2003).*

Morimoto et al (Vaccine 19: 3543-3551, 2001).*

Schnell et al (Journal of Neurovirology 11:76-81, 2005).*

A. Flamand et al., "An RNA polymerase activity in purified rabies virions", J. Gen. Virol., 1978, pp. 233-238, vol. 40, Society for General Microbiology, United Kingdom.

A. Flamand et at., Avirulent mutants of rabies virus and their use as live vaccine, Trends. Microbiol., Nov. 1993, pp. 317-320, vol. 1, No. 8, Elsevier Science Publishers Ltd, Cambridge,U.K.

A. Kawai et al., "Nucleocapsid formation and/or subsequent conformational change of rabies virus nucleoprotein (N) is a prerequisite step for acquiring the phosphatase-sensitive epitope of monoclonal antibody 5-2-26", Virology, 1999, pp. 395-407, vol. 263, Academic Press, San Diego, CA.

A. Kawai, "Transcriptase Activity Associated With Rabies Virion", J. Virol., Dec. 1977, pp. 826-835, vol. 24, No. 3, American Society for Microbiology, Washington, DC.

A. Kouznetzoff et at., "Identification of a region of the rabies virus N protein involved in direct binding to the viral RNA", J. Gen. Virol., 1998, pp. 1005-1013, vol. 79, Society of General Microbiology, United Kingdom.

A. Trejos et al., "Laboratory investigations of neuroparalytic accidents associated with suckling mouse brain rabies vaccine. I.—Encephalitogenicity and virological studies", Ann. Immunol. (Paris—Inst. Pasteur), 1971, pp. 917-924, vol. 125.

A. Wandeler et al., "Oral Immunization of Wildlife Against Rabies: Concept and First Field Experiments", Rev. Infect. Dis., Nov.-Dec. 1988, pp. S649-S653, vol. 10, Suppl. 4, The University of Chicago Press, Chicago, IL.

(Continued)

*Primary Examiner*—Mary E Mosher
(74) *Attorney, Agent, or Firm*—Bingham McCutchen LLP

(57) ABSTRACT

A mutant virus is provided which contains a mutation at a phosphorylation site in one or more of the proteins of the virus, which mutation causes the virus to be attenuated, and therefore, an improved vaccine composition can be produced therewith. The invention also relates to vaccine compositions which contain the mutant virus, as well as to methods of inducing an immune response, and of protecting mammals from infection by rabies virus. Also included in the invention are methods of producing the mutant virus and mutant viral proteins, including producing the mutant virus in a host cell which produces or even overproduces a wild-type counterpart of the mutant viral protein, which complements the other viral proteins such that production of the mutant viral particle is optimized. The invention also includes those host cells in which viral production is optimized, as well as vaccine compositions including the viral proteins, either alone or in combination with the intact virus, and to methods of inducing an immune response or protecting a mammal from infection, using the same. Also included in the invention are vectors suitable for delivering a gene to a cell of a human or animal, as well methods of delivery thereof.

14 Claims, 39 Drawing Sheets

OTHER PUBLICATIONS

A.B. Sabin et al., "History of the Sabin attenuated po(iovirus oral live vaccine strains", J. Biol. Stand., 1973, pp. 115-118, vol. 1, No. 2, Academic Press Inc., London, UK.
A.H. Robbins et al., "Prevention of the spread of rabies to wildlife by oral vaccination of raccoons in Massachusetts", J. Am. Vet. Med. Assoc., Nov. 15, 1998, pp. 1407-1412, vol. 213, No. 10, Journalof the American Veterinary Medical Association, Schaumburg, IL.
A.K. Banerjee et at., "Structure and Function of the RNA Polymerase of Vesicular Stomatitis Virus", Advances in Virus Research, 1990, pp. 99-124, vol. 38, Academic Press.
A.K. Pattnaik et al., "Cells that express all five proteins of vesicular stomatitis virus from cloned cDNAs support replication, assembly, and budding of defective interfering particles", Proc. Natl. Acad. Sci. USA, Feb. 1991, pp. 1379-1383, vol. 88, The National Academy of Sciences, Washington, DC.
A.K. Pattnaik et al., "Replication and amplification of defective interfering particle RNAs of vesicular stomatitis virus in cells expressing viral proteins from vectors containing cloned cDNAs", J. Virol., Jun. 1990, pp. 2948-2957, vol. 64, No. 6, American Society of Microbiology, Washington, DC.
A.M. Arvin, "Measles vaccines—a positive step toward eradicating a negative strand", Nature Med., Jul. 2000, pp. 744-745, vol. 6, No. 7, Nature America Inc., New York, NY.
Anonymous. Compendium of Animal Rabies Prevention and Control, 2000, National Association of State Public Health Veterinarians, Inc., MMWR, pp. 21-30, vol. 49, No. RR-8.
Anonymous. Rabies Vaccine Failures [editorial], Lancet, Apr. 23, 1988, p. 917, vol. 1, The Lancet Publishing Group, London, UK.
Anzai J. et al., "Identificaiton of a Phosphatase-Sensitive Epitope of Rabies Virus Nucleoprotein which is Recognized by a Monoclonal Antibody 5-22-26," Microbiology and Immunology, 1997, pp. 229-240, vol. 41, No. 3, Tokyo, Japan.
B. Brochier et al., "Use of recombinant vaccinia-rabies virus for oral vaccination of wildlife against rabies: innocuity to several non-target bait consuming species", J. Wild!. Dis., 1989, pp. 540-547, vol. 25, Wildlife Disease Association, Lawrence, Kansas.
B. Dietzschold et al., "Characterization of an antigenic determinant of the glycoprotein that correlates with pathogenicity of rabies virus", Proc. Natl. Acad. Sci. USA, Jan. 1983, pp. 70-74, vol. 80, No. 1, The National Academy of Sciences, Washington, DC.
B. Dietzschold et al., "Differences in cell-to-cell spread of pathogenic and apathogenic rabies virus in vivo and in vitro", J. Virol., Oct. 1985, pp. 12-18, vol. 56, No. 1, American Society forMicrobiology, Washington, DC.
B. Dietzschold et at., "Localization and immunological characterization of antigenic domains of rabies virus internal N and NS proteins", Virus Res., 1987, pp. 103-125, vol. 8, ElsevierScience Publishers B.V., The Netherlands.
B. Perbal, "A Practical Guide to Molecular Cloning", 1988, John Wiley & Sons, Inc., New York, NY.
B.P. Wilcock et al., "Focal cutaneous vasculitis and alopecia at sites of rabies vaccination in dogs", J. Am. Vet. Med. Assoc., May 15, 1986, pp. 1174-1177, vol. 188, No. 10, American Veterinary Medical Association, Schaumburg, IL.
C. Mitmoonpitak et al., "Rabies in Thailand", Epidemiol. Infect., 1998, pp. 165-169, vol. 120, Cambridge University Press, UK.
C.A. Hanlon et al., "First North American field release of a vaccinia-rabies glycoprotein recombinant virus", J. Wild!. Dis., 1998, pp. 228-239, vol. 34(2), Wildlife Disease Association, Lawrence, Kansas.
C.E. Rupprecht et al., "Oral immunization and protection of raccoons (*Procyon /otor*) with a vaccinia-rabies glycoprotein recombinant virus vaccine", Proc. Natl. Acad. Sci. USA, 1986, pp. 7947-7950, vol. 83, The National Academy of Sciences, Washington, DC.
C.E. Rupprecht et al., "Oral wildlife rabies vaccination: development of a recombinant virus vaccine", Trans. 57th N.A. Wild!. Natl. Res. Conf., 1992, pp. 439-452.
C.E. Rupprecht et al., "The Ascension of Wildlife Rabies: A Cause for Public Health Concern or Intervention?", Emerging Infect. Dis., Oct.-Dec. 1995, pp. 107-114, vol. 1, No. 4, Centers for Disease Control, Atlanta, Georgia.
C.E. Rupprecht et at., "Human infection due to recombinant vaccinia-rabies glycoprotein virus", N. Engl. J. Med., Aug. 23, 2001, pp. 582-586, vol. 345, No. 8, Massachusetts Medical Society, Waltham, Massachusetts.
C.J. Noren et al., "A General Method for Site-Specific Incorporation of Unnatural Amino Acids into Proteins", Science, Apr. 1989, pp. 182-188, vol. 244.
C.L. Schumacher et al., "SAG-2 oral rabies vaccine", Onderstepoort J. Vet. Res., 1993, pp. 459-462, vol. 60, No. 4, Agricultural Research Council, Pretoria, South Africa.
Clark et el., "Temperature -Sensitive Mutant of Rabies Virus in Mice: a Mutant (ts 2) Revertant Mixture Selectively Pathogenic by the Peripheral Route of Inoculation,"Infection and Immunity, vol. 13, No. 5, 141B-1425 (1976).
D. Spadafora et al., "Constitutive Phosphorylation of The Vesicular Stomatitis Virus P Protein Modulates Polymerase Complex Formation But Is Not Essential For Transcription or Replication", J. Virol., Jul. 1996, pp. 4538-4548, vol. 70, No. 7, American Society for Microbiology, Washington, DC.
D.A. Henderson, "Smallpox Eradication", Public Health Rep., Jan.-Feb. 1980, pp. 422-426, vol. 95, No. 1, U.S. Department of Health, Education and Welfare, Washington, DC.
D.E. Roscoe et al., "Efficacy of an oral vaccinia-rabies glycoprotein recombinant vaccine in controlling epidemic raccoon rabies in New Jersey", J. Wildl. Dis., Oct. 1998, pp. 752-763, vol. 34(4), Wildlife Disease Association, Lawrence, Kansas.
D.J. Briggs et al., "Safety and immunogenicity of *Lyssavac berna* human diploid cell rabies vaccine in healthy adults", Vaccine, 1996, pp. 1361-1365, vol. 14, No. 14, Elsevier Science Ltd., Great Britain.
D.L. Lodmell et al., "DNA immunization protects nonhuman primates against rabies virus", Nature Medicine, Aug. 1998, pp. 949-952, vol. 4, No. 8, Macmillan Publishers Ltd., Hampshire, England.
Drings A. et al, "Is there an advantage to including the nucleoprotein in a rabies glycoprotein subunit vaccines?", *Vaccine*, Mar. 1999, pp. 1549-1557, vol. 17, Nos. 11-12.
E. Fuenzalida, "Human pre-exposure rabies immunization with suckling mouse brain vaccine", Bulletin of The World Health Organization, 1972, pp. 561-563, vol. 46, No. 4, World Health Organization Publications, Geneva, Switzerland.
E. Jay et al., "Chemical Synthesis of a Biologically Active Gene for Human Immune Interferony", J. Biol. Chem., May 25, 1984, pp. 6311-6317, vol. 259, No. 10, The American Society for Biochemistry and Molecular Biology, Bethesda, Maryland.
E. Masson et al., "Safety study of the SAG2 rabies virus mutant in several non-target species with a view to its future use for the immunization of foxes in Europe", Vaccine, 1996, pp. 1506-1510, vol. 14, No. 16, Elsevier Science Ltd., Great Britain.
E.B. Flanagan et al., "Moving the glycoprotein gene of vesicular stomatitis virus to promotor- proximal positions accelerates and enhances the protective immune response", J. Virol., Sep. 2000, pp. 7895-7902, vol. 74, No. 17, American Society for Microbiology, Washington, DC.
E.J. Reed et al., "A simple method of estimating fifty percent endpoints", Am. J. Hyg., May 1938, pp. 493-497, vol 27, No. 3, School of Hygiene and Public Health of the Johns Hopkins University.
"Epidemiologic Notes and Reports Systemic Allergic Reactions Following Immunization with Human Diploid Cell Rabies Vaccine," MMWR Weekly, Apr. 13, 1984, vol. 33, No. 14, pp. 185-187, Centers for Disease Control, Atlanta, Georgia.
F. Lafay et al., "Vaccination against rabies: construction and characterization of SAG-2, a double avirulent derivative of SADBern", Vaccine, 1994, pp. 317-320, vol. 12, No. 4, Butterworth-Heinemann Ltd., Oxford, U.K.
F. Sokol et al., "Phosphoproteins, Structural Components of Rhabdoviruses", Virol., 1973, pp. 246-263, vol. 52, Academic Press, Inc., San Diego, CA.
F.-X. Meslin et al., "Rationale and prospects for rabies elimination in developing countries", Current Topics in Microbiology and Immunology, 1994, pp. 1-26, vol. 187, Springer-Verlag, Heidelberg, Germany.

Fu Z. et. al., "Immunoprotection by Rabies Virus Nucleoprotein," Current Topics in Microbiology and Immunology, 1994, pp. 161-172, Springer, Berlin, Germany.
G. Gosztonyi et al., "Rabies and borna disease. A comparative pathogenetic study of two neurovirulent agents", Lab. Invest., 1993, pp. 285-295, vol. 68, No. 3, The United States and Canadian Academy of Pathology, Inc., U.S.A.
G.M. Baer, "Oral Rabies Vaccination: An Overiew", Rev. Infect. Dis., Nov.-Dec. 1988, pp. S644-S647, vol. 10, Suppl. 4, Centers for Disease Control, Lawrencevile, Georgia.
G.W. Wertz et al., "Gene rearrangement attenuates expression and lethality of a nonsegmented negative strand RNA virus", Proc. Natl. Acad. Sci. USA, Mar. 1998, pp. 3501-3506, vol. 95, The National Academy of Sciences, Washington, DC.
G.W. Wertz et at., "The role of proteins in vesicular stomatitis virus RNA replication", R.R. Wagner (Ed.), The Rhabdoviruses, 1987, pp. 271-296, Plenum Press, New York.
H. Le Blois et al., "Oral immunization of foxes with avirulent rabies virus mutants", Veterinary Microbiology, 1990, pp. 259-266, vol. 23, Elsevier Science Publishers B.V., The Netherlands.
H.O. Aghomo et al., "The serological response of young dogs to the Flury LEP strain of rabies virusvaccine," Vet. Res. Commun., 1990, pp. 415-425, vol. 14, Kluwer Academic Publishers Group, The Netherlands.
I. Seif et al., "Rabies virulence: effect on pathogenicity and sequence characterization of rabies virus mutations affecting antigenic site III of the glycoprotein", J. Virol., 1985, pp. 926-934, vol. 53, No. 3, American Society for Microbiology, Washington, DC.
J. Barr et al., "Sequence of the major nucleocapsid protein gene of pneumonia virus of mice: Sequence comparisons suggest structural homology between nucleocapsid proteins of pneumoviruses, paramyxoviruses, rhabdoviruses and filoviruses", J. Gen. Virol., 1991, pp. 677-685, vol. 72, Society of General Microbiology, Great Britain.
J. Blancou et al., "Oral vaccination of the fox against rabies using a live recombinant vacciniavirus", Nature, Jul. 1986, pp. 373-375, vol. 322, Macmillan Publishers Ltd., Hampshire, England.
J. Yang et al., "Phosphorylation of rabies virus nucleoprotein regulates viral RNA transcription and replication by modulating leader RNA encapsidation", J. Virol., 1999, pp. 1661-1664, vol. 73, No. 2, American Society for Microbiology, Washington, DC.
J. Yang et al., "The specificity of rabies virus RNA encapsidation by nucleoprotein", Virology, 1998, pp. 107-117, vol. 242, Academic Press.
J.B. Esh et al., "Vaccine-induced rabies in four cats", J. Am. Vet. Med. Assoc., 1982, pp. 1336-1339, vol. 180, No. 11, American Veterinary Medical Association, Schaumburg, Illinois.
J.E. Osorio et al., "Immunization of dogs and cats with a DNA vaccine against rabies virus", Vaccine, 1999, pp. 1109-1116, vol. 17, Elsevier Science Ltd., Great Britain.
J.H. Cox et al., "Rabies virus glycoprotein. II. Biological and serological characterization", Infect Immun., Jun. 1977, pp. 754-759, vol. 16, American Society for Microbiology, Washington, DC.
J.S. Smith et al., "Molecular epidemiology of rabies in the United States. A Case Report", Sem. Virol., 1995, pp. 387-400, vol. 6, Academic Press Ltd., London, U.K.
J.S. Smith et al., "Unexplained Rabies in Three Immigrants in the United States. A Virologic Investigation", N. Engl. J. Med., Jan. 24, 1991, pp. 205-211, vol. 324, Massachusetts Medical Society, Waltham, Massachusetts.
J.W. Krebs et at., "Mammalian. reservoirs and epidemiology of rabies diagnosed in human beings in the United States, 1981-1998", Ann. NY Acad. Sci., 2000, pp. 345-353, vol. 916, New York Academy of Sciences, New York, NY.
J.W. Krebs et at., "Rabies surveillance in the United States during 1999", J. Am. Vet. Med. Assoc., Dec. 15, 2000, pp. 1799-1811, vol. 217, No. 12, American Veterinary Medical Association, Schaumburg, IL.
K. Hable, "Hable test for potency In. Laboratory techniques in rabies", 4th edition, F.X. Meslin et al.(Ed)., 1996, pp. 369-373, World Health Organization, Geneva, Switzerland.
K.A. Clark et al., "Post-exposure rabies prophylaxis and pre-exposure rabies vaccination failure in domestic animals", J. Am. Vet. Med. Assoc., Jun. 1, 1996, pp. 1827-1830, vol. 208, No. 11, American Veterinary Medical Association, Schaumburg, Illinois.
K.-K. Conzelmann et al., "Molecular cloning and complete nucleotide sequence of the attenuated rabies virus SAD B19", J. Virol., 1990, pp. 485-499, vol. 175, Academic Press, Inc., Duluth, MN.
K.-K. Conzelmann et al., "Rescue of synthetic genomic RNA analogs of rabies virus by plasmid-encoded proteins", J. Virol., Feb. 1994, pp. 713-719, vol. 68, No. 2, American Society for Microbiology, Washington, DC.
K.M. Charlton et al., "Oral rabies vaccination of skunks and foxes with a recombinant human adenovirus vaccine", Arch. Virol., 1992, pp. 169-179, vol. 123, Springer-Verlag, Austria.
K.P. Nambair et al., "Total Synthesis and Cloning of a Gene Coding for the Ribonuclease S Protein", Science, Jan. 1984, pp. 1299-1301, vol. 223.
K.S. Lundberg et al., "High-fidelity amplification using a thermostable DNA polymerase isolated from *Pyrococcus furiosus*", Gene, 1991, pp. 1-6, vol. 108, Elsevier Science Publishers B.V., The Netherlands.
L. Pasteur et al., "Pasteur and Rabies: An Interview of 1882", Medical History, 1996, pp. 373-377, vol. 40.
L. Prevec et al., "A Recombinant Human Adenovirus Vaccine Against Rabies", J. Infect. Dis., Jan. 1990, pp. 27-30, vol. 161, No. 1, The University of Chicago Press, Chicago, IL.
L.A. Ball et at., "Phenotypic Consequences of Rearranging the P. M, and G Genes of Vesicular Stomatitis Virus", J. Viral., Jun. 1999, pp. 4705-4712, vol. 73, No. 6, American Society for Microbiology, Washington, DC.
L.G. Schneider et al., "Current Oral Rabies Vaccination in Europe: An Interim Balance", Rev. Infect. Dis., Nov.-Dec. 1988, pp. S654-S659, vol. 10, Suppl. 4, The University of Chicago.
M. Enami et al., "Introduction of site- specific mutations into the genome of influenza virus", Proc. Natl. Acad. Sci. USA, May 1990, pp. 3802-3805, vol. 87, The National Academy of Sciences, Washington, DC.
M. Shill et al., "Fatal rabies encephalitis despite appropriate post-exposure prophylaxis", N. Engl. J. Med., May 14, 1987, pp. 1257-1258, vol. 316, No. 20, Massachusetts Medical Society, Waltham, Massachusetts.
M.C. Anderson et al., "The role of specific IgE and beta-propiolactone in reactions resultingfrom booster doses of human diploid cell rabies vaccine", J. Allergy Clin. Immunol., Dec. 1987,pp. 861-868, vol. 80, Food and Drug Administration, Bethesda, MD.
M.C. Swanson et al., "IgE and IgG antibodies to J3-Propiolactone and human serum albumin associated with urticarial reactions to rabies vaccine", J. Infect. Dis., May 1987, pp. 909-913, vol. 155, No. 5, The University of Chicago Press, Chicago, IL.
M.D. Edge et al., Total synthesis of a human leukocyte interferon gene, Nature, Aug. 20, 1981, pp. 756-762, vol. 292, Macmillan Publishers Ltd., Hampshire, England.
M.G. Fearneyhough et al., "Results of an oral rabies vaccination program for coyotes", J. Am. Vet. Med. Assoc., Feb. 15, 1998, pp. 498-502, vol. 212, No. 4, American Veterinary Medical Association, Schaumburg, Illinois.
M.I. Meltzer, "Assessing the Costs and Benefits of an Oral Vaccine for Raccoon Rabies: A Possible Model", Emerging Infect. Dis., Oct.-Dec. 1996, pp. 343-349, vol. 2, No. 4, Centers for Disease Control, Atlanta, Georgia.
M.J. Schnell et al., "Infectious rabies viruses from cloned cDNA", EMBO J., 1994, pp. 4195-4203, vol. 13, No. 18, Oxford University Press, Oxford, U.K.
M.J. Schnell et al., "Recombinant rabies virus as potential live-viral vaccines for HIV-1", Proc. Natl. Acad. Sci. USA, Mar. 28, 2000, pp. 3544-3549, vol. 97, No. 7, The National Academy of Sciences, Washington, DC.
M.P. Kieny et al., "Expression of rabies virus glycoprotein from a recombinant vaccinia virus", Nature, Nov. 8, 1984, pp. 163-166, vol. 312, Macmillan Publishers Ltd., Hampshire, England.
M.P. Weiner et al., "Site-directed mutagenesis of double-stranded DNA by the polymerase chain reaction", Gene, 1994, pp. 119-123, vol. 151, Elsevier Science B.V., The Netherlands.

Mebatsion T. et al., "Pathogenicity of different rabies virus variants inversely correlates with apoptosis and rabies virus glycoprotein expression in infected primary neuron cultures," JnL. Of Virology, Jan. 1999, pp. 510-518, vol. 73, No. 1 Amer. Soc. For Microbiolgy.

Morimoto, Kinjiro et al. "Genetic engineering of live rabies vaccines," Vaccine , May 14, 2001, pp. 3543-3551, vol. 19, No. 25-26, Butterworth Scientific, Guildford, GB.

Morimoto, Kinjiro et al. "Pathogencity fo different rabies variants inversely correlates with apoptosis and rabies virus glycoprotein expression in infected primary neuron cultures," Jnl. Of Virology, Jan. 1999, pp. 510-518, vol. 73, No. 1, Amer. Soc. For Microbiolgy, U.S.

N. Tordo et at., "Primary structure of leader RNA and nucleoprotein genes of rabies genome: Segmented homology with VSV", Nucleic Acids Res., 1986, pp. 2671-2683, vol. 14, No. 6, IRL Press Limited, Oxford, England.

N.B. Ray et al., "Nanogram quantities of plasmid DNA encoding the rabies virus glycoprotein protect mice against lethal rabies virus infection", Vaccine, 1997, pp. 892-895, vol. 15, No. 8, Elsevier Science Ltd., Great Britain.

N.D. Lawson et al., "Recombinant vesicular stomatitis viruses from DNA", Proc. Natl. Sci. USA, May 1995, pp. 4477-4481, vol. 92, The National Academy of Sciences, Washington, DC.

P. Boudinot et al., "Viral haemorrhagic septicaemia virus induces vig-2, a new intereron-responsive gene in rainbow trout", Fish & Shellfish Immunol., 2001, pp. 383-397, vol. 11, Academic Press.

P. Coulon et al., "Invasion of the peripheral nervous systems of adult mice by the CVS strain of rabies virus and its avirulent derivative AvOI", J. Virol., Aug. 1989, pp. 3550-3554, vol. 63, No. 8, American Society for Microbiology, Washington, DC.

P. Khawplod et al., "Immunogenicity of purified duck embryo rabies vaccine (Lyssavac-N) with use of the WHO-approved intradermal postexposure regimen", Clin. Infect. Dis., 1995, pp. 646-651, vol. 20, The University of Chicago Press, Chicago, IL.

P. Lumbiganon et al., "International Notes Human Rabies Despite Treatment With Rabies Immune Globulin and Human Diploid Cell Rabies Vaccine- Thailand", MMWR, 1987, p. 759, vol. 36, Centers for Disease Control, Atlanta, Georgia.

P. Suntharasamai et al., "New Purified Vero-Cell Vaccine Prevents Rabies in Patients Bitten by Rabid Animals", Lancet, Jul. 19, 1986, pp. 129-131, vol. 2, The Lancet Publishing Group, London, UK.

R. Barth et at., "A new inactivated tissue culture rabies vaccine for use in man. Evaluation ofPCEC-vaccine by laboratory tests", J. Biol. Stand., 1984, pp. 29-64, vol. 12, The InternationalAssociation of Biological Standardization, Academic Press.

R. Etessami et at., "Spread and pathogenic characteristics of a G-deficient rabies virus recombinant: an in vitro and in vivo study", J. Gen. Virol., 2000, pp. 2147-2153, vol. 81, Society of General Microbiology, United Kingdom.

R.C. Littell et al., "SAS system for mixed models", 1996, SAS Institute Inc., Cary, North Carolina.

R.J. Warrington et al., "Immunologic studies in subjects with a serum sickness-like illness after immunization with human diploid cell rabies vaccine", J. Allergy Clin. Immunol., Apr. 1987, pp. 605-610, vol. 79, American Academy of Allergy, Asthma & Immunology, Elsevier Science, London, UK.

R.R. Wagner et at., "Rhabdoviridae: The Viruses and Their Replication", In B.N. Fields et al. (Ed.), Fields Virology, 3rd Ed., 1996, pp. 1121-1136, Lippincott-Raven, Philadelphia, PA.

S. Finke et al., "Ambisense gene expression from recombinant rabies virus: random packaging of positive- and negative-strand ribonucleoprotein complexes into rabies virions",J. Virol., Oct. 1997, pp. 7281-7288, vol. 71, No. 10, American Society for Microbiology, Washington, DC.

S. Finke et al., "Differential transcription attenuation of rabies virus genes by intergenic regions: generation of recombinant viruses overexpressing the polymerase gene", J Virol., Aug. 2000, pp. 7261-7269, vol. 74, No. 16, American Society for Microbiology, Washington, DC.

S. Sehgal et al., "Ten year longitudinal study of efficacy and safety of purified chick embryo cell vaccine for pre- and post-exposure prophylaxis of rabies in Indian population", J. Com. Dis., Mar. 1995,pp. 36-43, vol. 27, No. 4, The Indian Society for Malaria and Other Communicable Diseases (India).

S.P.J. Whelan et al., "Efficient recovery of infectious vesicular stomatitis virus entirely from cDNA clones", Proc. Natl. Acad. Sci. USA, 1995, pp. 8388-8392, vol. 92, The National Academy of Sciences, Washington, DC.

S.U. Emerson, "Reconstitution studies detect a single polymerase entry site on the vesicular stomatitis vuris genome", Cell, Dec. 1982, pp. 635-642, vol. 31, Cell Press, Cambridge, Massachusetts.

Supplementary European Search Report.

Supplementary Partial European Search Report.

T. Tims et al., "Adult dogs receiving a rabies booster dose with a recombinant adenovirus expressing rabies virus glycoprotein develop high titers of neutralizing antibodies", Vaccine, 2000, pp. 2804-2807, vol. 18, Elsevier Science Ltd., Great Britain.

T.J. Wiktor et al., "Cultivation of rabies virus in human diploid cell strain WI-38", J. Immunol., 1964, pp. 353-366, vol. 93, The Williams & Wilkins Co., USA.

T.R. Fuerst et al., "Eukaryotic transient-expression system based on recombinant vaccinia virus that synthesizes bacteriophage T7 RNA polymerase", Proc. Natl. Acad. Sci. USA, Nov. 1986, pp. 8122-8126, vol. 83, The National Academy of Sciences, Washington, DC.

Tartaglia J. et al., "NYVAC: A Highly Attenuated Strain of Vaccina Virus,"Virology, May 1, 1992, pp. 217-232, vol. 188, No. 1 Academic Press, Orlando, FL.

U.J. Buchholz et al., "Generation of Bovine Respiratory Syncytial Virus (BRSV) From cDNA:BRSV NS2 Is Not Essential For Virus Replication In Tissue Culture, And The Human RSV LeaderRegion Acts as a Functional BRSV Genome Promoter", J. Virol., Jan. 1999, pp. 251-259, vol. 73, No. 1, American Society for Microbiology, Washington, DC.

W.G. Winkler et at., "Oral rabies vaccine: evaluation of its infectivity in three species of rodents", Am. J. Epidemiol., 1976, pp. 294-298, vol. 104, No. 3, The Johns Hopkins University School of Hygiene and Public Health, USA.

W.H. Wunner, "The chemical composition and molecular structure of rabies viruses. In: Natural History of Rabies", 2nd Edition, G.M. Baer (Ed.), 1991, pp. 31-67, CRC Press, Inc., Boca Raton, Florida.

X. Wu et al., "Both viral transcription and replication are reduced when the rabies virus nucleoprotein is not phosphorylated", J. Virol., 2002, pp. 4153-4161, vol. 76, American Society for Microbiology, Washington, DC.

Y. Wang et al., "The Use of an EI-Deleted, Replication-Defective Adenovirus Recombinant Expressing the Rabies Virus Glycoprotein for Early Vaccination of Mice Against Rabies Virus", J. Virol., 1997, pp. 3677-3683, vol. 71, No. 5, American Society for Microbiology, Washington, DC.

Z.F. Fu et al., "Both the N- and C-terminal domains of the nominal phosphoprotein of rabies virus are involved in binding to the nucleoprotein", Virology, 1994, pp. 590-597, vol. 200, Academic Press, Inc., San Diego, CA.

Z.F. Fu et al., "Inhibition of rabies virus infection by an oligodeoxynucleotide complementary torabies virus genomic RNA", Antisense and Nucleic Acid Drug Development, 1996, pp. 87-93, vol. 6, Mary Ann Liebert, Inc., Larchmont, New York.

Z.F. Fu et al., "Oral vaccination of raccoons (*Procyon lotor*) with baculovirus-expressed rabies virus glycoprotein", Vaccine, 1993, pp. 925-928, vol. 11, Butterworth-Heinemann Ltd., Oxford, U.K.

Z.F. Fu et at., "Rabies virus nucleoprotein expressed in and purified from insect cells is efficacious as a vaccine", Proc. Natl. Acad. Sci. USA, Mar. 1991, pp. 2001-2005, vol. 88, The National Academy of Sciences, Washington, DC.

Brochier, B., et al., "Large-scale eradication of rabies using recombinant vaccinia-rabies vaccine", Nature, Dec. 1991, pp. 520-522, vol. 354, Macmillan Publishers Ltd., Hampshire, England.

Fu, Z.F., et al., "Rabies and rabies research: past, present and future", Vaccine, 1997, pp. S20-S24, vol. 15, Suppl., Elsevier Science Ltd., Great Britain.

Xiang, Z.Q., et al., "Vaccination with a plasmid vector carrying the rabies virus glycoprotein gene induces protective immunity against rabies virus", Virology, 1994, pp. 132-140, vol. 199, Academic Press, Inc., San Diego, CA.

Xiang, Z.Q., et al., "A replication-defective human adenovirus recombinant serves as a highly efficacious vaccine carrier", Virology, 1996, pp. 220-227, vol. 219.

* cited by examiner

| | | L16 | A | D | E |
|---|---|---|---|---|---|
| N | Genomic RNA | 100% | 10.4% | 45% | 100% |
| N | mRNA | 100% | 28% | 65% | 100% |
| G | Genomic RNA | 100% | 12.2% | 41% | 100% |
| G | mRNA | 100% | 21% | 60% | 100% |

| | L16 | A | D | E |
|---|---|---|---|---|
| mRNA (6h) | 100% | 10% | 53% | 91% |
| mRNA (12h) | 100% | 12% | 61% | 95% |
| mRNA (24h) | 100% | 8% | 65% | 100% |

Infected cells

Genome (-)

| | L16 | A | D | E |
|---|---|---|---|---|
| % of (-/+) | 71 | 74 | 73 | 72 |

antigenome (+)

| L16 | A | D | E |
|---|---|---|---|
| 27 | 25 | 27 | 27 |

| Ratio | L16 | A | D | E |
|---|---|---|---|---|
| -/+ | 3 | 3 | 3 | 3 |

Purified virions

| | L16 | A | D | E |
|---|---|---|---|---|
| % of (-/+) | 95 | 95 | 95 | 94 |

| L16 | A | D | E |
|---|---|---|---|
| 5 | 5 | 5 | 6 |

| Ratio | L16 | A | D | E |
|---|---|---|---|---|
| -/+ | 19 | 19 | 19 | 16 |

Model of N Phosphorylation and its Effects on Viral Transcription and Replication

Fig. 9A-1

```
   1 acgcttaaca accagatcaa agaaaaaaca gacattgtca attgcaaagc aaaaatgtaa
  61 cacccctaca atggatgccg acaagattgt attcaaagtc aataatcagg tggtctcttt
 121 gaagcctgag attatcgtgg atcaatatga gtacaagtac cctgccatca aagatttgaa
 181 aaagccctgt ataaccctag gaaaggctcc cgatttaaat aaagcataca agtcagtttt
 241 gtcaggcatg agcgccgcca aacttaatcc tgacgatgta tgttcctatt tggcagcggc
 301 aatgcagttt tttgagggga catgtccgga agactggacc agctatggaa ttgtgattgc
 361 acgaaaagga gataagatca ccccaggttc tctggtggag ataaaacgta ctgatgtaga
 421 agggaattgg gctctgacag gaggcatgga actgacaaga gaccccactg tccctgagca
 481 tgcgtcctta gtcggtcttc tcttgagtct gtataggttg agcaaaatat ccgggcaaaa
 541 cactggtaac tataagacaa acattgcaga caggatagag cagatttttg agacagcccc
 601 ttttgttaaa atcgtggaac accatactct aatgacaact cacaaaatgt gtgctaattg
 661 gagtactata ccaaacttca gatttttggc cggaacctat gacatgtttt tctcccggat
 721 tgagcatcta tattcagcaa tcagagtggg cacagttgtc actgcttatg aagactgttc
 781 aggactggta tcatttactg ggttcataaa acaaatcaat ctcaccgcta gagaggcaat
 841 actatatttc ttccacaaga actttgagga agagataaga agaatgtttg agccagggca
 901 ggagacagct gttcctcact cttatttcat ccacttccgt tcactaggct tgagtgggaa
 961 atctccttat tcatcaaatg ctgttggtca cgtgttcaat ctcattcact ttgtaggatg
1021 ctatatgggt caagtcagat ccctaaatgc aacggttatt gctgcatgtg ctcctcatga
1081 aatgtctgtt ctagggggct atctgggaga ggaattcttc gggaaaggga catttgaaag
1141 aagattcttc agagatgaga aagaacttca agaatacgag gcggctgaac tgacaaagac
1201 tgacgtagca ctggcagatg atggaactgt caacTCTgac gacgaggact acttttcagg
1261 tgaaaccaga agtccggagg ctgtttatac tcgaatcatg atgaatggag gtcgactaaa
1321 gagatctcac atacggagat atgtctcagt cagttccaat catcaagccc gtccaaactc
1381 attcgccgag tttctaaaca agacatattc gagtgactca taagaagttg aataacaaaa
1441 tgccggaaat ctacggattg tgtatatcca tcatgaaaaa aactaacacc cctcctttcg
1501 aaccatccca aacatgagca agatctttgt caatcctagt gctattagag ccggtctggc
1561 cgatcttgag atggctgaag aaactgttga tctgatcaat agaaatatcg aagacaatca
1621 ggctcatctc caaggggaac ccatagaggt ggacaatctc cctgaggata tggggcgact
1681 tcacctggat gatggaaaat cgcccaacca tggtgagata gccaaggtgg gagaaggcaa
1741 gtatcgagag gactttcaga tggatgaagg agaggatcct agcttcctgt tccagtcata
```

Fig. 9A-2

```
1801 cctggaaaat gttggagtcc aaatagtcag acaaatgagg tcaggagaga gatttctcaa
1861 gatatggtca cagaccgtag aagagattat atcctatgtc gcggtcaact ttcccaaccc
1921 tccaggaaag tcttcagagg ataaatcaac ccagactact ggccgagagc tcaagaagga
1981 gacaacaccc actccttctc agagagaaag ccaatcatcg aaagccagga tggcggctca
2041 aattgcttct ggccctccag cccttgaatg gtcggctacc aatgaagagg atgatctatc
2101 agtggaggct gagatcgctc accagattgc agaaagtttc tccaaaaaat ataagtttcc
2161 ctctcgatcc tcagggatac tcttgtataa ttttgagcaa ttgaaaatga accttgatga
2221 tatagttaaa gaggcaaaaa atgtaccagg tgtgacccgt ttagcccatg acgggtccaa
2281 actcccccta agatgtgtac tgggatgggt cgctttggcc aactctaaga aattccagtt
2341 gttagtcgaa tccgacaagc tgagtaaaat catgcaagat gacttgaatc gctatacatc
2401 ttgctaaccg aacctctccc ctcagtccct ctagacaata aaatccgaga tgtcccaaag
2461 tcaacatgaa aaaaacaggc aacaccactg ataaaatgaa cctcctacgt aagatagtga
2521 aaaaccgcag ggacgaggac actcaaaaat cctctcccgc gtcagcccct ctggatgacg
2581 atgacttgtg gcttccaccc cctgaatacg tcccgctgaa agaacttaca ggcaagaaga
2641 acatgaggaa cttttgtatc aacggaaggg ttaaagtgtg tagcccgaat ggttactcgt
2701 tcaggatcct gcggcacatt ctgaaatcat tcgacgagat atattctggg aatcatagga
2761 tgatcgggtt agtcaaagtg gttattggac tggctttgtc aggatctcca gtccctgagg
2821 gcctgaactg ggtatacaaa ttgaggagaa cctttatctt ccagtgggct gattccaggg
2881 gccctcttga aggggaggag ttggaatact ctcaggagat cacttgggat gatgatactg
2941 agttcgtcgg attgcaaata agagtgattg caaaacagtg tcatatccag ggcagagtct
3001 ggtgtatcaa catgaacccg agagcatgtc aactatggtc tgacatgtct cttcagacac
3061 aaaggtccga agaggacaaa gattcctctc tgcttctaga ataatcagat tatatcccgc
3121 aaatttatca cttgtttacc tctggaggag agaacatatg ggctcaactc caacccttgg
3181 gagcaatata acaaaaaaca tgttatggtg ccattaaacc gctgcatttc atcaaagtca
3241 agttgattac ctttacattt tgatcctctt ggatgtgaaa aaaactatta acatccctca
3301 aaagactcaa ggaaagatgg ttcctcaggc tctcctgttt gtaccccttc tggtttttcc
3361 attgtgtttt gggaaattcc ctatttacac gataccagac aagcttggtc cctggagtcc
3421 gattgacata catcacctca gctgcccaaa caatttggta gtggaggacg aaggatgcac
3481 caacctgtca gggttctcct acatggaact taaagttgga tacatcttag ccataaaagt
3541 gaacgggttc acttgcacag gcgttgtgac ggaggctgaa acctacacta acttcgttgg
```

Fig. 9A-3

```
3601 ttatgtcaca accacgttca aaagaaagca tttccgccca acaccagatg catgtagagc
3661 cgcgtacaac tggaagatgg ccggtgaccc cagatatgaa gagtctctac acaatccgta
3721 ccctgactac cgctggcttc gaactgtaaa aaccaccaag gagtctctcg ttatcatatc
3781 tccaagtgtg gcagatttgg acccatatga cagatccctt cactcgaggg tcttccctag
3841 cgggaagtgc tcaggagtag cggtgtcttc tacctactgc tccactaacc acgattacac
3901 catttggatg cccgagaatc cgagactagg gatgtcttgt gacattttta ccaatagtag
3961 agggaagaga gcatccaaag ggagtgagac ttgcggcttt gtagatgaaa gaggcctata
4021 taagtcttta aaaggagcat gcaaactcaa gttatgtgga gttctaggac ttagacttat
4081 ggatggaaca tgggtctcga tgcaaacatc aaatgaaacc aaatggtgcc ctcccgataa
4141 gttggtgaac ctgcacgact ttcgctcaga cgaaattgag caccttgttg tagaggagtt
4201 ggtcaggaag agagaggagt gtctggatgc actagagtcc atcatgacaa ccaagtcagt
4261 gagtttcaga cgtctcagtc atttaagaaa acttgtccct gggtttggaa aagcatatac
4321 catattcaac aagaccttga tggaagccga tgctcactac aagtcagtca gaacttggaa
4381 tgagatcctc ccttcaaaag ggtgtttaag agttgggggg aggtgtcatc ctcatgtgaa
4441 cggggtgttt ttcaatggta taatattagg acctgacggc aatgtcttaa tcccagagat
4501 gcaatcatcc ctcctccagc aacatatgga gttgttggaa tcctcggtta tcccccttgt
4561 gcaccccctg gcagacccgt ctaccgtttt caaggacggt gacgaggctg aggattttgt
4621 tgaagttcac cttcccgatg tgcacaatca ggtctcagga gttgacttgg gtctcccgaa
4681 ctgggggaag tatgtattac tgagtgcagg ggccctgact gccttgatgt tgataatttt
4741 cctgatgaca tgttgtagaa gagtcaatcg atcagaacct acgcaacaca atctcagagg
4801 gacagggagg gaggtgtcag tcactcccca aagcgggaag atcatatctt catgggaatc
4861 acacaagagt gggggtgaga ccagactgta aggactggcc gtcctttcaa cgatccaagt
4921 cctgaagatc acctcccctt ggggggttct ttttgaaaaa cctgggttca atagtcctcc
4981 ttgaactcca tgcaactggg tagattcaag agtcatgaga ttttcattaa tcctctcagt
5041 tgatcaagca agatcatgtc gattctcata ataggggaga tcttctagca gtttcagtga
5101 ctaacggtac tttcattctc caggaactga caccaacagt tgtagacaaa ccacggggtg
5161 tctcgggtga ctctgtgctt gggcacagac aaaggtcatg gtgtgttcca tgatagcgga
5221 ctcaggatga gttaattgag agaggcagtc ttcctcccgt gaaggacata agcagtagct
5281 cacaatcatc tcgcgtctca gcaaagtgtg cataattata aagtgctggg tcatctaagc
5341 ttttcagtcg agaaaaaaac attagatcag aagaacaact ggcaacactt ctcaacctga
```

Fig. 9A-4

```
5401 gacttacttc aagatgctcg atcctggaga ggtctatgat gaccctattg acccaatcga
5461 gttagaggct gaacccagag gaaccccat tgtccccaac atcttgagga actctgacta
5521 caatctcaac tctcctttga tagaagatcc tgctagacta atgttagaat ggttaaaaac
5581 agggaataga ccttatcgga tgactctaac agacaattgc tccaggtctt tcagagtttt
5641 gaaagattat ttcaagaagg tagatttggg ttctctcaag gtgggcggaa tggctgcaca
5701 gtcaatgatt tctctctggt tatatggtgc ccactctgaa tccaacagga gccggagatg
5761 tataacagac ttggcccatt tctattccaa gtcgtccccc atagagaagc tgttgaatct
5821 cacgctagga aatagagggc tgagaatccc cccagaggga gtgttaagtt gccttgagag
5881 ggttgattat gataatgcat ttggaaggta tcttgccaac acgtattcct cttacttgtt
5941 cttccatgta atcaccttat acatgaacgc cctagactgg gatgaagaaa agaccatcct
6001 agcattatgg aaagatttaa cctcagtgga catcgggaag gacttggtaa agttcaaaga
6061 ccaaatatgg ggactgctga tcgtgacaaa ggactttgtt tactcccaaa gttccaattg
6121 tctttttgac agaaactaca cacttatgct aaaagatctt ttcttgtctc gcttcaactc
6181 cttaatggtc ttgctctctc cccagagcc ccgatactca gatgacttga tatctcaact
6241 atgccagctg tacattgctg gggatcaagt cttgtctatg tgtggaaact ccggctatga
6301 agtcatcaaa atattggagc catatgtcgt gaatagttta gtccagagag cagaaaagtt
6361 taggcctctc attcattcct tgggagactt tcctgtattt ataaaagaca aggtaagtca
6421 acttgaagag acgttcggtc cctgtgcaag aaggttcttt agggctctgg atcaattcga
6481 caacatacat gacttggttt ttgtgtttgg ctgttacagg cattgggggc acccatatat
6541 agattatcga aagggtctgt caaaactata tgatcaggtt caccttaaaa aaatgataga
6601 taagtcctac caggagtgct tagcaagcga cctagccagg aggatcctta gatggggttt
6661 tgataagtac tccaagtggt atctggattc aagattccta gcccgagacc acccccttgac
6721 tccttatatc aaaacccaaa catggccacc caaacatatt gtagacttgg tgggggatac
6781 atggcacaag ctcccgatca cgcagatctt tgagattcct gaatcaatgg atccgtcaga
6841 aatattggat gacaaatcac attctttcac cagaacgaga ctagcttctt ggctgtcaga
6901 aaaccgaggg gggcctgttc ctagcgaaaa agttattatc acggccctgt ctaagccgcc
6961 tgtcaatccc cgagagtttc tgaggtctat agacctcgga ggattgccag atgaagactt
7021 gataattggc ctcaagccaa aggaacggga attgaagatt gaaggtcgat tctttgctct
7081 aatgtcatgg aatctaagat tgtattttgt catcactgaa aaactcttgg ccaactacat
7141 cttgccactt tttgacgcgc tgactatgac agacaacctg aacaaggtgt ttaaaaagct
```

Fig. 9A-5

7201 gatcgacagg gtcaccgggc aagggctttt ggactattca agggtcacat atgcatttca
7261 cctggactat gaaaagtgga acaaccatca aagattagag tcaacagagg atgtattttc
7321 tgtcctagat caagtgtttg gattgaagag agtgttttct agaacacacg agtttttca
7381 aaaggcctgg atctattatt cagacagatc agacctcatc gggttacggg aggatcaaat
7441 atactgctta gatgcgtcca acggcccaac ctgttggaat ggccaggatg gcgggctaga
7501 aggcttacgg cagaagggct ggagtctagt cagcttattg atgatagata gagaatctca
7561 aatcaggaac acaagaacca aaatactagc tcaaggagac aaccaggttt tatgtccgac
7621 atacatgttg tcgccagggc tatctcaaga ggggctcctc tatgaattgg agagaatatc
7681 aaggaatgca ctttcgatat acagagccgt cgaggaaggg gcatctaagc tagggctgat
7741 catcaagaaa gaagagacca tgtgtagtta tgacttcctc atctatggaa aaaccccttt
7801 gtttagaggt aacatattgg tgcctgagtc caaaagatgg gccagagtct cttgcgtctc
7861 taatgaccaa atagtcaacc tcgccaatat aatgtcgaca gtgtccacca atgcgctaac
7921 agtggcacaa cactctcaat ctttgatcaa accgatgagg gattttctgc tcatgtcagt
7981 acaggcagtc tttcactacc tgctatttag cccaatctta aagggaagag tttacaagat
8041 tctgagcgct gaaggggaga gctttctcct agccatgtca aggataatct atctagatcc
8101 ttctttggga gggatatctg gaatgtccct cggaagattc catatacgac agttctcaga
8161 ccctgtctct gaagggttat ccttctggag agagatctgg ttaagctccc aagagtcctg
8221 gattcacgcg ttgtgtcaag aggctggaaa cccagatctt ggagagagaa cactcgagag
8281 cttcactcgc cttctagaag atccgaccac cttaaatatc agaggagggg ccagtcctac
8341 cattctactc aaggatgcaa tcagaaaggc tttatatgac gaggtggaca aggtggaaaa
8401 ttcagagttt cgagaggcaa tcctgttgtc caagacccat agagataatt ttatactctt
8461 cttaatatct gttgagcctc tgtttcctcg atttctcagt gagctattca gttcgtcttt
8521 tttgggaatc cccgagtcaa tcattggatt gatacaaaac tcccgaacga taagaaggca
8581 gtttagaaag agtctctcaa aaactttaga agaatccttc tacaactcag agatccacgg
8641 gattagtcgg atgacccaga cacctcagag ggttgggggg gtgtggcctt gctcttcaga
8701 gagggcagat ctacttaggg agatctcttg ggaagaaaa gtggtaggca cgacagttcc
8761 tcacccttct gagatgttgg gattacttcc caagtcctct atttcttgca cttgtggagc
8821 aacaggagga ggcaatccta gagtttctgt atcagtactc ccgtcctttg atcagtcatt
8881 tttttcacga ggcccctaa agggatactt gggctcgtcc acctctatgt cgacccagct
8941 attccatgca tgggaaaaag tcactaatgt tcatgtggtg aagagagctc tatcgttaaa

Fig. 9A-6

```
9001 agaatctata aactggttca ttactagaga ttccaacttg gctcaagctc taattaggaa
9061 cattatgtct ctgacaggcc ctgatttccc tctagaggag gcccctgtct tcaaaaggac
9121 ggggtcagcc ttgcataggt tcaagtctgc cagatacagc gaaggagggt attcttctgt
9181 ctgcccgaac ctcctctctc atatttctgt tagtacagac accatgtctg atttgaccca
9241 agacgggaag aactacgatt tcatgttcca gccattgatg ctttatgcac agacatggac
9301 atcagagctg gtacagagag acacaaggct aagagactct acgtttcatt ggcacctccg
9361 atgcaacagg tgtgtgagac ccattgacga cgtgaccctg gagacctctc agatcttcga
9421 gtttccggat gtgtcgaaaa gaatatccag aatggtttct ggggctgtgc ctcacttcca
9481 gaggcttccc gatatccgtc tgagaccagg agattttgaa tctctaagcg gtagagaaaa
9541 gtctcaccat atcggatcag ctcaggggct cttatactca atcttagtgg caattcacga
9601 ctcaggatac aatgatggaa ccatcttccc tgtcaacata tacggcaagg tttcccctag
9661 agactatttg agagggctcg caaggggagt attgatagga tcctcgattt gcttcttgac
9721 aagaatgaca aatatcaata ttaatagacc tcttgaattg gtctcagggg taatctcata
9781 tattctcctg aggctagata accatccctc cttgtacata atgctcagag aaccgtctct
9841 tagaggagag atattttcta tccctcagaa aatccccgcc gcttatccaa ccactatgaa
9901 agaaggcaac agatcaatct tgtgttatct ccaacatgtg ctacgctatg agcgagagat
9961 aatcacggcg tctccagaga atgactggct atggatcttt tcagacttta gaagtgccaa
10021 aatgacgtac ctatccctca ttacttacca gtctcatctt ctactccaga gggttgagag
10081 aaacctatct aagagtatga gagataacct gcgacaattg agttctttga tgaggcaggt
10141 gctgggcggg cacggagaag ataccttaga gtcagacgac aacattcaac gactgctaaa
10201 agactcttta cgaaggacaa gatgggtgga tcaagaggtg cgccatgcag ctagaaccat
10261 gactggagat tacagcccca acaagaaggt gtcccgtaag gtaggatgtt cagaatgggt
10321 ctgctctgct caacaggttg cagtctctac ctcagcaaac ccggcccctg tctcggagct
10381 tgacataagg gccctctcta agaggttcca gaaccctttg atctcgggct tgagagtggt
10441 tcagtgggca accggtgctc attataagct taagcctatt ctagatgatc tcaatgtttt
10501 cccatctctc tgccttgtag ttggggacgg gtcagggggg atatcaaggg cagtcctcaa
10561 catgtttcca gatgccaagc ttgtgttcaa cagtctttta gaggtgaatg acctgatggc
10621 ttccggaaca catccactgc ctccttcagc aatcatgagg ggaggaaatg atatcgtctc
10681 cagagtgata gatcttgact caatctggga aaaaccgtcc gacttgagaa acttggcaac
10741 ctggaaatac ttccagtcag tccaaaagca ggtcaacatg tcctatgacc tcattatttg
```

Fig. 9A-7

```
10801 cgatgcagaa gttactgaca ttgcatctat caaccggatc accctgttaa tgtccgattt
10861 tgcattgtct atagatggac cactctattt ggtcttcaaa acttatggga ctatgctagt
10921 aaatccaaac tacaaggcta ttcaacacct gtcaagagcg ttcccctcgg tcacagggtt
10981 tatcacccaa gtaacttcgt ctttttcatc tgagctctac ctccgattct ccaaacgagg
11041 gaagtttttc agagatgctg agtacttgac ctcttccacc cttcgagaaa tgagccttgt
11101 gttattcaat tgtagcagcc ccaagagtga gatgcagaga gctcgttcct tgaactatca
11161 ggatcttgtg agaggatttc ctgaagaaat catatcaaat ccttacaatg agatgatcat
11221 aactctgatt gacagtgatg tagaatcttt tctagtccac aagatggttg atgatcttga
11281 gttacagagg ggaactctgt ctaaagtggc tatcattata gccatcatga tagttttctc
11341 caacagagtc ttcaacgttt ccaaacccct aactgacccc tcgttctatc caccgtctga
11401 tcccaaaatc ctgaggcact tcaacatatg ttgcagtact atgatgtatc tatctactgc
11461 tttaggtgac gtccctagct tcgcaagact tcacgacctg tataacagac ctataactta
11521 ttacttcaga aagcaagtca ttcgagggaa cgtttatcta tcttggagtt ggtccaacga
11581 cacctcagtg ttcaaaaggg tagcctgtaa ttctagcctg agtctgtcat ctcactggat
11641 caggttgatt tacaagatag tgaagactac cagactcgtt ggcagcatca aggatctatc
11701 cagagaagtg gaaagacacc ttcataggta caacaggtgg atcaccctag aggatatcag
11761 atctagatca tccctactag actacagttg cctgtgaacc ggatactcct ggaagcctgc
11821 ccatgctaag actcttgtgt gatgtatctt gaaaaaaaca agatcctaaa tctgaacctt
11881 tggttgtttg attgtttttc tcatttttgt tgtttatttg ttaagcgt
```

Fig. 9B-1

```
   1 acgcttaaca accagatcaa agaaaaaaca gacattgtca attgcaaagc aaaaatgtaa
  61 cacccctaca atggatgccg acaagattgt attcaaagtc aataatcagg tggtctcttt
 121 gaagcctgag attatcgtgg atcaatatga gtacaagtac cctgccatca aagatttgaa
 181 aaagccctgt ataaccctag gaaaggctcc cgatttaaat aaagcataca agtcagtttt
 241 gtcaggcatg agcgccgcca aacttaatcc tgacgatgta tgttcctatt tggcagcggc
 301 aatgcagttt tttgagggga catgtccgga agactggacc agctatggaa ttgtgattgc
 361 acgaaaagga gataagatca ccccaggttc tctggtggag ataaaacgta ctgatgtaga
 421 agggaattgg gctctgacag gaggcatgga actgacaaga gaccccactg tccctgagca
 481 tgcgtcctta gtcggtcttc tcttgagtct gtataggttg agcaaaatat ccgggcaaaa
 541 cactggtaac tataagacaa acattgcaga caggatagag cagatttttg agacagcccc
 601 ttttgttaaa atcgtggaac accatactct aatgacaact cacaaaatgt gtgctaattg
 661 gagtactata ccaaacttca gatttttggc cggaacctat gacatgtttt tctcccggat
 721 tgagcatcta tattcagcaa tcagagtggg cacagttgtc actgcttatg aagactgttc
 781 aggactggta tcatttactg ggttcataaa acaaatcaat ctcaccgcta gagaggcaat
 841 actatatttc ttccacaaga actttgagga agagataaga agaatgtttg agccagggca
 901 ggagacagct gttcctcact cttatttcat ccacttccgt tcactaggct tgagtgggaa
 961 atctccttat tcatcaaatg ctgttggtca cgtgttcaat ctcattcact ttgtaggatg
1021 ctatatgggt caagtcagat ccctaaatgc aacggttatt gctgcatgtg ctcctcatga
1081 aatgtctgtt ctagggggct atctgggaga ggaattcttc gggaaaggga catttgaaag
1141 aagattcttc agagatgaga aagaacttca agaatacgag gcggctgaac tgacaaagac
1201 tgacgtagca ctggcagatg atggaactgt caacGCTgac gacgaggact acttttcagg
1261 tgaaaccaga agtccggagg ctgtttatac tcgaatcatg atgaatggag gtcgactaaa
1321 gagatctcac atacggagat atgtctcagt cagttccaat catcaagccc gtccaaactc
1381 attcgccgag tttctaaaca agacatattc gagtgactca taagaagttg aataacaaaa
1441 tgccggaaat ctacggattg tgtatatcca tcatgaaaaa aactaacacc cctcctttcg
1501 aaccatccca aacatgagca agatctttgt caatcctagt gctattagag ccggtctggc
1561 cgatcttgag atggctgaag aaactgttga tctgatcaat agaaatatcg aagacaatca
1621 ggctcatctc caaggggaac ccatagaggt ggacaatctc cctgaggata tggggcgact
1681 tcacctggat gatggaaaat cgcccaacca tggtgagata gccaaggtgg gagaaggcaa
1741 gtatcgagag gactttcaga tggatgaagg agaggatcct agcttcctgt tccagtcata
1801 cctggaaaat gttggagtcc aaatagtcag acaaatgagg tcaggagaga gatttctcaa
```

Fig. 9B-2

```
1861 gatatggtca cagaccgtag aagagattat atcctatgtc gcggtcaact ttcccaaccc
1921 tccaggaaag tcttcagagg ataaatcaac ccagactact ggccgagagc tcaagaagga
1981 gacaacaccc actccttctc agagagaaag ccaatcatcg aaagccagga tggcggctca
2041 aattgcttct ggccctccag cccttgaatg gtcggctacc aatgaagagg atgatctatc
2101 agtggaggct gagatcgctc accagattgc agaaagtttc tccaaaaaat ataagtttcc
2161 ctctcgatcc tcagggatac tcttgtataa ttttgagcaa ttgaaaatga accttgatga
2221 tatagttaaa gaggcaaaaa atgtaccagg tgtgacccgt ttagcccatg acgggtccaa
2281 actcccccta agatgtgtac tgggatgggt cgctttggcc aactctaaga aattccagtt
2341 gttagtcgaa tccgacaagc tgagtaaaat catgcaagat gacttgaatc gctatacatc
2401 ttgctaaccg aacctctccc ctcagtccct ctagacaata aaatccgaga tgtcccaaag
2461 tcaacatgaa aaaaacaggc aacaccactg ataaaatgaa cctcctacgt aagatagtga
2521 aaaaccgcag ggacgaggac actcaaaaat cctctcccgc gtcagcccct ctggatgacg
2581 atgacttgtg gcttccaccc cctgaatacg tcccgctgaa agaacttaca ggcaagaaga
2641 acatgaggaa cttttgtatc aacggaaggg ttaaagtgtg tagcccgaat ggttactcgt
2701 tcaggatcct gcggcacatt ctgaaatcat tcgacgagat atattctggg aatcatagga
2761 tgatcgggtt agtcaaagtg gttattggac tggctttgtc aggatctcca gtccctgagg
2821 gcctgaactg ggtatacaaa ttgaggagaa cctttatctt ccagtgggct gattccaggg
2881 gccctcttga aggggaggag ttggaatact ctcaggagat cacttgggat gatgatactg
2941 agttcgtcgg attgcaaata agagtgattg caaaacagtg tcatatccag ggcagagtct
3001 ggtgtatcaa catgaacccg agagcatgtc aactatggtc tgacatgtct cttcagacac
3061 aaaggtccga agaggacaaa gattcctctc tgcttctaga ataatcagat tatatcccgc
3121 aaatttatca cttgtttacc tctggaggag agaacatatg ggctcaactc caacccttgg
3181 gagcaatata acaaaaaaca tgttatggtg ccattaaacc gctgcatttc atcaaagtca
3241 agttgattac ctttacattt tgatcctctt ggatgtgaaa aaaactatta acatccctca
3301 aaagactcaa ggaaagatgg ttcctcaggc tctcctgttt gtaccccttc tggtttttcc
3361 attgtgtttt gggaaattcc ctatttacac gataccagac aagcttggtc cctggagtcc
3421 gattgacata catcacctca gctgcccaaa caatttggta gtggaggacg aaggatgcac
3481 caacctgtca gggttctcct acatggaact taaagttgga tacatcttag ccataaaagt
3541 gaacgggttc acttgcacag gcgttgtgac ggaggctgaa acctacacta acttcgttgg
3601 ttatgtcaca accacgttca aaagaaagca tttccgccca acaccagatg catgtagagc
```

Fig. 9B-3

```
3661 cgcgtacaac tggaagatgg ccggtgaccc cagatatgaa gagtctctac acaatccgta
3721 ccctgactac cgctggcttc gaactgtaaa aaccaccaag gagtctctcg ttatcatatc
3781 tccaagtgtg gcagatttgg acccatatga cagatccctt cactcgaggg tcttccctag
3841 cgggaagtgc tcaggagtag cggtgtcttc tacctactgc tccactaacc acgattacac
3901 catttggatg cccgagaatc cgagactagg gatgtcttgt gacattttta ccaatagtag
3961 agggaagaga gcatccaaag ggagtgagac ttgcggcttt gtagatgaaa gaggcctata
4021 taagtcttta aaaggagcat gcaaactcaa gttatgtgga gttctaggac ttagacttat
4081 ggatggaaca tgggtctcga tgcaaacatc aaatgaaacc aaatggtgcc ctcccgataa
4141 gttggtgaac ctgcacgact ttcgctcaga cgaaattgag caccttgttg tagaggagtt
4201 ggtcaggaag agagaggagt gtctggatgc actagagtcc atcatgacaa ccaagtcagt
4261 gagtttcaga cgtctcagtc atttaagaaa acttgtccct gggtttggaa aagcatatac
4321 catattcaac aagaccttga tggaagccga tgctcactac aagtcagtca gaacttggaa
4381 tgagatcctc ccttcaaaag ggtgtttaag agttgggggg aggtgtcatc ctcatgtgaa
4441 cggggtgttt ttcaatggta taatattagg acctgacggc aatgtcttaa tcccagagat
4501 gcaatcatcc ctcctccagc aacatatgga gttgttggaa tcctcggtta tccccccttgt
4561 gcacccccctg gcagacccgt ctaccgtttt caaggacggt gacgaggctg aggattttgt
4621 tgaagttcac cttcccgatg tgcacaatca ggtctcagga gttgacttgg gtctcccgaa
4681 ctgggggaag tatgtattac tgagtgcagg ggccctgact gccttgatgt tgataatttt
4741 cctgatgaca tgttgtagaa gagtcaatcg atcagaacct acgcaacaca atctcagagg
4801 gacagggagg gaggtgtcag tcactcccca aagcgggaag atcatatctt catgggaatc
4861 acacaagagt gggggtgaga ccagactgta aggactggcc gtcctttcaa cgatccaagt
4921 cctgaagatc acctcccctt ggggggttct ttttgaaaaa cctgggttca atagtcctcc
4981 ttgaactcca tgcaactggg tagattcaag agtcatgaga ttttcattaa tcctctcagt
5041 tgatcaagca agatcatgtc gattctcata ataggggaga tcttctagca gtttcagtga
5101 ctaacggtac tttcattctc caggaactga caccaacagt tgtagacaaa ccacggggtg
5161 tctcgggtga ctctgtgctt gggcacagac aaaggtcatg gtgtgttcca tgatagcgga
5221 ctcaggatga gttaattgag agaggcagtc ttcctcccgt gaaggacata agcagtagct
5281 cacaatcatc tcgcgtctca gcaaagtgtg cataattata aagtgctggg tcatctaagc
5341 ttttcagtcg agaaaaaaac attagatcag aagaacaact ggcaacactt ctcaacctga
5401 gacttacttc aagatgctcg atcctggaga ggtctatgat gaccctattg acccaatcga
```

Fig. 9B-4

```
5461 gttagaggct gaacccagag gaaccccat tgtccccaac atcttgagga actctgacta
5521 caatctcaac tctcctttga tagaagatcc tgctagacta atgttagaat ggttaaaaac
5581 agggaataga ccttatcgga tgactctaac agacaattgc tccaggtctt tcagagtttt
5641 gaaagattat ttcaagaagg tagatttggg ttctctcaag gtgggcggaa tggctgcaca
5701 gtcaatgatt tctctctggt tatatggtgc ccactctgaa tccaacagga gccggagatg
5761 tataacagac ttggcccatt tctattccaa gtcgtccccc atagagaagc tgttgaatct
5821 cacgctagga aatagagggc tgagaatccc cccagaggga gtgttaagtt gccttgagag
5881 ggttgattat gataatgcat ttggaaggta tcttgccaac acgtattcct cttacttgtt
5941 cttccatgta atcaccttat acatgaacgc cctagactgg gatgaagaaa agaccatcct
6001 agcattatgg aaagatttaa cctcagtgga catcgggaag gacttggtaa agttcaaaga
6061 ccaaatatgg ggactgctga tcgtgacaaa ggactttgtt tactcccaaa gttccaattg
6121 tctttttgac agaaactaca cacttatgct aaaagatctt ttcttgtctc gcttcaactc
6181 cttaatggtc ttgctctctc ccccagagcc ccgatactca gatgacttga tatctcaact
6241 atgccagctg tacattgctg ggatcaagt cttgtctatg tgtggaaact ccggctatga
6301 agtcatcaaa atattggagc catatgtcgt gaatagttta gtccagagag cagaaaagtt
6361 taggcctctc attcattcct tgggagactt tcctgtattt ataaaagaca aggtaagtca
6421 acttgaagag acgttcggtc cctgtgcaag aaggttcttt agggctctgg atcaattcga
6481 caacatacat gacttggttt ttgtgtttgg ctgttacagg cattgggggc acccatatat
6541 agattatcga aagggtctgt caaaactata tgatcaggtt caccttaaaa aaatgataga
6601 taagtcctac caggagtgct tagcaagcga cctagccagg aggatcctta gatggggttt
6661 tgataagtac tccaagtggt atctggattc aagattccta gcccgagacc acccccttgac
6721 tccttatatc aaaacccaaa catggccacc caaacatatt gtagacttgg tgggggatac
6781 atggcacaag ctcccgatca cgcagatctt tgagattcct gaatcaatgg atccgtcaga
6841 aatattggat gacaaatcac attctttcac cagaacgaga ctagcttctt ggctgtcaga
6901 aaaccgaggg gggcctgttc ctagcgaaaa agttattatc acggccctgt ctaagccgcc
6961 tgtcaatccc cgagagtttc tgaggtctat agacctcgga ggattgccag atgaagactt
7021 gataattggc ctcaagccaa aggaacggga attgaagatt gaaggtcgat tctttgctct
7081 aatgtcatgg aatctaagat tgtattttgt catcactgaa aaactcttgg ccaactacat
7141 cttgccactt tttgacgcgc tgactatgac agacaacctg aacaaggtgt ttaaaaagct
7201 gatcgacagg gtcaccgggc aagggctttt ggactattca agggtcacat atgcatttca
```

Fig. 9B-5

```
7261 cctggactat gaaaagtgga acaaccatca aagattagag tcaacagagg atgtattttc
7321 tgtcctagat caagtgtttg gattgaagag agtgttttct agaacacacg agtttttca
7381 aaaggcctgg atctattatt cagacagatc agacctcatc gggttacggg aggatcaaat
7441 atactgctta gatgcgtcca acggcccaac ctgttggaat ggccaggatg gcgggctaga
7501 aggcttacgg cagaagggct ggagtctagt cagcttattg atgatagata gagaatctca
7561 aatcaggaac acaagaacca aaatactagc tcaaggagac aaccaggttt tatgtccgac
7621 atacatgttg tcgccagggc tatctcaaga ggggctcctc tatgaattgg agagaatatc
7681 aaggaatgca ctttcgatat acagagccgt cgaggaaggg gcatctaagc tagggctgat
7741 catcaagaaa gaagagacca tgtgtagtta tgacttcctc atctatggaa aaaccccttt
7801 gtttagaggt aacatattgg tgcctgagtc caaaagatgg gccagagtct cttgcgtctc
7861 taatgaccaa atagtcaacc tcgccaatat aatgtcgaca gtgtccacca atgcgctaac
7921 agtggcacaa cactctcaat ctttgatcaa accgatgagg gattttctgc tcatgtcagt
7981 acaggcagtc tttcactacc tgctatttag cccaatctta aagggaagag tttacaagat
8041 tctgagcgct gaaggggaga gctttctcct agccatgtca aggataatct atctagatcc
8101 ttctttggga gggatatctg gaatgtccct cggaagattc catatacgac agttctcaga
8161 ccctgtctct gaagggttat ccttctggag agagatctgg ttaagctccc aagagtcctg
8221 gattcacgcg ttgtgtcaag aggctggaaa cccagatctt ggagagagaa cactcgagag
8281 cttcactcgc cttctagaag atccgaccac cttaaatatc agaggagggg ccagtcctac
8341 cattctactc aaggatgcaa tcagaaaggc tttatatgac gaggtggaca aggtggaaaa
8401 ttcagagttt cgagaggcaa tcctgttgtc caagacccat agagataatt ttatactctt
8461 cttaatatct gttgagcctc tgtttcctcg atttctcagt gagctattca gttcgtcttt
8521 tttgggaatc cccgagtcaa tcattggatt gatacaaaac tcccgaacga taagaaggca
8581 gtttagaaag agtctctcaa aaactttaga agaatccttc tacaactcag agatccacgg
8641 gattagtcgg atgacccaga cacctcagag ggttgggggg gtgtggcctt gctcttcaga
8701 gagggcagat ctacttaggg agatctcttg ggaagaaaaa gtggtaggca cgacagttcc
8761 tcacccttct gagatgttgg gattacttcc caagtcctct atttcttgca cttgtggagc
8821 aacaggagga ggcaatccta gagtttctgt atcagtactc ccgtcctttg atcagtcatt
8881 tttttcacga ggcccctaa agggatactt gggctcgtcc acctctatgt cgacccagct
8941 attccatgca tgggaaaaag tcactaatgt tcatgtggtg aagagagctc tatcgttaaa
9001 agaatctata aactggttca ttactagaga ttccaacttg gctcaagctc taattaggaa
```

Fig. 9B-6

```
9061 cattatgtct ctgacaggcc ctgatttccc tctagaggag gcccctgtct tcaaaaggac
9121 ggggtcagcc ttgcataggt tcaagtctgc cagatacagc gaaggagggt attcttctgt
9181 ctgcccgaac ctcctctctc atatttctgt tagtacagac accatgtctg atttgaccca
9241 agacgggaag aactacgatt tcatgttcca gccattgatg ctttatgcac agacatggac
9301 atcagagctg gtacagagag acacaaggct aagagactct acgtttcatt ggcacctccg
9361 atgcaacagg tgtgtgagac ccattgacga cgtgaccctg gagacctctc agatcttcga
9421 gtttccggat gtgtcgaaaa gaatatccag aatggtttct ggggctgtgc ctcacttcca
9481 gaggcttccc gatatccgtc tgagaccagg agattttgaa tctctaagcg gtagagaaaa
9541 gtctcaccat atcggatcag ctcaggggct cttatactca atcttagtgg caattcacga
9601 ctcaggatac aatgatggaa ccatcttccc tgtcaacata tacggcaagg tttcccctag
9661 agactatttg agagggctcg caagggggagt attgatagga tcctcgattt gcttcttgac
9721 aagaatgaca aatatcaata ttaatagacc tcttgaattg gtctcagggg taatctcata
9781 tattctcctg aggctagata accatccctc cttgtacata atgctcagag aaccgtctct
9841 tagaggagag atattttcta tccctcagaa aatccccgcc gcttatccaa ccactatgaa
9901 agaaggcaac agatcaatct tgtgttatct ccaacatgtg ctacgctatg agcgagagat
9961 aatcacggcg tctccagaga atgactggct atggatcttt tcagacttta gaagtgccaa
10021 aatgacgtac ctatccctca ttacttacca gtctcatctt ctactccaga gggttgagag
10081 aaacctatct aagagtatga gagataacct gcgacaattg agttctttga tgaggcaggt
10141 gctgggcggg cacggagaag ataccttaga gtcagacgac aacattcaac gactgctaaa
10201 agactcttta cgaaggacaa gatgggtgga tcaagaggtg cgccatgcag ctagaaccat
10261 gactggagat tacagcccca acaagaaggt gtcccgtaag gtaggatgtt cagaatgggt
10321 ctgctctgct caacaggttg cagtctctac ctcagcaaac ccggcccctg tctcggagct
10381 tgacataagg gccctctcta agaggttcca gaaccctttg atctcgggct tgagagtggt
10441 tcagtgggca accggtgctc attataagct taagcctatt ctagatgatc tcaatgtttt
10501 cccatctctc tgccttgtag ttggggacgg gtcagggggg atatcaaggg cagtcctcaa
10561 catgtttcca gatgccaagc ttgtgttcaa cagtctttta gaggtgaatg acctgatggc
10621 ttccggaaca catccactgc ctccttcagc aatcatgagg ggaggaaatg atatcgtctc
10681 cagagtgata gatcttgact caatctggga aaaaccgtcc gacttgagaa acttggcaac
10741 ctggaaatac ttccagtcag tccaaaagca ggtcaacatg tcctatgacc tcattatttg
10801 cgatgcagaa gttactgaca ttgcatctat caaccggatc accctgttaa tgtccgattt
10861 tgcattgtct atagatggac cactctattt ggtcttcaaa acttatggga ctatgctagt
10921 aaatccaaac tacaaggcta ttcaacacct gtcaagagcg ttcccctcgg tcacagggtt
10981 tatcacccaa gtaacttcgt ctttttcatc tgagctctac ctccgattct ccaaacgagg
11041 gaagtttttc agagatgctg agtacttgac ctcttccacc cttcgagaaa tgagccttgt
11101 gttattcaat tgtagcagcc ccaagagtga gatgcagaga gctcgttcct tgaactatca
11161 ggatcttgtg agaggatttc ctgaagaaat catatcaaat ccttacaatg agatgatcat
11221 aactctgatt gacagtgatg tagaatcttt tctagtccac aagatggttg atgatcttga
```

Fig. 9B-7

```
11281 gttacagagg ggaactctgt ctaaagtggc tatcattata gccatcatga tagttttctc
11341 caacagagtc ttcaacgttt ccaaacccct aactgacccc tcgttctatc caccgtctga
11401 tcccaaaatc ctgaggcact tcaacatatg ttgcagtact atgatgtatc tatctactgc
11461 tttaggtgac gtccctagct tcgcaagact tcacgacctg tataacagac ctataactta
11521 ttacttcaga aagcaagtca ttcgagggaa cgtttatcta tcttggagtt ggtccaacga
11581 cacctcagtg ttcaaaaggg tagcctgtaa ttctagcctg agtctgtcat ctcactggat
11641 caggttgatt tacaagatag tgaagactac cagactcgtt ggcagcatca aggatctatc
11701 cagagaagtg gaaagacacc ttcataggta caacaggtgg atcaccctag aggatatcag
11761 atctagatca tccctactag actacagttg cctgtgaacc ggatactcct ggaagcctgc
11821 ccatgctaag actcttgtgt gatgtatctt gaaaaaaaca agatcctaaa tctgaacctt
11881 tggttgtttg attgtttttc tcatttttgt tgtttatttg ttaagcgt
```

Fig. 9C-1

```
   1 acgcttaaca accagatcaa agaaaaaaca gacattgtca attgcaaagc aaaaatgtaa
  61 cacccctaca atggatgccg acaagattgt attcaaagtc aataatcagg tggtctcttt
 121 gaagcctgag attatcgtgg atcaatatga gtacaagtac cctgccatca aagatttgaa
 181 aaagccctgt ataaccctag gaaaggctcc cgatttaaat aaagcataca agtcagtttt
 241 gtcaggcatg agcgccgcca aacttaatcc tgacgatgta tgttcctatt tggcagcggc
 301 aatgcagttt tttgagggga catgtccgga agactggacc agctatggaa ttgtgattgc
 361 acgaaaagga gataagatca ccccaggttc tctggtggag ataaaacgta ctgatgtaga
 421 agggaattgg gctctgacag gaggcatgga actgacaaga gaccccactg tccctgagca
 481 tgcgtcctta gtcggtcttc tcttgagtct gtataggttg agcaaaatat ccgggcaaaa
 541 cactggtaac tataagacaa acattgcaga caggatagag cagatttttg agacagcccc
 601 ttttgttaaa atcgtggaac accatactct aatgacaact cacaaaatgt gtgctaattg
 661 gagtactata ccaaacttca gatttttggc cggaacctat gacatgtttt tctcccggat
 721 tgagcatcta tattcagcaa tcagagtggg cacagttgtc actgcttatg aagactgttc
 781 aggactggta tcatttactg ggttcataaa acaaatcaat ctcaccgcta gagaggcaat
 841 actatatttc ttccacaaga actttgagga agagataaga agaatgtttg agccagggca
 901 ggagacagct gttcctcact cttatttcat ccacttccgt tcactaggct tgagtgggaa
 961 atctccttat tcatcaaatg ctgttggtca cgtgttcaat ctcattcact ttgtaggatg
1021 ctatatgggt caagtcagat ccctaaatgc aacggttatt gctgcatgtg ctcctcatga
1081 aatgtctgtt ctagggggct atctgggaga ggaattcttc gggaaaggga catttgaaag
1141 aagattcttc agagatgaga aagaacttca agaatacgag gcggctgaac tgacaaagac
1201 tgacgtagca ctggcagatg atggaactgt caacCAAgac gacgaggact acttttcagg
1261 tgaaaccaga agtccggagg ctgtttatac tcgaatcatg atgaatggag gtcgactaaa
1321 gagatctcac atacggagat atgtctcagt cagttccaat catcaagccc gtccaaactc
1381 attcgccgag tttctaaaca agacatattc gagtgactca taagaagttg aataacaaaa
1441 tgccggaaat ctacggattg tgtatatcca tcatgaaaaa aactaacacc cctcctttcg
1501 aaccatccca aacatgagca agatctttgt caatcctagt gctattagag ccggtctggc
1561 cgatcttgag atggctgaag aaactgttga tctgatcaat agaaatatcg aagacaatca
1621 ggctcatctc caaggggaac ccatagaggt ggacaatctc cctgaggata tggggcgact
1681 tcacctggat gatggaaaat cgcccaacca tggtgagata gccaaggtgg gagaaggcaa
1741 gtatcgagag gactttcaga tggatgaagg agaggatcct agcttcctgt tccagtcata
1801 cctggaaaat gttggagtcc aaatagtcag acaaatgagg tcaggagaga gatttctcaa
```

Fig. 9C-2

```
1861 gatatggtca cagaccgtag aagagattat atcctatgtc gcggtcaact ttcccaaccc
1921 tccaggaaag tcttcagagg ataaatcaac ccagactact ggccgagagc tcaagaagga
1981 gacaacaccc actccttctc agagagaaag ccaatcatcg aaagccagga tggcggctca
2041 aattgcttct ggccctccag cccttgaatg gtcggctacc aatgaagagg atgatctatc
2101 agtggaggct gagatcgctc accagattgc agaaagtttc tccaaaaaat ataagtttcc
2161 ctctcgatcc tcagggatac tcttgtataa ttttgagcaa ttgaaaatga accttgatga
2221 tatagttaaa gaggcaaaaa atgtaccagg tgtgacccgt ttagcccatg acgggtccaa
2281 actcccccta agatgtgtac tgggatgggt cgctttggcc aactctaaga aattccagtt
2341 gttagtcgaa tccgacaagc tgagtaaaat catgcaagat gacttgaatc gctatacatc
2401 ttgctaaccg aacctctccc ctcagtccct ctagacaata aaatccgaga tgtcccaaag
2461 tcaacatgaa aaaaacaggc aacaccactg ataaaatgaa cctcctacgt aagatagtga
2521 aaaaccgcag ggacgaggac actcaaaaat cctctcccgc gtcagcccct ctggatgacg
2581 atgacttgtg gcttccaccc cctgaatacg tcccgctgaa agaacttaca ggcaagaaga
2641 acatgaggaa cttttgtatc aacggaaggg ttaaagtgtg tagcccgaat ggttactcgt
2701 tcaggatcct gcggcacatt ctgaaatcat tcgacgagat atattctggg aatcatagga
2761 tgatcgggtt agtcaaagtg gttattggac tggctttgtc aggatctcca gtccctgagg
2821 gcctgaactg ggtatacaaa ttgaggagaa cctttatctt ccagtgggct gattccaggg
2881 gccctcttga aggggaggag ttggaatact ctcaggagat cacttgggat gatgatactg
2941 agttcgtcgg attgcaaata agagtgattg caaaacagtg tcatatccag ggcagagtct
3001 ggtgtatcaa catgaacccg agagcatgtc aactatggtc tgacatgtct cttcagacac
3061 aaaggtccga agaggacaaa gattcctctc tgcttctaga ataatcagat tatatcccgc
3121 aaatttatca cttgtttacc tctggaggag agaacatatg ggctcaactc caacccttgg
3181 gagcaatata acaaaaaaca tgttatggtg ccattaaacc gctgcatttc atcaaagtca
3241 agttgattac ctttacattt tgatcctctt ggatgtgaaa aaaactatta acatccctca
3301 aaagactcaa ggaaagatgg ttcctcaggc tctcctgttt gtaccccttc tggtttttcc
3361 attgtgtttt gggaaattcc ctatttacac gataccagac aagcttggtc cctggagtcc
3421 gattgacata catcacctca gctgcccaaa caatttggta gtggaggacg aaggatgcac
3481 caacctgtca gggttctcct acatggaact taaagttgga tacatcttag ccataaaagt
3541 gaacgggttc acttgcacag gcgttgtgac ggaggctgaa acctacacta acttcgttgg
3601 ttatgtcaca accacgttca aaagaaagca tttccgccca acaccagatg catgtagagc
```

Fig. 9C-3

3661 cgcgtacaac tggaagatgg ccggtgaccc cagatatgaa gagtctctac acaatccgta
3721 ccctgactac cgctggcttc gaactgtaaa aaccaccaag gagtctctcg ttatcatatc
3781 tccaagtgtg gcagatttgg acccatatga cagatccctt cactcgaggg tcttccctag
3841 cgggaagtgc tcaggagtag cggtgtcttc tacctactgc tccactaacc acgattacac
3901 catttggatg cccgagaatc cgagactagg gatgtcttgt gacattttta ccaatagtag
3961 agggaagaga gcatccaaag ggagtgagac ttgcggcttt gtagatgaaa gaggcctata
4021 taagtcttta aaaggagcat gcaaactcaa gttatgtgga gttctaggac ttagacttat
4081 ggatggaaca tgggtctcga tgcaaacatc aaatgaaacc aaatggtgcc ctcccgataa
4141 gttggtgaac ctgcacgact ttcgctcaga cgaaattgag caccttgttg tagaggagtt
4201 ggtcaggaag agagaggagt gtctggatgc actagagtcc atcatgacaa ccaagtcagt
4261 gagtttcaga cgtctcagtc atttaagaaa acttgtccct gggtttggaa aagcatatac
4321 catattcaac aagaccttga tggaagccga tgctcactac aagtcagtca gaacttggaa
4381 tgagatcctc ccttcaaaag ggtgtttaag agttgggggg aggtgtcatc ctcatgtgaa
4441 cggggtgttt ttcaatggta taatattagg acctgacggc aatgtcttaa tcccagagat
4501 gcaatcatcc ctcctccagc aacatatgga gttgttggaa tcctcggtta tccccccttgt
4561 gcaccccctg gcagacccgt ctaccgtttt caaggacggt gacgaggctg aggattttgt
4621 tgaagttcac cttcccgatg tgcacaatca ggtctcagga gttgacttgg gtctcccgaa
4681 ctgggggaag tatgtattac tgagtgcagg ggccctgact gccttgatgt tgataatttt
4741 cctgatgaca tgttgtagaa gagtcaatcg atcagaacct acgcaacaca atctcagagg
4801 gacagggagg gaggtgtcag tcactcccca aagcgggaag atcatatctt catgggaatc
4861 acacaagagt gggggtgaga ccagactgta aggactggcc gtcctttcaa cgatccaagt
4921 cctgaagatc acctcccctt ggggggttct tttgaaaaaa cctgggttca atagtcctcc
4981 ttgaactcca tgcaactggg tagattcaag agtcatgaga ttttcattaa tcctctcagt
5041 tgatcaagca agatcatgtc gattctcata ataggggaga tcttctagca gtttcagtga
5101 ctaacggtac tttcattctc caggaactga caccaacagt tgtagacaaa ccacggggtg
5161 tctcgggtga ctctgtgctt gggcacagac aaaggtcatg gtgtgttcca tgatagcgga
5221 ctcaggatga gttaattgag agaggcagtc ttcctcccgt gaaggacata agcagtagct
5281 cacaatcatc tcgcgtctca gcaaagtgtg cataattata aagtgctggg tcatctaagc
5341 ttttcagtcg agaaaaaaac attagatcag aagaacaact ggcaacactt ctcaacctga
5401 gacttacttc aagatgctcg atcctggaga ggtctatgat gaccctattg acccaatcga

Fig. 9C-4

5461 gttagaggct gaacccagag gaaccccat tgtccccaac atcttgagga actctgacta
5521 caatctcaac tctcctttga tagaagatcc tgctagacta atgttagaat ggttaaaaac
5581 agggaataga ccttatcgga tgactctaac agacaattgc tccaggtctt tcagagtttt
5641 gaaagattat ttcaagaagg tagatttggg ttctctcaag gtgggcggaa tggctgcaca
5701 gtcaatgatt tctctctggt tatatggtgc ccactctgaa tccaacagga gccggagatg
5761 tataacagac ttggcccatt tctattccaa gtcgtccccc atagagaagc tgttgaatct
5821 cacgctagga aatagagggc tgagaatccc cccagaggga gtgttaagtt gccttgagag
5881 ggttgattat gataatgcat ttggaaggta tcttgccaac acgtattcct cttacttgtt
5941 cttccatgta atcaccttat acatgaacgc cctagactgg gatgaagaaa agaccatcct
6001 agcattatgg aaagatttaa cctcagtgga catcgggaag gacttggtaa agttcaaaga
6061 ccaaatatgg ggactgctga tcgtgacaaa ggactttgtt tactcccaaa gttccaattg
6121 tctttttgac agaaactaca cacttatgct aaaagatctt ttcttgtctc gcttcaactc
6181 cttaatggtc ttgctctctc ccccagagcc ccgatactca gatgacttga tatctcaact
6241 atgccagctg tacattgctg gggatcaagt cttgtctatg tgtggaaact ccggctatga
6301 agtcatcaaa atattggagc catatgtcgt gaatagttta gtccagagag cagaaaagtt
6361 taggcctctc attcattcct tgggagactt tcctgtattt ataaaagaca aggtaagtca
6421 acttgaagag acgttcggtc cctgtgcaag aaggttcttt agggctctgg atcaattcga
6481 caacatacat gacttggttt ttgtgtttgg ctgttacagg cattgggggc acccatatat
6541 agattatcga aagggtctgt caaaactata tgatcaggtt caccttaaaa aaatgataga
6601 taagtcctac caggagtgct tagcaagcga cctagccagg aggatcctta gatggggttt
6661 tgataagtac tccaagtggt atctggattc aagattccta gcccgagacc accccttgac
6721 tccttatatc aaaacccaaa catggccacc caaacatatt gtagacttgg tgggggatac
6781 atggcacaag ctcccgatca cgcagatctt tgagattcct gaatcaatgg atccgtcaga
6841 aatattggat gacaaatcac attctttcac cagaacgaga ctagcttctt ggctgtcaga
6901 aaaccgaggg gggcctgttc ctagcgaaaa agttattatc acggccctgt ctaagccgcc
6961 tgtcaatccc cgagagtttc tgaggtctat agacctcgga ggattgccag atgaagactt
7021 gataattggc ctcaagccaa aggaacggga attgaagatt gaaggtcgat tctttgctct
7081 aatgtcatgg aatctaagat tgtattttgt catcactgaa aaactcttgg ccaactacat
7141 cttgccactt tttgacgcgc tgactatgac agacaacctg aacaaggtgt ttaaaaagct
7201 gatcgacagg gtcaccgggc aagggctttt ggactattca agggtcacat atgcatttca

Fig. 9C-5

```
7261 cctggactat gaaaagtgga acaaccatca aagattagag tcaacagagg atgtattttc
7321 tgtcctagat caagtgtttg gattgaagag agtgttttct agaacacacg agtttttca
7381 aaaggcctgg atctattatt cagacagatc agacctcatc gggttacggg aggatcaaat
7441 atactgctta gatgcgtcca acggcccaac ctgttggaat ggccaggatg gcgggctaga
7501 aggcttacgg cagaagggct ggagtctagt cagcttattg atgatagata gagaatctca
7561 aatcaggaac acaagaacca aaatactagc tcaaggagac aaccaggttt tatgtccgac
7621 atacatgttg tcgccagggc tatctcaaga ggggctcctc tatgaattgg agagaatatc
7681 aaggaatgca ctttcgatat acagagccgt cgaggaaggg gcatctaagc tagggctgat
7741 catcaagaaa gaagagacca tgtgtagtta tgacttcctc atctatggaa aaaccccttt
7801 gtttagaggt aacatattgg tgcctgagtc caaaagatgg gccagagtct cttgcgtctc
7861 taatgaccaa atagtcaacc tcgccaatat aatgtcgaca gtgtccacca atgcgctaac
7921 agtggcacaa cactctcaat ctttgatcaa accgatgagg gattttctgc tcatgtcagt
7981 acaggcagtc tttcactacc tgctatttag cccaatctta aagggaagag tttacaagat
8041 tctgagcgct gaaggggaga gctttctcct agccatgtca aggataatct atctagatcc
8101 ttctttggga gggatatctg gaatgtccct cggaagattc catatacgac agttctcaga
8161 ccctgtctct gaagggttat ccttctggag agagatctgg ttaagctccc aagagtcctg
8221 gattcacgcg ttgtgtcaag aggctggaaa cccagatctt ggagagagaa cactcgagag
8281 cttcactcgc cttctagaag atccgaccac cttaaatatc agaggagggg ccagtcctac
8341 cattctactc aaggatgcaa tcagaaaggc tttatatgac gaggtggaca aggtggaaaa
8401 ttcagagttt cgagaggcaa tcctgttgtc caagacccat agagataatt ttatactctt
8461 cttaatatct gttgagcctc tgtttcctcg atttctcagt gagctattca gttcgtcttt
8521 tttgggaatc cccgagtcaa tcattggatt gatacaaaac tcccgaacga taagaaggca
8581 gtttagaaag agtctctcaa aaactttaga agaatccttc tacaactcag agatccacgg
8641 gattagtcgg atgacccaga cacctcagag ggttgggggg gtgtggcctt gctcttcaga
8701 gagggcagat ctacttaggg agatctcttg ggaagaaaa gtggtaggca cgacagttcc
8761 tcacccttct gagatgttgg gattacttcc caagtcctct atttcttgca cttgtggagc
8821 aacaggagga ggcaatccta gagtttctgt atcagtactc ccgtcctttg atcagtcatt
8881 tttttcacga ggccccctaa agggatactt gggctcgtcc acctctatgt cgacccagct
8941 attccatgca tgggaaaaag tcactaatgt tcatgtggtg aagagagctc tatcgttaaa
9001 agaatctata aactggttca ttactagaga ttccaacttg gctcaagctc taattaggaa
```

Fig. 9C-6

```
9061 cattatgtct ctgacaggcc ctgatttccc tctagaggag gcccctgtct tcaaaaggac
9121 ggggtcagcc ttgcataggt tcaagtctgc cagatacagc gaaggagggt attcttctgt
9181 ctgcccgaac ctcctctctc atatttctgt tagtacagac accatgtctg atttgaccca
9241 agacgggaag aactacgatt tcatgttcca gccattgatg ctttatgcac agacatggac
9301 atcagagctg gtacagagag acacaaggct aagagactct acgtttcatt ggcacctccg
9361 atgcaacagg tgtgtgagac ccattgacga cgtgaccctg gagacctctc agatcttcga
9421 gtttccggat gtgtcgaaaa gaatatccag aatggtttct ggggctgtgc ctcacttcca
9481 gaggcttccc gatatccgtc tgagaccagg agattttgaa tctctaagcg gtagagaaaa
9541 gtctcaccat atcggatcag ctcaggggct cttatactca atcttagtgg caattcacga
9601 ctcaggatac aatgatggaa ccatcttccc tgtcaacata tacggcaagg tttcccctag
9661 agactatttg agagggctcg caaggggagt attgatagga tcctcgattt gcttcttgac
9721 aagaatgaca aatatcaata ttaatagacc tcttgaattg gtctcagggg taatctcata
9781 tattctcctg aggctagata accatccctc cttgtacata atgctcagag aaccgtctct
9841 tagaggagag atattttcta tccctcagaa aatccccgcc gcttatccaa ccactatgaa
9901 agaaggcaac agatcaatct tgtgttatct ccaacatgtg ctacgctatg agcgagagat
9961 aatcacggcg tctccagaga atgactggct atggatcttt tcagacttta gaagtgccaa
10021 aatgacgtac ctatccctca ttacttacca gtctcatctt ctactccaga gggttgagag
10081 aaacctatct aagagtatga gagataacct gcgacaattg agttctttga tgaggcaggt
10141 gctgggcggg cacggagaag ataccttaga gtcagacgac aacattcaac gactgctaaa
10201 agactcttta cgaaggacaa gatgggtgga tcaagaggtg cgccatgcag ctagaaccat
10261 gactggagat tacagcccca acaagaaggt gtcccgtaag gtaggatgtt cagaatgggt
10321 ctgctctgct caacaggttg cagtctctac ctcagcaaac ccggcccctg tctcggagct
10381 tgacataagg gccctctcta agaggttcca gaaccctttg atctcgggct tgagagtggt
10441 tcagtgggca accggtgctc attataagct taagcctatt ctagatgatc tcaatgtttt
10501 cccatctctc tgccttgtag ttggggacgg gtcagggggg atatcaaggg cagtcctcaa
10561 catgtttcca gatgccaagc ttgtgttcaa cagtctttta gaggtgaatg acctgatggc
10621 ttccggaaca catccactgc ctccttcagc aatcatgagg ggaggaaatg atatcgtctc
10681 cagagtgata gatcttgact caatctggga aaaaccgtcc gacttgagaa acttggcaac
10741 ctggaaatac ttccagtcag tccaaaagca ggtcaacatg tcctatgacc tcattatttg
10801 cgatgcagaa gttactgaca ttgcatctat caaccggatc accctgttaa tgtccgattt
```

Fig. 9C-7

10861 tgcattgtct atagatggac cactctattt ggtcttcaaa acttatggga ctatgctagt
10921 aaatccaaac tacaaggcta ttcaacacct gtcaagagcg ttcccctcgg tcacagggtt
10981 tatcacccaa gtaacttcgt ctttttcatc tgagctctac ctccgattct ccaaacgagg
11041 gaagtttttc agagatgctg agtacttgac ctcttccacc cttcgagaaa tgagccttgt
11101 gttattcaat tgtagcagcc ccaagagtga gatgcagaga gctcgttcct tgaactatca
11161 ggatcttgtg agaggatttc ctgaagaaat catatcaaat ccttacaatg agatgatcat
11221 aactctgatt gacagtgatg tagaatcttt tctagtccac aagatggttg atgatcttga
11281 gttacagagg ggaactctgt ctaaagtggc tatcattata gccatcatga tagttttctc
11341 caacagagtc ttcaacgttt ccaaacccct aactgacccc tcgttctatc caccgtctga
11401 tcccaaaatc ctgaggcact tcaacatatg ttgcagtact atgatgtatc tatctactgc
11461 tttaggtgac gtccctagct tcgcaagact tcacgacctg tataacagac ctataactta
11521 ttacttcaga aagcaagtca ttcgagggaa cgtttatcta tcttggagtt ggtccaacga
11581 cacctcagtg ttcaaaaggg tagcctgtaa ttctagcctg agtctgtcat ctcactggat
11641 caggttgatt tacaagatag tgaagactac cagactcgtt ggcagcatca aggatctatc
11701 cagagaagtg gaaagacacc ttcataggta caacaggtgg atcaccctag aggatatcag
11761 atctagatca tccctactag actacagttg cctgtgaacc ggatactcct ggaagcctgc
11821 ccatgctaag actcttgtgt gatgtatctt gaaaaaaaca agatcctaaa tctgaacctt
11881 tggttgtttg attgtttttc tcatttttgt tgtttatttg ttaagcgt

Fig. 9D-1

```
   1 acgcttaaca accagatcaa agaaaaaaca gacattgtca attgcaaagc aaaaatgtaa
  61 cacccctaca atggatgccg acaagattgt attcaaagtc aataatcagg tggtctcttt
 121 gaagcctgag attatcgtgg atcaatatga gtacaagtac cctgccatca aagatttgaa
 181 aaagccctgt ataaccctag gaaaggctcc cgatttaaat aaagcataca agtcagtttt
 241 gtcaggcatg agcgccgcca aacttaatcc tgacgatgta tgttcctatt tggcagcggc
 301 aatgcagttt tttgagggga catgtccgga agactggacc agctatggaa ttgtgattgc
 361 acgaaaagga gataagatca ccccaggttc tctggtggag ataaaacgta ctgatgtaga
 421 agggaattgg gctctgacag gaggcatgga actgacaaga gaccccactg tccctgagca
 481 tgcgtcctta gtcggtcttc tcttgagtct gtataggttg agcaaaatat ccgggcaaaa
 541 cactggtaac tataagacaa acattgcaga caggatagag cagatttttg agacagcccc
 601 ttttgttaaa atcgtggaac accatactct aatgacaact cacaaaatgt gtgctaattg
 661 gagtactata ccaaacttca gatttttggc cggaacctat gacatgtttt tctcccggat
 721 tgagcatcta tattcagcaa tcagagtggg cacagttgtc actgcttatg aagactgttc
 781 aggactggta tcatttactg ggttcataaa acaaatcaat ctcaccgcta gagaggcaat
 841 actatatttc ttccacaaga actttgagga agagataaga agaatgtttg agccagggca
 901 ggagacagct gttcctcact cttatttcat ccacttccgt tcactaggct tgagtgggaa
 961 atctccttat tcatcaaatg ctgttggtca cgtgttcaat ctcattcact ttgtaggatg
1021 ctatatgggt caagtcagat ccctaaatgc aacggttatt gctgcatgtg ctcctcatga
1081 aatgtctgtt ctagggggct atctgggaga ggaattcttc gggaaaggga catttgaaag
1141 aagattcttc agagatgaga aagaacttca agaatacgag gcggctgaac tgacaaagac
1201 tgacgtagca ctggcagatg atggaactgt caacCAAgac gacgaggact acttttcagg
1261 tgaaaccaga agtccggagg ctgtttatac tcgaatcatg atgaatggag gtcgactaaa
1321 gagatctcac atacggagat atgtctcagt cagttccaat catcaagccc gtccaaactc
1381 attcgccgag tttctaaaca agacatattc gagtgactca taagaagttg aataacaaaa
1441 tgccggaaat ctacggattg tgtatatcca tcatgaaaaa aactaacacc cctcctttcg
1501 aaccatccca aacatgagca agatctttgt caatcctagt gctattagag ccggtctggc
1561 cgatcttgag atggctgaag aaactgttga tctgatcaat agaaatatcg aagacaatca
1621 ggctcatctc caaggggaac ccatagaggt ggacaatctc cctgaggata tggggcgact
1681 tcacctggat gatggaaaat cgcccaacca tggtgagata gccaaggtgg gagaaggcaa
1741 gtatcgagag gactttcaga tggatgaagg agaggatcct agcttcctgt tccagtcata
1801 cctggaaaat gttggagtcc aaatagtcag acaaatgagg tcaggagaga gatttctcaa
```

Fig. 9D-2

```
1861 gatatggtca cagaccgtag aagagattat atcctatgtc gcggtcaact ttcccaaccc
1921 tccaggaaag tcttcagagg ataaatcaac ccagactact ggccgagagc tcaagaagga
1981 gacaacaccc actccttctc agagagaaag ccaatcatcg aaagccagga tggcggctca
2041 aattgcttct ggccctccag cccttgaatg gtcggctacc aatgaagagg atgatctatc
2101 agtggaggct gagatcgctc accagattgc agaaagtttc tccaaaaaat ataagtttcc
2161 ctctcgatcc tcagggatac tcttgtataa ttttgagcaa ttgaaaatga accttgatga
2221 tatagttaaa gaggcaaaaa atgtaccagg tgtgacccgt ttagcccatg acgggtccaa
2281 actcccccta agatgtgtac tgggatgggt cgctttggcc aactctaaga aattccagtt
2341 gttagtcgaa tccgacaagc tgagtaaaat catgcaagat gacttgaatc gctatacatc
2401 ttgctaaccg aacctctccc ctcagtccct ctagacaata aaatccgaga tgtcccaaag
2461 tcaacatgaa aaaaacaggc aacaccactg ataaaatgaa cctcctacgt aagatagtga
2521 aaaaccgcag ggacgaggac actcaaaaat cctctcccgc gtcagcccct ctggatgacg
2581 atgacttgtg gcttccaccc cctgaatacg tcccgctgaa agaacttaca ggcaagaaga
2641 acatgaggaa cttttgtatc aacggaaggg ttaaagtgtg tagcccgaat ggttactcgt
2701 tcaggatcct gcggcacatt ctgaaatcat tcgacgagat atattctggg aatcatagga
2761 tgatcgggtt agtcaaagtg gttattggac tggctttgtc aggatctcca gtccctgagg
2821 gcctgaactg ggtatacaaa ttgaggagaa cctttatctt ccagtgggct gattccaggg
2881 gccctcttga aggggaggag ttggaatact ctcaggagat cacttgggat gatgatactg
2941 agttcgtcgg attgcaaata agagtgattg caaaacagtg tcatatccag ggcagagtct
3001 ggtgtatcaa catgaacccg agagcatgtc aactatggtc tgacatgtct cttcagacac
3061 aaaggtccga agaggacaaa gattcctctc tgcttctaga ataatcagat tatatcccgc
3121 aaatttatca cttgtttacc tctggaggag agaacatatg ggctcaactc caacccttgg
3181 gagcaatata acaaaaaaca tgttatggtg ccattaaacc gctgcatttc atcaaagtca
3241 agttgattac ctttacattt tgatcctctt ggatgtgaaa aaaactatta acatccctca
3301 aaagactcaa ggaaagatgg ttcctcaggc tctcctgttt gtaccccttc tggtttttcc
3361 attgtgtttt gggaaattcc ctatttacac gataccagac aagcttggtc cctggagtcc
3421 gattgacata catcacctca gctgcccaaa caatttggta gtggaggacg aaggatgcac
3481 caacctgtca gggttctcct acatggaact taaagttgga tacatcttag ccataaaagt
3541 gaacgggttc acttgcacag gcgttgtgac ggaggctgaa acctacacta acttcgttgg
3601 ttatgtcaca accacgttca aaagaaagca tttccgccca acaccagatg catgtagagc
```

Fig. 9D-3

```
3661 cgcgtacaac tggaagatgg ccggtgaccc cagatatgaa gagtctctac acaatccgta
3721 ccctgactac cgctggcttc gaactgtaaa aaccaccaag gagtctctcg ttatcatatc
3781 tccaagtgtg gcagatttgg acccatatga cagatccctt cactcgaggg tcttccctag
3841 cgggaagtgc tcaggagtag cggtgtcttc tacctactgc tccactaacc acgattacac
3901 catttggatg cccgagaatc cgagactagg gatgtcttgt gacattttta ccaatagtag
3961 agggaagaga gcatccaaag ggagtgagac ttgcggcttt gtagatgaaa gaggcctata
4021 taagtcttta aaaggagcat gcaaactcaa gttatgtgga gttctaggac ttagacttat
4081 ggatggaaca tgggtctcga tgcaaacatc aaatgaaacc aaatggtgcc ctcccgataa
4141 gttggtgaac ctgcacgact ttcgctcaga cgaaattgag caccttgttg tagaggagtt
4201 ggtcaggaag agagaggagt gtctggatgc actagagtcc atcatgacaa ccaagtcagt
4261 gagtttcaga cgtctcagtc atttaagaaa acttgtccct gggtttggaa aagcatatac
4321 catattcaac aagaccttga tggaagccga tgctcactac aagtcagtcG AAacttggaa
4381 tgagatcctc ccttcaaaag ggtgtttaag agttgggggg aggtgtcatc ctcatgtgaa
4441 cggggtgttt ttcaatggta taatattagg acctgacggc aatgtcttaa tcccagagat
4501 gcaatcatcc ctcctccagc aacatatgga gttgttggaa tcctcggtta tcccccttgt
4561 gcaccccctg gcagacccgt ctaccgtttt caaggacggt gacgaggctg aggattttgt
4621 tgaagttcac cttcccgatg tgcacaatca ggtctcagga gttgacttgg gtctcccgaa
4681 ctgggggaag tatgtattac tgagtgcagg ggccctgact gccttgatgt tgataatttt
4741 cctgatgaca tgttgtagaa gagtcaatcg atcagaacct acgcaacaca atctcagagg
4801 gacagggagg gaggtgtcag tcactcccca aagcgggaag atcatatctt catgggaatc
4861 acacaagagt gggggtgaga ccagactgta aggactggcc gtcctttcaa cgatccaagt
4921 cctgaagatc acctcccctt ggggggttct ttttgaaaaa cctgggttca atagtcctcc
4981 ttgaactcca tgcaactggg tagattcaag agtcatgaga ttttcattaa tcctctcagt
5041 tgatcaagca agatcatgtc gattctcata ataggggaga tcttctagca gtttcagtga
5101 ctaacggtac tttcattctc caggaactga caccaacagt tgtagacaaa ccacggggtg
5161 tctcgggtga ctctgtgctt gggcacagac aaaggtcatg gtgtgttcca tgatagcgga
5221 ctcaggatga gttaattgag agaggcagtc ttcctcccgt gaaggacata agcagtagct
5281 cacaatcatc tcgcgtctca gcaaagtgtg cataattata aagtgctggg tcatctaagc
5341 ttttcagtcg agaaaaaaac attagatcag aagaacaact ggcaacactt ctcaacctga
5401 gacttacttc aagatgctcg atcctggaga ggtctatgat gaccctattg acccaatcga
5461 gttagaggct gaacccagag gaacccccat tgtccccaac atcttgagga actctgacta
```

Fig. 9D-4

```
5521 caatctcaac tctcctttga tagaagatcc tgctagacta atgttagaat ggttaaaaac
5581 agggaataga ccttatcgga tgactctaac agacaattgc tccaggtctt tcagagtttt
5641 gaaagattat ttcaagaagg tagatttggg ttctctcaag gtgggcggaa tggctgcaca
5701 gtcaatgatt tctctctggt tatatggtgc ccactctgaa tccaacagga gccggagatg
5761 tataacagac ttggcccatt tctattccaa gtcgtccccc atagagaagc tgttgaatct
5821 cacgctagga aatagagggc tgagaatccc cccagaggga gtgttaagtt gccttgagag
5881 ggttgattat gataatgcat ttggaaggta tcttgccaac acgtattcct cttacttgtt
5941 cttccatgta atcaccttat acatgaacgc cctagactgg gatgaagaaa agaccatcct
6001 agcattatgg aaagatttaa cctcagtgga catcgggaag gacttggtaa agttcaaaga
6061 ccaaatatgg ggactgctga tcgtgacaaa ggactttgtt tactcccaaa gttccaattg
6121 tctttttgac agaaactaca cacttatgct aaaagatctt ttcttgtctc gcttcaactc
6181 cttaatggtc ttgctctctc ccccagagcc ccgatactca gatgacttga tatctcaact
6241 atgccagctg tacattgctg gggatcaagt cttgtctatg tgtggaaact ccggctatga
6301 agtcatcaaa atattggagc catatgtcgt gaatagttta gtccagagag cagaaaagtt
6361 taggcctctc attcattcct tgggagactt tcctgtattt ataaaagaca aggtaagtca
6421 acttgaagag acgttcggtc cctgtgcaag aaggttcttt agggctctgg atcaattcga
6481 caacatacat gacttggttt ttgtgtttgg ctgttacagg cattgggggc acccatatat
6541 agattatcga aagggtctgt caaaactata tgatcaggtt caccttaaaa aaatgataga
6601 taagtcctac caggagtgct tagcaagcga cctagccagg aggatcctta gatggggttt
6661 tgataagtac tccaagtggt atctggattc aagattccta gcccgagacc accccttgac
6721 tccttatatc aaaacccaaa catggccacc caaacatatt gtagacttgg tgggggatac
6781 atggcacaag ctcccgatca cgcagatctt tgagattcct gaatcaatgg atccgtcaga
6841 aatattggat gacaaatcac attctttcac cagaacgaga ctagcttctt ggctgtcaga
6901 aaaccgaggg gggcctgttc ctagcgaaaa agttattatc acggccctgt ctaagccgcc
6961 tgtcaatccc cgagagtttc tgaggtctat agacctcgga ggattgccag atgaagactt
7021 gataattggc ctcaagccaa aggaacggga attgaagatt gaaggtcgat tctttgctct
7081 aatgtcatgg aatctaagat tgtattttgt catcactgaa aaactcttgg ccaactacat
7141 cttgccactt tttgacgcgc tgactatgac agacaacctg aacaaggtgt ttaaaaagct
7201 gatcgacagg gtcaccgggc aagggctttt ggactattca agggtcacat atgcatttca
7261 cctggactat gaaaagtgga acaaccatca aagattagag tcaacagagg atgtattttc
```

Fig. 9D-5

```
7321 tgtcctagat caagtgtttg gattgaagag agtgttttct agaacacacg agttttttca
7381 aaaggcctgg atctattatt cagacagatc agacctcatc gggttacggg aggatcaaat
7441 atactgctta gatgcgtcca acggcccaac ctgttggaat ggccaggatg gcgggctaga
7501 aggcttacgg cagaagggct ggagtctagt cagcttattg atgatagata gagaatctca
7561 aatcaggaac acaagaacca aaatactagc tcaaggagac aaccaggttt tatgtccgac
7621 atacatgttg tcgccagggc tatctcaaga ggggctcctc tatgaattgg agagaatatc
7681 aaggaatgca ctttcgatat acagagccgt cgaggaaggg gcatctaagc tagggctgat
7741 catcaagaaa gaagagacca tgtgtagtta tgacttcctc atctatggaa aaaccccttt
7801 gtttagaggt aacatattgg tgcctgagtc caaaagatgg gccagagtct cttgcgtctc
7861 taatgaccaa atagtcaacc tcgccaatat aatgtcgaca gtgtccacca atgcgctaac
7921 agtggcacaa cactctcaat ctttgatcaa accgatgagg gattttctgc tcatgtcagt
7981 acaggcagtc tttcactacc tgctatttag cccaatctta aagggaagag tttacaagat
8041 tctgagcgct gaaggggaga gctttctcct agccatgtca aggataatct atctagatcc
8101 ttctttggga gggatatctg gaatgtccct cggaagattc catatacgac agttctcaga
8161 ccctgtctct gaagggttat ccttctggag agagatctgg ttaagctccc aagagtcctg
8221 gattcacgcg ttgtgtcaag aggctggaaa cccagatctt ggagagagaa cactcgagag
8281 cttcactcgc cttctagaag atccgaccac cttaaatatc agaggagggg ccagtcctac
8341 cattctactc aaggatgcaa tcagaaaggc tttatatgac gaggtggaca aggtggaaaa
8401 ttcagagttt cgagaggcaa tcctgttgtc caagacccat agagataatt ttatactctt
8461 cttaatatct gttgagcctc tgtttcctcg atttctcagt gagctattca gttcgtcttt
8521 tttgggaatc cccgagtcaa tcattggatt gatacaaaac tcccgaacga taagaaggca
8581 gtttagaaag agtctctcaa aaactttaga agaatccttc tacaactcag agatccacgg
8641 gattagtcgg atgacccaga cacctcagag ggttgggggg gtgtggcctt gctcttcaga
8701 gagggcagat ctacttaggg agatctcttg ggaagaaaaa gtggtaggca cgacagttcc
8761 tcacccttct gagatgttgg gattacttcc caagtcctct atttcttgca cttgtggagc
8821 aacaggagga ggcaatccta gagtttctgt atcagtactc ccgtcctttg atcagtcatt
8881 tttttcacga ggccccctaa agggatactt gggctcgtcc acctctatgt cgacccagct
8941 attccatgca tgggaaaaag tcactaatgt tcatgtggtg aagagagctc tatcgttaaa
9001 agaatctata aactggttca ttactagaga ttccaacttg gctcaagctc taattaggaa
9061 cattatgtct ctgacaggcc ctgatttccc tctagaggag gcccctgtct tcaaaaggac
```

Fig. 9D-6

```
 9121 ggggtcagcc ttgcataggt tcaagtctgc cagatacagc gaaggagggt attcttctgt
 9181 ctgcccgaac ctcctctctc atatttctgt tagtacagac accatgtctg atttgaccca
 9241 agacgggaag aactacgatt tcatgttcca gccattgatg ctttatgcac agacatggac
 9301 atcagagctg gtacagagag acacaaggct aagagactct acgtttcatt ggcacctccg
 9361 atgcaacagg tgtgtgagac ccattgacga cgtgaccctg gagacctctc agatcttcga
 9421 gtttccggat gtgtcgaaaa gaatatccag aatggtttct ggggctgtgc ctcacttcca
 9481 gaggcttccc gatatccgtc tgagaccagg agattttgaa tctctaagcg gtagagaaaa
 9541 gtctcaccat atcggatcag ctcaggggct cttatactca atcttagtgg caattcacga
 9601 ctcaggatac aatgatggaa ccatcttccc tgtcaacata tacggcaagg tttcccctag
 9661 agactatttg agagggctcg caaggggagt attgatagga tcctcgattt gcttcttgac
 9721 aagaatgaca aatatcaata ttaatagacc tcttgaattg gtctcagggg taatctcata
 9781 tattctcctg aggctagata accatccctc cttgtacata atgctcagag aaccgtctct
 9841 tagaggagag atatttctta tccctcagaa aatccccgcc gcttatccaa ccactatgaa
 9901 agaaggcaac agatcaatct tgtgttatct ccaacatgtg ctacgctatg agcgagagat
 9961 aatcacggcg tctccagaga atgactggct atggatcttt tcagacttta gaagtgccaa
10021 aatgacgtac ctatccctca ttacttacca gtctcatctt ctactccaga gggttgagag
10081 aaacctatct aagagtatga gagataacct gcgacaattg agttctttga tgaggcaggt
10141 gctgggcggg cacggagaag ataccttaga gtcagacgac aacattcaac gactgctaaa
10201 agactcttta cgaaggacaa gatgggtgga tcaagaggtg cgccatgcag ctagaaccat
10261 gactggagat tacagcccca acaagaaggt gtcccgtaag gtaggatgtt cagaatgggt
10321 ctgctctgct caacaggttg cagtctctac ctcagcaaac ccggcccctg tctcggagct
10381 tgacataagg gccctctcta agaggttcca gaaccctttg atctcgggct tgagagtggt
10441 tcagtgggca accggtgctc attataagct taagcctatt ctagatgatc tcaatgtttt
10501 cccatctctc tgccttgtag ttggggacgg gtcagggggg atatcaaggg cagtcctcaa
10561 catgtttcca gatgccaagc ttgtgttcaa cagtctttta gaggtgaatg acctgatggc
10621 ttccggaaca catccactgc ctccttcagc aatcatgagg ggaggaaatg atatcgtctc
10681 cagagtgata gatcttgact caatctggga aaaaccgtcc gacttgagaa acttggcaac
10741 ctggaaatac ttccagtcag tccaaaagca ggtcaacatg tcctatgacc tcattatttg
10801 cgatgcagaa gttactgaca ttgcatctat caaccggatc accctgttaa tgtccgattt
10861 tgcattgtct atagatggac cactctattt ggtcttcaaa acttatggga ctatgctagt
```

Fig. 9D-7

```
10921 aaatccaaac tacaaggcta ttcaacacct gtcaagagcg ttcccctcgg tcacagggtt
10981 tatcacccaa gtaacttcgt ctttttcatc tgagctctac ctccgattct ccaaacgagg
11041 gaagtttttc agagatgctg agtacttgac ctcttccacc cttcgagaaa tgagccttgt
11101 gttattcaat tgtagcagcc ccaagagtga gatgcagaga gctcgttcct tgaactatca
11161 ggatcttgtg agaggatttc ctgaagaaat catatcaaat ccttacaatg agatgatcat
11221 aactctgatt gacagtgatg tagaatcttt tctagtccac aagatggttg atgatcttga
11281 gttacagagg ggaactctgt ctaaagtggc tatcattata gccatcatga tagttttctc
11341 caacagagtc ttcaacgttt ccaaacccct aactgacccc tcgttctatc caccgtctga
11401 tcccaaaatc ctgaggcact tcaacatatg ttgcagtact atgatgtatc tatctactgc
11461 tttaggtgac gtccctagct tcgcaagact tcacgacctg tataacagac ctataactta
11521 ttacttcaga aagcaagtca ttcgagggaa cgtttatcta tcttggagtt ggtccaacga
11581 cacctcagtg ttcaaaaggg tagcctgtaa ttctagcctg agtctgtcat ctcactggat
11641 caggttgatt tacaagatag tgaagactac cagactcgtt ggcagcatca aggatctatc
11701 cagagaagtg gaaagacacc ttcataggta caacaggtgg atcaccctag aggatatcag
11761 atctagatca tccctactag actacagttg cctgtgaacc ggatactcct ggaagcctgc
11821 ccatgctaag actcttgtgt gatgtatctt gaaaaaaaca agatcctaaa tctgaacctt
11881 tggttgtttg attgtttttc tcatttttgt tgtttatttg ttaagcgt
```

Fig. 10A

Rabies virus G amino acid sequence (wt, Arginine 333 underlined):

MVPQALLFVPLLVFPLCFGKFPIYTIPDKLGPWSPIDIHHLSCPNNLVVEDEGCTNLSGFSY
MELKVGYILAIKVNGFTCTGVVTEAETYTNFVGYVTTTFKRKHFRPTPDACRAAYNWMAGDP
RYEESLHNPYPDYRWLRTVKTTKESLVIISPSVADLDPYDRSLHSRVFPSGKCSGVAVSSTY
CSTNHDYTIWMPENPRLGMSCDIFTNSRGKRASKGSETCGFVDERGLYKSLKGACKLKLCGV
LGLRLMDGTWVSMQTSNETKWCPPDKLVNLHDFRSDEIEHLVVEELVRKREECLDALESIMT
TKSVSFRRLSHLRKLVPGFGKAYTIFNKTLMEADAHYKSV<u>R</u>TWNEILPSKGCLRVGGRCHPH
VNGVFFNGIILGPDGNVLIPEMQSSLLQQHMELLESSVIPLVHPLADPSTVFKDGDEAEDFV
EVHLPDVHNQVSGVDLGLPNWGKYVLLSAGALTALMLIIFLMTCCRRVNRSEPTQHNLRGTG
REVSVTPQSGKIISSWESHKSGGETRL

Fig. 10B

Rabies virus G amino acid sequence (wt, Arginine 333 mutated to Glutamic acid, underlined):

MVPQALLFVPLLVFPLCFGKFPIYTIPDKLGPWSPIDIHHLSCPNNLVVEDEGCTNLSGFSY
MELKVGYILAIKVNGFTCTGVVTEAETYTNFVGYVTTTFKRKHFRPTPDACRAAYNWMAGDP
RYEESLHNPYPDYRWLRTVKTTKESLVIISPSVADLDPYDRSLHSRVFPSGKCSGVAVSSTY
CSTNHDYTIWMPENPRLGMSCDIFTNSRGKRASKGSETCGFVDERGLYKSLKGACKLKLCGV
LGLRLMDGTWVSMQTSNETKWCPPDKLVNLHDFRSDEIEHLVVEELVRKREECLDALESIMT
TKSVSFRRLSHLRKLVPGFGKAYTIFNKTLMEADAHYKSV<u>E</u>TWNEILPSKGCLRVGGRCHPH
VNGVFFNGIILGPDGNVLIPEMQSSLLQQHMELLESSVIPLVHPLADPSTVFKDGDEAEDFV
EVHLPDVHNQVSGVDLGLPNWGKYVLLSAGALTALMLIIFLMTCCRRVNRSEPTQHNLRGTG
REVSVTPQSGKIISSWESHKSGGETRL

Fig. 11A

Rabies virus N amino acid sequence (wt, phosphorylated serine underlined):

MDADKIVFKVNNQVVSLKPEIIVDQYEYKYPAIKDLKKPCITLGKAPDLNKAYKSVLSGMSAA
KLNPDDVCSYLAAAMQFFEGTCPEDWTSYGIVIARKGDKITPGSLVEIKRTDVEGNWALTGGM
ELTRDPTVPEHASLVGLLLSLYRLSKISGQNTGNYKTNIADRIEQIFETAPFVKIVEHHTLMT
THKMCANWSTIPNFRFLAGTYDMFFSRIEHLYSAIRVGTVVTAYEDCSGLVSFTGFIKQINLT
AREAILYFFHKNFEEEIRRMFEPGQETAVPHSYFIHFRSLGLSGKSPYSSNAVGHVFNLIHFV
GCYMGQVRSLNATVIAACAPHEMSVLGGYLGEEFFGKGTFERRFFRDEKELQEYEAAELTKTD
VALADDGTVNSDDEDYFSGETRSPEAVYTRIMMNGGRLKRSHIRRYVSVSSNHQARPNSFAEF
LNKTYSSDS

Fig. 11B

Rabies virus N amino acid sequence (Serine to Alanine, see underlined):

MDADKIVFKVNNQVVSLKPEIIVDQYEYKYPAIKDLKKPCITLGKAPDLNKAYKSVLSGMSAA
KLNPDDVCSYLAAAMQFFEGTCPEDWTSYGIVIARKGDKITPGSLVEIKRTDVEGNWALTGGM
ELTRDPTVPEHASLVGLLLSLYRLSKISGQNTGNYKTNIADRIEQIFETAPFVKIVEHHTLMT
THKMCANWSTIPNFRFLAGTYDMFFSRIEHLYSAIRVGTVVTAYEDCSGLVSFTGFIKQINLT
AREAILYFFHKNFEEEIRRMFEPGQETAVPHSYFIHFRSLGLSGKSPYSSNAVGHVFNLIHFV
GCYMGQVRSLNATVIAACAPHEMSVLGGYLGEEFFGKGTFERRFFRDEKELQEYEAAELTKTD
VALADDGTVNADDEDYFSGETRSPEAVYTRIMMNGGRLKRSHIRRYVSVSSNHQARPNSFAEF
LNKTYSSDS

Fig. 11C

Rabies virus N amino acid sequence (Serine to Glycine, see underlined):

MDADKIVFKVNNQVVSLKPEIIVDQYEYKYPAIKDLKKPCITLGKAPDLNKAYKSVLSGMSAA
KLNPDDVCSYLAAAMQFFEGTCPEDWTSYGIVIARKGDKITPGSLVEIKRTDVEGNWALTGGM
ELTRDPTVPEHASLVGLLLSLYRLSKISGQNTGNYKTNIADRIEQIFETAPFVKIVEHHTLMT
THKMCANWSTIPNFRFLAGTYDMFFSRIEHLYSAIRVGTVVTAYEDCSGLVSFTGFIKQINLT
AREAILYFFHKNFEEEIRRMFEPGQETAVPHSYFIHFRSLGLSGKSPYSSNAVGHVFNLIHFV
GCYMGQVRSLNATVIAACAPHEMSVLGGYLGEEFFGKGTFERRFFRDEKELQEYEAAELTKTD
VALADDGTVNGDDEDYFSGETRSPEAVYTRIMMNGGRLKRSHIRRYVSVSSNHQARPNSFAEF
LNKTYSSDS

Fig. 11D

Rabies virus N amino acid sequence (Serine to Glutamine, see underlined):

MDADKIVFKVNNQVVSLKPEIIVDQYEYKYPAIKDLKKPCITLGKAPDLNKAYKSVLSGMSAA
KLNPDDVCSYLAAAMQFFEGTCPEDWTSYGIVIARKGDKITPGSLVEIKRTDVEGNWALTGGM
ELTRDPTVPEHASLVGLLLSLYRLSKISGQNTGNYKTNIADRIEQIFETAPFVKIVEHHTLMT
THKMCANWSTIPNFRFLAGTYDMFFSRIEHLYSAIRVGTVVTAYEDCSGLVSFTGFIKQINLT
AREAILYFFHKNFEEEIRRMFEPGQETAVPHSYFIHFRSLGLSGKSPYSSNAVGHVFNLIHFV
GCYMGQVRSLNATVIAACAPHEMSVLGGYLGEEFFGKGTFERRFFRDEKELQEYEAAELTKTD
VALADDGTVNQDDEDYFSGETRSPEAVYTRIMMNGGRLKRSHIRRYVSVSSNHQARPNSFAEF
LNKTYSSDS

SEQUENCE LISTING

```
<160> NUMBER OF SEQ ID NOS: 64

<210> SEQ ID NO 1
<211> LENGTH: 31
<212> TYPE: DNA
<213> ORGANISM: Artificial Sequence
<220> FEATURE:
<223> OTHER INFORMATION: primer

<400> SEQUENCE: 1

gatgatggaa ctgtcaacgc tgacgacgag g                                     31


<210> SEQ ID NO 2
<211> LENGTH: 30
<212> TYPE: DNA
<213> ORGANISM: Artificial Sequence
<220> FEATURE:
<223> OTHER INFORMATION: primer

<400> SEQUENCE: 2

gtagtcctcg tcgtcagcgt tgacagttcc                                       30


<210> SEQ ID NO 3
<211> LENGTH: 31
<212> TYPE: DNA
<213> ORGANISM: Artificial Sequence
<220> FEATURE:
<223> OTHER INFORMATION: primer

<400> SEQUENCE: 3

gatgatggaa ctgtcaacgg tgacgacgag g                                     31


<210> SEQ ID NO 4
<211> LENGTH: 30
<212> TYPE: DNA
<213> ORGANISM: Artificial Sequence
<220> FEATURE:
<223> OTHER INFORMATION: primer

<400> SEQUENCE: 4

gtagtcctcg tcgtcaccgt tgacagttcc                                       30


<210> SEQ ID NO 5
<211> LENGTH: 30
<212> TYPE: DNA
<213> ORGANISM: Artificial Sequence
<220> FEATURE:
<223> OTHER INFORMATION: primer

<400> SEQUENCE: 5

gatgatggaa ctgtcaagat gacgacgagg                                       30


<210> SEQ ID NO 6
<211> LENGTH: 30
<212> TYPE: DNA
```

-continued

<213> ORGANISM: Artificial Sequence
<220> FEATURE:
<223> OTHER INFORMATION: primer

<400> SEQUENCE: 6
gtagtcctcg tcgtcatcgt tgacagttcc 30

<210> SEQ ID NO 7
<211> LENGTH: 31
<212> TYPE: DNA
<213> ORGANISM: Artificial Sequence
<220> FEATURE:
<223> OTHER INFORMATION: primer

<400> SEQUENCE: 7
gatgatggaa ctgtcaacaa tgacgacgag g 31

<210> SEQ ID NO 8
<211> LENGTH: 30
<212> TYPE: DNA
<213> ORGANISM: Artificial Sequence
<220> FEATURE:
<223> OTHER INFORMATION: primer

<400> SEQUENCE: 8
gtagtcctcg tcgtcattgt tgacagttcc 30

<210> SEQ ID NO 9
<211> LENGTH: 31
<212> TYPE: DNA
<213> ORGANISM: Artificial Sequence
<220> FEATURE:
<223> OTHER INFORMATION: primer

<400> SEQUENCE: 9
gatgatggaa ctgtcaacga agacgacgag g 31

<210> SEQ ID NO 10
<211> LENGTH: 30
<212> TYPE: DNA
<213> ORGANISM: Artificial Sequence
<220> FEATURE:
<223> OTHER INFORMATION: primer

<400> SEQUENCE: 10
gtagtcctcg tcgtcttcgt tgacagttcc 30

<210> SEQ ID NO 11
<211> LENGTH: 31
<212> TYPE: DNA
<213> ORGANISM: Artificial Sequence
<220> FEATURE:
<223> OTHER INFORMATION: primer

<400> SEQUENCE: 11
gatgatggaa ctgtcaacca agacgacgag g 31

<210> SEQ ID NO 12
<211> LENGTH: 30
<212> TYPE: DNA
<213> ORGANISM: Artificial Sequence
<220> FEATURE:
<223> OTHER INFORMATION: primer

<400> SEQUENCE: 12
gtagtcctcg tcgtcttggt tgacagttcc 30

-continued

<210> SEQ ID NO 13
<211> LENGTH: 16
<212> TYPE: DNA
<213> ORGANISM: Artificial Sequence
<220> FEATURE:
<223> OTHER INFORMATION: primer

<400> SEQUENCE: 13
ctacaatgga tgccga 16

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
ttgacgaaga tcttgctcat 20

<210> SEQ ID NO 15
<211> LENGTH: 17
<212> TYPE: DNA
<213> ORGANISM: Artificial Sequence
<220> FEATURE:
<223> OTHER INFORMATION: primer

<400> SEQUENCE: 15
gtaggatgct atatggg 17

<210> SEQ ID NO 16
<211> LENGTH: 30
<212> TYPE: DNA
<213> ORGANISM: Artificial Sequence
<220> FEATURE:
<223> OTHER INFORMATION: primer

<400> SEQUENCE: 16
atgctcacta caagtgaaac ttggaatcag 30

<210> SEQ ID NO 17
<211> LENGTH: 30
<212> TYPE: DNA
<213> ORGANISM: Artificial Sequence
<220> FEATURE:
<223> OTHER INFORMATION: primer

<400> SEQUENCE: 17
ggaggatctc attccaagtt tcacttgtag 30

<210> SEQ ID NO 18
<211> LENGTH: 24
<212> TYPE: DNA
<213> ORGANISM: Artificial Sequence
<220> FEATURE:
<223> OTHER INFORMATION: primer

<400> SEQUENCE: 18
acacccctcc tttcgaacca tccc 24

<210> SEQ ID NO 19
<211> LENGTH: 27
<212> TYPE: DNA
<213> ORGANISM: Artificial Sequence
<220> FEATURE:

-continued

<223> OTHER INFORMATION: primer

<400> SEQUENCE: 19 cattttttgct ttgcaattga caatgtc 27

<210> SEQ ID NO 20
<211> LENGTH: 29
<212> TYPE: DNA
<213> ORGANISM: Artificial Sequence
<220> FEATURE:
<223> OTHER INFORMATION: primer

<400> SEQUENCE: 20
tcaacatgaa aaaaacagtt aacaccact 29

<210> SEQ ID NO 21
<211> LENGTH: 29
<212> TYPE: DNA
<213> ORGANISM: Artificial Sequence
<220> FEATURE:
<223> OTHER INFORMATION: primer

<400> SEQUENCE: 21
aggggtgtta actgtttttt tcatgttga 29

<210> SEQ ID NO 22
<211> LENGTH: 21
<212> TYPE: DNA
<213> ORGANISM: Artificial Sequence
<220> FEATURE:
<223> OTHER INFORMATION: primer

<400> SEQUENCE: 22
acacccctac aatggatgcc g 21

<210> SEQ ID NO 23
<211> LENGTH: 24
<212> TYPE: DNA
<213> ORGANISM: Artificial Sequence
<220> FEATURE:
<223> OTHER INFORMATION: primer

<400> SEQUENCE: 23
gtttttttca tgatggatat acac 24

<210> SEQ ID NO 24
<211> LENGTH: 21
<212> TYPE: DNA
<213> ORGANISM: Artificial Sequence
<220> FEATURE:
<223> OTHER INFORMATION: primer

<400> SEQUENCE: 24
atggaaaaaa acaggcaact g 21

<210> SEQ ID NO 25
<211> LENGTH: 21
<212> TYPE: DNA
<213> ORGANISM: Artificial Sequence
<220> FEATURE:
<223> OTHER INFORMATION: primer

<400> SEQUENCE: 25
agttgcctgt ttttttccat g 21

-continued

<210> SEQ ID NO 26
<211> LENGTH: 28
<212> TYPE: DNA
<213> ORGANISM: Artificial Sequence
<220> FEATURE:
<223> OTHER INFORMATION: primer

<400> SEQUENCE: 26
gatgtgaaaa aaactgttaa catccctc 28

<210> SEQ ID NO 27
<211> LENGTH: 28
<212> TYPE: DNA
<213> ORGANISM: Artificial Sequence
<220> FEATURE:
<223> OTHER INFORMATION: primer

<400> SEQUENCE: 27
agggatgtta acagtttttt tcacatcc 28

<210> SEQ ID NO 28
<211> LENGTH: 24
<212> TYPE: DNA
<213> ORGANISM: Artificial Sequence
<220> FEATURE:
<223> OTHER INFORMATION: primer

<400> SEQUENCE: 28
tgaaaaaaac tattaacatc cctc 24

<210> SEQ ID NO 29
<211> LENGTH: 24
<212> TYPE: DNA
<213> ORGANISM: Artificial Sequence
<220> FEATURE:
<223> OTHER INFORMATION: primer

<400> SEQUENCE: 29
agggatgtta atagtttttt tcac 24

<210> SEQ ID NO 30
<211> LENGTH: 26
<212> TYPE: DNA
<213> ORGANISM: Artificial Sequence
<220> FEATURE:
<223> OTHER INFORMATION: primer

<400> SEQUENCE: 30
cagaagaaca actgttaaca cttctc 26

<210> SEQ ID NO 31
<211> LENGTH: 25
<212> TYPE: DNA
<213> ORGANISM: Artificial Sequence
<220> FEATURE:
<223> OTHER INFORMATION: primer

<400> SEQUENCE: 31
agaagtgtta acagttgttc ttctg 25

<210> SEQ ID NO 32
<211> LENGTH: 20
<212> TYPE: DNA
<213> ORGANISM: Artificial Sequence
<220> FEATURE:
<223> OTHER INFORMATION: primer -continued

<400> SEQUENCE: 32
aacaactggc aacacttctc 20

<210> SEQ ID NO 33
<211> LENGTH: 20
<212> TYPE: DNA
<213> ORGANISM: Artificial Sequence
<220> FEATURE:
<223> OTHER INFORMATION: primer

<400> SEQUENCE: 33
agaagtgttg ccagttgttc 20

<210> SEQ ID NO 34
<211> LENGTH: 22
<212> TYPE: DNA
<213> ORGANISM: Artificial Sequence
<220> FEATURE:
<223> OTHER INFORMATION: primer

<400> SEQUENCE: 34
acatccctca aaagactcaa gg 22

<210> SEQ ID NO 35
<211> LENGTH: 24
<212> TYPE: DNA
<213> ORGANISM: Artificial Sequence
<220> FEATURE:
<223> OTHER INFORMATION: primer

<400> SEQUENCE: 35
atagtttttt tcacatccaa gagg 24

<210> SEQ ID NO 36
<211> LENGTH: 25
<212> TYPE: DNA
<213> ORGANISM: Artificial Sequence
<220> FEATURE:
<223> OTHER INFORMATION: primer

<400> SEQUENCE: 36
agaaagaaca actggcaaca cccct 25

<210> SEQ ID NO 37
<211> LENGTH: 25
<212> TYPE: DNA
<213> ORGANISM: Artificial Sequence
<220> FEATURE:
<223> OTHER INFORMATION: primer

<400> SEQUENCE: 37
ggggtgttgc cagttgttct ttctg 25

<210> SEQ ID NO 38
<211> LENGTH: 24
<212> TYPE: DNA
<213> ORGANISM: Artificial Sequence
<220> FEATURE:
<223> OTHER INFORMATION: primer

<400> SEQUENCE: 38
acacccctcc tttcgaacca tccc 24

<210> SEQ ID NO 39
<211> LENGTH: 24

-continued

<212> TYPE: DNA
<213> ORGANISM: Artificial Sequence
<220> FEATURE:
<223> OTHER INFORMATION: primer

<400> SEQUENCE: 39
atagtttttt tcacatccaa gagg 24

<210> SEQ ID NO 40
<211> LENGTH: 25
<212> TYPE: DNA
<213> ORGANISM: Artificial Sequence
<220> FEATURE:
<223> OTHER INFORMATION: primer

<400> SEQUENCE: 40
agaaagaaca actggcaaca cccct 25

<210> SEQ ID NO 41
<211> LENGTH: 24
<212> TYPE: DNA
<213> ORGANISM: Artificial Sequence
<220> FEATURE:
<223> OTHER INFORMATION: primer

<400> SEQUENCE: 41
acaccactga taaaatgaac ctcc 24

<210> SEQ ID NO 42
<211> LENGTH: 24
<212> TYPE: DNA
<213> ORGANISM: Artificial Sequence
<220> FEATURE:
<223> OTHER INFORMATION: primer

<400> SEQUENCE: 42
gtttttttca tgatggatat agag 24

<210> SEQ ID NO 43
<211> LENGTH: 26
<212> TYPE: DNA
<213> ORGANISM: Artificial Sequence
<220> FEATURE:
<223> OTHER INFORMATION: primer

<400> SEQUENCE: 43
cctgtttttt tcatgttgac tttggg 26

<210> SEQ ID NO 44
<211> LENGTH: 21
<212> TYPE: DNA
<213> ORGANISM: Artificial Sequence
<220> FEATURE:
<223> OTHER INFORMATION: primer

<400> SEQUENCE: 44
acatccctca aagactcaag g 21

<210> SEQ ID NO 45
<211> LENGTH: 25
<212> TYPE: DNA
<213> ORGANISM: Artificial Sequence
<220> FEATURE:
<223> OTHER INFORMATION: primer

<400> SEQUENCE: 45

-continued aacaccactg ataaaatgaa cctcc 25

<210> SEQ ID NO 46
<211> LENGTH: 25
<212> TYPE: DNA
<213> ORGANISM: Artificial Sequence
<220> FEATURE:
<223> OTHER INFORMATION: primer

<400> SEQUENCE: 46
aatagttttt ttcacatcca agagg 25

<210> SEQ ID NO 47
<211> LENGTH: 28
<212> TYPE: DNA
<213> ORGANISM: Artificial Sequence
<220> FEATURE:
<223> OTHER INFORMATION: primer

<400> SEQUENCE: 47
gatgtgaaaa aaactgttaa cacttctc 28

<210> SEQ ID NO 48
<211> LENGTH: 28
<212> TYPE: DNA
<213> ORGANISM: Artificial Sequence
<220> FEATURE:
<223> OTHER INFORMATION: primer

<400> SEQUENCE: 48
agaagtgtta acagtttttt tcacatcc 28

<210> SEQ ID NO 49
<211> LENGTH: 25
<212> TYPE: DNA
<213> ORGANISM: Artificial Sequence
<220> FEATURE:
<223> OTHER INFORMATION: primer

<400> SEQUENCE: 49
gatgtgaaaa aaactattaa caccc 25

<210> SEQ ID NO 50
<211> LENGTH: 25
<212> TYPE: DNA
<213> ORGANISM: Artificial Sequence
<220> FEATURE:
<223> OTHER INFORMATION: primer

<400> SEQUENCE: 50
ggtgttaata gtttttttca catcc 25

<210> SEQ ID NO 51
<211> LENGTH: 25
<212> TYPE: DNA
<213> ORGANISM: Artificial Sequence
<220> FEATURE:
<223> OTHER INFORMATION: primer

<400> SEQUENCE: 51
agaagaacaa ctgttaacac cactg 25

<210> SEQ ID NO 52
<211> LENGTH: 25
<212> TYPE: DNA
<213> ORGANISM: Artificial Sequence -continued
<220> FEATURE:
<223> OTHER INFORMATION: primer

<400> SEQUENCE: 52
agtggtgtta acagttgttc ttctg 25

<210> SEQ ID NO 53
<211> LENGTH: 25
<212> TYPE: DNA
<213> ORGANISM: Artificial Sequence
<220> FEATURE:
<223> OTHER INFORMATION: primer

<400> SEQUENCE: 53
agaagaacaa ctaagaacac cactg 25

<210> SEQ ID NO 54
<211> LENGTH: 25
<212> TYPE: DNA
<213> ORGANISM: Artificial Sequence
<220> FEATURE:
<223> OTHER INFORMATION: primer

<400> SEQUENCE: 54
agtggtgttc ttagttgttc ttctg 25

<210> SEQ ID NO 55
<211> LENGTH: 11928
<212> TYPE: DNA
<213> ORGANISM: Rabies virus

<400> SEQUENCE: 55
acgcttaaca accagatcaa agaaaaaaca gacattgtca attgcaaagc aaaaatgtaa 60 caccccctaca atggatgccg acaagattgt attcaaagtc aataatcagg tggtctcttt 120
gaagcctgag attatcgtgg atcaatatga gtacaagtac cctgccatca aagatttgaa 180
aaagccctgt ataaccctag gaaaggctcc cgatttaaat aaagcataca agtcagtttt 240
gtcaggcatg agcgccgcca aacttaatcc tgacgatgta tgttcctatt tggcagcggc 300
aatgcagttt tttgaggggga catgtccgga agactggacc agctatggaa ttgtgattgc 360
acgaaaagga gataagatca ccccaggttc tctggtggag ataaaacgta ctgatgtaga 420
agggaattgg gctctgacag gaggcatgga actgacaaga gaccccactg tccctgagca 480
tgcgtcctta gtcggtcttc tcttgagtct gtataggttg agcaaaatat ccgggcaaaa 540
cactggtaac tataagacaa acattgcaga caggatagag cagatttttg agacagcccc 600
ttttgttaaa atcgtggaac accatactct aatgacaact cacaaaatgt gtgctaattg 660
gagtactata ccaaacttca gatttttggc cggaacctat gacatgtttt tctcccggat 720
tgagcatcta tattcagcaa tcagagtggg cacagttgtc actgcttatg aagactgttc 780
aggactggta tcatttactg ggttcataaa acaaatcaat ctcaccgcta gagaggcaat 840
actatatttc ttccacaaga actttgagga agagataaga agaatgtttg agccagggca 900
ggagacagct gttcctcact cttatttcat ccacttccgt tcactaggct tgagtgggaa 960
atctccttat tcatcaaatg ctgttggtca cgtgttcaat ctcattcact ttgtaggatg 1020
ctatatgggt caagtcagat ccctaaatgc aacggttatt gctgcatgtg ctcctcatga 1080
aatgtctgtt ctagggggct atctgggaga ggaattcttc gggaaaggga catttgaaag 1140
aagattcttc agagatgaga aagaacttca agaatacgag gcggctgaac tgacaaagac 1200

-continued

```
tgacgtagca ctggcagatg atggaactgt caactctgac gacgaggact acttttcagg   1260
tgaaaccaga agtccggagg ctgtttatac tcgaatcatg atgaatggag gtcgactaaa   1320
gagatctcac atacggagat atgtctcagt cagttccaat catcaagccc gtccaaactc   1380
attcgccgag tttctaaaca agacatattc gagtgactca taagaagttg aataacaaaa   1440
tgccggaaat ctacggattg tgtatatcca tcatgaaaaa aactaacacc cctcctttcg   1500
aaccatccca aacatgagca agatctttgt caatcctagt gctattagag ccggtctggc   1560
cgatcttgag atggctgaag aaactgttga tctgatcaat agaaatatcg aagacaatca   1620
ggctcatctc caaggggaac ccatagaggt ggacaatctc cctgaggata tggggcgact   1680
tcacctggat gatggaaaat cgcccaacca tggtgagata gccaaggtgg gagaaggcaa   1740
gtatcgagag gactttcaga tggatgaagg agaggatcct agcttcctgt tccagtcata   1800
cctggaaaat gttggagtcc aaatagtcag acaaatgagg tcaggagaga gatttctcaa   1860
gatatggtca cagaccgtag aagagattat atcctatgtc gcggtcaact ttcccaaccc   1920
tccaggaaag tcttcagagg ataaatcaac ccagactact ggccgagagc tcaagaagga   1980
gacaacaccc actccttctc agagagaaag ccaatcatcg aaagccagga tggcggctca   2040
aattgcttct ggccctccag cccttgaatg gtcggctacc aatgaagagg atgatctatc   2100
agtggaggct gagatcgctc accagattgc agaaagtttc tccaaaaaat ataagtttcc   2160
ctctcgatcc tcagggatac tcttgtataa ttttgagcaa ttgaaaatga accttgatga   2220
tatagttaaa gaggcaaaaa atgtaccagg tgtgacccgt ttagcccatg acgggtccaa   2280
actcccccta agatgtgtac tgggatgggt cgctttggcc aactctaaga aattccagtt   2340
gttagtcgaa tccgacaagc tgagtaaaat catgcaagat gacttgaatc gctatacatc   2400
ttgctaaccg aacctctccc ctcagtccct ctagacaata aaatccgaga tgtcccaaag   2460
tcaacatgaa aaaaacaggc aacaccactg ataaaatgaa cctcctacgt aagatagtga   2520
aaaaccgcag ggacgaggac actcaaaaat cctctcccgc gtcagcccct ctggatgacg   2580
atgacttgtg gcttccaccc cctgaatacg tcccgctgaa agaacttaca ggcaagaaga   2640
acatgaggaa cttttgtatc aacggaaggg ttaaagtgtg tagcccgaat ggttactcgt   2700
tcaggatcct gcggcacatt ctgaaatcat tcgacgagat atattctggg aatcatagga   2760
tgatcgggtt agtcaaagtg gttattggac tggctttgtc aggatctcca gtccctgagg   2820
gcctgaactg ggtatacaaa ttgaggagaa cctttatctt ccagtgggct gattccaggg   2880
gccctcttga aggggaggag ttggaatact ctcaggagat cacttgggat gatgatactg   2940
agttcgtcgg attgcaaata agagtgattg caaaacagtg tcatatccag ggcagagtct   3000
ggtgtatcaa catgaacccg agagcatgtc aactatggtc tgacatgtct cttcagacac   3060
aaaggtccga agaggacaaa gattcctctc tgcttctaga ataatcagat tatatcccgc   3120
aaatttatca cttgtttacc tctggaggag agaacatatg ggctcaactc caacccttgg   3180
gagcaatata acaaaaaaca tgttatggtg ccattaaacc gctgcatttc atcaaagtca   3240
agttgattac ctttacattt tgatcctctt ggatgtgaaa aaaactatta acatccctca   3300
aaagactcaa ggaaagatgg ttcctcaggc tctcctgttt gtaccccttc tggtttttcc   3360
attgtgtttt gggaaattcc ctatttacac gataccagac aagcttggtc cctggagtcc   3420
gattgacata catcacctca gctgcccaaa caatttggta gtggaggacg aaggatgcac   3480
caacctgtca gggttctcct acatggaact taaagttgga tacatcttag ccataaaagt   3540
gaacgggttc acttgcacag gcgttgtgac ggaggctgaa acctacacta acttcgttgg   3600
```

-continued

```
ttatgtcaca accacgttca aaagaaagca tttccgccca acaccagatg catgtagagc   3660
cgcgtacaac tggaagatgg ccggtgaccc cagatatgaa gagtctctac acaatccgta   3720
ccctgactac cgctggcttc gaactgtaaa aaccaccaag gagtctctcg ttatcatatc   3780
tccaagtgtg gcagatttgg acccatatga cagatccctt cactcgaggg tcttccctag   3840
cgggaagtgc tcaggagtag cggtgtcttc tacctactgc tccactaacc acgattacac   3900
catttggatg cccgagaatc cgagactagg gatgtcttgt gacattttta ccaatagtag   3960
agggaagaga gcatccaaag ggagtgagac ttgcggcttt gtagatgaaa gaggcctata   4020
taagtcttta aaaggagcat gcaaactcaa gttatgtgga gttctaggac ttagacttat   4080
ggatggaaca tgggtctcga tgcaaacatc aaatgaaacc aaatggtgcc ctcccgataa   4140
gttggtgaac ctgcacgact ttcgctcaga cgaaattgag caccttgttg tagaggagtt   4200
ggtcaggaag agagaggagt gtctggatgc actagagtcc atcatgacaa ccaagtcagt   4260
gagtttcaga cgtctcagtc atttaagaaa acttgtccct gggtttggaa aagcatatac   4320
catattcaac aagaccttga tggaagccga tgctcactac aagtcagtca gaacttggaa   4380
tgagatcctc ccttcaaaag ggtgtttaag agttgggggg aggtgtcatc ctcatgtgaa   4440
cggggtgttt ttcaatggta taatattagg acctgacggc aatgtcttaa tcccagagat   4500
gcaatcatcc ctcctccagc aacatatgga gttgttggaa tcctcggtta tccccccttgt   4560
gcaccccctg gcagacccgt ctaccgtttt caaggacggt gacgaggctg aggattttgt   4620
tgaagttcac cttcccgatg tgcacaatca ggtctcagga gttgacttgg gtctcccgaa   4680
ctgggggaag tatgtattac tgagtgcagg ggccctgact gccttgatgt tgataatttt   4740
cctgatgaca tgttgtagaa gagtcaatcg atcagaacct acgcaacaca atctcagagg   4800
gacagggagg gaggtgtcag tcactcccca aagcgggaag atcatatctt catgggaatc   4860
acacaagagt gggggtgaga ccagactgta aggactggcc gtcctttcaa cgatccaagt   4920
cctgaagatc acctcccctt ggggggttct ttttgaaaaa cctgggttca atagtcctcc   4980
ttgaactcca tgcaactggg tagattcaag agtcatgaga ttttcattaa tcctctcagt   5040
tgatcaagca agatcatgtc gattctcata ataggggaga tcttctagca gtttcagtga   5100
ctaacggtac tttcattctc caggaactga caccaacagt tgtagacaaa ccacggggtg   5160
tctcgggtga ctctgtgctt gggcacagac aaaggtcatg gtgtgttcca tgatagcgga   5220
ctcaggatga gttaattgag agaggcagtc ttcctcccgt gaaggacata agcagtagct   5280
cacaatcatc tcgcgtctca gcaaagtgtg cataattata aagtgctggg tcatctaagc   5340
ttttcagtcg agaaaaaaac attagatcag aagaacaact ggcaacactt ctcaacctga   5400
gacttacttc aagatgctcg atcctggaga ggtctatgat gaccctattg acccaatcga   5460
gttagaggct gaacccagag gaacccccat tgtccccaac atcttgagga actctgacta   5520
caatctcaac tctcctttga tagaagatcc tgctagacta atgttagaat ggttaaaaac   5580
agggaataga ccttatcgga tgactctaac agacaattgc tccaggtctt tcagagtttt   5640
gaaagattat ttcaagaagg tagatttggg ttctctcaag gtgggcggaa tggctgcaca   5700
gtcaatgatt tctctctggt tatatggtgc ccactctgaa tccaacagga gccggagatg   5760
tataacagac ttggcccatt tctattccaa gtcgtccccc atagagaagc tgttgaatct   5820
cacgctagga aatagagggc tgagaatccc cccagaggga gtgttaagtt gccttgagag   5880
ggttgattat gataatgcat ttggaaggta tcttgccaac acgtattcct cttacttgtt   5940
```

-continued cttccatgta atcaccttat acatgaacgc cctagactgg gatgaagaaa agaccatcct 6000
agcattatgg aaagatttaa cctcagtgga catcgggaag gacttggtaa agttcaaaga 6060
ccaaatatgg ggactgctga tcgtgacaaa ggactttgtt tactcccaaa gttccaattg 6120
tctttttgac agaaactaca cacttatgct aaaagatctt ttcttgtctc gcttcaactc 6180
cttaatggtc ttgctctctc ccccagagcc ccgatactca gatgacttga tatctcaact 6240
atgccagctg tacattgctg ggatcaagt cttgtctatg tgtggaaact ccggctatga 6300
agtcatcaaa atattggagc catatgtcgt gaatagttta gtccagagag cagaaaagtt 6360
taggcctctc attcattcct tgggagactt tcctgtattt ataaaagaca aggtaagtca 6420
acttgaagag acgttcggtc cctgtgcaag aaggttcttt agggctctgg atcaattcga 6480
caacatacat gacttggttt ttgtgtttgg ctgttacagg cattgggggc acccatatat 6540
agattatcga aagggtctgt caaaactata tgatcaggtt caccttaaaa aaatgataga 6600
taagtcctac caggagtgct tagcaagcga cctagccagg aggatcctta gatggggttt 6660
tgataagtac tccaagtggt atctggattc aagattccta gcccgagacc accccttgac 6720
tccttatatc aaaacccaaa catggccacc caaacatatt gtagacttgg tgggggatac 6780
atggcacaag ctcccgatca cgcagatctt tgagattcct gaatcaatgg atccgtcaga 6840
aatattggat gacaaatcac attctttcac cagaacgaga ctagcttctt ggctgtcaga 6900
aaaccgaggg gggcctgttc ctagcgaaaa agttattatc acggccctgt ctaagccgcc 6960
tgtcaatccc cgagagtttc tgaggtctat agacctcgga ggattgccag atgaagactt 7020
gataattggc ctcaagccaa aggaacggga attgaagatt gaaggtcgat tctttgctct 7080
aatgtcatgg aatctaagat tgtattttgt catcactgaa aaactcttgg ccaactacat 7140
cttgccactt tttgacgcgc tgactatgac agacaacctg aacaaggtgt ttaaaaagct 7200
gatcgacagg gtcaccgggc aagggctttt ggactattca agggtcacat atgcatttca 7260
cctggactat gaaaagtgga acaaccatca aagattagag tcaacagagg atgtattttc 7320
tgtcctagat caagtgtttg gattgaagag agtgttttct agaacacacg agtttttca 7380 aaaggcctgg atctattatt cagacagatc agacctcatc gggttacggg aggatcaaat 7440
atactgctta gatgcgtcca acggcccaac ctgttggaat ggccaggatg gcgggctaga 7500
aggcttacgg cagaagggct ggagtctagt cagcttattg atgatagata gagaatctca 7560
aatcaggaac acaagaacca aaatactagc tcaaggagac aaccaggttt tatgtccgac 7620
atacatgttg tcgccagggc tatctcaaga ggggctcctc tatgaattgg agagaatatc 7680
aaggaatgca ctttcgatat acagagccgt cgaggaaggg gcatctaagc tagggctgat 7740
catcaagaaa gaagagacca tgtgtagtta tgacttcctc atctatggaa aaacccccttt 7800 gtttagaggt aacatattgg tgcctgagtc caaaagatgg gccagagtct cttgcgtctc 7860
taatgaccaa atagtcaacc tcgccaatat aatgtcgaca gtgtccacca atgcgctaac 7920
agtggcacaa cactctcaat ctttgatcaa accgatgagg gattttctgc tcatgtcagt 7980
acaggcagtc tttcactacc tgctatttag cccaatctta aagggaagag tttacaagat 8040
tctgagcgct gaaggggaga gctttctcct agccatgtca aggataatct atctagatcc 8100
ttctttggga gggatatctg gaatgtccct cggaagattc catatacgac agttctcaga 8160
ccctgtctct gaagggttat ccttctggag agagatctgg ttaagctccc aagagtcctg 8220
gattcacgcg ttgtgtcaag aggctggaaa cccagatctt ggagagagaa cactcgagag 8280
cttcactcgc cttctagaag atccgaccac cttaaatatc agaggagggg ccagtcctac 8340

-continued

```
cattctactc aaggatgcaa tcagaaaggc tttatatgac gaggtggaca aggtggaaaa   8400
ttcagagttt cgagaggcaa tcctgttgtc caagacccat agagataatt ttatactctt   8460
cttaatatct gttgagcctc tgtttcctcg atttctcagt gagctattca gttcgtcttt   8520
tttgggaatc cccgagtcaa tcattggatt gatacaaaac tcccgaacga taagaaggca   8580
gtttagaaag agtctctcaa aaactttaga agaatccttc tacaactcag agatccacgg   8640
gattagtcgg atgacccaga cacctcagag ggttgggggg gtgtggcctt gctcttcaga   8700
gagggcagat ctacttaggg agatctcttg ggaagaaaaa gtggtaggca cgacagttcc   8760
tcacccttct gagatgttgg gattacttcc caagtcctct atttcttgca cttgtggagc   8820
aacaggagga ggcaatccta gagtttctgt atcagtactc ccgtcctttg atcagtcatt   8880
tttttcacga ggccccctaa agggatactt gggctcgtcc acctctatgt cgacccagct   8940
attccatgca tgggaaaaag tcactaatgt tcatgtggtg aagagagctc tatcgttaaa   9000
agaatctata aactggttca ttactagaga ttccaacttg gctcaagctc taattaggaa   9060
cattatgtct ctgacaggcc ctgatttccc tctagaggag gcccctgtct tcaaaaggac   9120
ggggtcagcc ttgcataggt tcaagtctgc cagatacagc gaaggagggt attcttctgt   9180
ctgcccgaac ctcctctctc atatttctgt tagtacagac accatgtctg atttgaccca   9240
agacgggaag aactacgatt tcatgttcca gccattgatg ctttatgcac agacatggac   9300
atcagagctg gtacagagag acacaaggct aagagactct acgtttcatt ggcacctccg   9360
atgcaacagg tgtgtgagac ccattgacga cgtgaccctg gagacctctc agatcttcga   9420
gtttccggat gtgtcgaaaa gaatatccag aatggtttct ggggctgtgc ctcacttcca   9480
gaggcttccc gatatccgtc tgagaccagg agattttgaa tctctaagcg gtagagaaaa   9540
gtctcaccat atcggatcag ctcaggggct cttatactca atcttagtgg caattcacga   9600
ctcaggatac aatgatggaa ccatcttccc tgtcaacata tacggcaagg tttcccctag   9660
agactatttg agagggctcg caaggggagt attgatagga tcctcgattt gcttcttgac   9720
aagaatgaca aatatcaata ttaatagacc tcttgaattg gtctcagggg taatctcata   9780
tattctcctg aggctagata accatccctc cttgtacata atgctcagag aaccgtctct   9840
tagaggagag atattttcta tccctcagaa aatccccgcc gcttatccaa ccactatgaa   9900
agaaggcaac agatcaatct tgtgttatct ccaacatgtg ctacgctatg agcgagagat   9960
aatcacggcg tctccagaga atgactggct atggatcttt tcagacttta gaagtgccaa  10020
aatgacgtac ctatccctca ttacttacca gtctcatctt ctactccaga gggttgagag  10080
aaacctatct aagagtatga gagataacct gcgacaattg agttctttga tgaggcaggt  10140
gctgggcggg cacggagaag ataccttaga gtcagacgac aacattcaac gactgctaaa  10200
agactcttta cgaaggacaa gatgggtgga tcaagaggtg cgccatgcag ctagaaccat  10260
gactggagat tacagcccca acaagaaggt gtcccgtaag gtaggatgtt cagaatgggt  10320
ctgctctgct caacaggttg cagtctctac ctcagcaaac ccggcccctg tctcggagct  10380
tgacataagg gccctctcta agaggttcca gaaccctttg atctcgggct tgagagtggt  10440
tcagtgggca accggtgctc attataagct taagcctatt ctagatgatc tcaatgtttt  10500
cccatctctc tgccttgtag ttggggacgg gtcagggggg atatcaaggg cagtcctcaa  10560
catgtttcca gatgccaagc ttgtgttcaa cagtctttta gaggtgaatg acctgatggc  10620
ttccggaaca catccactgc ctccttcagc aatcatgagg ggaggaaatg atatcgtctc  10680
```

-continued

```
cagagtgata gatcttgact caatctggga aaaaccgtcc gacttgagaa acttggcaac  10740

ctggaaatac ttccagtcag tccaaaagca ggtcaacatg tcctatgacc tcattatttg  10800

cgatgcagaa gttactgaca ttgcatctat caaccggatc accctgttaa tgtccgattt  10860

tgcattgtct atagatggac cactctattt ggtcttcaaa acttatggga ctatgctagt  10920

aaatccaaac tacaaggcta ttcaacacct gtcaagagcg ttcccctcgg tcacagggtt  10980

tatcacccaa gtaacttcgt ctttttcatc tgagctctac ctccgattct ccaaacgagg  11040

gaagtttttc agagatgctg agtacttgac ctcttccacc cttcgagaaa tgagccttgt  11100

gttattcaat tgtagcagcc ccaagagtga gatgcagaga gctcgttcct tgaactatca  11160

ggatcttgtg agaggatttc ctgaagaaat catatcaaat ccttacaatg agatgatcat  11220

aactctgatt gacagtgatg tagaatcttt tctagtccac aagatggttg atgatcttga  11280

gttacagagg ggaactctgt ctaaagtggc tatcattata gccatcatga tagttttctc  11340

caacagagtc ttcaacgttt ccaaacccct aactgacccc tcgttctatc caccgtctga  11400

tcccaaaatc ctgaggcact tcaacatatg ttgcagtact atgatgtatc tatctactgc  11460

tttaggtgac gtccctagct tcgcaagact tcacgacctg tataacagac ctataactta  11520

ttacttcaga aagcaagtca ttcgagggaa cgtttatcta tcttggagtt ggtccaacga  11580

cacctcagtg ttcaaaaggg tagcctgtaa ttctagcctg agtctgtcat ctcactggat  11640

caggttgatt tacaagatag tgaagactac cagactcgtt ggcagcatca aggatctatc  11700

cagagaagtg gaaagacacc ttcataggta caacaggtgg atcaccctag aggatatcag  11760

atctagatca tccctactag actacagttg cctgtgaacc ggatactcct ggaagcctgc  11820

ccatgctaag actcttgtgt gatgtatctt gaaaaaaaca agatcctaaa tctgaacctt  11880

tggttgtttg attgtttttc tcatttttgt tgtttatttg ttaagcgt               11928
```

```
<210> SEQ ID NO 56
<211> LENGTH: 11928
<212> TYPE: DNA
<213> ORGANISM: Rabies virus

<400> SEQUENCE: 56

acgcttaaca accagatcaa agaaaaaaca gacattgtca attgcaaagc aaaaatgtaa     60

cacccctaca atggatgccg acaagattgt attcaaagtc aataatcagg tggtctcttt    120

gaagcctgag attatcgtgg atcaatatga gtacaagtac cctgccatca aagatttgaa    180

aaagccctgt ataaccctag gaaaggctcc cgatttaaat aaagcataca agtcagtttt    240

gtcaggcatg agcgccgcca aacttaatcc tgacgatgta tgttcctatt tggcagcggc    300

aatgcagttt tttgagggga catgtccgga agactggacc agctatggaa ttgtgattgc    360

acgaaaagga gataagatca ccccaggttc tctggtggag ataaaacgta ctgatgtaga    420

agggaattgg gctctgacag gaggcatgga actgacaaga gaccccactg tccctgagca    480

tgcgtcctta gtcggtcttc tcttgagtct gtataggttg agcaaaatat ccgggcaaaa    540

cactggtaac tataagacaa acattgcaga caggatagag cagattttg agacagcccc     600

ttttgttaaa atcgtggaac accatactct aatgacaact cacaaaatgt gtgctaattg    660

gagtactata ccaaacttca gatttttggc cggaacctat gacatgtttt tctcccggat    720

tgagcatcta tattcagcaa tcagagtggg cacagttgtc actgcttatg aagactgttc    780

aggactggta tcatttactg ggttcataaa acaaatcaat ctcaccgcta gagaggcaat    840

actatatttc ttccacaaga actttgagga agagataaga agaatgtttg agccagggca    900
```

-continued

```
ggagacagct gttcctcact cttatttcat ccacttccgt tcactaggct tgagtgggaa    960
atctccttat tcatcaaatg ctgttggtca cgtgttcaat ctcattcact ttgtaggatg   1020
ctatatgggt caagtcagat ccctaaatgc aacggttatt gctgcatgtg ctcctcatga   1080
aatgtctgtt ctagggggct atctgggaga ggaattcttc gggaaaggga catttgaaag   1140
aagattcttc agagatgaga aagaacttca agaatacgag gcggctgaac tgacaaagac   1200
tgacgtagca ctggcagatg atggaactgt caacgctgac gacgaggact acttttcagg   1260
tgaaaccaga agtccggagg ctgtttatac tcgaatcatg atgaatggag gtcgactaaa   1320
gagatctcac atacggagat atgtctcagt cagttccaat catcaagccc gtccaaactc   1380
attcgccgag tttctaaaca agacatattc gagtgactca taagaagttg aataacaaaa   1440
tgccggaaat ctacggattg tgtatatcca tcatgaaaaa aactaacacc cctcctttcg   1500
aaccatccca aacatgagca agatctttgt caatcctagt gctattagag ccggtctggc   1560
cgatcttgag atggctgaag aaactgttga tctgatcaat agaaatatcg aagacaatca   1620
ggctcatctc caaggggaac ccatagaggt ggacaatctc cctgaggata tggggcgact   1680
tcacctggat gatggaaaat cgcccaacca tggtgagata gccaaggtgg gagaaggcaa   1740
gtatcgagag gactttcaga tggatgaagg agaggatcct agcttcctgt tccagtcata   1800
cctggaaaat gttggagtcc aaatagtcag acaaatgagg tcaggagaga gatttctcaa   1860
gatatggtca cagaccgtag aagagattat atcctatgtc gcggtcaact ttcccaaccc   1920
tccaggaaag tcttcagagg ataaatcaac ccagactact ggccgagagc tcaagaagga   1980
gacaacaccc actccttctc agagagaaag ccaatcatcg aaagccagga tggcggctca   2040
aattgcttct ggccctccag cccttgaatg gtcggctacc aatgaagagg atgatctatc   2100
agtggaggct gagatcgctc accagattgc agaaagtttc tccaaaaaat ataagtttcc   2160
ctctcgatcc tcagggatac tcttgtataa ttttgagcaa ttgaaaatga accttgatga   2220
tatagttaaa gaggcaaaaa atgtaccagg tgtgacccgt ttagcccatg acgggtccaa   2280
actcccccta agatgtgtac tgggatgggt cgctttggcc aactctaaga aattccagtt   2340
gttagtcgaa tccgacaagc tgagtaaaat catgcaagat gacttgaatc gctatacatc   2400
ttgctaaccg aacctctccc ctcagtccct ctagacaata aaatccgaga tgtcccaaag   2460
tcaacatgaa aaaaacaggc aacaccactg ataaaatgaa cctcctacgt aagatagtga   2520
aaaaccgcag ggacgaggac actcaaaaat cctctcccgc gtcagcccct ctggatgacg   2580
atgacttgtg gcttccaccc cctgaatacg tcccgctgaa agaacttaca ggcaagaaga   2640
acatgaggaa cttttgtatc aacggaaggg ttaaagtgtg tagcccgaat ggttactcgt   2700
tcaggatcct gcggcacatt ctgaaatcat tcgacgagat atattctggg aatcatagga   2760
tgatcgggtt agtcaaagtg gttattggac tggctttgtc aggatctcca gtccctgagg   2820
gcctgaactg ggtatacaaa ttgaggagaa cctttatctt ccagtgggct gattccaggg   2880
gccctcttga aggggaggag ttggaatact ctcaggagat cacttgggat gatgatactg   2940
agttcgtcgg attgcaaata agagtgattg caaaacagtg tcatatccag ggcagagtct   3000
ggtgtatcaa catgaacccg agagcatgtc aactatggtc tgacatgtct cttcagacac   3060
aaaggtccga agaggacaaa gattcctctc tgcttctaga ataatcagat tatatcccgc   3120
aaatttatca cttgtttacc tctggaggag agaacatatg ggctcaactc caacccttgg   3180
gagcaatata acaaaaaaca tgttatggtg ccattaaacc gctgcatttc atcaaagtca   3240
```

-continued

```
agttgattac ctttacattt tgatcctctt ggatgtgaaa aaaactatta acatccctca   3300
aaagactcaa ggaaagatgg ttcctcaggc tctcctgttt gtaccccttc tggtttttcc   3360
attgtgtttt gggaaattcc ctatttacac gataccagac aagcttggtc cctggagtcc   3420
gattgacata catcacctca gctgcccaaa caatttggta gtggaggacg aaggatgcac   3480
caacctgtca gggttctcct acatggaact taaagttgga tacatcttag ccataaaagt   3540
gaacgggttc acttgcacag gcgttgtgac ggaggctgaa acctacacta acttcgttgg   3600
ttatgtcaca accacgttca aaagaaagca tttccgccca acaccagatg catgtagagc   3660
cgcgtacaac tggaagatgg ccggtgaccc cagatatgaa gagtctctac acaatccgta   3720
ccctgactac cgctggcttc gaactgtaaa aaccaccaag gagtctctcg ttatcatatc   3780
tccaagtgtg gcagatttgg acccatatga cagatccctt cactcgaggg tcttccctag   3840
cgggaagtgc tcaggagtag cggtgtcttc tacctactgc tccactaacc acgattacac   3900
catttggatg cccgagaatc cgagactagg gatgtcttgt gacattttta ccaatagtag   3960
agggaagaga gcatccaaag ggagtgagac ttgcggcttt gtagatgaaa gaggcctata   4020
taagtcttta aaaggagcat gcaaactcaa gttatgtgga gttctaggac ttagacttat   4080
ggatggaaca tgggtctcga tgcaaacatc aaatgaaacc aaatggtgcc ctcccgataa   4140
gttggtgaac ctgcacgact ttcgctcaga cgaaattgag caccttgttg tagaggagtt   4200
ggtcaggaag agagaggagt gtctggatgc actagagtcc atcatgacaa ccaagtcagt   4260
gagtttcaga cgtctcagtc atttaagaaa acttgtccct gggtttggaa aagcatatac   4320
catattcaac aagaccttga tggaagccga tgctcactac aagtcagtca gaacttggaa   4380
tgagatcctc ccttcaaaag ggtgtttaag agttgggggg aggtgtcatc ctcatgtgaa   4440
cggggtgttt ttcaatggta taatattagg acctgacggc aatgtcttaa tcccagagat   4500
gcaatcatcc ctcctccagc aacatatgga gttgttggaa tcctcggtta tcccccttgt   4560
gcacccccctg gcagacccgt ctaccgtttt caaggacggt gacgaggctg aggattttgt   4620
tgaagttcac cttcccgatg tgcacaatca ggtctcagga gttgacttgg gtctcccgaa   4680
ctgggggaag tatgtattac tgagtgcagg ggccctgact gccttgatgt tgataatttt   4740
cctgatgaca tgttgtagaa gagtcaatcg atcagaacct acgcaacaca atctcagagg   4800
gacagggagg gaggtgtcag tcactcccca aagcgggaag atcatatctt catgggaatc   4860
acacaagagt gggggtgaga ccagactgta aggactggcc gtcctttcaa cgatccaagt   4920
cctgaagatc acctcccctt ggggggttct ttttgaaaaa cctgggttca atagtcctcc   4980
ttgaactcca tgcaactggg tagattcaag agtcatgaga ttttcattaa tcctctcagt   5040
tgatcaagca agatcatgtc gattctcata ataggggaga tcttctagca gtttcagtga   5100
ctaacggtac tttcattctc caggaactga caccaacagt tgtagacaaa ccacggggtg   5160
tctcgggtga ctctgtgctt gggcacagac aaaggtcatg gtgtgttcca tgatagcgga   5220
ctcaggatga gttaattgag agaggcagtc ttcctcccgt gaaggacata agcagtagct   5280
cacaatcatc tcgcgtctca gcaaagtgtg cataattata aagtgctggg tcatctaagc   5340
ttttcagtcg agaaaaaaac attagatcag aagaacaact ggcaacactt ctcaacctga   5400
gacttacttc aagatgctcg atcctggaga ggtctatgat gaccctattg acccaatcga   5460
gttagaggct gaacccagag gaacccccat tgtccccaac atcttgagga actctgacta   5520
caatctcaac tctcctttga tagaagatcc tgctagacta atgttagaat ggttaaaaac   5580
agggaataga ccttatcgga tgactctaac agacaattgc tccaggtctt tcagagtttt   5640
```

-continued

```
gaaagattat ttcaagaagg tagatttggg ttctctcaag gtgggcggaa tggctgcaca   5700
gtcaatgatt tctctctggt tatatggtgc ccactctgaa tccaacagga gccggagatg   5760
tataacagac ttggcccatt tctattccaa gtcgtccccc atagagaagc tgttgaatct   5820
cacgctagga aatagagggc tgagaatccc cccagaggga gtgttaagtt gccttgagag   5880
ggttgattat gataatgcat ttggaaggta tcttgccaac acgtattcct cttacttgtt   5940
cttccatgta atcaccttat acatgaacgc cctagactgg gatgaagaaa agaccatcct   6000
agcattatgg aaagatttaa cctcagtgga catcgggaag gacttggtaa agttcaaaga   6060
ccaaatatgg ggactgctga tcgtgacaaa ggactttgtt tactcccaaa gttccaattg   6120
tctttttgac agaaactaca cacttatgct aaaagatctt ttcttgtctc gcttcaactc   6180
cttaatggtc ttgctctctc ccccagagcc ccgatactca gatgacttga tatctcaact   6240
atgccagctg tacattgctg gggatcaagt cttgtctatg tgtggaaact ccggctatga   6300
agtcatcaaa atattggagc catatgtcgt gaatagttta gtccagagag cagaaaagtt   6360
taggcctctc attcattcct tgggagactt tcctgtattt ataaaagaca aggtaagtca   6420
acttgaagag acgttcggtc cctgtgcaag aaggttcttt agggctctgg atcaattcga   6480
caacatacat gacttggttt ttgtgtttgg ctgttacagg cattgggggc acccatatat   6540
agattatcga aagggtctgt caaaactata tgatcaggtt caccttaaaa aaatgataga   6600
taagtcctac caggagtgct tagcaagcga cctagccagg aggatcctta gatggggttt   6660
tgataagtac tccaagtggt atctggattc aagattccta gcccgagacc acccccttgac   6720
tccttatatc aaaacccaaa catggccacc caaacatatt gtagacttgg tgggggatac   6780
atggcacaag ctcccgatca cgcagatctt tgagattcct gaatcaatgg atccgtcaga   6840
aatattggat gacaaatcac attctttcac cagaacgaga ctagcttctt ggctgtcaga   6900
aaaccgaggg gggcctgttc ctagcgaaaa agttattatc acggccctgt ctaagccgcc   6960
tgtcaatccc cgagagtttc tgaggtctat agacctcgga ggattgccag atgaagactt   7020
gataattggc ctcaagccaa aggaacggga attgaagatt gaaggtcgat tctttgctct   7080
aatgtcatgg aatctaagat tgtattttgt catcactgaa aaactcttgg ccaactacat   7140
cttgccactt tttgacgcgc tgactatgac agacaacctg aacaaggtgt ttaaaaagct   7200
gatcgacagg gtcaccgggc aagggctttt ggactattca agggtcacat atgcatttca   7260
cctggactat gaaaagtgga acaaccatca aagattagag tcaacagagg atgtattttc   7320
tgtcctagat caagtgtttg gattgaagag agtgttttct agaacacacg agtttttttca   7380
aaaggcctgg atctattatt cagacagatc agacctcatc gggttacggg aggatcaaat   7440
atactgctta gatgcgtcca acggcccaac ctgttggaat ggccaggatg gcgggctaga   7500
aggcttacgg cagaagggct ggagtctagt cagcttattg atgatagata gagaatctca   7560
aatcaggaac acaagaacca aaatactagc tcaaggagac aaccaggttt tatgtccgac   7620
atacatgttg tcgccagggc tatctcaaga ggggctcctc tatgaattgg agagaatatc   7680
aaggaatgca ctttcgatat acagagccgt cgaggaaggg gcatctaagc tagggctgat   7740
catcaagaaa gaagagacca tgtgtagtta tgacttcctc atctatggaa aaaccccttt   7800
gtttagaggt aacatattgg tgcctgagtc caaaagatgg gccagagtct cttgcgtctc   7860
taatgaccaa atagtcaacc tcgccaatat aatgtcgaca gtgtccacca atgcgctaac   7920
agtggcacaa cactctcaat ctttgatcaa accgatgagg gattttctgc tcatgtcagt   7980
```

-continued acaggcagtc tttcactacc tgctatttag cccaatctta aagggaagag tttacaagat 8040
tctgagcgct gaaggggaga gctttctcct agccatgtca aggataatct atctagatcc 8100
ttctttggga gggatatctg gaatgtccct cggaagattc catatacgac agttctcaga 8160
ccctgtctct gaagggttat ccttctggag agagatctgg ttaagctccc aagagtcctg 8220
gattcacgcg ttgtgtcaag aggctggaaa cccagatctt ggagagagaa cactcgagag 8280
cttcactcgc cttctagaag atccgaccac cttaaatatc agaggagggg ccagtcctac 8340
cattctactc aaggatgcaa tcagaaaggc tttatatgac gaggtggaca aggtggaaaa 8400
ttcagagttt cgagaggcaa tcctgttgtc caagacccat agagataatt ttatactctt 8460
cttaatatct gttgagcctc tgtttcctcg atttctcagt gagctattca gttcgtcttt 8520
tttgggaatc cccgagtcaa tcattggatt gatacaaaac tcccgaacga taagaaggca 8580
gtttagaaag agtctctcaa aaactttaga agaatccttc tacaactcag agatccacgg 8640
gattagtcgg atgacccaga cacctcagag ggttgggggg gtgtggcctt gctcttcaga 8700
gagggcagat ctacttaggg agatctcttg gggaagaaaa gtggtaggca cgacagttcc 8760
tcacccttct gagatgttgg gattacttcc caagtcctct atttcttgca cttgtggagc 8820
aacaggagga ggcaatccta gagtttctgt atcagtactc ccgtcctttg atcagtcatt 8880
tttttcacga ggcccccta a agggatactt gggctcgtcc acctctatgt cgacccagct 8940
attccatgca tgggaaaaag tcactaatgt tcatgtggtg aagagagctc tatcgttaaa 9000
agaatctata aactggttca ttactagaga ttccaacttg gctcaagctc taattaggaa 9060
cattatgtct ctgacaggcc ctgatttccc tctagaggag gcccctgtct tcaaaaggac 9120
ggggtcagcc ttgcataggt tcaagtctgc cagatacagc gaaggagggt attcttctgt 9180
ctgcccgaac ctcctctctc atatttctgt tagtacagac accatgtctg atttgaccca 9240
agacgggaag aactacgatt tcatgttcca gccattgatg ctttatgcac agacatggac 9300
atcagagctg gtacagagag acacaaggct aagagactct acgtttcatt ggcacctccg 9360
atgcaacagg tgtgtgagac ccattgacga cgtgaccctg gagacctctc agatcttcga 9420
gtttccggat gtgtcgaaaa gaatatccag aatggtttct ggggctgtgc ctcacttcca 9480
gaggcttccc gatatccgtc tgagaccagg agattttgaa tctctaagcg gtagagaaaa 9540
gtctcaccat atcggatcag ctcaggggct cttatactca atcttagtgg caattcacga 9600
ctcaggatac aatgatggaa ccatcttccc tgtcaacata tacggcaagg tttcccctag 9660
agactatttg agagggctcg caaggggagt attgatagga tcctcgattt gcttcttgac 9720
aagaatgaca aatatcaata ttaatagacc tcttgaattg gtctcagggg taatctcata 9780
tattctcctg aggctagata accatccctc cttgtacata atgctcagag aaccgtctct 9840
tagaggagag atattttcta tccctcagaa aatccccgcc gcttatccaa ccactatgaa 9900
agaaggcaac agatcaatct tgtgttatct ccaacatgtg ctacgctatg agcgagagat 9960
aatcacggcg tctccagaga atgactggct atggatcttt tcagacttta gaagtgccaa 10020
aatgacgtac ctatccctca ttacttacca gtctcatctt ctactccaga gggttgagag 10080
aaacctatct aagagtatga gagataacct gcgacaattg agttctttga tgaggcaggt 10140
gctgggcggg cacggagaag ataccttaga gtcagacgac aacattcaac gactgctaaa 10200
agactcttta cgaaggacaa gatgggtgga tcaagaggtg cgccatgcag ctagaaccat 10260
gactggagat tacagcccca acaagaaggt gtcccgtaag gtaggatgtt cagaatgggt 10320
ctgctctgct caacaggttg cagtctctac ctcagcaaac ccggcccctg tctcggagct 10380

-continued

```
tgacataagg gccctctcta agaggttcca gaaccctttg atctcgggct tgagagtggt  10440
tcagtgggca accggtgctc attataagct taagcctatt ctagatgatc tcaatgtttt  10500
cccatctctc tgccttgtag ttggggacgg gtcagggggg atatcaaggg cagtcctcaa  10560
catgtttcca gatgccaagc ttgtgttcaa cagtctttta gaggtgaatg acctgatggc  10620
ttccggaaca catccactgc ctccttcagc aatcatgagg ggaggaaatg atatcgtctc  10680
cagagtgata gatcttgact caatctggga aaaaccgtcc gacttgagaa acttggcaac  10740
ctggaaatac ttccagtcag tccaaaagca ggtcaacatg tcctatgacc tcattatttg  10800
cgatgcagaa gttactgaca ttgcatctat caaccggatc accctgttaa tgtccgattt  10860
tgcattgtct atagatggac cactctattt ggtcttcaaa acttatggga ctatgctagt  10920
aaatccaaac tacaaggcta ttcaacacct gtcaagagcg ttcccctcgg tcacagggtt  10980
tatcacccaa gtaacttcgt ctttttcatc tgagctctac ctccgattct ccaaacgagg  11040
gaagtttttc agagatgctg agtacttgac ctcttccacc cttcgagaaa tgagccttgt  11100
gttattcaat tgtagcagcc ccaagagtga gatgcagaga gctcgttcct tgaactatca  11160
ggatcttgtg agaggatttc ctgaagaaat catatcaaat ccttacaatg agatgatcat  11220
aactctgatt gacagtgatg tagaatcttt tctagtccac aagatggttg atgatcttga  11280
gttacagagg ggaactctgt ctaaagtggc tatcattata gccatcatga tagttttctc  11340
caacagagtc ttcaacgttt ccaaacccct aactgacccc tcgttctatc caccgtctga  11400
tcccaaaatc ctgaggcact tcaacatatg ttgcagtact atgatgtatc tatctactgc  11460
tttaggtgac gtccctagct tcgcaagact tcacgacctg tataacagac ctataactta  11520
ttacttcaga aagcaagtca ttcgagggaa cgtttatcta tcttggagtt ggtccaacga  11580
cacctcagtg ttcaaaaggg tagcctgtaa ttctagcctg agtctgtcat ctcactggat  11640
caggttgatt tacaagatag tgaagactac cagactcgtt ggcagcatca aggatctatc  11700
cagagaagtg gaaagacacc ttcataggta caacaggtgg atcaccctag aggatatcag  11760
atctagatca tccctactag actacagttg cctgtgaacc ggatactcct ggaagcctgc  11820
ccatgctaag actcttgtgt gatgtatctt gaaaaaaaca agatcctaaa tctgaacctt  11880
tggttgtttg attgtttttc tcatttttgt tgtttatttg ttaagcgt              11928
```

<210> SEQ ID NO 57
<211> LENGTH: 11928
<212> TYPE: DNA
<213> ORGANISM: Rabies virus

<400> SEQUENCE: 57

```
acgcttaaca accagatcaa agaaaaaaca gacattgtca attgcaaagc aaaaatgtaa     60
cacccctaca atggatgccg acaagattgt attcaaagtc aataatcagg tggtctcttt    120
gaagcctgag attatcgtgg atcaatatga gtacaagtac cctgccatca aagatttgaa    180
aaagccctgt ataaccctag gaaaggctcc cgatttaaat aaagcataca agtcagtttt    240
gtcaggcatg agcgccgcca aacttaatcc tgacgatgta tgttcctatt tggcagcggc    300
aatgcagttt tttgagggga catgtccgga agactggacc agctatggaa ttgtgattgc    360
acgaaaagga gataagatca ccccaggttc tctggtggag ataaaacgta ctgatgtaga    420
agggaattgg gctctgacag gaggcatgga actgacaaga gaccccactg tccctgagca    480
tgcgtcctta gtcggtcttc tcttgagtct gtataggttg agcaaaatat ccgggcaaaa    540
```

-continued

```
cactggtaac tataagacaa acattgcaga caggatagag cagatttttg agacagcccc    600
ttttgttaaa atcgtggaac accatactct aatgacaact cacaaaatgt gtgctaattg    660
gagtactata ccaaacttca gatttttggc cggaacctat gacatgtttt tctcccggat    720
tgagcatcta tattcagcaa tcagagtggg cacagttgtc actgcttatg aagactgttc    780
aggactggta tcatttactg ggttcataaa acaaatcaat ctcaccgcta gagaggcaat    840
actatatttc ttccacaaga actttgagga agagataaga agaatgtttg agccagggca    900
ggagacagct gttcctcact cttatttcat ccacttccgt tcactaggct tgagtgggaa    960
atctccttat tcatcaaatg ctgttggtca cgtgttcaat ctcattcact ttgtaggatg   1020
ctatatgggt caagtcagat ccctaaatgc aacggttatt gctgcatgtg ctcctcatga   1080
aatgtctgtt ctagggggct atctgggaga ggaattcttc gggaaaggga catttgaaag   1140
aagattcttc agagatgaga aagaacttca agaatacgag gcggctgaac tgacaaagac   1200
tgacgtagca ctggcagatg atggaactgt caaccaagac gacgaggact actttttcagg   1260
tgaaaccaga agtccggagg ctgtttatac tcgaatcatg atgaatggag gtcgactaaa   1320
gagatctcac atacggagat atgtctcagt cagttccaat catcaagccc gtccaaactc   1380
attcgccgag tttctaaaca agacatattc gagtgactca taagaagttg aataacaaaa   1440
tgccggaaat ctacggattg tgtatatcca tcatgaaaaa aactaacacc cctcctttcg   1500
aaccatccca aacatgagca agatctttgt caatcctagt gctattagag ccggtctggc   1560
cgatcttgag atggctgaag aaactgttga tctgatcaat agaaatatcg aagacaatca   1620
ggctcatctc caaggggaac ccatagaggt ggacaatctc cctgaggata tggggcgact   1680
tcacctggat gatggaaaat cgcccaacca tggtgagata gccaaggtgg gagaaggcaa   1740
gtatcgagag gactttcaga tggatgaagg agaggatcct agcttcctgt tccagtcata   1800
cctggaaaat gttggagtcc aaatagtcag acaaatgagg tcaggagaga gatttctcaa   1860
gatatggtca cagaccgtag aagagattat atcctatgtc gcggtcaact ttcccaaccc   1920
tccaggaaag tcttcagagg ataaatcaac ccagactact ggccgagagc tcaagaagga   1980
gacaacaccc actccttctc agagagaaag ccaatcatcg aaagccagga tggcggctca   2040
aattgcttct ggccctccag cccttgaatg gtcggctacc aatgaagagg atgatctatc   2100
agtggaggct gagatcgctc accagattgc agaaagtttc tccaaaaaat ataagtttcc   2160
ctctcgatcc tcagggatac tcttgtataa ttttgagcaa ttgaaaatga accttgatga   2220
tatagttaaa gaggcaaaaa atgtaccagg tgtgacccgt ttagcccatg acgggtccaa   2280
actcccccta agatgtgtac tgggatgggt cgctttggcc aactctaaga aattccagtt   2340
gttagtcgaa tccgacaagc tgagtaaaat catgcaagat gacttgaatc gctatacatc   2400
ttgctaaccg aacctctccc ctcagtccct ctagacaata aaatccgaga tgtcccaaag   2460
tcaacatgaa aaaaacaggc aacaccactg ataaaatgaa cctcctacgt aagatagtga   2520
aaaaccgcag ggacgaggac actcaaaaat cctctcccgc gtcagcccct ctggatgacg   2580
atgacttgtg gcttccaccc cctgaatacg tcccgctgaa agaacttaca ggcaagaaga   2640
acatgaggaa cttttgtatc aacggaaggg ttaaagtgtg tagcccgaat ggttactcgt   2700
tcaggatcct gcggcacatt ctgaaatcat tcgacgagat atattctggg aatcatagga   2760
tgatcgggtt agtcaaagtg gttattggac tggctttgtc aggatctcca gtccctgagg   2820
gcctgaactg ggtatacaaa ttgaggagaa cctttatctt ccagtgggct gattccaggg   2880
gccctcttga aggggaggag ttggaatact ctcaggagat cacttgggat gatgatactg   2940
```

-continued

```
agttcgtcgg attgcaaata agagtgattg caaaacagtg tcatatccag ggcagagtct   3000
ggtgtatcaa catgaacccg agagcatgtc aactatggtc tgacatgtct cttcagacac   3060
aaaggtccga agaggacaaa gattcctctc tgcttctaga ataatcagat tatatcccgc   3120
aaatttatca cttgtttacc tctggaggag agaacatatg ggctcaactc caacccttgg   3180
gagcaatata acaaaaaaca tgttatggtg ccattaaacc gctgcatttc atcaaagtca   3240
agttgattac ctttacattt tgatcctctt ggatgtgaaa aaaactatta acatccctca   3300
aaagactcaa ggaaagatgg ttcctcaggc tctcctgttt gtaccccttc tggtttttcc   3360
attgtgtttt gggaaattcc ctatttacac gataccagac aagcttggtc cctggagtcc   3420
gattgacata catcacctca gctgcccaaa caatttggta gtggaggacg aaggatgcac   3480
caacctgtca gggttctcct acatggaact taaagttgga tacatcttag ccataaaagt   3540
gaacgggttc acttgcacag gcgttgtgac ggaggctgaa acctacacta acttcgttgg   3600
ttatgtcaca accacgttca aaagaaagca tttccgccca acaccagatg catgtagagc   3660
cgcgtacaac tggaagatgg ccggtgaccc cagatatgaa gagtctctac acaatccgta   3720
ccctgactac cgctggcttc gaactgtaaa aaccaccaag gagtctctcg ttatcatatc   3780
tccaagtgtg gcagatttgg acccatatga cagatccctt cactcgaggg tcttccctag   3840
cgggaagtgc tcaggagtag cggtgtcttc tacctactgc tccactaacc acgattacac   3900
catttggatg cccgagaatc cgagactagg gatgtcttgt gacattttta ccaatagtag   3960
agggaagaga gcatccaaag ggagtgagac ttgcggcttt gtagatgaaa gaggcctata   4020
taagtcttta aaaggagcat gcaaactcaa gttatgtgga gttctaggac ttagacttat   4080
ggatggaaca tgggtctcga tgcaaacatc aaatgaaacc aaatggtgcc ctcccgataa   4140
gttggtgaac ctgcacgact ttcgctcaga cgaaattgag caccttgttg tagaggagtt   4200
ggtcaggaag agagaggagt gtctggatgc actagagtcc atcatgacaa ccaagtcagt   4260
gagtttcaga cgtctcagtc atttaagaaa acttgtccct gggtttggaa aagcatatac   4320
catattcaac aagaccttga tggaagccga tgctcactac aagtcagtca gaacttggaa   4380
tgagatcctc ccttcaaaag ggtgtttaag agttgggggg aggtgtcatc ctcatgtgaa   4440
cggggtgttt ttcaatggta taatattagg acctgacggc aatgtcttaa tcccagagat   4500
gcaatcatcc ctcctccagc aacatatgga gttgttggaa tcctcggtta tcccccttgt   4560
gcacccccctg gcagacccgt ctaccgtttt caaggacggt gacgaggctg aggattttgt   4620
tgaagttcac cttcccgatg tgcacaatca ggtctcagga gttgacttgg gtctcccgaa   4680
ctgggggaag tatgtattac tgagtgcagg ggccctgact gccttgatgt tgataatttt   4740
cctgatgaca tgttgtagaa gagtcaatcg atcagaacct acgcaacaca atctcagagg   4800
gacagggagg gaggtgtcag tcactcccca aagcgggaag atcatatctt catgggaatc   4860
acacaagagt gggggtgaga ccagactgta aggactggcc gtcctttcaa cgatccaagt   4920
cctgaagatc acctcccctt ggggggttct ttttgaaaaa cctgggttca atagtcctcc   4980
ttgaactcca tgcaactggg tagattcaag agtcatgaga ttttcattaa tcctctcagt   5040
tgatcaagca agatcatgtc gattctcata ataggggaga tcttctagca gtttcagtga   5100
ctaacggtac tttcattctc caggaactga caccaacagt tgtagacaaa ccacggggtg   5160
tctcgggtga ctctgtgctt gggcacagac aaaggtcatg gtgtgttcca tgatagcgga   5220
ctcaggatga gttaattgag agaggcagtc ttcctcccgt gaaggacata agcagtagct   5280
```

-continued

```
cacaatcatc tcgcgtctca gcaaagtgtg cataattata aagtgctggg tcatctaagc   5340
ttttcagtcg agaaaaaaac attagatcag aagaacaact ggcaacactt ctcaacctga   5400
gacttacttc aagatgctcg atcctggaga ggtctatgat gaccctattg acccaatcga   5460
gttagaggct gaacccagag gaaccccccat tgtccccaac atcttgagga actctgacta   5520
caatctcaac tctcctttga tagaagatcc tgctagacta atgttagaat ggttaaaaac   5580
agggaataga ccttatcgga tgactctaac agacaattgc tccaggtctt tcagagtttt   5640
gaaagattat ttcaagaagg tagatttggg ttctctcaag gtgggcggaa tggctgcaca   5700
gtcaatgatt tctctctggt tatatggtgc ccactctgaa tccaacagga gccggagatg   5760
tataacagac ttggcccatt tctattccaa gtcgtccccc atagagaagc tgttgaatct   5820
cacgctagga aatagagggc tgagaatccc cccagaggga gtgttaagtt gccttgagag   5880
ggttgattat gataatgcat ttggaaggta tcttgccaac acgtattcct cttacttgtt   5940
cttccatgta atcaccttat acatgaacgc cctagactgg gatgaagaaa agaccatcct   6000
agcattatgg aaagatttaa cctcagtgga catcgggaag gacttggtaa agttcaaaga   6060
ccaaatatgg ggactgctga tcgtgacaaa ggactttgtt tactcccaaa gttccaattg   6120
tctttttgac agaaactaca cacttatgct aaaagatctt ttcttgtctc gcttcaactc   6180
cttaatggtc ttgctctctc ccccagagcc ccgatactca gatgacttga tatctcaact   6240
atgccagctg tacattgctg gggatcaagt cttgtctatg tgtggaaact ccggctatga   6300
agtcatcaaa atattggagc catatgtcgt gaatagttta gtccagagag cagaaaagtt   6360
taggcctctc attcattcct tgggagactt tcctgtattt ataaaagaca aggtaagtca   6420
acttgaagag acgttcggtc cctgtgcaag aaggttcttt agggctctgg atcaattcga   6480
caacatacat gacttggttt ttgtgtttgg ctgttacagg cattgggggc acccatatat   6540
agattatcga aagggtctgt caaaactata tgatcaggtt caccttaaaa aaatgataga   6600
taagtcctac caggagtgct tagcaagcga cctagccagg aggatcctta gatggggttt   6660
tgataagtac tccaagtggt atctggattc aagattccta gcccgagacc accccttgac   6720
tccttatatc aaaacccaaa catggccacc caaacatatt gtagacttgg tgggggatac   6780
atggcacaag ctcccgatca cgcagatctt tgagattcct gaatcaatgg atccgtcaga   6840
aatattggat gacaaatcac attctttcac cagaacgaga ctagcttctt ggctgtcaga   6900
aaaccgaggg ggcctgttc ctagcgaaaa agttattatc acggccctgt ctaagccgcc   6960
tgtcaatccc cgagagtttc tgaggtctat agacctcgga ggattgccag atgaagactt   7020
gataattggc ctcaagccaa aggaacggga attgaagatt gaaggtcgat tctttgctct   7080
aatgtcatgg aatctaagat tgtattttgt catcactgaa aaactcttgg ccaactacat   7140
cttgccactt tttgacgcgc tgactatgac agacaacctg aacaaggtgt ttaaaaagct   7200
gatcgacagg gtcaccgggc aagggctttt ggactattca agggtcacat atgcatttca   7260
cctggactat gaaaagtgga acaaccatca aagattagag tcaacagagg atgtattttc   7320
tgtcctagat caagtgtttg gattgaagag agtgttttct agaacacacg agtttttca   7380
aaaggcctgg atctattatt cagacagatc agacctcatc gggttacggg aggatcaaat   7440
atactgctta gatgcgtcca acggcccaac ctgttggaat ggccaggatg gcgggctaga   7500
aggcttacgg cagaagggct ggagtctagt cagcttattg atgatagata gagaatctca   7560
aatcaggaac acaagaacca aaatactagc tcaaggagac aaccaggttt tatgtccgac   7620
atacatgttg tcgccagggc tatctcaaga ggggctcctc tatgaattgg agagaatatc   7680
```

-continued

```
aaggaatgca ctttcgatat acagagccgt cgaggaaggg gcatctaagc tagggctgat   7740
catcaagaaa gaagagacca tgtgtagtta tgacttcctc atctatggaa aaacccccttt  7800
gtttagaggt aacatattgg tgcctgagtc caaaagatgg gccagagtct cttgcgtctc   7860
taatgaccaa atagtcaacc tcgccaatat aatgtcgaca gtgtccacca atgcgctaac   7920
agtggcacaa cactctcaat ctttgatcaa accgatgagg gattttctgc tcatgtcagt   7980
acaggcagtc tttcactacc tgctatttag cccaatctta aagggaagag tttacaagat   8040
tctgagcgct gaaggggaga gctttctcct agccatgtca aggataatct atctagatcc   8100
ttctttggga gggatatctg gaatgtccct cggaagattc catatacgac agttctcaga   8160
ccctgtctct gaagggttat ccttctggag agagatctgg ttaagctccc aagagtcctg   8220
gattcacgcg ttgtgtcaag aggctggaaa cccagatctt ggagagagaa cactcgagag   8280
cttcactcgc cttctagaag atccgaccac cttaaatatc agaggagggg ccagtcctac   8340
cattctactc aaggatgcaa tcagaaaggc tttatatgac gaggtggaca aggtggaaaa   8400
ttcagagttt cgagaggcaa tcctgttgtc caagacccat agagataatt ttatactctt   8460
cttaatatct gttgagcctc tgtttcctcg atttctcagt gagctattca gttcgtcttt   8520
tttgggaatc cccgagtcaa tcattggatt gatacaaaac tcccgaacga taagaaggca   8580
gtttagaaag agtctctcaa aaactttaga agaatccttc tacaactcag agatccacgg   8640
gattagtcgg atgacccaga cacctcagag ggttgggggg gtgtggcctt gctcttcaga   8700
gagggcagat ctacttaggg agatctcttg ggaagaaaa gtggtaggca cgacagttcc    8760
tcacccttct gagatgttgg gattacttcc caagtcctct atttcttgca cttgtggagc   8820
aacaggagga ggcaatccta gagtttctgt atcagtactc ccgtcctttg atcagtcatt   8880
tttttcacga ggcccccctaa agggatactt gggctcgtcc acctctatgt cgacccagct  8940
attccatgca tgggaaaaag tcactaatgt tcatgtggtg aagagagctc tatcgttaaa   9000
agaatctata aactggttca ttactagaga ttccaacttg gctcaagctc taattaggaa   9060
cattatgtct ctgacaggcc ctgatttccc tctagaggag gcccctgtct tcaaaaggac   9120
ggggtcagcc ttgcataggt tcaagtctgc cagatacagc gaaggagggt attcttctgt   9180
ctgcccgaac ctcctctctc atatttctgt tagtacagac accatgtctg atttgaccca   9240
agacgggaag aactacgatt tcatgttcca gccattgatg ctttatgcac agacatggac   9300
atcagagctg gtacagagag acacaaggct aagagactct acgtttcatt ggcacctccg   9360
atgcaacagg tgtgtgagac ccattgacga cgtgaccctg gagacctctc agatcttcga   9420
gtttccggat gtgtcgaaaa gaatatccag aatggtttct ggggctgtgc ctcacttcca   9480
gaggcttccc gatatccgtc tgagaccagg agattttgaa tctctaagcg gtagagaaaa   9540
gtctcaccat atcggatcag ctcaggggct cttatactca atcttagtgg caattcacga   9600
ctcaggatac aatgatggaa ccatcttccc tgtcaacata tacggcaagg tttcccctag   9660
agactatttg agagggctcg caaggggagt attgatagga tcctcgattt gcttcttgac   9720
aagaatgaca aatatcaata ttaatagacc tcttgaattg gtctcagggg taatctcata   9780
tattctcctg aggctagata accatccctc cttgtacata atgctcagag aaccgtctct   9840
tagaggagag atattttcta tccctcagaa aatcccccgcc gcttatccaa ccactatgaa  9900
agaaggcaac agatcaatct tgtgttatct ccaacatgtg ctacgctatg agcgagagat   9960
aatcacggcg tctccagaga atgactggct atggatcttt tcagacttta gaagtgccaa  10020
```

-continued

```
aatgacgtac ctatccctca ttacttacca gtctcatctt ctactccaga gggttgagag  10080

aaacctatct aagagtatga gagataacct gcgacaattg agttctttga tgaggcaggt  10140

gctgggcggg cacggagaag ataccttaga gtcagacgac aacattcaac gactgctaaa  10200

agactcttta cgaaggacaa gatgggtgga tcaagaggtg cgccatgcag ctagaaccat  10260

gactggagat tacagcccca acaagaaggt gtcccgtaag gtaggatgtt cagaatgggt  10320

ctgctctgct caacaggttg cagtctctac ctcagcaaac ccggcccctg tctcggagct  10380

tgacataagg gccctctcta agaggttcca gaaccctttg atctcgggct tgagagtggt  10440

tcagtgggca accggtgctc attataagct taagcctatt ctagatgatc tcaatgtttt  10500

cccatctctc tgccttgtag ttggggacgg gtcagggggg atatcaaggg cagtcctcaa  10560

catgtttcca gatgccaagc ttgtgttcaa cagtctttta gaggtgaatg acctgatggc  10620

ttccggaaca catccactgc ctccttcagc aatcatgagg ggaggaaatg atatcgtctc  10680

cagagtgata gatcttgact caatctggga aaaaccgtcc gacttgagaa acttggcaac  10740

ctggaaatac ttccagtcag tccaaaagca ggtcaacatg tcctatgacc tcattatttg  10800

cgatgcagaa gttactgaca ttgcatctat caaccggatc accctgttaa tgtccgattt  10860

tgcattgtct atagatggac cactctattt ggtcttcaaa acttatggga ctatgctagt  10920

aaatccaaac tacaaggcta ttcaacacct gtcaagagcg ttcccctcgg tcacagggtt  10980

tatcacccaa gtaacttcgt ctttttcatc tgagctctac ctccgattct ccaaacgagg  11040

gaagtttttc agagatgctg agtacttgac ctcttccacc cttcgagaaa tgagccttgt  11100

gttattcaat tgtagcagcc ccaagagtga gatgcagaga gctcgttcct tgaactatca  11160

ggatcttgtg agaggatttc ctgaagaaat catatcaaat ccttacaatg agatgatcat  11220

aactctgatt gacagtgatg tagaatcttt tctagtccac aagatggttg atgatcttga  11280

gttacagagg ggaactctgt ctaaagtggc tatcattata gccatcatga tagttttctc  11340

caacagagtc ttcaacgttt ccaaacccct aactgacccc tcgttctatc caccgtctga  11400

tcccaaaatc ctgaggcact tcaacatatg ttgcagtact atgatgtatc tatctactgc  11460

tttaggtgac gtccctagct tcgcaagact tcacgacctg tataacagac ctataactta  11520

ttacttcaga aagcaagtca ttcgagggaa cgtttatcta tcttggagtt ggtccaacga  11580

cacctcagtg ttcaaaaggg tagcctgtaa ttctagcctg agtctgtcat ctcactggat  11640

caggttgatt tacaagatag tgaagactac cagactcgtt ggcagcatca aggatctatc  11700

cagagaagtg gaaagacacc ttcataggta caacaggtgg atcaccctag aggatatcag  11760

atctagatca tccctactag actacagttg cctgtgaacc ggatactcct ggaagcctgc  11820

ccatgctaag actcttgtgt gatgtatctt gaaaaaaaca agatcctaaa tctgaacctt  11880

tggttgtttg attgttttc tcatttttgt tgtttatttg ttaagcgt              11928
```

<210> SEQ ID NO 58
<211> LENGTH: 11928
<212> TYPE: DNA
<213> ORGANISM: Rabies virus

<400> SEQUENCE: 58

```
acgcttaaca accagatcaa agaaaaaaca gacattgtca attgcaaagc aaaaatgtaa     60

cacccctaca atggatgccg acaagattgt attcaaagtc aataatcagg tggtctcttt    120

gaagcctgag attatcgtgg atcaatatga gtacaagtac cctgccatca aagatttgaa    180

aaagccctgt ataaccctag gaaaggctcc cgatttaaat aaagcataca agtcagtttt    240
```

-continued

```
gtcaggcatg agcgccgcca aacttaatcc tgacgatgta tgttcctatt tggcagcggc    300
aatgcagttt tttgagggga catgtccgga agactggacc agctatggaa ttgtgattgc    360
acgaaaagga gataagatca ccccaggttc tctggtggag ataaaacgta ctgatgtaga    420
agggaattgg gctctgacag gaggcatgga actgacaaga gaccccactg tccctgagca    480
tgcgtcctta gtcggtcttc tcttgagtct gtataggttg agcaaaatat ccgggcaaaa    540
cactggtaac tataagacaa acattgcaga caggatagag cagatttttg agacagcccc    600
ttttgttaaa atcgtggaac accatactct aatgacaact cacaaaatgt gtgctaattg    660
gagtactata ccaaacttca gatttttggc cggaacctat gacatgtttt tctcccggat    720
tgagcatcta tattcagcaa tcagagtggg cacagttgtc actgcttatg aagactgttc    780
aggactggta tcatttactg ggttcataaa acaaatcaat ctcaccgcta gagaggcaat    840
actatatttc ttccacaaga actttgagga agagataaga agaatgtttg agccagggca    900
ggagacagct gttcctcact cttatttcat ccacttccgt tcactaggct tgagtgggaa    960
atctccttat tcatcaaatg ctgttggtca cgtgttcaat ctcattcact ttgtaggatg   1020
ctatatgggt caagtcagat ccctaaatgc aacggttatt gctgcatgtg ctcctcatga   1080
aatgtctgtt ctagggggct atctgggaga ggaattcttc gggaaaggga catttgaaag   1140
aagattcttc agagatgaga aagaacttca agaatacgag gcggctgaac tgacaaagac   1200
tgacgtagca ctggcagatg atggaactgt caaccaagac gacgaggact acttttcagg   1260
tgaaaccaga agtccggagg ctgtttatac tcgaatcatg atgaatggag gtcgactaaa   1320
gagatctcac atacggagat atgtctcagt cagttccaat catcaagccc gtccaaactc   1380
attcgccgag tttctaaaca agacatattc gagtgactca taagaagttg aataacaaaa   1440
tgccggaaat ctacggattg tgtatatcca tcatgaaaaa aactaacacc cctcctttcg   1500
aaccatccca aacatgagca agatctttgt caatcctagt gctattagag ccggtctggc   1560
cgatcttgag atggctgaag aaactgttga tctgatcaat agaaatatcg aagacaatca   1620
ggctcatctc caaggggaac ccatagaggt ggacaatctc cctgaggata tggggcgact   1680
tcacctggat gatggaaaat cgcccaacca tggtgagata gccaaggtgg gagaaggcaa   1740
gtatcgagag gactttcaga tggatgaagg agaggatcct agcttcctgt tccagtcata   1800
cctggaaaat gttggagtcc aaatagtcag acaaatgagg tcaggagaga gatttctcaa   1860
gatatggtca cagaccgtag aagagattat atcctatgtc gcggtcaact ttcccaaccc   1920
tccaggaaag tcttcagagg ataaatcaac ccagactact ggccgagagc tcaagaagga   1980
gacaacaccc actccttctc agagagaaag ccaatcatcg aaagccagga tggcggctca   2040
aattgcttct ggccctccag cccttgaatg gtcggctacc aatgaagagg atgatctatc   2100
agtggaggct gagatcgctc accagattgc agaaagtttc tccaaaaaat ataagtttcc   2160
ctctcgatcc tcagggatac tcttgtataa ttttgagcaa ttgaaaatga accttgatga   2220
tatagttaaa gaggcaaaaa atgtaccagg tgtgacccgt ttagcccatg acgggtccaa   2280
actcccccta agatgtgtac tgggatgggt cgctttggcc aactctaaga aattccagtt   2340
gttagtcgaa tccgacaagc tgagtaaaat catgcaagat gacttgaatc gctatacatc   2400
ttgctaaccg aacctctccc ctcagtccct ctagacaata aaatccgaga tgtcccaaag   2460
tcaacatgaa aaaaacaggc aacaccactg ataaaatgaa cctcctacgt aagatagtga   2520
aaaaccgcag ggacgaggac actcaaaaat cctctcccgc gtcagcccct ctggatgacg   2580
```

-continued

```
atgacttgtg gcttccaccc cctgaatacg tcccgctgaa agaacttaca ggcaagaaga   2640
acatgaggaa cttttgtatc aacggaaggg ttaaagtgtg tagcccgaat ggttactcgt   2700
tcaggatcct gcggcacatt ctgaaatcat tcgacgagat atattctggg aatcatagga   2760
tgatcgggtt agtcaaagtg gttattggac tggctttgtc aggatctcca gtccctgagg   2820
gcctgaactg ggtatacaaa ttgaggagaa cctttatctt ccagtgggct gattccaggg   2880
gccctcttga aggggaggag ttggaatact ctcaggagat cacttgggat gatgatactg   2940
agttcgtcgg attgcaaata agagtgattg caaaacagtg tcatatccag ggcagagtct   3000
ggtgtatcaa catgaacccg agagcatgtc aactatggtc tgacatgtct cttcagacac   3060
aaaggtccga agaggacaaa gattcctctc tgcttctaga ataatcagat tatatcccgc   3120
aaatttatca cttgtttacc tctggaggag agaacatatg ggctcaactc caacccttgg   3180
gagcaatata acaaaaaaca tgttatggtg ccattaaacc gctgcatttc atcaaagtca   3240
agttgattac ctttacattt tgatcctctt ggatgtgaaa aaaactatta acatccctca   3300
aaagactcaa ggaaagatgg ttcctcaggc tctcctgttt gtacccccttc tggtttttcc   3360
attgtgtttt gggaaattcc ctatttacac gataccagac aagcttggtc cctggagtcc   3420
gattgacata catcacctca gctgcccaaa caatttggta gtggaggacg aaggatgcac   3480
caacctgtca gggttctcct acatggaact taaagttgga tacatcttag ccataaaagt   3540
gaacgggttc acttgcacag gcgttgtgac ggaggctgaa acctacacta acttcgttgg   3600
ttatgtcaca accacgttca aaagaaagca tttccgccca acaccagatg catgtagagc   3660
cgcgtacaac tggaagatgg ccggtgaccc cagatatgaa gagtctctac acaatccgta   3720
ccctgactac cgctggcttc gaactgtaaa aaccaccaag gagtctctcg ttatcatatc   3780
tccaagtgtg gcagatttgg acccatatga cagatccctt cactcgaggg tcttccctag   3840
cgggaagtgc tcaggagtag cggtgtcttc tacctactgc tccactaacc acgattacac   3900
catttggatg cccgagaatc cgagactagg gatgtcttgt gacattttta ccaatagtag   3960
agggaagaga gcatccaaag ggagtgagac ttgcggcttt gtagatgaaa gaggcctata   4020
taagtcttta aaaggagcat gcaaactcaa gttatgtgga gttctaggac ttagacttat   4080
ggatggaaca tgggtctcga tgcaaacatc aaatgaaacc aaatggtgcc ctcccgataa   4140
gttggtgaac ctgcacgact ttcgctcaga cgaaattgag caccttgttg tagaggagtt   4200
ggtcaggaag agagaggagt gtctggatgc actagagtcc atcatgacaa ccaagtcagt   4260
gagtttcaga cgtctcagtc atttaagaaa acttgtccct gggtttggaa aagcatatac   4320
catattcaac aagaccttga tggaagccga tgctcactac aagtcagtcg aaacttggaa   4380
tgagatcctc ccttcaaaag ggtgtttaag agttgggggg aggtgtcatc ctcatgtgaa   4440
cggggtgttt ttcaatggta taatattagg acctgacggc aatgtcttaa tcccagagat   4500
gcaatcatcc ctcctccagc aacatatgga gttgttggaa tcctcggtta tccccccttgt   4560
gcacccccctg gcagacccgt ctaccgtttt caaggacggt gacgaggctg aggattttgt   4620
tgaagttcac cttcccgatg tgcacaatca ggtctcagga gttgacttgg gtctcccgaa   4680
ctgggggaag tatgtattac tgagtgcagg ggccctgact gccttgatgt tgataatttt   4740
cctgatgaca tgttgtagaa gagtcaatcg atcagaacct acgcaacaca atctcagagg   4800
gacagggagg gaggtgtcag tcactcccca aagcgggaag atcatatctt catgggaatc   4860
acacaagagt gggggtgaga ccagactgta aggactggcc gtcctttcaa cgatccaagt   4920
cctgaagatc acctcccctt ggggggttct tttgaaaaa cctgggttca atagtcctcc   4980
```

-continued

```
ttgaactcca tgcaactggg tagattcaag agtcatgaga ttttcattaa tcctctcagt   5040
tgatcaagca agatcatgtc gattctcata ataggggaga tcttctagca gtttcagtga   5100
ctaacggtac tttcattctc caggaactga caccaacagt tgtagacaaa ccacggggtg   5160
tctcgggtga ctctgtgctt gggcacagac aaaggtcatg gtgtgttcca tgatagcgga   5220
ctcaggatga gttaattgag agaggcagtc ttcctcccgt gaaggacata agcagtagct   5280
cacaatcatc tcgcgtctca gcaaagtgtg cataattata aagtgctggg tcatctaagc   5340
ttttcagtcg agaaaaaaac attagatcag aagaacaact ggcaacactt ctcaacctga   5400
gacttacttc aagatgctcg atcctggaga ggtctatgat gaccctattg acccaatcga   5460
gttagaggct gaacccagag gaacccccat tgtccccaac atcttgagga actctgacta   5520
caatctcaac tctcctttga tagaagatcc tgctagacta atgttagaat ggttaaaaac   5580
agggaataga ccttatcgga tgactctaac agacaattgc tccaggtctt tcagagtttt   5640
gaaagattat ttcaagaagg tagatttggg ttctctcaag gtgggcggaa tggctgcaca   5700
gtcaatgatt tctctctggt tatatggtgc ccactctgaa tccaacagga gccggagatg   5760
tataacagac ttggcccatt tctattccaa gtcgtccccc atagagaagc tgttgaatct   5820
cacgctagga aatagagggc tgagaatccc cccagaggga gtgttaagtt gccttgagag   5880
ggttgattat gataatgcat ttggaaggta tcttgccaac acgtattcct cttacttgtt   5940
cttccatgta atcaccttat acatgaacgc cctagactgg gatgaagaaa agaccatcct   6000
agcattatgg aaagatttaa cctcagtgga catcgggaag gacttggtaa agttcaaaga   6060
ccaaatatgg ggactgctga tcgtgacaaa ggactttgtt tactcccaaa gttccaattg   6120
tctttttgac agaaactaca cacttatgct aaaagatctt ttcttgtctc gcttcaactc   6180
cttaatggtc ttgctctctc ccccagagcc ccgatactca gatgacttga tatctcaact   6240
atgccagctg tacattgctg gggatcaagt cttgtctatg tgtggaaact ccggctatga   6300
agtcatcaaa atattggagc catatgtcgt gaatagttta gtccagagag cagaaaagtt   6360
taggcctctc attcattcct tgggagactt tcctgtattt ataaaagaca aggtaagtca   6420
acttgaagag acgttcggtc cctgtgcaag aaggttcttt agggctctgg atcaattcga   6480
caacatacat gacttggttt ttgtgtttgg ctgttacagg cattgggggc acccatatat   6540
agattatcga aagggtctgt caaaactata tgatcaggtt caccttaaaa aaatgataga   6600
taagtcctac caggagtgct tagcaagcga cctagccagg aggatcctta gatggggttt   6660
tgataagtac tccaagtggt atctggattc aagattccta gcccgagacc accccttgac   6720
tccttatatc aaaacccaaa catggccacc caaacatatt gtagacttgg tgggggatac   6780
atggcacaag ctcccgatca cgcagatctt tgagattcct gaatcaatgg atccgtcaga   6840
aatattggat gacaaatcac attctttcac cagaacgaga ctagcttctt ggctgtcaga   6900
aaaccgaggg gggcctgttc ctagcgaaaa agttattatc acggccctgt ctaagccgcc   6960
tgtcaatccc cgagagtttc tgaggtctat agacctcgga ggattgccag atgaagactt   7020
gataattggc ctcaagccaa aggaacggga attgaagatt gaaggtcgat tctttgctct   7080
aatgtcatgg aatctaagat tgtattttgt catcactgaa aaactcttgg ccaactacat   7140
cttgccactt tttgacgcgc tgactatgac agacaacctg aacaaggtgt ttaaaaagct   7200
gatcgacagg gtcaccgggc aagggctttt ggactattca agggtcacat atgcatttca   7260
cctggactat gaaaagtgga acaaccatca aagattagag tcaacagagg atgtattttc   7320
```

-continued

```
tgtcctagat caagtgtttg gattgaagag agtgttttct agaacacacg agttttttca   7380
aaaggcctgg atctattatt cagacagatc agacctcatc gggttacggg aggatcaaat   7440
atactgctta gatgcgtcca acggcccaac ctgttggaat ggccaggatg gcgggctaga   7500
aggcttacgg cagaagggct ggagtctagt cagcttattg atgatagata gagaatctca   7560
aatcaggaac acaagaacca aaatactagc tcaaggagac aaccaggttt tatgtccgac   7620
atacatgttg tcgccagggc tatctcaaga ggggctcctc tatgaattgg agagaatatc   7680
aaggaatgca ctttcgatat acagagccgt cgaggaaggg gcatctaagc tagggctgat   7740
catcaagaaa gaagagacca tgtgtagtta tgacttcctc atctatggaa aaaccccttt   7800
gtttagaggt aacatattgg tgcctgagtc caaaagatgg gccagagtct cttgcgtctc   7860
taatgaccaa atagtcaacc tcgccaatat aatgtcgaca gtgtccacca atgcgctaac   7920
agtggcacaa cactctcaat ctttgatcaa accgatgagg gattttctgc tcatgtcagt   7980
acaggcagtc tttcactacc tgctatttag cccaatctta aagggaagag tttacaagat   8040
tctgagcgct gaaggggaga gctttctcct agccatgtca aggataatct atctagatcc   8100
ttctttggga gggatatctg gaatgtccct cggaagattc catatacgac agttctcaga   8160
ccctgtctct gaagggttat ccttctggag agagatctgg ttaagctccc aagagtcctg   8220
gattcacgcg ttgtgtcaag aggctggaaa cccagatctt ggagagagaa cactcgagag   8280
cttcactcgc cttctagaag atccgaccac cttaaatatc agaggagggg ccagtcctac   8340
cattctactc aaggatgcaa tcagaaaggc tttatatgac gaggtggaca aggtggaaaa   8400
ttcagagttt cgagaggcaa tcctgttgtc caagacccat agagataatt ttatactctt   8460
cttaatatct gttgagcctc tgtttcctcg atttctcagt gagctattca gttcgtcttt   8520
tttgggaatc cccgagtcaa tcattggatt gatacaaaac tcccgaacga taagaaggca   8580
gtttagaaag agtctctcaa aaactttaga agaatccttc tacaactcag agatccacgg   8640
gattagtcgg atgacccaga cacctcagag ggttgggggg gtgtggcctt gctcttcaga   8700
gagggcagat ctacttaggg agatctcttg ggaagaaaaa gtggtaggca cgacagttcc   8760
tcacccttct gagatgttgg gattacttcc caagtcctct atttcttgca cttgtggagc   8820
aacaggagga ggcaatccta gagtttctgt atcagtactc ccgtcctttg atcagtcatt   8880
tttttcacga ggcccccctaa agggatactt gggctcgtcc acctctatgt cgacccagct   8940
attccatgca tgggaaaaag tcactaatgt tcatgtggtg aagagagctc tatcgttaaa   9000
agaatctata aactggttca ttactagaga ttccaacttg gctcaagctc taattaggaa   9060
cattatgtct ctgacaggcc ctgatttccc tctagaggag gcccctgtct tcaaaaggac   9120
ggggtcagcc ttgcataggt tcaagtctgc cagatacagc gaaggagggt attcttctgt   9180
ctgcccgaac ctcctctctc atatttctgt tagtacagac accatgtctg atttgaccca   9240
agacgggaag aactacgatt tcatgttcca gccattgatg ctttatgcac agacatggac   9300
atcagagctg gtacagagag acacaaggct aagagactct acgtttcatt ggcacctccg   9360
atgcaacagg tgtgtgagac ccattgacga cgtgaccctg gagacctctc agatcttcga   9420
gtttccggat gtgtcgaaaa gaatatccag aatggtttct ggggctgtgc ctcacttcca   9480
gaggcttccc gatatccgtc tgagaccagg agattttgaa tctctaagcg gtagagaaaa   9540
gtctcaccat atcggatcag ctcaggggct cttatactca atcttagtgg caattcacga   9600
ctcaggatac aatgatggaa ccatcttccc tgtcaacata tacggcaagg tttcccctag   9660
agactatttg agagggctcg caaggggagt attgatagga tcctcgattt gcttcttgac   9720
```

-continued

```
aagaatgaca aatatcaata ttaatagacc tcttgaattg gtctcagggg taatctcata   9780
tattctcctg aggctagata accatccctc cttgtacata atgctcagag aaccgtctct   9840
tagaggagag atattttcta tccctcagaa aatccccgcc gcttatccaa ccactatgaa   9900
agaaggcaac agatcaatct tgtgttatct ccaacatgtg ctacgctatg agcgagagat   9960
aatcacggcg tctccagaga atgactggct atggatcttt tcagacttta gaagtgccaa  10020
aatgacgtac ctatccctca ttacttacca gtctcatctt ctactccaga gggttgagag  10080
aaacctatct aagagtatga gagataacct gcgacaattg agttctttga tgaggcaggt  10140
gctgggcggg cacggagaag ataccttaga gtcagacgac aacattcaac gactgctaaa  10200
agactcttta cgaaggacaa gatgggtgga tcaagaggtg cgccatgcag ctagaaccat  10260
gactggagat tacagcccca acaagaaggt gtcccgtaag gtaggatgtt cagaatgggt  10320
ctgctctgct caacaggttg cagtctctac ctcagcaaac ccggcccctg tctcggagct  10380
tgacataagg gccctctcta agaggttcca gaaccctttg atctcgggct tgagagtggt  10440
tcagtgggca accggtgctc attataagct taagcctatt ctagatgatc tcaatgtttt  10500
cccatctctc tgccttgtag ttggggacgg gtcagggggg atatcaaggg cagtcctcaa  10560
catgtttcca gatgccaagc ttgtgttcaa cagtctttta gaggtgaatg acctgatggc  10620
ttccggaaca catccactgc ctccttcagc aatcatgagg ggaggaaatg atatcgtctc  10680
cagagtgata gatcttgact caatctggga aaaaccgtcc gacttgagaa acttggcaac  10740
ctggaaatac ttccagtcag tccaaaagca ggtcaacatg tcctatgacc tcattatttg  10800
cgatgcagaa gttactgaca ttgcatctat caaccggatc accctgttaa tgtccgattt  10860
tgcattgtct atagatggac cactctattt ggtcttcaaa acttatggga ctatgctagt  10920
aaatccaaac tacaaggcta ttcaacacct gtcaagagcg ttcccctcgg tcacagggtt  10980
tatcacccaa gtaacttcgt ctttttcatc tgagctctac ctccgattct ccaaacgagg  11040
gaagttttc agagatgctg agtacttgac ctcttccacc cttcgagaaa tgagccttgt  11100
gttattcaat tgtagcagcc ccaagagtga gatgcagaga gctcgttcct tgaactatca  11160
ggatcttgtg agaggatttc ctgaagaaat catatcaaat ccttacaatg agatgatcat  11220
aactctgatt gacagtgatg tagaatcttt tctagtccac aagatggttg atgatcttga  11280
gttacagagg ggaactctgt ctaaagtggc tatcattata gccatcatga tagttttctc  11340
caacagagtc ttcaacgttt ccaaaccccct aactgacccc tcgttctatc caccgtctga  11400
tcccaaaatc ctgaggcact tcaacatatg ttgcagtact atgatgtatc tatctactgc  11460
tttaggtgac gtccctagct tcgcaagact tcacgacctg tataacagac ctataactta  11520
ttacttcaga aagcaagtca ttcgagggaa cgtttatcta tcttggagtt ggtccaacga  11580
cacctcagtg ttcaaaaggg tagcctgtaa ttctagcctg agtctgtcat ctcactggat  11640
caggttgatt tacaagatag tgaagactac cagactcgtt ggcagcatca aggatctatc  11700
cagagaagtg gaaagacacc ttcataggta caacaggtgg atcaccctag aggatatcag  11760
atctagatca tccctactag actacagttg cctgtgaacc ggatactcct ggaagcctgc  11820
ccatgctaag actcttgtgt gatgtatctt gaaaaaaaca agatcctaaa tctgaacctt  11880
tggttgtttg attgtttttc tcatttttgt tgtttatttg ttaagcgt              11928
```

<210> SEQ ID NO 59
<211> LENGTH: 523
<212> TYPE: PRT

-continued

<213> ORGANISM: Rabies virus

<400> SEQUENCE: 59

```
Met Val Pro Gln Ala Leu Leu Phe Val Pro Leu Leu Val Phe Pro Leu
 1               5                  10                  15

Cys Phe Gly Lys Phe Pro Ile Tyr Thr Ile Pro Asp Lys Leu Gly Pro
            20                  25                  30

Trp Ser Pro Ile Asp Ile His His Leu Ser Cys Pro Asn Asn Leu Val
        35                  40                  45

Val Glu Asp Glu Gly Cys Thr Asn Leu Ser Gly Phe Ser Tyr Met Glu
    50                  55                  60

Leu Lys Val Gly Tyr Ile Leu Ala Ile Lys Val Asn Gly Phe Thr Cys
65                  70                  75                  80

Thr Gly Val Val Thr Glu Ala Glu Thr Tyr Thr Asn Phe Val Gly Tyr
                85                  90                  95

Val Thr Thr Thr Phe Lys Arg Lys His Phe Arg Pro Thr Pro Asp Ala
            100                 105                 110

Cys Arg Ala Ala Tyr Asn Trp Met Ala Gly Asp Pro Arg Tyr Glu Glu
        115                 120                 125

Ser Leu His Asn Pro Tyr Pro Asp Tyr Arg Trp Leu Arg Thr Val Lys
    130                 135                 140

Thr Thr Lys Glu Ser Leu Val Ile Ile Ser Pro Ser Val Ala Asp Leu
145                 150                 155                 160

Asp Pro Tyr Asp Arg Ser Leu His Ser Arg Val Phe Pro Ser Gly Lys
                165                 170                 175

Cys Ser Gly Val Ala Val Ser Ser Thr Tyr Cys Ser Thr Asn His Asp
            180                 185                 190

Tyr Thr Ile Trp Met Pro Glu Asn Pro Arg Leu Gly Met Ser Cys Asp
        195                 200                 205

Ile Phe Thr Asn Ser Arg Gly Lys Arg Ala Ser Lys Gly Ser Glu Thr
    210                 215                 220

Cys Gly Phe Val Asp Glu Arg Gly Leu Tyr Lys Ser Leu Lys Gly Ala
225                 230                 235                 240

Cys Lys Leu Lys Leu Cys Gly Val Leu Gly Leu Arg Leu Met Asp Gly
                245                 250                 255

Thr Trp Val Ser Met Gln Thr Ser Asn Glu Thr Lys Trp Cys Pro Pro
            260                 265                 270

Asp Lys Leu Val Asn Leu His Asp Phe Arg Ser Asp Glu Ile Glu His
        275                 280                 285

Leu Val Val Glu Glu Leu Val Arg Lys Arg Glu Glu Cys Leu Asp Ala
    290                 295                 300

Leu Glu Ser Ile Met Thr Thr Lys Ser Val Ser Phe Arg Arg Leu Ser
305                 310                 315                 320

His Leu Arg Lys Leu Val Pro Gly Phe Gly Lys Ala Tyr Thr Ile Phe
                325                 330                 335

Asn Lys Thr Leu Met Glu Ala Asp Ala His Tyr Lys Ser Val Arg Thr
            340                 345                 350

Trp Asn Glu Ile Leu Pro Ser Lys Gly Cys Leu Arg Val Gly Gly Arg
        355                 360                 365

Cys His Pro His Val Asn Gly Val Phe Phe Asn Gly Ile Ile Leu Gly
    370                 375                 380

Pro Asp Gly Asn Val Leu Ile Pro Glu Met Gln Ser Ser Leu Leu Gln
385                 390                 395                 400
```

-continued

```
Gln His Met Glu Leu Leu Glu Ser Ser Val Ile Pro Leu Val His Pro
                405                 410                 415

Leu Ala Asp Pro Ser Thr Val Phe Lys Asp Gly Asp Glu Ala Glu Asp
            420                 425                 430

Phe Val Glu Val His Leu Pro Asp Val His Asn Gln Val Ser Gly Val
        435                 440                 445

Asp Leu Gly Leu Pro Asn Trp Gly Lys Tyr Val Leu Leu Ser Ala Gly
    450                 455                 460

Ala Leu Thr Ala Leu Met Leu Ile Ile Phe Leu Met Thr Cys Cys Arg
465                 470                 475                 480

Arg Val Asn Arg Ser Glu Pro Thr Gln His Asn Leu Arg Gly Thr Gly
                485                 490                 495

Arg Glu Val Ser Val Thr Pro Gln Ser Gly Lys Ile Ile Ser Ser Trp
            500                 505                 510

Glu Ser His Lys Ser Gly Gly Glu Thr Arg Leu
        515                 520


<210> SEQ ID NO 60
<211> LENGTH: 523
<212> TYPE: PRT
<213> ORGANISM: Rabies virus

<400> SEQUENCE: 60

Met Val Pro Gln Ala Leu Leu Phe Val Pro Leu Leu Val Phe Pro Leu
 1               5                  10                  15

Cys Phe Gly Lys Phe Pro Ile Tyr Thr Ile Pro Asp Lys Leu Gly Pro
            20                  25                  30

Trp Ser Pro Ile Asp Ile His His Leu Ser Cys Pro Asn Asn Leu Val
        35                  40                  45

Val Glu Asp Glu Gly Cys Thr Asn Leu Ser Gly Phe Ser Tyr Met Glu
    50                  55                  60

Leu Lys Val Gly Tyr Ile Leu Ala Ile Lys Val Asn Gly Phe Thr Cys
65                  70                  75                  80

Thr Gly Val Val Thr Glu Ala Glu Thr Tyr Thr Asn Phe Val Gly Tyr
                85                  90                  95

Val Thr Thr Thr Phe Lys Arg Lys His Phe Arg Pro Thr Pro Asp Ala
            100                 105                 110

Cys Arg Ala Ala Tyr Asn Trp Met Ala Gly Asp Pro Arg Tyr Glu Glu
        115                 120                 125

Ser Leu His Asn Pro Tyr Pro Asp Tyr Arg Trp Leu Arg Thr Val Lys
    130                 135                 140

Thr Thr Lys Glu Ser Leu Val Ile Ile Ser Pro Ser Val Ala Asp Leu
145                 150                 155                 160

Asp Pro Tyr Asp Arg Ser Leu His Ser Arg Val Phe Pro Ser Gly Lys
                165                 170                 175

Cys Ser Gly Val Ala Val Ser Ser Thr Tyr Cys Ser Thr Asn His Asp
            180                 185                 190

Tyr Thr Ile Trp Met Pro Glu Asn Pro Arg Leu Gly Met Ser Cys Asp
        195                 200                 205

Ile Phe Thr Asn Ser Arg Gly Lys Arg Ala Ser Lys Gly Ser Glu Thr
    210                 215                 220

Cys Gly Phe Val Asp Glu Arg Gly Leu Tyr Lys Ser Leu Lys Gly Ala
225                 230                 235                 240

Cys Lys Leu Lys Leu Cys Gly Val Leu Gly Leu Arg Leu Met Asp Gly
                245                 250                 255
```

-continued

```
Thr Trp Val Ser Met Gln Thr Ser Asn Glu Thr Lys Trp Cys Pro Pro
            260                 265                 270

Asp Lys Leu Val Asn Leu His Asp Phe Arg Ser Asp Glu Ile Glu His
        275                 280                 285

Leu Val Val Glu Glu Leu Val Arg Lys Arg Glu Glu Cys Leu Asp Ala
    290                 295                 300

Leu Glu Ser Ile Met Thr Thr Lys Ser Val Ser Phe Arg Arg Leu Ser
305                 310                 315                 320

His Leu Arg Lys Leu Val Pro Gly Phe Gly Lys Ala Tyr Thr Ile Phe
                325                 330                 335

Asn Lys Thr Leu Met Glu Ala Asp Ala His Tyr Lys Ser Val Glu Thr
            340                 345                 350

Trp Asn Glu Ile Leu Pro Ser Lys Gly Cys Leu Arg Val Gly Gly Arg
        355                 360                 365

Cys His Pro His Val Asn Gly Val Phe Phe Asn Gly Ile Ile Leu Gly
    370                 375                 380

Pro Asp Gly Asn Val Leu Ile Pro Glu Met Gln Ser Ser Leu Leu Gln
385                 390                 395                 400

Gln His Met Glu Leu Leu Glu Ser Ser Val Ile Pro Leu Val His Pro
                405                 410                 415

Leu Ala Asp Pro Ser Thr Val Phe Lys Asp Gly Asp Glu Ala Glu Asp
            420                 425                 430

Phe Val Glu Val His Leu Pro Asp Val His Asn Gln Val Ser Gly Val
        435                 440                 445

Asp Leu Gly Leu Pro Asn Trp Gly Lys Tyr Val Leu Leu Ser Ala Gly
    450                 455                 460

Ala Leu Thr Ala Leu Met Leu Ile Ile Phe Leu Met Thr Cys Cys Arg
465                 470                 475                 480

Arg Val Asn Arg Ser Glu Pro Thr Gln His Asn Leu Arg Gly Thr Gly
                485                 490                 495

Arg Glu Val Ser Val Thr Pro Gln Ser Gly Lys Ile Ile Ser Ser Trp
            500                 505                 510

Glu Ser His Lys Ser Gly Gly Glu Thr Arg Leu
        515                 520


<210> SEQ ID NO 61
<211> LENGTH: 450
<212> TYPE: PRT
<213> ORGANISM: Rabies virus

<400> SEQUENCE: 61

Met Asp Ala Asp Lys Ile Val Phe Lys Val Asn Asn Gln Val Val Ser
 1               5                  10                  15

Leu Lys Pro Glu Ile Ile Val Asp Gln Tyr Glu Tyr Lys Tyr Pro Ala
            20                  25                  30

Ile Lys Asp Leu Lys Lys Pro Cys Ile Thr Leu Gly Lys Ala Pro Asp
        35                  40                  45

Leu Asn Lys Ala Tyr Lys Ser Val Leu Ser Gly Met Ser Ala Ala Lys
    50                  55                  60

Leu Asn Pro Asp Asp Val Cys Ser Tyr Leu Ala Ala Ala Met Gln Phe
65                  70                  75                  80

Phe Glu Gly Thr Cys Pro Glu Asp Trp Thr Ser Tyr Gly Ile Val Ile
                85                  90                  95

Ala Arg Lys Gly Asp Lys Ile Thr Pro Gly Ser Leu Val Glu Ile Lys
```

-continued

```
            100                 105                 110

Arg Thr Asp Val Glu Gly Asn Trp Ala Leu Thr Gly Gly Met Glu Leu
        115                 120                 125

Thr Arg Asp Pro Thr Val Pro Glu His Ala Ser Leu Val Gly Leu Leu
    130                 135                 140

Leu Ser Leu Tyr Arg Leu Ser Lys Ile Ser Gly Gln Asn Thr Gly Asn
145                 150                 155                 160

Tyr Lys Thr Asn Ile Ala Asp Arg Ile Glu Gln Ile Phe Glu Thr Ala
                165                 170                 175

Pro Phe Val Lys Ile Val Glu His His Thr Leu Met Thr Thr His Lys
            180                 185                 190

Met Cys Ala Asn Trp Ser Thr Ile Pro Asn Phe Arg Phe Leu Ala Gly
        195                 200                 205

Thr Tyr Asp Met Phe Phe Ser Arg Ile Glu His Leu Tyr Ser Ala Ile
    210                 215                 220

Arg Val Gly Thr Val Val Thr Ala Tyr Glu Asp Cys Ser Gly Leu Val
225                 230                 235                 240

Ser Phe Thr Gly Phe Ile Lys Gln Ile Asn Leu Thr Ala Arg Glu Ala
                245                 250                 255

Ile Leu Tyr Phe Phe His Lys Asn Phe Glu Glu Glu Ile Arg Arg Met
            260                 265                 270

Phe Glu Pro Gly Gln Glu Thr Ala Val Pro His Ser Tyr Phe Ile His
        275                 280                 285

Phe Arg Ser Leu Gly Leu Ser Gly Lys Ser Pro Tyr Ser Ser Asn Ala
    290                 295                 300

Val Gly His Val Phe Asn Leu Ile His Phe Val Gly Cys Tyr Met Gly
305                 310                 315                 320

Gln Val Arg Ser Leu Asn Ala Thr Val Ile Ala Ala Cys Ala Pro His
                325                 330                 335

Glu Met Ser Val Leu Gly Gly Tyr Leu Gly Glu Glu Phe Phe Gly Lys
            340                 345                 350

Gly Thr Phe Glu Arg Arg Phe Phe Arg Asp Glu Lys Glu Leu Gln Glu
        355                 360                 365

Tyr Glu Ala Ala Glu Leu Thr Lys Thr Asp Val Ala Leu Ala Asp Asp
    370                 375                 380

Gly Thr Val Asn Ser Asp Asp Glu Asp Tyr Phe Ser Gly Glu Thr Arg
385                 390                 395                 400

Ser Pro Glu Ala Val Tyr Thr Arg Ile Met Met Asn Gly Gly Arg Leu
                405                 410                 415

Lys Arg Ser His Ile Arg Arg Tyr Val Ser Val Ser Ser Asn His Gln
            420                 425                 430

Ala Arg Pro Asn Ser Phe Ala Glu Phe Leu Asn Lys Thr Tyr Ser Ser
        435                 440                 445

Asp Ser
    450


<210> SEQ ID NO 62
<211> LENGTH: 450
<212> TYPE: PRT
<213> ORGANISM: Rabies virus

<400> SEQUENCE: 62

Met Asp Ala Asp Lys Ile Val Phe Lys Val Asn Asn Gln Val Val Ser
 1               5                  10                  15
```

-continued

```
Leu Lys Pro Glu Ile Ile Val Asp Gln Tyr Glu Tyr Lys Tyr Pro Ala
            20                  25                  30

Ile Lys Asp Leu Lys Lys Pro Cys Ile Thr Leu Gly Lys Ala Pro Asp
        35                  40                  45

Leu Asn Lys Ala Tyr Lys Ser Val Leu Ser Gly Met Ser Ala Ala Lys
    50                  55                  60

Leu Asn Pro Asp Asp Val Cys Ser Tyr Leu Ala Ala Ala Met Gln Phe
65                  70                  75                  80

Phe Glu Gly Thr Cys Pro Glu Asp Trp Thr Ser Tyr Gly Ile Val Ile
                85                  90                  95

Ala Arg Lys Gly Asp Lys Ile Thr Pro Gly Ser Leu Val Glu Ile Lys
            100                 105                 110

Arg Thr Asp Val Glu Gly Asn Trp Ala Leu Thr Gly Gly Met Glu Leu
        115                 120                 125

Thr Arg Asp Pro Thr Val Pro Glu His Ala Ser Leu Val Gly Leu Leu
    130                 135                 140

Leu Ser Leu Tyr Arg Leu Ser Lys Ile Ser Gly Gln Asn Thr Gly Asn
145                 150                 155                 160

Tyr Lys Thr Asn Ile Ala Asp Arg Ile Glu Gln Ile Phe Glu Thr Ala
                165                 170                 175

Pro Phe Val Lys Ile Val Glu His His Thr Leu Met Thr Thr His Lys
            180                 185                 190

Met Cys Ala Asn Trp Ser Thr Ile Pro Asn Phe Arg Phe Leu Ala Gly
        195                 200                 205

Thr Tyr Asp Met Phe Phe Ser Arg Ile Glu His Leu Tyr Ser Ala Ile
    210                 215                 220

Arg Val Gly Thr Val Val Thr Ala Tyr Glu Asp Cys Ser Gly Leu Val
225                 230                 235                 240

Ser Phe Thr Gly Phe Ile Lys Gln Ile Asn Leu Thr Ala Arg Glu Ala
                245                 250                 255

Ile Leu Tyr Phe Phe His Lys Asn Phe Glu Glu Glu Ile Arg Arg Met
            260                 265                 270

Phe Glu Pro Gly Gln Glu Thr Ala Val Pro His Ser Tyr Phe Ile His
        275                 280                 285

Phe Arg Ser Leu Gly Leu Ser Gly Lys Ser Pro Tyr Ser Ser Asn Ala
    290                 295                 300

Val Gly His Val Phe Asn Leu Ile His Phe Val Gly Cys Tyr Met Gly
305                 310                 315                 320

Gln Val Arg Ser Leu Asn Ala Thr Val Ile Ala Ala Cys Ala Pro His
                325                 330                 335

Glu Met Ser Val Leu Gly Gly Tyr Leu Gly Glu Glu Phe Phe Gly Lys
            340                 345                 350

Gly Thr Phe Glu Arg Arg Phe Phe Arg Asp Glu Lys Glu Leu Gln Glu
        355                 360                 365

Tyr Glu Ala Ala Glu Leu Thr Lys Thr Asp Val Ala Leu Ala Asp Asp
    370                 375                 380

Gly Thr Val Asn Ala Asp Asp Glu Asp Tyr Phe Ser Gly Glu Thr Arg
385                 390                 395                 400

Ser Pro Glu Ala Val Tyr Thr Arg Ile Met Met Asn Gly Gly Arg Leu
                405                 410                 415

Lys Arg Ser His Ile Arg Arg Tyr Val Ser Val Ser Ser Asn His Gln
            420                 425                 430

Ala Arg Pro Asn Ser Phe Ala Glu Phe Leu Asn Lys Thr Tyr Ser Ser
```

-continued

```
        435                 440                 445

Asp Ser
    450


<210> SEQ ID NO 63
<211> LENGTH: 450
<212> TYPE: PRT
<213> ORGANISM: Rabies virus

<400> SEQUENCE: 63

Met Asp Ala Asp Lys Ile Val Phe Lys Val Asn Asn Gln Val Val Ser
 1               5                  10                  15

Leu Lys Pro Glu Ile Ile Val Asp Gln Tyr Glu Tyr Lys Tyr Pro Ala
            20                  25                  30

Ile Lys Asp Leu Lys Lys Pro Cys Ile Thr Leu Gly Lys Ala Pro Asp
        35                  40                  45

Leu Asn Lys Ala Tyr Lys Ser Val Leu Ser Gly Met Ser Ala Ala Lys
    50                  55                  60

Leu Asn Pro Asp Asp Val Cys Ser Tyr Leu Ala Ala Ala Met Gln Phe
65                  70                  75                  80

Phe Glu Gly Thr Cys Pro Glu Asp Trp Thr Ser Tyr Gly Ile Val Ile
                85                  90                  95

Ala Arg Lys Gly Asp Lys Ile Thr Pro Gly Ser Leu Val Glu Ile Lys
            100                 105                 110

Arg Thr Asp Val Glu Gly Asn Trp Ala Leu Thr Gly Gly Met Glu Leu
        115                 120                 125

Thr Arg Asp Pro Thr Val Pro Glu His Ala Ser Leu Val Gly Leu Leu
    130                 135                 140

Leu Ser Leu Tyr Arg Leu Ser Lys Ile Ser Gly Gln Asn Thr Gly Asn
145                 150                 155                 160

Tyr Lys Thr Asn Ile Ala Asp Arg Ile Glu Gln Ile Phe Glu Thr Ala
                165                 170                 175

Pro Phe Val Lys Ile Val Glu His His Thr Leu Met Thr Thr His Lys
            180                 185                 190

Met Cys Ala Asn Trp Ser Thr Ile Pro Asn Phe Arg Phe Leu Ala Gly
        195                 200                 205

Thr Tyr Asp Met Phe Phe Ser Arg Ile Glu His Leu Tyr Ser Ala Ile
    210                 215                 220

Arg Val Gly Thr Val Val Thr Ala Tyr Glu Asp Cys Ser Gly Leu Val
225                 230                 235                 240

Ser Phe Thr Gly Phe Ile Lys Gln Ile Asn Leu Thr Ala Arg Glu Ala
                245                 250                 255

Ile Leu Tyr Phe Phe His Lys Asn Phe Glu Glu Glu Ile Arg Arg Met
            260                 265                 270

Phe Glu Pro Gly Gln Glu Thr Ala Val Pro His Ser Tyr Phe Ile His
        275                 280                 285

Phe Arg Ser Leu Gly Leu Ser Gly Lys Ser Pro Tyr Ser Ser Asn Ala
    290                 295                 300

Val Gly His Val Phe Asn Leu Ile His Phe Val Gly Cys Tyr Met Gly
305                 310                 315                 320

Gln Val Arg Ser Leu Asn Ala Thr Val Ile Ala Ala Cys Ala Pro His
                325                 330                 335

Glu Met Ser Val Leu Gly Gly Tyr Leu Gly Glu Glu Phe Phe Gly Lys
            340                 345                 350
```

-continued

```
Gly Thr Phe Glu Arg Arg Phe Phe Arg Asp Glu Lys Glu Leu Gln Glu
        355                 360                 365

Tyr Glu Ala Ala Glu Leu Thr Lys Thr Asp Val Ala Leu Ala Asp Asp
    370                 375                 380

Gly Thr Val Asn Gly Asp Asp Glu Asp Tyr Phe Ser Gly Glu Thr Arg
385                 390                 395                 400

Ser Pro Glu Ala Val Tyr Thr Arg Ile Met Met Asn Gly Gly Arg Leu
                405                 410                 415

Lys Arg Ser His Ile Arg Arg Tyr Val Ser Val Ser Ser Asn His Gln
            420                 425                 430

Ala Arg Pro Asn Ser Phe Ala Glu Phe Leu Asn Lys Thr Tyr Ser Ser
        435                 440                 445

Asp Ser
    450
```

<210> SEQ ID NO 64
<211> LENGTH: 450
<212> TYPE: PRT
<213> ORGANISM: Rabies virus

<400> SEQUENCE: 64

```
Met Asp Ala Asp Lys Ile Val Phe Lys Val Asn Asn Gln Val Val Ser
 1               5                  10                  15

Leu Lys Pro Glu Ile Ile Val Asp Gln Tyr Glu Tyr Lys Tyr Pro Ala
            20                  25                  30

Ile Lys Asp Leu Lys Lys Pro Cys Ile Thr Leu Gly Lys Ala Pro Asp
        35                  40                  45

Leu Asn Lys Ala Tyr Lys Ser Val Leu Ser Gly Met Ser Ala Ala Lys
    50                  55                  60

Leu Asn Pro Asp Asp Val Cys Ser Tyr Leu Ala Ala Ala Met Gln Phe
65                  70                  75                  80

Phe Glu Gly Thr Cys Pro Glu Asp Trp Thr Ser Tyr Gly Ile Val Ile
                85                  90                  95

Ala Arg Lys Gly Asp Lys Ile Thr Pro Gly Ser Leu Val Glu Ile Lys
            100                 105                 110

Arg Thr Asp Val Glu Gly Asn Trp Ala Leu Thr Gly Gly Met Glu Leu
        115                 120                 125

Thr Arg Asp Pro Thr Val Pro Glu His Ala Ser Leu Val Gly Leu Leu
    130                 135                 140

Leu Ser Leu Tyr Arg Leu Ser Lys Ile Ser Gly Gln Asn Thr Gly Asn
145                 150                 155                 160

Tyr Lys Thr Asn Ile Ala Asp Arg Ile Glu Gln Ile Phe Glu Thr Ala
                165                 170                 175

Pro Phe Val Lys Ile Val Glu His His Thr Leu Met Thr Thr His Lys
            180                 185                 190

Met Cys Ala Asn Trp Ser Thr Ile Pro Asn Phe Arg Phe Leu Ala Gly
        195                 200                 205

Thr Tyr Asp Met Phe Phe Ser Arg Ile Glu His Leu Tyr Ser Ala Ile
    210                 215                 220

Arg Val Gly Thr Val Val Thr Ala Tyr Glu Asp Cys Ser Gly Leu Val
225                 230                 235                 240

Ser Phe Thr Gly Phe Ile Lys Gln Ile Asn Leu Thr Ala Arg Glu Ala
                245                 250                 255

Ile Leu Tyr Phe Phe His Lys Asn Phe Glu Glu Glu Ile Arg Arg Met
            260                 265                 270
```

-continued

```
Phe Glu Pro Gly Gln Glu Thr Ala Val Pro His Ser Tyr Phe Ile His
        275                 280                 285

Phe Arg Ser Leu Gly Leu Ser Gly Lys Ser Pro Tyr Ser Ser Asn Ala
    290                 295                 300

Val Gly His Val Phe Asn Leu Ile His Phe Val Gly Cys Tyr Met Gly
305                 310                 315                 320

Gln Val Arg Ser Leu Asn Ala Thr Val Ile Ala Ala Cys Ala Pro His
                325                 330                 335

Glu Met Ser Val Leu Gly Gly Tyr Leu Gly Glu Glu Phe Phe Gly Lys
            340                 345                 350

Gly Thr Phe Glu Arg Arg Phe Phe Arg Asp Glu Lys Glu Leu Gln Glu
        355                 360                 365

Tyr Glu Ala Ala Glu Leu Thr Lys Thr Asp Val Ala Leu Ala Asp Asp
    370                 375                 380

Gly Thr Val Asn Gln Asp Asp Glu Asp Tyr Phe Ser Gly Glu Thr Arg
385                 390                 395                 400

Ser Pro Glu Ala Val Tyr Thr Arg Ile Met Met Asn Gly Gly Arg Leu
                405                 410                 415

Lys Arg Ser His Ile Arg Arg Tyr Val Ser Val Ser Ser Asn His Gln
            420                 425                 430

Ala Arg Pro Asn Ser Phe Ala Glu Phe Leu Asn Lys Thr Tyr Ser Ser
        435                 440                 445

Asp Ser
    450
```

ATTENUATED RABIES VIRUS WITH NUCLEOPROTEIN MUTATION AT THE PHOSPHORYLATION SITE FOR VACCINATION AGAINST RABIES AND GENE THERAPY IN THE CNS

CROSS-REFERENCE TO RELATE APPLICATION

This application is a divisional of U.S. patent application Ser. No. 10/739,029, filed Dec. 9, 2003, now U.S. Pat. No. 7,419,816 which is a divisional of U.S. patent application Ser. No. 10/199,024, filed Jul. 22, 2002, which issued as U.S Pat. No. 6,706,523 on Mar. 16, 2004, which claims priority from U.S. Provisional Patent Application Ser. No. 60/331,354, filed Jul. 20, 2001, now expired, which are incorporated herein in their entirety for all purposes and relied upon for priority purposes pursuant to 35 U.S.C. §§ 119, 120, and/or 365.

GOVERNMENTAL SUPPORT

This work was supported partially by Public Health Service grant AI-33029 (Z.F.F.) from the National Institute of Allergy and Infectious Diseases. The government has certain rights in the present application.

BACKGROUND OF THE INVENTION

1. Field of the Invention

The present invention relates generally to a vaccine composition and methods of preventing and treating infection in humans and animals therewith. More specifically, the invention relates to a mutant rabies virus wherein the nucleoprotein is mutated at the amino acid wherein phosphorylation occurs. The invention also relates to vectors for delivering a gene to a human or animal, and methods of delivering the gene thereto.

2. Description of the Related Art

Within the Rhabdoviridae family, rabies virus is the prototype of the *Lyssavirus* genus and vesicular stomatitis virus (VSV) is the prototype of the *Vesiculovirus* genus (Wagner and Rose, 1996). The genomic RNA is encapsidated with nucleoprotein (N) and this N-RNA complex, together with the phosphoprotein (P, also termed as NS) and RNA-dependent RNA polymerase (L), forms the RNP complex. The N protein of the rhabdoviruses, like the N protein from other members in the order of the mononegavirales, plays vital roles in regulating viral RNA transcription and replication by encapsidating de novo synthesized viral genomic RNA. Although rabies virus N and VSV N do not share a high degree of homology in the primary nucleotide and protein sequences, they do have conserved regions and similar protein characteristics. For example, the N protein of rabies virus has four conserved amino acid stretches homologous with those of VSV (Tordo et al., 1986). In addition, a similar helical structure of N protein exists in both rabies virus and VSV, with an α-helix continuing from the N-terminus through most of the protein, and a β-turn towards the C-terminus (Barr et al., 1991).

One major structural difference, however, exists between rabies virus N and VSV N. Rabies virus N is phosphoryiated while VSV N is not (Sokol and Clark, 1973). The phosphorylation has been mapped to serine residue at position 389 of the rabies virus N (Dietzschold et al., 1987). Previously, it was demonstrated that dephosphorylation of rabies virus N or mutation of the serine 389 to alanine resulted in increased binding to in vitro-synthesized leader RNA (Yang et al., 1999). Furthermore, mutation of the phosphorylated serine to alanine resulted in reduction of viral transcription and replication of a rabies virus minigenomic RNA (Yang et al., 1999). However, in the minigenome system, viral proteins necessary for viral transcription and replication were synthesized by T7 polymerase, and thus their synthesis was not under the control of rabies virus regulatory machinery.

Rabies has always had an aura of tragedy and mystery. Its dramatic clinical expression and almost always fatal outcome guarantee that rabies prevention is given high priority. Despite significant progress in biological research, rabies remains a significant global disease. Annually, more than 70,000 human fatalities are estimated, and millions of others require post-exposure treatment (Meslin et al., 1994; Anonymous, 1993). Although humans are the dead-end host, the disease is epizootic or enzootic in domestic animals as well as in wildlife (Fu, 1997; Rupprecht et al., 1995; Smith et al., 1995). Dogs remain the most important reservoir in Asia, Africa, and Latin America where most human rabies cases occur (Fu, 1997). In countries where dog rabies is controlled through animal vaccination, the number of human cases has been reduced considerably (Smith et al., 1995). However, rabies in wildlife presents a more challenging problem in these countries (Rupprecht et al., 1995; Smith et al., 1995). Fox rabies has been endemic in Europe and North America for many years, although a recent endeavor in oral vaccination has been successful in reducing or even eliminating rabies in many parts of Europe (Brochier et al., 1991). In the United Sates, wildlife rabies accounted for more than 90% of the reported rabies cases (more than 7,000 each year) in the past decade (Rupprecht et al., 1995; Smith et al., 1995; Krebs et al., 2000a; Krebs et al., 2000b) and there are at least five major wildlife rabies reservoirs that maintain concurrent epizootics (Smith et al., 1995). Epizootic raccoon rabies continues to occur in all the states along the eastern seaboard, and it is spreading westwards to Ohio, West Virginia, and Alabama (Krebs et al., 2000b). Skunk rabies remains enzootic in the central states and California (Krebs et al., 2000b). Fox rabies occurs sporadically in Arizona, Alaska, and Texas and also in the eastern states where raccoon rabies is epizootic (Krebs et al., 2000b). Bat rabies is widely distributed throughout the 48 contiguous states (Krebs et al., 2000b). These epizootics of wildlife rabies present a health threat for humans. Therefore, controlling rabies and protecting humans from rabies virus infection requires multi-layered control strategies, particularly vaccination of humans before or after exposure, regular vaccination of pet animals, and vaccination of wildlife.

Vaccination of humans after exposure can be dated back to the time of Pasteur when he injected Joseph Meister with attenuated rabies virus made from neuronal tissue (Pasteur et al., 1996). Since then, human rabies vaccines have gone through successive improvements, particularly the development of human diploid cell culture vaccine (HDCV) by Koprowski and associates at the Wistar Institute (Wiktor et al., 1964). The tissue culture vaccine is not only safe compared with the old brain vaccines because it does not contain neuronal tissues, but it is also more effective. People immunized with HDCV developed high virus neutralizing antibody (VNA) titers as early as 10 days after inoculation, compared with those immunized with the nervous tissue vaccine in whom neutralizing antibody titers do not reach protective levels until 30 days after the immunization (Wiktor et al., 1964). Today, many of the derivatives of tissue culture vaccines are similar to HDCV, and they are both effective and well tolerated. They include the purified chicken embryo cell vaccine (PCEC, Barth et al., 1984; Sehgal et al., 1993), the purified Vero cell rabies vaccine (PVRV, Suntharasamai et al., 1986) and the purified duck embryo cell vaccine (PDRV, Khawplod et al., 1995). A typical post-exposure treatment for an individual bitten by a rabid or a suspected rabid animal consists of the prompt administration of multiple injections of one of the above-mentioned tissue culture vaccines. Depending upon the nature and severity of the bite, it is also recommended that individuals receive antirabies antiserum prepared either in animals (usually equine) or preferably in humans (human rabies immune globulins, or HRIG) (Anonymous, 2000). Less frequently and under special circumstances, humans considered at risk of inapparent rabies exposure, such as animal control officers, veterinarians, and laboratory personnel working with the virus, are immunized against rabies, which is known as pre-exposure vaccination (Anonymous, 2000).

Although the tissue culture vaccines are safe and effective, there are problems. Because all these vaccines are made from inactivated viruses, multiple doses over an extended time period are required to stimulate optimal immune responses (Anonymous, 2000). Failure to complete the whole series of vaccination may result in the development of diseases (Shill et al., 1987; Lumbiganon et al., 1987; Anonymous, 1988). Allergic reactions to proteins contained within cell culture vaccines occur in approximately 6% of the vaccines given booster injections (CDC, 1984). Indeed, there is some evidence that the most serious adverse reactions are to human albumin denatured by the β-propiolactone used to inactivate the virus (Warrington et al., 1987; Swanson et al., 1987; Anderson et al., 1987). Furthermore, the high cost of these tissue culture vaccines makes it difficult to effectively utilize in developing countries where it is needed most. Post-exposure treatment may exceed $2,000 to 3,000 dollars (in the United States) per case (Melter, 1996). Most human rabies cases occur in developing countries, where vaccines cannot afford to pay this amount. Thus, a frequently used vaccine for rabies in developing countries is from animal neural tissue, usually produced either in livestock or in suckling mouse brains (Fuenzalida vaccine) (Fuenzalida, 1972). Twenty-one doses of the nervous tissue vaccine are usually required by intraperitoneal injection, and such vaccines may cause neurological diseases (Trejos et al., 1974).

Vaccination of pets (dogs and cats) in the United States is carried out as recommended in the Compendium of Animal Rabies Prevention and Control by the National Association of State Public Health Veterinarians (Anonymous, 2000). Usually pet animals are immunized at 6 weeks of age and revaccinated annually or triennially depending on the vaccines used (Anonymous, 2000). Most of the licensed rabies vaccines for pets are inactivated rabies viruses. Recently, a recombinant canary pox virus expressing rabies virus G was approved for cat immunization (Anonymous, 2000). Although these vaccines provide adequate protection in dogs ant cats, the vaccines do induce local reactions (Wilcock et al., 1986). Furthermore, multiple immunizations are required to maintain sufficient immunity throughout life (Anonymous, 2000). Dogs immunized repeatedly with commercial vaccines may not always maintain adequate titers, and only one-third of the dogs showed VNA titers above the 1:5 base line (Tims et al., 2000). In addition, vaccination of puppies less than 3 months of age fails to induce protective immunity, although the maternal antibodies transferred from bitches declined to undetectable levels by 6 weeks of age (Aghomo et al., 1990). There is a period from the time of the waning of maternal antibody to the time of active immunity in which the young animals may not be protected (Mitmoonpitak et al., 1998; Clark et al., 1996).

Wildlife rabies exists in many countries and continues to present a major public health threat. Efforts to control wildlife rabies during the past two decades in both Europe and North America have been directed towards oral vaccination (Baer, 1988). Initially, an attenuated rabies virus, Street Alabama Dufferin B19 (SAD) strain was used, and it did not cause rabies when orally administered to foxes (Baer, 1988). Field trials to vaccinate red foxes in European countries with SAD in chicken-head baits resulted in more than 60% of rabies immune foxes and stopped the spread of the disease into untreated areas (Wandeler et al., 1998; Schneider et al., 1988). However, SAD still causes disease in rodents (Winkler et al., 1976) and in domestic animals (Esh et al., 1982). Subsequently, a recombinant vaccinia virus expressing the rabies virus G (VRG) was developed (Kieny et al., 1984) and was found to be an effective oral immunogen for raccoons and foxes under laboratory conditions (Rupprecht et al., 1986; Blancou et al., 1986). Further testing of VRG in fishmeal baits was carried out in animals in the wild, and it has been demonstrated that VRG is safe (Brochier et al., 1989; Rupprecht et al., 1993). Neither vaccine-associated morbidity or mortality nor gross lesions or detrimental side effects have been associated with vaccination in target and non-target animal species. The vaccine is also efficacious in inducing protective immunity and field application with VRG resulted in large-scale elimination of fox rabies in vaccinated areas in Europe (Brochier et al., 1991). Similar application of VRG in the United States has resulted in a blockade of coyote rabies spreading in Texas (Fearneyhough et al., 1998), and raccoon rabies spreading in other states (Hanlon et al., 1998; Robbins et al., 1998; Roscoe et al., 1998). Although VRG is safe in vaccinated animals and efficacious in stimulating immunity in target animal species, a recent incident involving a pregnant woman underscores the risks of using such recombinant vaccines even in wildlife animals, particularly in densely populated areas (Rupprecht et al., 2001). The woman was bitten on the finger and left forearm when she tried to remove a VRG recombinant virus-laden bait from her dog's mouth. Within 10 days she developed an intensive local inflammatory reaction around two necrotic lesions at the forearm bite sites and adenitis. She went on to develop generalized erythroderma that eventually subsided after exfoliation (Rupprecht et al., 2001). This incident casts doubts on the future use of VRG as a rabies vaccine for wildlife.

It is clear that current vaccines used in humans and other animals have problems in safety, effectiveness, and cost. More effective, safe, and inexpensive vaccines are needed for controlling rabies in animals and prevent human rabies. Many novel vaccines are being developed and tested including DNA vaccines and other recombinant vaccines. DNA vectors expressing rabies virus G have been found to stimulate both T helper cells and the production of rabies virus VNA (Xiang et al., 1994). Furthermore, immunization of mice with these DNA vectors protected mice and monkeys against subsequent challenge infections with lethal rabies virus (Xiang et al., 1994; Ray et al., 1997; Lodmell et al., 1998). However, induction of immune responses by DNA vaccines usually takes longer, and the magnitude of the immune response is lower compared with conventional vaccines (Xiang et al., 1994; Osorio et al., 1999). Recombinant human adenoviruses expressing rabies virus G have also been developed (Prevec et al., 1990; Xiang et al., 1996). The recombinant adenovirus vaccines can induce VNA and protect vaccinated animals (mice, dogs, skunks, and foxes) against challenge infection (Tims et al., 2000; Prevec et al., 1990; Xiang et al., 1996; Charlton et al., 1992; Wang et al., 1997). There is concern with the adenoviral vector in the immune responses directed to the adenoviral proteins (Wang et al., 1997). Preexisting anti-adenoviral immunity may prevent the uptake of the vaccine by cells needed for expression of the target gene and, thus, impair the active immune response to the target antigen. Furthermore, revaccination or vaccination with adenoviral vector expressing a different target antigen may no longer be effective.

Live-attenuated virus vaccines have long been known to be more effective in inducing long-lasting humoral and cell-mediated immunity, and many diseases are controlled or eradicated by using live modified viral vaccines. The global eradication of small pox is essentially achieved by using a less virulent cowpox virus vaccine (Henderson, 1980). Poliomyelitis is on the verge of global eradication because of the mass vaccination with the live polio vaccines (Sabin et al., 1973). Many other viral diseases such as measles, mumps, and rubella, just to name a few, are brought under control by live modified virus vaccines (Arvin, 2000). Thus, a live modified rabies virus vaccine may have the advantage over currently licensed vaccines by providing long-lasting immunity and reducing the doses required. As a result, the cost will be lowered markedly. However, such live modified rabies vaccines must be completely avirulent, particularly for humans. To this end, the SAD strain of rabies virus, which was initially used for wildlife vaccination in the 1980s (Baer, 1988; Wandeler et al., 1998; Schneider et al., 1988), was further attenuated by successive selection using neutralizing monoclonal antibodies (Mab), resulting in the selection of strains SAG1 and SAG2 (Le Blois et al., 1990; Flamand et al., 1993; Schumacher et al., 1993; Lafay et al., 1994). The selection of SAG1 and SAG2 using Mabs was based on earlier findings that mutation of the glycoprotein at arginine 333 reduced the virulence of the rabies virus (Dietzschold et al., 1983; Seif et al., 1985). The SAG1 virus possesses one mutation at position 333, where arginine is replaced by lysine (Lafay et al., 1994). Compared with the SAD strain, which is still pathogenic in adult mice by intracerebral (i.c.) route of inoculation, the SAG1 virus is avirulent when given to adult mice by i.c., intramuscular (i.m.), and per os (Le Blois et al., 1990; Lafay et al., 1994). The SAG1 virus is as effective as SAD in vaccinating foxes via the oral route (Le Blois et al., 1990). To stabilize the avirulent virus, a SAG2 virus was selected with an additional Mab (Lafay et al., 1994). SAG2 bears double mutations at position 333, changing from arginine (AGA) to glutamic acid (GAA), which reduces further the possibility of the virus to revert to virulent wild-type (wt) (Schumacher et al., 1993; Lafay et al., 1994). The SAG2 virus is avirulent for adult rodents, foxes, cats, and dogs by any route of inoculation (Schumacher et al., 1993; Lafay et al., 1994). Oral vaccination of foxes and dogs has resulted in the protection against a lethal challenge with rabies virus. Field trials with SAG2 in immunizing foxes and dogs demonstrated its safety and immunogenicity (Masson et al., 1996). However, SAG2 can induce rabies in suckling animals by i.c. inoculation (Schumacher et al., 1993; Lafay et al., 1994), raising the possibility that younger animals or immunocompromised animals may still be infected with the virus and develop disease.

These selected mutant viruses with changes on the arginine 333 of the G replicate well in cell culture, suggesting that the rate of viral replication of these viruses is not affected (Lafay et al., 1994). However, investigation of the ability of these viruses to invade the nervous system revealed that the virus can invade the first order neurons but fails to spread to secondary or tertiary neurons, indicating that the ability of these mutant viruses to spread in the nervous system via synaptic junctions is reduced (Coulon et al., 1989). Synaptic spreading is the major route for virus dissemination in the adult CNS (Gosztonyi et al., 1993). In the neonatal animals, synaptic spreading may not be the only way for virus dissemination. Because myelin development may not be complete in neonatal animals, the rabies virus may also spread from infected to uninfected neurons in neonatal animals by budding from infected neurons and infecting other uninfected neurons, more or less like that in cell cultures (Dietzschold et al., 1985). Therefore, reducing the rate of viral replication may be necessary to develop avirulent rabies virus vaccines. Like other single-stranded, non-segmented RNA viruses, rabies virus transcription and replication is regulated by the complicated interaction between the components within the ribonucleoprotein complex (RNP). RNP is composed of the genomic RNA, which is encapsidated by the nucleoprotein (N), together with the phosphoprotein (P) and the RNA-dependent RNA polymerase (L) (Wunner, 1991). Theoretically, mutation of these viral proteins may result in a reduced rate of replication for the rabies virus. With the recent development of reverse genetics technology for negative-stranded RNA viruses (Enami et al., 1990; Pattnaik et al., 1990; Pattnaik et al., 1991; Conzelmann et al., 1994; Schnell et al., 1994), manipulation of the viral genome for this group of viruses became possible (Conzelmann et al., 1994; Schnell et al., 1994; Lawson et al., 1995; Whelan et al., 1995). Application of this technology has resulted in a better understanding of how this group of viruses regulates their transcription and replication (Enami et al., 1990; Pattnaik et al., 1990; Pattnaik et al., 1991; Conzelmann et al., 1994; Schnell et al., 1994; Lawson et al., 1995; Whelan et al., 1995) and how each of the viral proteins functions in the replication cycle (Pattnaik et al., 1990) and in their pathogenicity (Etessami et al., 2000). Application of this technology has also resulted in attenuation of these viruses and some of them could be developed as vaccines (Wertz et al., 1998) or vectors for gene therapy (Finke et al., 1997).

N is the first product transcribed from the viral genome and is expressed abundantly in infected cells for all the negative-stranded RNA viruses (Wunner, 1991). N has been proposed to play a crucial role in the transition from RNA transcription to replication by encapsidating the nascent genomic RNA (Wunner, 1991). Mutation of the N could potentially lead to an attenuated phenotype. Indeed, moving the nucleoprotein (N) to other locations on the viral genome resulted in attenuation of vesicular stomatitis virus (VSV) (Wertz et al., 1998). This is caused by the inhibition of viral replication because of the reduced expression of the N protein. Recently, we have constructed mutant rabies virus with changes on the phosphorylation site of the N and found that the rate of viral replication was reduced by more than five-fold and the virus production was reduced by more than 10,000 times, indicating attenuation of the mutant rabies viruses (Wu et al., 2002).

Rabies still presents a public health threat causing more than 70,000 human deaths each year. Humans get infected with the rabies virus mostly through bites from rabid domestic and wildlife animals. Controlling rabies virus infection in domestic and wildlife animals, therefore, not only reduces the mortality in these animals but also reduces the risks of human exposure. Pre-exposure vaccinations for people who are constantly at risk further prevent human rabies, as do post-exposure immunizations for people who are bitten by rabid or suspected rabid animals. In the past few years, a recombinant vaccinia virus expressing rabies virus glycoprotein (VRG) has been used to control rabies in wildlife. Inactivated rabies virus vaccines are used to immunize domestic animals, particularly pets. Purified and inactivated rabies virus vaccines are used for humans in the pre- or post-exposure settings.

Although these vaccines are effective, annual vaccinations are required to maintain adequate immunity in pets. For humans, multiple doses of the inactivated tissue culture vaccines are required to stimulate optimal immune responses. Furthermore, current tissue culture vaccines are expensive; thus most people in need of vaccinations (in developing countries) cannot afford them. Hence, there is a need to develop more efficacious and affordable rabies virus vaccines.

Therefore, in view of the aforementioned deficiencies attendant with prior art methods of vaccinating humans and animals against rabies virus, it should be apparent that there still exists a need in the art for a safe and cost-effective method therefore.

SUMMARY OF THIS INVENTION

In accordance with the present invention, a mutant virus is provided which contains a mutation at a phosphorylation site in one or more of the proteins of the virus, which mutation causes the virus to be attenuated, and therefore, an improved vaccine composition can be produced therewith.

In particular, a mutant rabies virus is provided, wherein the virus contains a mutant rabies virus N protein which has an amino acid other than serine at position 389. Additionally, the mutant virus may contain one or more mutations within the N protein, or in other of the viral proteins, for example, in the G glycoprotein.

The invention also relates to vaccine compositions which contain the mutant virus, as well as to methods of inducing an immune response, and of protecting mammals from infection by rabies virus.

Also included in the invention are methods of producing the mutant virus and mutant viral proteins, including producing the mutant virus in a host cell which produces or even overproduces a wild-type counterpart of the mutant viral protein, which complements the other viral proteins such that production of the mutant viral particle is optimized. The invention also includes those host cells in which viral production is optimized.

Also included within the invention are nucleic acids which encode the mutant viral protein(s), and nucleic acids which encode a portion of, or the entire viral nucleic acid sequence. In addition, the invention includes vectors containing the nucleic acid sequences, including expression vectors, and host cells transformed with the nucleic acid sequences.

The invention also includes the viral proteins encoded by the mutant nucleic acids, vaccine compositions including the viral proteins, either alone or in combination with the intact virus, and to methods of inducing an immune response or protecting a mammal from infection, using the same.

The invention also includes antibodies to the intact mutant virus and to the mutant viral proteins, and to methods of making and using the same.

Also included in the invention are vectors suitable for delivering a gene to a cell of a human or animal, as well methods of delivery thereof.

BRIEF DESCRIPTION OF THE DRAWINGS

FIG. 9 shows the complete rabies nucleic acid sequence. (L16 (nt 1235-1237), TCT encoding serine on N protein is bolded and underlined.) FIG. 9A shows the wild-type L16 sequence (SEQ ID NO:55). FIG. 9B shows the L16A sequence (SEQ ID NO:56), wherein serine has been replaced with alanine on the N sequence. FIG. 9C shows the L16Q sequence (SEQ ID NO:57), wherein serine has been replaced with glutamine on the N sequence. FIG. 9D shows the L16QG333 sequence (SEQ ID NO:58), wherein serine has been replaced with glutamine on the N protein at nt 1235-1237 [TCT to CAA] (underlined and bolded) and arginine has been replaced with glutamic acid at nt 4370-4372 [AGA to GAA] (underlined, bolded and italicized).

FIG. 10 shows the nucleic acid sequence of the rabies virus G protein. FIG. 10A (SEQ ID NO:59) shows the Arg 333 as underlined. FIG. 10B (SEQ ID NO:60) shows Glu which has replaced Arg at position 333.

FIG. 11 shows the nucleic acid sequence of the rabies virus N protein. FIG. 11A shows wild-type sequence (SEQ ID NO:61), in which the phosphorylated serine is underlined. FIG. 11B (SEQ ID NO:62) shows the Serine to Alanine mutation (underlined). FIG. 11C (SEQ ID NO:63) shows the Serine to Glycine mutation (underlined). FIG. 11D (SEQ ID NO:64) shows the Serine to Glutamine mutation (underlined).

DETAILED DESCRIPTION

Figure 1:
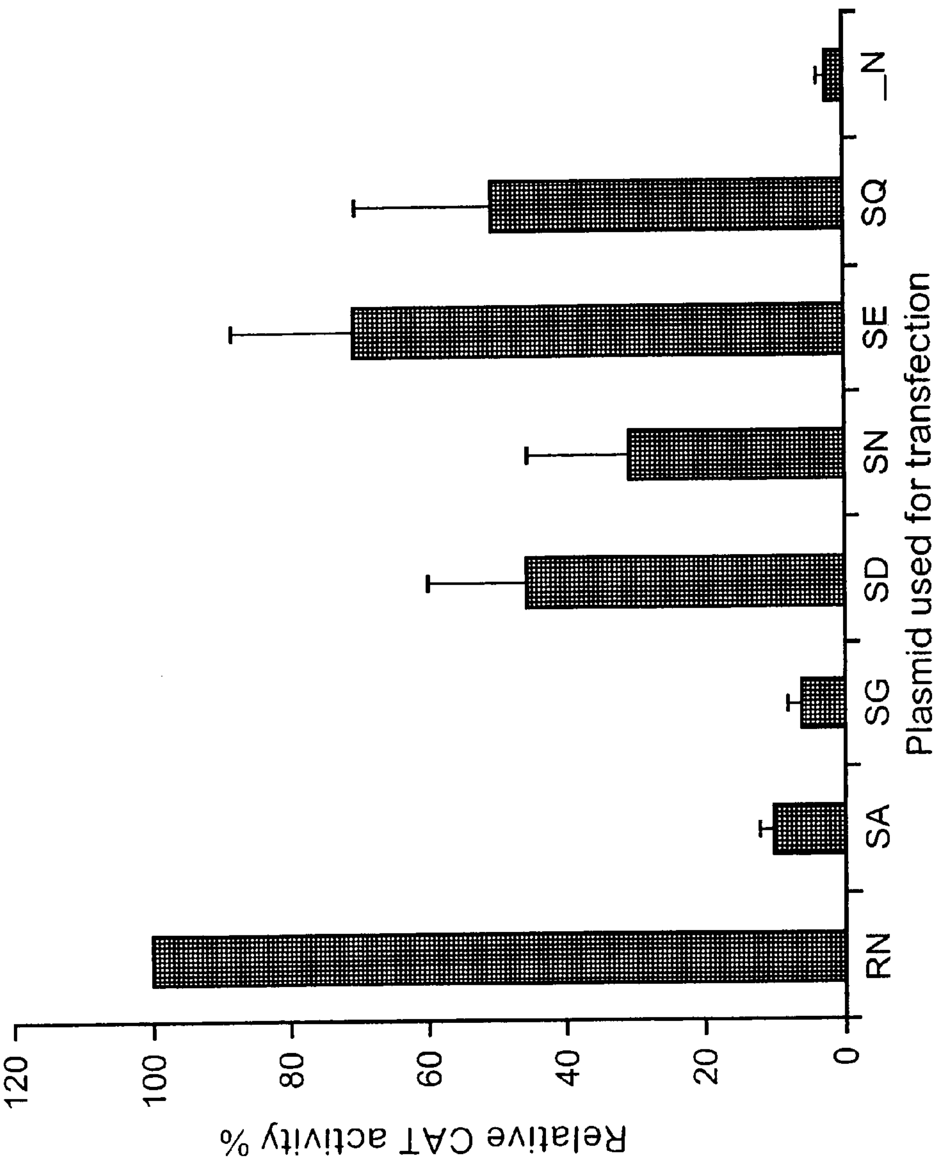
FIG. 1 shows that N phosphorylation affects viral RNA transcription in the minigenome. BSR cells were infected with recombinant vaccinia virus vTF7-3 and then transfected with plasmid pRP, pT7T-L, pSDI-CAT together with pRN (RN), pRN-SA (SA), pRN-SG (SG), pRN-SD (SD), pRN-SN (SN), pRN-SE (SE) or pRN-SQ (SQ). Cells transfected with other plasmids but without N expressing plasmid (-N) were included as controls. Cells were harvested for measurement of CAT activity by the Quan-T-CAT assay. Error bars, standard deviations.

The present invention relates to effective and affordable virus vaccines for humans as well as for animals, to methods of making the same, and to methods of using the same for inducing an immune response, preferably a protective immune response in animals and humans. Suitable viruses include, but are not limited to, measles, Respiratory Syncytial virus (RSV), ebola virus and influenza virus, Sendai virus, and bovine RSV.

In particular, the invention relates to avirulent live virus vaccines containing mutant virus in which the phosphorylation on the N nucleoprotein has been disrupted. Suitable viruses include, but are not limited to, measles, Respiratory Syncytial virus (RSV), ebola virus and influenza virus, which are all phosphorylated on the N protein. The phosphorylation is disrupted by any suitable means, including alteration of the phosphorylation site by insertion, deletion or preferably by substitution. In addition, the phosphorylation may be disrupted by changes in other portions of the N protein, such as a consensus sequence at another site in the N protein. Preferably, the N protein has an amino acid other than serine at position 389, preferably a neutral amino acid, and more preferably, alanine. Preferably, the mutant rabies virus is encoded by one of the sequences of FIG. 8, the mutant rabies virus N protein is encoded by one of the sequences of FIG. 9, and/or the mutant rabies virus G protein is encoded by one of the sequences of FIG. 10.

The N protein may be mutated so as to affect the binding of the N protein to RNA, to a phosphate moiety, or to itself. This modulation of the binding properties of the N nucleoprotein affects vital functions of the virus, such as replication.

In a preferred embodiment, the present invention is directed to avirulent live rabies virus vaccines containing mutant virus in which the phosphorylation on the N nucleoprotein has been disrupted, either by insertion, deletion, substitution, or other appropriate means. Preferably, the virus has a reduced rate of viral replication (by mutating the nucleoprotein N or by reshuffling the genes within the rabies virus genome). In a preferred embodiment a serine at position 389 of the N nucleoprotein is substituted with alanine, glycine, glutamine, glutamic acid, aspartic acid or asparagine.

In a preferred embodiment, the viruses also have a reduced ability to spread in the nervous system (by mutation of the glycoprotein G), preferably at position 333 of the G glycoprotein.

The mutant viruses may also preferably have more than one change in either or both of the N and G proteins, such that the chances of reversion to a wild-type (WT) phenotype are reduced.

Any strain of rabies virus can be used in which the phosphorylation site is conserved. The phosphorylation site on the N protein of all presently known rabies viruses is conserved.

In addition, the mutant virus of the invention may contain a G glycoprotein of another type of virus, in order to direct the tropism of the virus within the body. Thus, the viruses of the present invention are likewise useful in gene therapy, for administering therapeutic or immunogenic proteins to the human or animal in which it is administered.

In particular, the rabies virus G glycoprotein causes a tropism for CNS cells, and thus is suitable for treating diseases of the CNS such as cancer, including but not limited to neuroblastoma, and neurodegenerative diseases including, but not limited to, Alzheimer's Disease, Parkinson's Disease, Huntington's Disease. Likewise, the human immunodeficiency virus (HIV) G protein causes a tropism for T cells, and thus is suitable for treating T-cell mediated disorders by gene delivery thereto, including various cancers, and diseases affecting T-cells, including HIV.

The vesicular stomatitis. virus (VSV) G glycoprotein is pantropic, and thus may be used for administration to various cell types. The RSV G glycoprotein causes a tropism for epithelia, and thus is suitable for direction to the lung and treatment of disorders thereof, including, but not limited to, cystic fibrosis.

The invention also relates to methods of using the mutant virus for inducing an immune response, and preferably, a protective immune response in a human or animal.

Also included in the invention are host cells for producing the mutant virus, as well as a method of producing the same. Preferably, the host cell is a mammalian host cell which produces a wild-type rabies virus N protein, preferably a hamster cell, more preferably a BHK cell, and most preferably, a host cell which was deposited at the American Type Culture Collection, 10801 University Boulevard, Manassas, Va. 20110-2209, USA, as deposit number ATCC PTA-3544 on Jul. 20, 2001.

Mutation on both the G and N or relocation of these genes leads to attenuation of the virus to an extent that the virus no longer causes disease in animals at any age and by any route of infection; yet, it can induce immune responses that provide protection against virulent rabies virus challenge. This is based on recent studies showing the following. 1) Mutation of the phosphorylated serine at 389 of the N to alanine reduced the rate of viral replication by more than five-fold and virus production by more than 10,000 times. 2) Mutation of the G at residue 333 reduced dramatically the virulence and pathogenicity of rabies virus. 3) Rearrangement of the genes in a related virus, vesicular stomatitis virus (VSV), resulted in attenuation and enhancement of its immune responses. Rabies viruses with mutations on both the G and N or with rearranged genes are further attenuated than currently available attenuated rabies viruses (still induce rabies in neonatal animals). Further attenuated rabies viruses which are incapable of inducing diseases in experimental animals at any age and by any route of inoculation, yet remain immunogenic, can be developed into modified live rabies vaccines for humans and animals.

Alternatively, the vaccine of the present invention may contain isolated mutant N protein, in the absence of intact virus. Because the N phosphorylation mutant aggregates to a larger extent than its wild-type counterpart, it may have increased adjuvant effects compared to compositions containing wild-type N.

The vaccine compositions of the invention may contain an adjuvant, including, but not limited to, hepatitis B surface antigen (HbsAg) or the rabies virus G protein. The vaccine may be prepared using any pharmaceutically acceptable carrier or vehicle, including Hanks basic salt solution (HBSS) or phosphate buffered saline (PBS). The vaccine compositions can be administered by any known route, including intradermal, intramuscular and subcutaneous, which are preferred, as well as oral, via skin (epidermal abrasion) or intranasal.

In accordance with the present invention there may be employed conventional molecular biology, microbiology, immunology, and recombinant DNA techniques within the skill of the art. Such techniques are explained fully in the literature. See, e.g., Sambrook et al, "Molecular Cloning: A Laboratory Manual" ($3^{rd}$ edition, 2001); "Current Protocols in Molecular Biology" Volumes I-III [Ausubel, R. M., ed. (1999 and updated bimonthly)]; "Cell Biology: A Laboratory Handbook" Volumes I-III [J. E. Celis, ed. (1994)]; "Current Protocols in Immunology" Volumes I-IV [Coligan, J. E., ed, (1999 and updated bimonthly)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Culture of Animal Cells, $4^{th}$ edition" [R. I. Freshney, ed. (2000)]; "Immobilized Cells And Enzymes" [IRL Press, (1986)]; B. Perbal, "A Practical Guide To Molecular Cloning" (1988); *Using Antibodies: A Laboratory Manual: Portable Protocol No. I*, Harlow, Ed and Lane, David (Cold Spring Harbor Press, 1998); *Using Antibodies: A Laboratory Manual*, Harlow, Ed and Lane, David (Cold Spring Harbor Press, 1999).

Therefore, if appearing herein, the following terms shall have the definitions set out below.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide," as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15-25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

It is well known in the art that the following codons can be used interchangeably to code for each specific amino acid:

| | |
|---|---|
| Phenylalanine (Phe or F) | UUU or UUC |
| Leucine (Leu or L) | UUA or UUG or CUU or CUC or CUA or CUG |
| Isoleucine (Ile or I) | AUU or AUC or AUA |
| Methionine (Met or M) | AUG |
| Valine (Val or V) | GUU or GUC of GUA or GUG |
| Serine (Ser or S) | UCU or UCC or UCA or UCG or AGU or AGC |
| Proline (Pro or P) | CCU or CCC or CCA or CCG |
| Threonine (Thr or T) | ACU or ACC or ACA or ACG |

-continued

| | |
|---|---|
| Alanine (Ala or A) | GCU or GCG or GCA or GCG |
| Tyrosine (Tyr or Y) | UAU or UAC |
| Histidine (His or H) | CAU or CAC |
| Glutamine (Gln or Q) | CAA or CAG |
| Asparagine (Asn or N) | AAU or AAC |
| Lysine (Lys or K) | AAA or AAG |
| Aspartic Acid (Asp or D) | GAU or GAC |
| Glutamic Acid (Glu or E) | GAA or GAG |
| Cysteine (Cys or C) | UGU or UGC |
| Arginine (Arg or R) | CGU or CGC or CGA or CGG or AGA or AGG |
| Glycine (Gly or G) | GGU or GGC or GGA or GGG |
| Tryptophan (Trp or W) | UGG |
| Termination codon | UAA (ochre) or UAG (amber) or UGA (opal) |

It should be understood that the codons specified above are for RNA sequences. The corresponding codons for DNA have a T substituted for U.

Mutations can be made in the various viral proteins such that a particular codon is changed to a codon which codes for a different amino acid. Such a mutation may be easily made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein, such as changes induced by the lack of phosphorylation on the N nucleoprotein. It may be preferable, in some cases, to effect more than one change in the viral protein, so as to reduce the possibility of reversion to the wild-type phenotype.

The following is one example of various groupings of amino acids:

Amino Acids with Nonpolar R Groups
Alanine
Valine
Leucine
Isoleucine
Proline
Phenylalanine
Tryptophan
Methionine Amino Acids with Uncharged Polar R Groups
Glycine
Serine
Threonine
Cysteine
Tyrosine Asparagine
Glutamine Amino Acids with Charged Polar R Groups (Negatively Charged at ph 6.0)
Aspartic acid
Glutamic acid Basic Amino Acids (Positively Charged at pH 6.0)
Lysine
Arginine
Histidine (at pH 6.0)

Another grouping may be those amino acids with phenyl groups:
Phenylalanine
Tryptophan
Tyrosine Another grouping may be according to molecular weight (i.e., size of R groups):

| | |
|---|---|
| Glycine | 75 |
| Alanine | 89 |
| Serine | 105 |
| Proline | 115 |
| Valine | 117 |
| Threonine | 119 |
| Cysteine | 121 |
| Leucine | 131 |
| Isoleucine | 131 |
| Asparagine | 132 |
| Aspartic acid | 133 |
| Glutamine | 146 |
| Lysine | 146 |
| Glutamic acid | 147 |
| Methionine | 149 |
| Histidine (at pH 6.0) | 155 |
| Phenylalanine | 165 |
| Arginine | 174 |
| Tyrosine | 181 |
| Tryptophan | 204 |

Particularly preferred substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $NH_2$ can be maintained.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces Æ-turns in the protein's structure.

Two amino acid sequences are "substantially homologous" when at least about 70% of the amino acid residues (preferably at least about 80%, and most preferably at least about 90 or 95%) are identical, or represent conservative substitutions.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', $F(ab')_2$ and F(v), which portions are preferred for use in the therapeutic methods described herein.

Fab and $F(ab')_2$ portions of antibody molecules are prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from $F(ab')_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

The phrase "pharmaceutically acceptable" refers to molecular entities and compositions that are physiologically tolerable and do not typically produce an allergic or similar untoward reaction, such as gastric upset, dizziness and the like, when administered to a human.

The phrase "sufficient to protect an animal from infection" is used herein to mean an amount sufficient to prevent, and preferably reduce by at least about 30 percent, more preferably by at least 50 percent, most preferably by at least 90 percent, a clinically significant change in at least one feature of pathology normally caused by the disease.

Clinically, the first symptoms of rabies in people may be nonspecific flu-like signs, such as malaise, fever, or headache. There may be discomfort or paresthesia at the site of exposure (bite), progressing within days to symptoms of cerebral dysfunction, anxiety, confusion, agitation, progressing to delirium, abnormal behavior, hallucinations, and insomnia.

Cellular pathology of rabies infection is defined by encephalitis and myelitis, including perivascular infiltration with lymphocytes, polymorphonuclear leukocytes, and plasma cells throughout the entire CNS. There may be cytoplasmic eosinophilic inclusion bodies (Negri bodies) in neuronal cells, including pyramidal cells of the hippocampus and Purkinje cells of the cerebellum, and within neurons of the cortex and other regions of the CNS, including the spinal ganglia.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "stringent hybridization conditions" refers to salt and temperature conditions substantially equivalent to 5×SSC and 65° C. for both hybridization and wash. However, one skilled in the art will appreciate that such "stringent hybridization conditions" are dependent on particular conditions including the concentration of sodium and magnesium in the buffer, nucleotide sequence length and concentration, percent mismatch, percent formamide, and the like. Also important in the determination of "stringent hybridization conditions" is whether the two sequences hybridizing are RNA-RNA, DNA-DNA or RNA-DNA. Such stringent hybridization conditions are easily determined by one skilled in the art according to well known formulae, wherein hybridization is typically 10-20° C. below the predicted or determined $T_m$ with washes of higher stringency, if desired.

The present invention further contemplates therapeutic compositions useful in practicing the therapeutic methods of this invention. A subject therapeutic composition includes, in admixture, a pharmaceutically acceptable excipient (carrier) and one or more of a mutant rabies virus, a mutant rabies virus polypeptide or fragment thereof, as described herein as an active ingredient. In a preferred embodiment, the composition comprises an antigen capable of inducing an immune response, and preferably a protective immune response against rabies.

The preparation of therapeutic compositions which contain polypeptides, analogs or active fragments as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A virus, polypeptide, or fragment thereof can be formulated into a therapeutic and/or immunogenic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic and/or immunogenic virus-, polypeptide-, or fragment-containing compositions are conventionally administered in a unit dose, for example. The term "unit dose" when used in reference to a therapeutic composition of the present invention refers to physically discrete units suitable as unitary dosage for humans, each unit containing a predetermined quantity of active material calculated to produce the desired therapeutic and/or immunogenic effect in association with the required diluent; i.e., carrier, or vehicle.

The compositions are administered in a manner compatible with the dosage formulation, and in a therapeutically or immunogenically effective amount. The quantity to be administered depends on the subject to be treated, capacity of the subject's immune system to utilize the active ingredient, and degree of expression desired. Precise amounts of active ingredient required to be administered depend on the judgment of the practitioner and are peculiar to each individual. However, for polypeptide administration, suitable dosages may range from about 0.1 to 20, preferably about 0.5 to about 10, and more preferably one to several, milligrams of active ingredient per kilogram body weight of individual per day and depend on the route of administration. For viral administration, suitable dosages may be from $10^5$ infectious units (i.u.) to $10^7$ i.u. Suitable regimes for initial administration and booster shots are also variable, but are typified by an initial administration followed by repeated doses at 7 day intervals by a subsequent injection or other administration.

The therapeutic compositions may further include one or more of the following active ingredients: an antibiotic, a steroid.

Another feature of this invention is the expression of the DNA sequences operably inserted into the viruses disclosed herein. As is well known in the art, DNA sequences may be expressed by operatively linking them to an expression control sequence in an appropriate expression vector and employing that expression vector to transform an appropriate host.

Such operative linking of a DNA sequence of this invention to an expression control sequence, of course, includes, if not already part of the DNA sequence, the provision of an initiation codon, ATG, in the correct reading frame upstream of the DNA sequence.

A wide variety of host/expression vector combinations may be employed in expressing the DNA sequences encoding viral proteins of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids col El, pCR1, pBR322, pMB9 and their derivatives, plasmids such as RP4; phage DNAS, e.g., the numerous derivatives of phageλ, e.g., NM989, and other phage DNA, e.g., M13 and filamentous single stranded phage DNA; yeast plasmids such as the 2μ plasmid or derivatives thereof; vectors useful in eukaryotic cells, such as vectors useful in insect (baculovirus) or mammalian cells; vectors derived from combinations of plasmids and phage DNAs, such as plasmids that have been modified to employ phage DNA or other expression control sequences; and the like.

Any of a wide variety of expression control sequences—sequences that control the expression of a DNA sequence operatively linked to it—may be used in these vectors to express the DNA sequences of this invention. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage λ, the control regions of fd coat protein, the promoter for 3-phosphoglycerate kinase or other glycolytic enzymes, the promoters of acid phosphatase (e.g., Pho5), the promoters of the yeast α-mating factors, and other sequences known to control the expression of genes of prokaryotic or eukaryotic cells or their viruses, and various combinations thereof.

A wide variety of host cells are also useful in expressing the DNA sequences encoding viral proteins of this invention. These hosts may include well known eukaryotic and prokaryotic hosts, such as strains of *E. coli, Pseudomonas, Bacillus, Streptomyces*, fungi such as yeasts, and animal cells, such as CHO, R1.1, B-W and L-M cells, African Green Monkey kidney cells (e.g., COS 1, COS 7, BSC1, BSC40, and BMT10), insect cells (e.g., Sf9), BHK cells, and human cells and plant cells in tissue culture.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable mutant viral vectors will be selected by consideration of, e.g., their replicative capacity as well as the toxicity to the host of the product encoded by the DNA sequences to be expressed, or by the mutant virus.

Considering these and other factors a person skilled in the art will be able to construct a variety of vector/expression control sequence/host combinations that will express the DNA sequences of this invention.

It is further intended that other mutant viral proteins may be prepared from nucleotide sequences of the present invention. Analogs, such as fragments, may be produced, for example, by pepsin digestion of viral polypeptide material. Other analogs, such as muteins, can be produced by standard site-directed mutagenesis of sequences encoding viral proteins. Mutants exhibiting immunogenic or protective activity, may be identified by known in vivo and/or in vitro assays.

As mentioned above, a DNA sequence encoding the virus or viral proteins can be prepared synthetically rather than cloned. The complete sequence is assembled from overlapping oligonucleotides prepared by standard methods and assembled into a complete coding sequence. See, e.g., Edge, *Nature,* 292:756 (1981); Nambair et al., *Science,* 223:1299 (1984); Jay et al., *J. Biol. Chem.,* 259:6311 (1984).

Synthetic DNA sequences allow convenient construction of genes which will express viral protein mutants or "muteins". Alternatively, DNA encoding muteins can be made by site-directed mutagenesis of native viral genes or cDNAs, and muteins can be made directly using conventional polypeptide synthesis.

A general method for site-specific incorporation of unnatural amino acids into proteins is described in Christopher J. Noren, Spencer J. Anthony-Cahill, Michael C. Griffith, Peter G. Schultz, *Science,* 244:182-188 (April 1989). This method may be used to create analogs with unnatural amino acids.

The following examples are presented in order to more fully illustrate the preferred embodiments of the invention. They should in no way be construed, however, as limiting the broad scope of the invention.

EXAMPLE 1

Rabies virus N preferentially encapsidates genomic RNA. Rabies virus N, like other N from negative-stranded RNA viruses, plays important roles in the regulation of viral transcription and replication by encapsidating de novo synthesized genomic RNA (Yang et al., 1998). To investigate the function of rabies virus N, rabies virus N was expressed in the baculovirus system and purified the N to near homogeneity by affinity chromatography (Fu et al., 1991). When the purified N was used to encapsidate RNA, it was found that N bound to all RNA transcripts tested (Yang et al., 1998). These include rabies virus positive-stranded leader RNA (L-70), the 5' end of rabies virus N mRNA (N-70), and a control nonviral RNA (bluescript RNA, B-70). However, the interaction between recombinant N and the rabies virus leader RNA was at least three times greater than that between recombinant N and N mRNA and 10 times greater than that between recombinant N and the control RNA, indicating that N preferentially encapsidates the positive-stranded leader RNA.

EXAMPLE 2

Phosphorylation of rabies virus N modulates viral transcription and replication. Rabies virus N is phosphorylated (Sokol et al., 1973) and its phosphorylation site has been identified as serine at position 389 (Dietzschold et al., 1987). Because N plays important roles in regulating viral transcription and replication by encapsidating de novo synthesized genomic RNA (Wunner, 1991), phosphorylation of N may affect viral transcription and replication. To determine whether phosphorylation of N plays a regulatory role in viral transcription and replication, the reverse genetics system described by Conzelmann and Schnell (Conzelmann et al., 1994) was used to express a rabies virus minigenome and directly test the effects of N phosphorylation on viral RNA transcription and replication. The minigenome was expressed from the plasmid pSDI-CAT directed by T7 polymerase. When expressed in cells, the minigenomic RNA contains 68 nucleotides from the 3' end and 169 nucleotides from the 5' end of the rabies virus genome flanked by the CAT coding sequences in between (Conzelmann et al., 1994). Plasmid pSDI-CAT, together with pRP, pT7T-L, pT7T-G, pT7T-M, and pRN or pRN-S389A, was transfected into BHK cells, and the cells were harvested 48 hr after transfection. CAT activity was measured from the cellular extract by using the standard CAT assay. Strong CAT activity was detected in cells transfected with pRN. When the wt N was replaced with the mutated N (serine to alanine), only about 20% CAT activity was detected suggesting that the absence of N phosphorylation results in a decrease of viral transcription. However, when both the wt N and the mutant N were present, about 80% CAT activity was detected, indicating that the unphosphorylated N is not a dominant negative regulator (Yang et al., 1999, Appendix 1).

To determine if N phosphorylation also affects viral replication, passage experiments were performed. The supernatant from the initial transfection was harvested and used for infection of fresh BHK cells transfected with pRP, pT7T-L, and pRN or pRN-S389A. The cells were harvested 48 hrs later for measurement of CAT activity. The highest CAT activity (100%) was detected when the wt N was used in both the initial transfection and the subsequent passage experiment. When wt N was used in the initial transfection and the mutated N in the passage experiment, 43% CAT activity was detected; indicating that phosphorylation of N indeed affects transcription of the minigenome. When the mutated N was used in the initial transfection and the wt N in the passage experiment, 61% CAT activity was detected, indicating that the mutant N supported replication of the minigenome in the initial transfection, albeit with lower efficiency. However, only 13% CAT activity was detected when the mutant N was used in both the initial transfection and the passage experiment, suggesting that the absence of N phosphorylation result in decreases of both viral RNA transcription and replication (Yang et al., 1999; Appendix 1).

EXAMPLE 3

The serine at position 389 was mutated to alanine, aspartic acid, or glutamic acid and the effects of these mutations on rabies virus transcription and replication in the minigenome as well as with the full infectious virus were examined. Mutation of the serine to each of the other amino acids resulted in the synthesis of an unphosphorylated N and reduction of viral transcription and replication in the minigenome. Mutations from S to A and S to D also resulted in reduction of both viral transcription and replication in full-length infectious viruses. Growth curve studies indicated that production of the mutant virus with the S-to-A mutation (L16A) was as much as 10,000-fold less than that of the wild-type virus (L16). Northern blot hybridization with rabies virus gene probes revealed that the rates of viral transcription and replication were reduced by as much as 10-fold in the mutant viruses when the N was not phosphorylated. Interpretation of the data from the minigenome system and the full-length infectious virus indicates that phosphorylation of rabies virus N is necessary for replication. Further studies involving cycloheximide treatment of infected cells revealed that viral transcription was also reduced when the N was not phosphorylated. Taken together, these results provide definitive evidence that N phosphorylation plays an important role in the processes of rabies virus transcription and replication.

Cells, virus, plasmids, and antibodies. BSR (a clone of BHK) and BSR T7/5 (BSR cells stably expressing T7 polymerases, [Buchholz et al., 1999]) were grown in Dubecco's minimal essential medium and transfected with plasmids as described previously (Yang et al., 1999). Recombinant vaccinia virus expressing bacterial T7 RNA polymerase (vTF7-3) was prepared as described (Fuerst et al., 1986). Plasmids used for expression of the full infectious virus (pSAD-L16), rabies virus minigenome (pSDI-CAT), rabies virus L (pT7T-L), glycoprotein (pT7T-G), and matrix protein (pT7T-M) (Buchholz et al., 1999; Conzelmann et al., 1987; Schnell et al., 1984) were obtained from Dr. K. Conzelmann. Plasmids for expression of N (pRN) and P (pRP) were constructed previously (Fu et al., 1994). Polyclonal antiserum against rabies virus N was prepared in rabbits as described previously (Fu et al., 1991).

Site-directed mutagenesis. Mutation of the serine 389 of the rabies virus N to A, G, D, N, E, or Q was carried out by site-directed mutagenesis, using the method of Weiner et al (1994). Six pairs of primers were synthesized as summarized in Table 1 and were designed to contain one or two nucleotide changes that resulted in the mutation of the serine codon. PCR was performed with each of the three primer pairs using pRN (Fu et al., 1994) as a template. The PCR products were subjected to digestion with DpnI, which digests methylated and hemimethylated DNA at the $G^{me}$ATC site, thereby digesting the pRN DNA template. The undigested PCR products (not methylated) were used to transform competent XL-1 Blue cells. The mutations in the plasmids were confirmed by nucleotide sequencing.

TABLE 1

Primers used to make mutations from serine at position 389 to alanine, aspartic acid, and glutamic acid on rabies virus N. (Bold letters represent the mutated codon)

| Primer ID | Primer sequence | Amino acid changed to |
|---|---|---|
| SA5 (SEQ ID NO:1) | 5'GATGATGGAACTGTCAAC**GCT**GACGACGAGG3' | Alanine |
| SA3 (SEQ ID NO:2) | 5'GTAGTCCTCGTCGTC**AGC**GTTGACAGTTCC3' | |
| SG5 (SEQ ID NO:3) | 5'GATGATGGAACTGTCAAC**GGT**GACGACGAGG3' | Glycine |
| SG3 (SEQ ID NO:4) | 5'GTAGTCCTCGTCGTC**ACC**GTTGACAGTTCC3' | |
| SD5 (SEQ ID NO:5) | 5'GATGATGGAACTGTCAAC **GAT**GACGACGAGG3' | Aspartic acid |
| SD3 (SEQ ID NO:6) | 5'GTAGTCCTCGTCGTC**ATC**GTTGACAGTTCC3' | |
| SN5 (SEQ ID NO:7) | 5'GATGATGGAACTGTCAAC**AAT**GACGACGAGG3' | Asparagine |
| SN3 (SEQ ID NO:8) | 5'GTAGTCCTCGTCGTC**ATT**GTTGACAGTTCC3' | |

TABLE 1-continued

Primers used to make mutations from serine at position 389 to alanine, aspartic acid, and glutamic acid on rabies virus N. (Bold letters represent the mutated codon)

| Primer ID | Primer sequence | Amino acid changed to |
| --- | --- | --- |
| SE5 (SEQ ID NO:9) | 5'GATGATGGAACTGTCAAC **GAA**GACGACGAGG3' | Glutamic acid |
| SE3 (SEQ ID NO:10) | 5'GTAGTCCTCGTCGTC**TTC**GTTGACAGTTCC3' | |
| SQ5 (SEQ ID NO:11) | 5'GATGATGGAACTGTCAAC**CAA**GACGACGAGG3' | Glutamine |
| SQ3 (SEQ ID NO:12) | 5'GTAGTCCTCGTCGTCTTGGTTGACAGTTCC3' | |

To introduce the mutations on rabies virus N into the infectious clone, an SphI fragment containing the serine codon of the N from the full infectious clone (pSAD-L16) (nucleotide sequences 482-4041 of the rabies virus genome [Conzelmann et al., 1990]) was cloned into the SphI site of pGEM-3Z. The resulting plasmid was used as the template for construction of the mutations as described above for pRN. The serine at position 389 was mutated to alanine, aspartic acid, or glutamic acid in the surrogate vector. After confirmation by sequence analysis, each of the mutated SphI fragments was cloned back to pSAD-L16. Three mutated clones with the expected mutation and correct orientation were obtained and designated pSAD-L16A, pSAD-L16D, and pSAD-L16E, respectively.

Transfection. Transfection of BSR cells with plasmids was performed as described previously (Yang et al., 1999). Briefly, BSR cells were infected with recombinant vaccinia virus (vTF7-3) at a multiplicity of infection (moi) of 5 plaque-forming units (pfu) per cell. One h after infection, cells were transfected with different combinations of mixed plasmids using Lipofectamine (Life Technologies, Rockville, Md.). Transfected cells were harvested at indicated time points for further analysis.

Chloremphenicol actyl transferase (CAT) assay. CAT activities were measured with the Quan-T-CAT assay (Amersham Pharmacia Biotech, Piscataway, N.J.) according to the manufacturer's protocol. Transfected cells were lysed, and the supernatants were incubated with biotinylated chloramphenicol and [$^3$H] acetyl coenzyme A. Then streptavidin-coated beads were added to the reaction. After the free radioactive materials were removed, the pellets were resuspended in scintillation fluid for quantitation by scintillation spectrometry. The CAT activities were expressed as counts per minute. The relative CAT activities in cells transfected with each of the mutated N proteins were calculated using the CAT activity in cells transfected with wt N as 100%.

Radiolabeling and immunoprecipitation of proteins. Transfected or infected BSR cells were labeled with either [$^{35}$S] methionine or [$^{32}$P] phosphoric acid (Amersham Pharmacia Biotech) as described previously (Yang et al., 1999). Cells were harvested and subjected to immunoprecipitation with anti-N antibodies followed by electrophoresis on 12% polyacrylamide/10% SDS gel and autoradiography.

Northern and Western blotting. Transfected or infected BSR cells, or purified viruses were subjected to Northern and/or Western blotting. For Northern blotting, BSR cells were lysed with Trizon reagent (Life Technologies) and total RNA was prepared according to the manufacturer's specifications. Poly A+mRNA was purified from total RNA by using the mRNA isolation kit (Roche, Indianapolis, Ind.). RNA preparations were denatured with a 10 mM sodium phosphate buffer (pH 7.4) containing 50% (v/v) formamide at 65° C. for 15 min and electrophoresed on a 1.1% agarose gel containing 1.1 M formaldehyde and 10 mM sodium phosphate. The RNA then was transferred and covalently fixed onto a nylon membrane for hybridization with CAT, rabies virus gene, or β-actin probes. Quantitation of RNA bands was done by densitometry. For Western blots, BSR cells were lysed with RIPA buffer, and proteins were directly separated by SDS-PAGE. After transfer to a nitrocellulose membrane, rabies virus N was detected by rabbit anti-N polyclonal antibodies as described (Fu et al., 1991).

Selection of mutant rabies viruses. Selection of mutant viruses was performed either in BSR cells infected with vTF7-3 (Fuerst et al., 1986), or in BSR T7/5 cells (Buchholz et al., 1999; Schnell et al., 2000). Briefly, BSR cells were infected with vTF7-3 at a moi of 1. One h later, the cells were transfected with 10 mg of pRN, 2.5 mg of pRP, 1.5 mg of pT7T-L, and 10 mg of pSAD-L16, pSAD-L16A, pSAD-L16D, or pSAD-L16E. After incubation for 48 hr, cells were resuspended with the medium and subjected to three cycles of freezing and thawing to release cell-associated virus. Vaccinia virus was eliminated by centrifugation and then filtration through a 0.2 m filter unit (Millipore) as described previously (Schnell et al 1994). Alternatively, BSR T7/5 cells were transfected with 10 mg of pSAD-16 or pSAD-L16A, together with 10 mg of pTIT-N, 2.5 mg of pTIT-P, and 2.5 mg TIT-L as described (Schnell et al., 2000). To confirm that the mutant viruses contain the desired mutations, total RNA was extracted from BSR cells infected with each of these viruses and subjected to PCR amplification for the N gene using primers (SEQ ID NOS:13-14) 10 g (5'CTACAATGGATGCC-GAC3') and 304 (5'TTGACGAAGATCTTGCT-CAT3') as described previously (Smith et al., 1991). These primers can amplify the complete N coding sequence from the genomic RNA. The amplified fragment was directly sequenced using primer (SEQ ID NO:15) 113 (5'GTAGGATGCTATATGGG3') (Smith et al., 1991), which immediately precedes the area of the mutations on the N gene. The mutant viruses bearing S to A, S to D, and S to E mutations were designated L16A, L16D, and L16E, respectively.

Virus growth curve. BSR cells growing in six-well plates were infected with wt or mutant rabies viruses at a moi of 1 ffu/cell. After incubation at 37° C. for 1 hr, virus inocula were removed and cells were washed with PBS to remove any unabsorbed virus. The cells were replenished with fresh medium, and 100 ml of culture supernatant were removed at 6, 12, 24, 36, 48, 60, and 72 hr after infection. Virus aliquots were titrated in duplicate in BSR cells as described previously (Fu et al., 1996).

Treatment of infected cells with CHX. Cycloheximide (CHX) was purchased from Sigma (St. Louis, Mo.) and was added into cells infected with rabies virus at a final concentration of 150 μg/ml 1 h after infection as described previously (3). At 6, 12, and 24 h after infection, cells were harvested and RNA was extracted for Northern blot hybridization.

The effects of N phosphorylation on viral transcription and replication are probably caused at least in part by the net negative charge of the phosphate moiety. Previously, it was demonstrated that phosphorylation of rabies virus N plays important roles in the process of viral transcription and replication (Yang et al., 1999). Mutation of the phosphoserine to alanine results in reduced transcription and replication of a rabies virus minigenome. To determine whether the effects of rabies virus N phosphorylation on viral transcription and replication are caused by the net negative charge of the phosphate moiety or the structure of S or both, the phosphorylated serine at position 389 of the N was mutated to A, G, D, N, E and Q. BSR cells were infected with recombinant vaccinia virus vTF7-3 followed by transfection with plasmids expressing the rabies virus minigenome (pSDI-CAT), rabies virus L (pT7T-L), and rabies virus P (pRP), together with plasmids expressing rabies N or mutant N (pRN, pRN-SA, pRN-SG, pRN-SD, pRN-SN, pRN-SE or pRN-SQ), as described previously (Conzelmann and Schnell, 1994; Yang et al., 1999). After incubation for 48 h, BSR cells were harvested, and CAT activities were measured using the Quan-T-CAT assay. The relative CAT activities, which are a measure of minigenome transcription in cells transfected with each of the mutated N plasmids, were calculated using the CAT activity in cells transfected with wt N as 100%. The results are summarized in FIG. 1. The CAT activities relative to wt N were 6, 9, 28, 40, 46, and 62%, in cells transfected with pRN-SG, pRN-SA, pRN-SN, pRN-SD, pRN-SQ, and pRN-SE, respectively. In cells transfected with all other plasmids but lacking an N-expressing plasmid, the relative CAT activity was less than 2% (data not shown). These results suggest that the effects of N phosphorylation on viral transcription or replication, or both, are probably caused at least in part by the net negative charge of the phosphate moiety and the structure of the serine residue.

Figure 2:
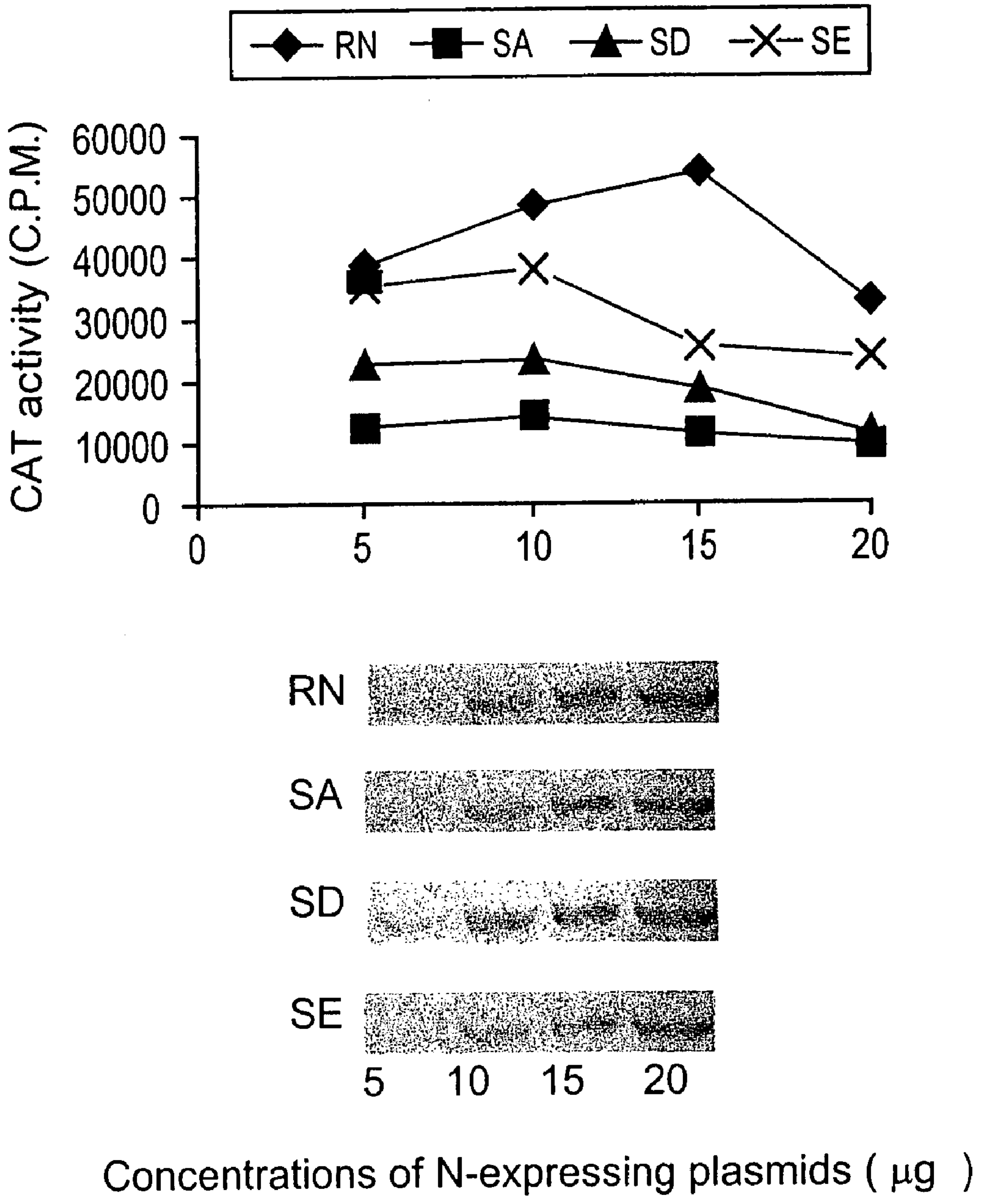
FIG. 2 demonstrates that rabies virus N phosphorylation affects both viral RNA transcription and replication. BSR cells infected and transfected as described in FIG. 1 were harvested for Northern blot hybridization or immunoprecipitation. Message RNA was purified from total RNA and genomic analogues were purified from immunoprecipitated RNP with polyclonal anti-N antibodies. These RNA preparations were hybridized with CAT cDNA probe. Total RNA was hybridized with a sense oligo probe for measurement of negative-sense RNA transcribed from the plasmid expressing the minigenome. N protein expressed in the cells were immunoprecipitated with polyclonal anti-N antibodies.

Increasing or decreasing the concentrations of N-expressing plasmid cannot compensate for the effects of N phosphorylation on viral transcription and replication. In studying the effects of phosphorylation of VSV P protein, Spadafora et al. (1996) observed that unphosphorylated P was much less active in supporting viral transcription at low concentrations. To determine if N concentration has any effect on the ability of the mutant N proteins to achieve optimal transcription and replication of the rabies virus minigenome, various concentrations (5, 10, 15 and 20 mg) of the plasmids expressing N or mutant N (pRN-SA, pRN-SD, or pRN-SE) were used for transfection, and the cells were harvested for CAT assay. As presented in FIG. 2, 10 mg of each mutant N-expressing plasmid and 15 mg of the wt N (pRN) resulted in the optimal CAT activities. A larger or smaller amount led to slightly reduced CAT activities (20%), indicating that increasing or decreasing the concentration of N does not have a major impact on viral transcription for either the wt N or the mutant N. To ensure that the levels of N expressed corresponded to the amount of N-expressing plasmid added, transfected cells were lysed with RIPA buffer, and the cell lysates were subjected to analysis by SDS-PAGE, followed by Western blotting using the polyclonal anti-N antibodies (Fu et al., 1994). As shown in the bottom of FIG. 2, the amount of N expressed for each of the wt or the mutant N proteins was proportional to the concentrations of N-expressing plasmid added.

Figure 3:
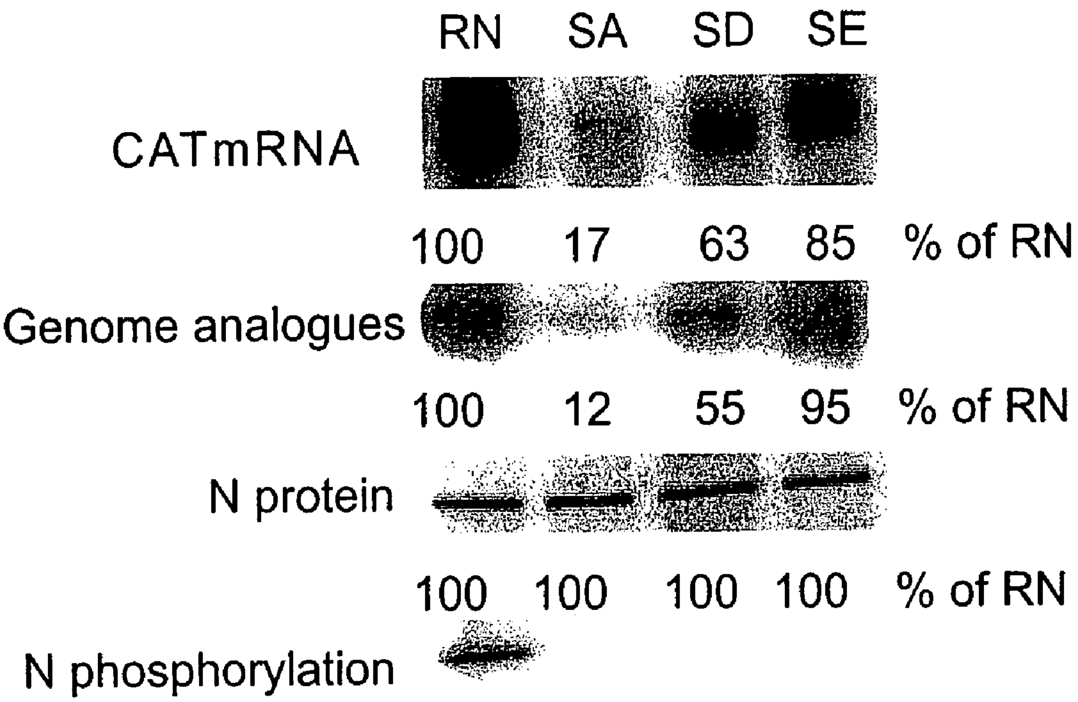
FIG. 3 depicts the effects of N concentrations on viral transcription. BSR cells were infected with recombinant vaccinia virus vTF7-3 and then transfected with plasmids pRP, pT7T-L, pSDI-CAT together with pRN, pRN-SA (SA), pRN-SD (SD), or pRN-SE (SE). Various concentrations (5, 10, 15, and 20 μg) of N or mutant N plasmids were used. Cells were harvested for CAT assay.

Phosphorylation of rabies virus N affects both transcription and replication of the rabies virus minigenome. In a previous study (Yang et al., 1999) and the study described above, only CAT activities were assayed to measure viral transcription and replication. To further determine whether N phosphorylation affects viral transcription or replication, or both, Northern blot hybridization was performed to measure the transcripts and the genomic analogues in the transfected cells. To measure viral transcription, total RNA was prepared from transfected cells, and polyA+mRNA was purified from the total RNA. To measure viral replication, transfected cells were extracted with distilled $H_2O$, and the RNP complex was immunoprecipitated with polyclonal anti-N antibodies. The complex was subjected to treatment with Trizon reagent to obtain genomic analogues. The RNA preparations were hybridized with a CAT probe labeled with [a-$^{32}$P]-dCTP by nick translation from CAT cDNA. As shown in FIG. 3, the amounts of CAT transcripts and the genomic RNA analogues were reduced when the N is unphosphorylated. The transcription and replication activities ranged from high to low in the order of wt N, N with mutation S to E, S to D, and S to A. The amounts of CAT transcripts in the cells transfected with pRN-SA, pRN-SD, or pRN-SE were 17, 63, and 85% of the wt N (pRN), respectively. These correspond well with the relative CAT activities shown in FIG. 1. The amounts of genomic analogues in the cells transfected with pRN-SA, pRN-SD, or pRN-SE were 12, 55, and 95% of the amount in cells expressing wt N (pRN), respectively, demonstrating that the synthesis of both viral transcripts and genomic analogues in the minigenome system is affected by N phosphorylation.

To, exclude the possibility that the reduced transcription and replication in the cells transfected with mutant N-expressing plasmids was caused by different levels of N synthesized, transfected cells were labeled with [$^{35}$S]methionine and lysed with RIPA buffer. The labeled N was immunoprecipitated with anti-N antibodies and analyzed by SDS-PAGE. As shown in FIG. 3, similar amounts of N or mutant N were immunoprecipitated in the cells transfected with different N constructs. To confirm that the N mutants are indeed unphosphorylated, transfected cells were labeled with [$^{32}$P]phosphoric acid. After lysis with RIPA buffer, the labeled N was immunoprecipitated with anti-N antibodies and analyzed by SDS-PAGE. Only the wt N was phosphorylated, whereas all the mutant N proteins were not (FIG. 3).

Construction and selection of mutant rabies viruses. In the minigenome system, viral proteins necessary for viral transcription and replication were synthesized by T7 polymerase, and thus their synthesis was not under the control of rabies virus regulatory machinery. Therefore, it was necessary to determine the effects of rabies virus N phosphorylation on viral transcription and replication in the full infectious virus. To this end, mutations of the serine 389 on the N to alanine (L16A), aspartic acid (L16D), or glutamic acid (L16E) were introduced into the full-length infectious clone (Schnell et al., 1994). (L16A, L16D and L16E were deposited at the American Type Culture Collection, 10801 University Boulevard, Manassas, Va. 20110-2209, USA, as deposit numbers ATCC PTA-3541, PTA-3542 and PTA-3543, respectively, on Jul. 20, 2001. After transfection of these clones into BSR cells, wt virus L16 as well as mutant viruses L16D, and L16E were obtained. However, L16A was not rescued in BSR cells. Therefore, BSR T7/5 cells (Buchholz et al., 1999) were used for selection of L16A and L16A was successfully rescued. RT-PCR and direct sequencing confirmed that these mutant viruses contained the desired mutations. The genomic RNA of the wt virus (L16) retained the codon for serine (UCU) at position 389, whereas the genomic RNAs from L16A, L16D, and L16E viruses have the serine (UCU) substituted with alanine (GCU), aspartic acid (GAU), and glutamic acid (GAA), respectively. To confirm that the mutant viruses express unphosphorylated N, BSR cells infected with each of the viruses were labeled with either [$^{35}$S]methionine or [$^{32}$P] phosphoric acid and subjected to immunoprecipitation and PAGE analysis. As was the case in the minigenome system, [$^{35}$S]methionine-labeled N was detected in BSR cells infected with each of the viruses, whereas [$^{32}$P]phosphoric acid-labeled N was detected only in BSR cells infected with L16 (data not shown), indicating that mutation of serine at position 389 abolishes N phosphorylation in the full infectious virus.

Figure 4:
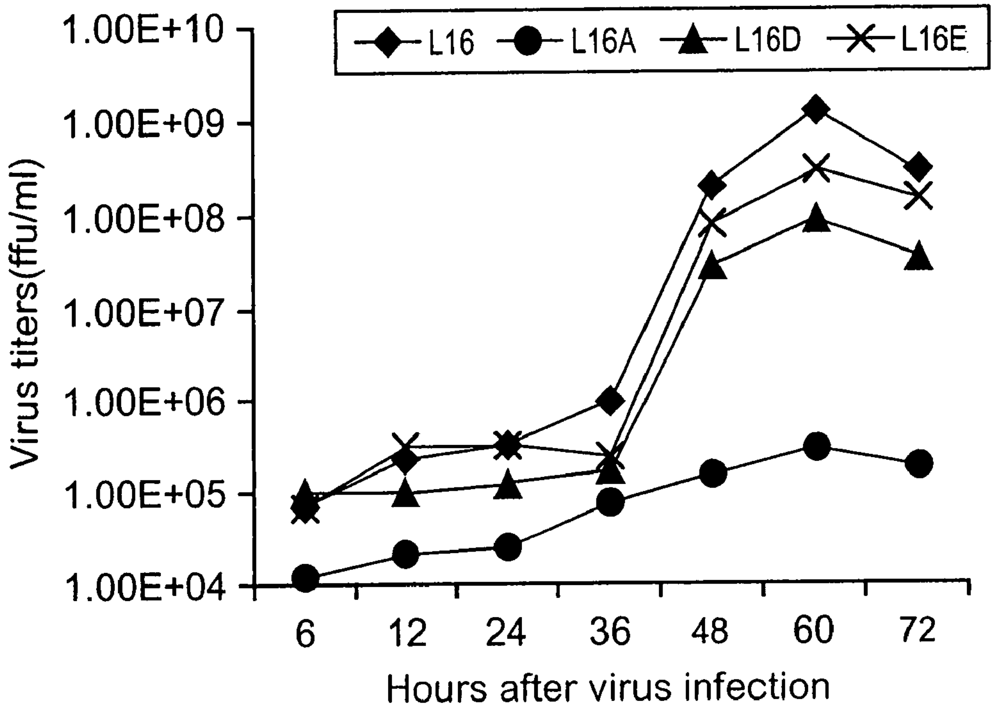
FIG. 4 depicts the virus growth curves for wt and mutant rabies viruses in BSR cells. BSR cells were infected with wt virus (L16) and mutant viruses (L16A, L16D, or L16E) at a multiplicity of infection (moi) of 1 ffu/cell and virus aliquots were removed at indicated time points and subjected to virus titration.

The mutant rabies viruses replicate more slowly than the wt virus. Initially, wt rabies virus (L16), mutant viruses L16D, and L16E grew to high titers (>$10^7$ ffu/ml) in BSR cells at 37° C., but L16A grew poorly (titers<$10^4$ ffu/ml). To overcome this difficulty, L16A was propagated in BSR cells at 31° C. as described for mutant VSV (Wertz et al., 1998) and L16A grew to higher titers (>$10^5$ FU/ml). The growth curves of the wt as well as mutant rabies viruses were investigated by infecting BSR cells with each of the viruses at a moi of 1 ffu per cell. As shown in FIG. 4, the wt virus (L16) consistently grew better than the mutant viruses and reached a titer more than $10^9$ pfu/ml at the peak of virus production (60 h). At this time, the rate of growth for the mutant viruses lagged behind, particularly for L16A. Its yield was only $10^5$ pfu/cell, at least 4 log units (10,000 times) lower than the wt virus. These data indicate that N phosphorylation promotes virus production, possibly through regulation or modulation of rabies virus transcription and replication.

Figure 5:
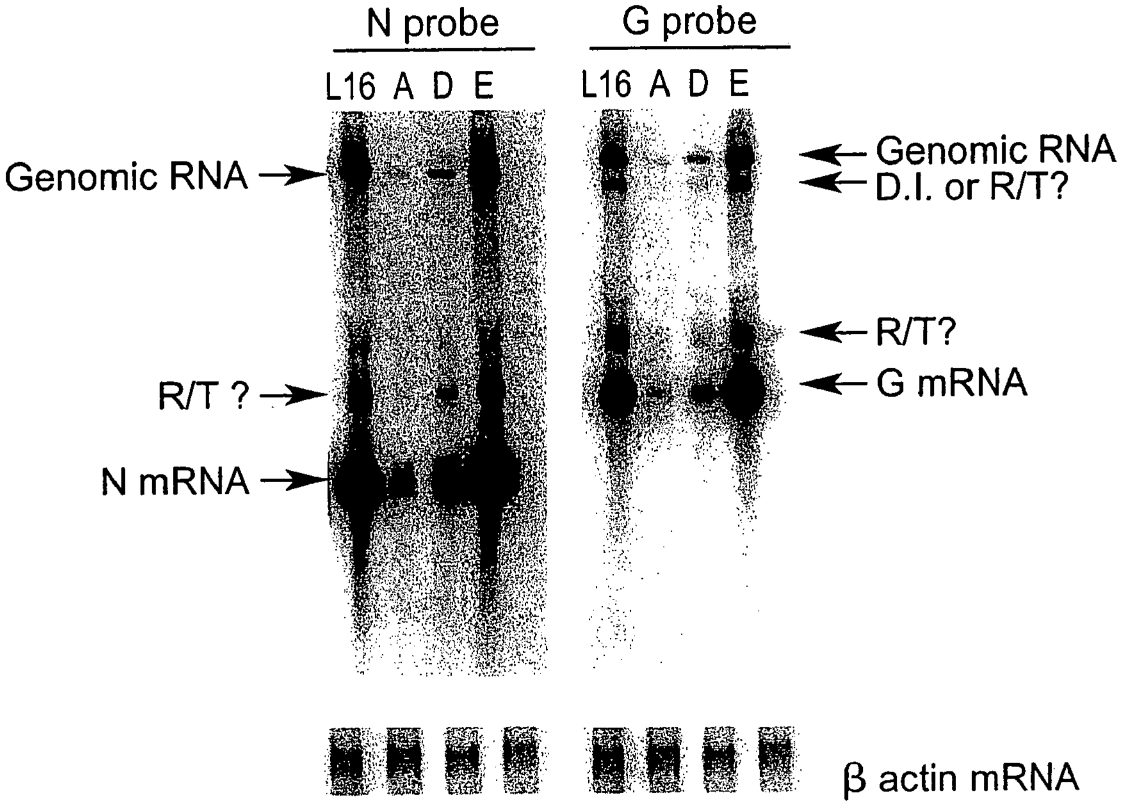
FIG. 5 shows the detection of viral transcripts and genomic RNA with either rabies virus N or G probe. Total RNA was prepared from BSR cells infected with L16, L16A (A), L16D (D), or L16E (E) and was hybridized with N probe (left panel) or the G probe (right panel). The respective mRNAs, the genomic RNA, and the possible readthrough (RT) transcripts and/or defective-interfering (DI) RNA are also indicated. The total RNA was also hybridized with a β actin probe (lower panel). The amount of N and G transcripts and genomic RNA products in relation to that of the wt virus were quantitated by densitometry.

N phosphorylation modulates both viral transcription and replication in the full infectious rabies virus. The growth curve data presented in FIG. 4 indicate that growth of the mutant viruses with unphosphorylated N, particularly the mutant virus L16A, was severely reduced. This could result from the inhibition of viral transcription or replication, or both. To investigate if both viral transcription and replication were inhibited in the mutant infectious rabies viruses, BSR cells were infected at a moi of 1 with the wt virus L16 as well as the mutant viruses L16A, L16D, or L16E. Total RNA isolated 40 hr p.i. was analyzed by Northern blot hybridization using probes made from both the N (Fu et al., 1991) or the glycoprotein (G) cDNAs (Fu et al., 1993). These probes can distinguish the N or G transcripts (1.4 kb and 1.8 kb) from the genomic RNA (12 kb). As illustrated in FIG. 5, each probe detected both genomic RNA and N or G transcripts. In addition, readthrough (RT) transcripts and/or defective-interfering (DI) RNA were also detected. The bands immediately above the N or the G transcripts, when hybridized with either G or N probes, may represent RT transcripts. The band immediately below the genomic RNA, when hybridized with the G probe, may represent RT transcript (G or L) or DI RNA. For the L16A virus, the amounts of viral genomic RNA and transcripts were 10-12% and 21-28% of the wt virus, respectively. For the L16D virus, the amounts of viral genomic RNA and transcripts were 41-45% and 60-65% of the wt virus, respectively. For the L16E virus, the amounts of viral genomic RNA and transcripts were 100% of the wt virus. Generally, the inhibition in viral replication (10-12% and 41-54%) was more severe than that in transcription (21-28% and 60-65%) in cells infected with L16A and L16D viruses. These observations, together with the data obtained from the minigenome system, indicate that unphosphorylated N results in reduction of viral replication. In the minigenome system viral replication is not dependent on viral transcription because N transcription was under control of T7 polymerase and the level of unphosphorylated N was similar to that of the wt N. Yet the amounts of genomic RNA are reduced when the N is not phosphorylated (FIG. 2), demonstrating that N phosphorylation is required for optimal viral replication.

Figure 6A:
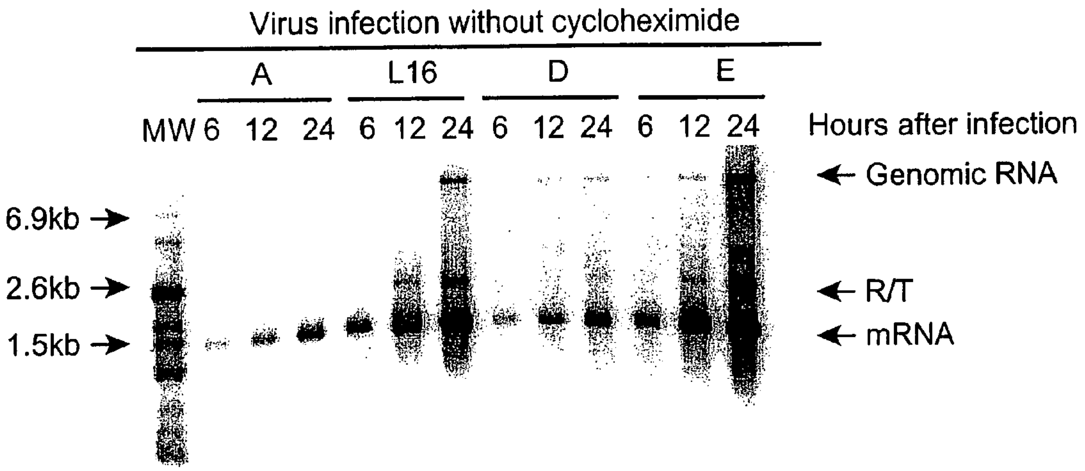
FIG. 6 shows that N phosphorylation also modulates viral transcription. BSR cells were infected with L16, L16A (A), L16D (D), or L16E (E); treated 1 hour later either without (A) or with (B) CHX; and harvested at the indicated time points for total-RNA isolation. The RNA was hybridized with an N probe. The respective mRNAs, the genomic RNA, and the possible RT transcripts are also indicated. The total RNA was also hybridized with a β actin probe (bottom). The amounts of N transcripts in relation to that for the wt virus were quantitated by densitometry.
Figure 6B:
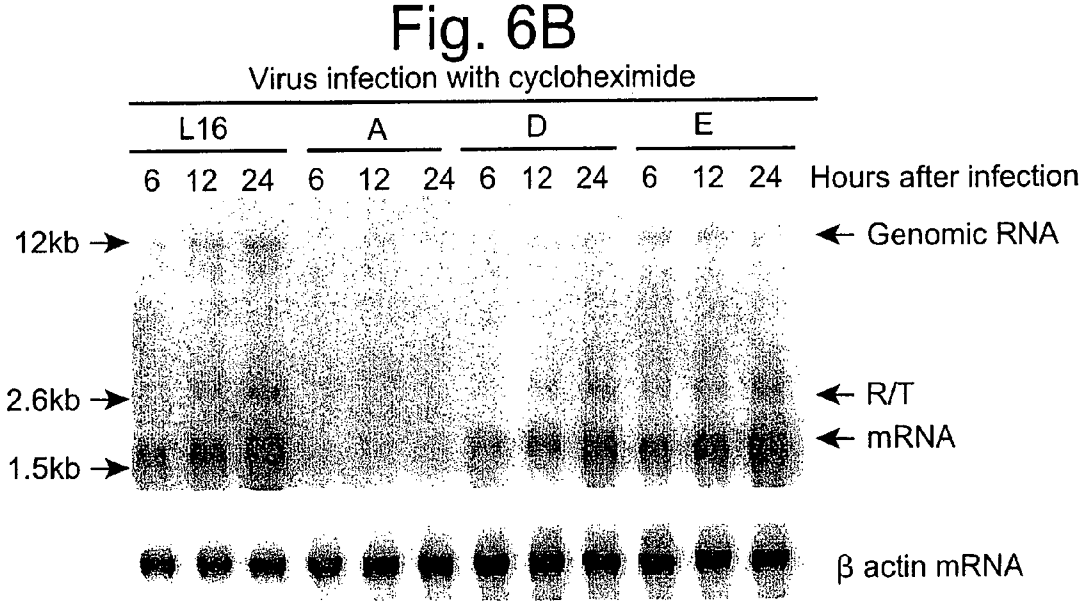

To further determine if N phosphorylation also affects viral transcription, experiments were performed to uncouple the transcription process from the replication process by inhibiting de novo protein synthesis in the infected cells with CHX. BSR cells were infected with each of the viruses at a MOI of 3 FFU per cell, and at 1 h after infection CHX was added to the culture medium at a final concentration of 150 μg/ml to completely inhibit protein synthesis (3). Infected cells without treatment with CHX were included as controls. At 6, 12, and 24 h after infection, cells were harvested and RNA was extracted for Northern blot hybridization with the rabies virus N probe. Without CHX, all the viruses replicated because the amounts of genomic RNA increased for each of the viruses as a function of time (FIG. 6A). The efficiency in viral transcription and replication for each of the viruses was similar to that shown in FIG. 5 at each time point. With the addition of CHX to the culture medium, virus replication was inhibited because the amount of genomic RNA did not increase for any of the viruses at each of the time points (FIG. 6B). Furthermore, rabies virus N protein synthesis was inhibited in BSR cells treated with CHX (data not shown). However, the amounts of transcripts for each of the viruses increased during the same period of time. Quantitation of the transcripts at each time point for each of the viruses in relation to the amount for wt L16 indicated that the transcription efficiencies for L16A, L16D, and L16E were 8 to 12%, 53 to 65%, and 91 to 100%, respectively, of that for wt virus L16. The results demonstrate definitively that unphosphorylated N, except the N with mutation from S to E, also inhibits viral transcription.

Figure 7:
FIG. 7 shows the quantitation of the ratio between genomic RNA and antigenomic RNA in the infected cells and purified virions. Total RNAs from infected cells or purified virions were hybridized with either the sense probe or the antisense riboprobes prepared from pRN by in vitro transcription. The levels of genomic and antigenomic RNA were determined by densitometry.
Figure 7:
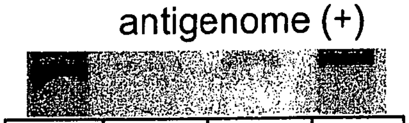
Figure 7:
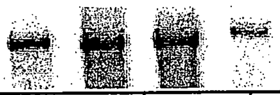
Figure 7:
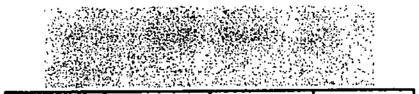

Unphosphorylated N did not alter the ratio between the genomic RNA and the antigenomic RNA. Unphosphorylated N bound more strongly to the leader RNA than the phosphorylated N (Yang et al., 1999). Therefore, it is possible that N phosphorylation plays a role in viral transcription and replication by encapsidating more antigenomic RNA than genomic RNA. This is because the unphosphorylated N, due to its stronger binding to the antigenomic RNA (Yang et al., 1999), the first step in viral replication, may reduce the synthesis of the progeny negative-strand genomic RNA, thus changing the ration of genomic to antigenomic RNA. To test this hypothesis, total RNA extracted from BSR cells infected with each of the wt or mutant viruses were subjected to Northern blot hybridization with sense (transcribed by T7 polymerase) or antisense (transcribed by SP6 polymerase) riboprobes made from pRN template. RNA was also prepared from virions purified from BSR cells infected with each of the viruses. The ratios of genomic RNA and antigenomic RNA in the infected cells for the wt and mutant viruses was roughly similar (3:1) (FIG. 7). The ratios for these viruses found in the purified virions were also similar (16:1 to 19:1) for each of these viruses. These data indicate that N phosphorylation probably does not affect the preferential encapsidation and packaging of the genomic RNA over antigenomic RNA.

That both rabies virus transcription and replication are reduced when the phosphorylated serine of the N is mutated, has ben demonstrated both in the minigenomic system and with infectious virus. When N was unphosphorylated, the rates of transcription and replication were reduced as much as 10-fold when compared with the phosphorylated N. The viral yield for these mutant viruses was reduced as much as 10,000-fold, particularly when the phosphorylated serine was mutated to alanine. These data suggest that phosphorylation of rabies virus N, although it is not absolutely necessary, is important in modulation of rabies virus transcription and replication. Furthermore, interpretation of the data also suggest that the effects of phosphorylation of rabies virus N on viral transcription and replication are due to a combination of the structure of the serine and the net negative charge of the phosphate moiety. Mutation of the phosphorylated serine of rabies virus N to the neutral amino acids alanine and glycine reduced viral transcription and replication by as much as 10-fold. Alternatively, mutation of the phosphoserine to aspartic acid or glutamic acid, both of which contain acidic side chains that are negatively charged at physiological pH, restored the viral transcription and replication activities to more than 60% and 80% of that of the phosphorylated N. However, when the S was mutated to N or Q, both of which have structures similar to those of D and E but lack the negative charge, viral transcription activities were reduced by at least one-third but were still higher than those resulting from S to A or S to G mutations. Furthermore, the fact that mutant virus L16A grow better at 31° C. than at 37° C. indicates the temperature sensitivity of the mutant virus. These results suggest that both the structure of the amino acid and the net negative charge of the phosphate moiety are important for viral transcription and replication.

Rabies virus N, like its counterpart in VSV, plays vital roles in regulating viral RNA transcription and replication by encapsidating de novo synthesized viral genomic RNA (Wagner and Rose, 1996; Wertz et al., 1987; Wunner, 1991, 23, 25, 27). The fact that rabies virus N, but not VSV N, is phosphorylated has raised questions as to how the phosphorylation is involved in the regulation of rabies virus RNA transcription and replication (Wunner, 1991). Yang et al., 1999, and studies presented herein suggest that both viral transcription and replication of the minigenome as well as the full infectious virus were inhibited when the N is not phosphorylated. The amounts of both viral transcripts and genomic analogues were lower in cells transfected with unphosphorylated N constructs than in cells transfected with the phosphorylated N. Similarly, the amounts of both viral transcripts and genomic RNA were lower in cells infected with the mutant viruses expressing the unphosphorylated N than in cells infected with the wt virus. In the minigenome system, the observed reduction in viral transcription and replication was not because of differences in expression of the mutant N proteins in the transfected cells, because no differences in the level of N expression were detected in the assays.

This study also addressed whether N phosphorylation affects viral transcription, replication, or both. One possible scenario would be that N phosphorylation affects viral transcription, replication, or both. Quantitation of viral transcripts and genomic RNA in the minigenome and the infectious virus indicated that both viral transcript and genomic RNA (or analogue) levels were reduced when N was not phosphorylated (FIG. 2 and 5). However, these data do not necessarily mean that unphosphorylated N inhibits both viral transcription and replication because of the inherent complexity of viral transcription and replication in the infected cells (Wagner and Rose, 1996). Reduction in viral genome replication results in fewer templates for transcription, and this likely will decrease the accumulation of viral mRNA. On the other hand, reduction in transcription reduces the N pool and eventually led to reduction in replication. Nevertheless, one can conclude from the data obtained in the minigenome system that phosphorylated N favors viral replication. Viral replication is reduced when the N is not phosphorylated in the minigenome system (see FIG. 2) despite the fact that, in the minigenome system, viral replication is not dependent on viral transcription because N transcription is under the control of T7 polymerase. Indeed, immunoprecipitation indicated that the level of unphosphorylated N was similar to that of the wt N in the minigenomic system.

To further demonstrate if and how N phosphorylation also affects viral transcription, we uncoupled viral transcription from viral replication by inhibiting protein synthesis by treating infected cells with CHX. Viral replication is dependent on the de novo synthesis of viral N protein while transcription is not (25). Under these conditions, viral replication was reduced but transcription was not (FIG. 6), which allowed the assessment of the effects of N phosphorylation on viral transcription independent of viral replication. The data demonstrate that N phosphorylation also modulates viral transcription because viral transcription was inhibited by almost 90% when N was not phosphorylated, particularly when the phosphorylated S was mutated to A. Thus, the data demonstrate that N phosphorylation favors both viral transcription and replication.

As in all the single-stranded negative-sense RNA viruses, in rabies virus the RNP complex is the infectious unit (Wunner, 1991). The complicated interaction between the components within the RNP complex brings about rabies virus transcription and replication (Wagner and Rose, 1996; Wertz et al., 1987). Previously, it was demonstrated that dephosphorylation of purified rabies virus N encapsidated more leader RNA than phosphorylated N (Yang et al., 1999). Mutation of the serine at position 389 of the rabies virus N to alanine also resulted in increased binding to leader RNA in comparison to that for wt N. N phosphorylation affects both viral transcription and replication. It is thus possible that strong binding of unphosphorylated N to RNA may prevent L from gaining access to the genomic RNA to initiate viral transcription and replication. Although N remains bound to genomic RNA during the transcription and replication processes through the phosphate backbone (Emerson, 1982), the template-associated N has to unfold transiently such that L can gain contact with the template RNA (Bannerjee and Chattopadhyay, 1990). N phosphorylation may weaken the interaction between N and genomic RNA and therefore enables the L to gain access to and bind the RNA template to initiate transcription and replication. This hypothesis is supported by data in both the minigenomic system and the infectious virus. When the phosphorylated serine was mutated to the neutral amino acids A and G, viral transcription and replication were reduced the most. When the phosphorylated serine was mutated to the negative-charged aspartic acid or glutamic acid, transcription and replication activities were restored to more than 60 to 90% of the wt N levels. The amount of transcript and replication product in cells infected with mutant virus L16E (serine changed to glutamic acid) was essentially equivalent to that in cells infected with the wt virus L16. This occurred even though the virus production in cells infected with L16E was slightly less than in cells infected with L16. Because the genomic RNA is the template for both transcription and replication (Wagner and Rose, 1996), it is conceivable that phosphorylated N would facilitate the initiation of both transcription and replication.

Because N phosphorylation affects its efficiency of encapsidating leader RNA (Yang et al., 1999), it is possible that N phosphorylation leads to encapsidation of more antigenomic than genomic RNA (Wunner, 1991). Unphosphorylated N, by strongly binding to the antigenomic RNA, the first step in viral replication, may reduce the synthesis of the genomic RNA. The ratio between genomic RNA and antigenomic RNA remained constant in cells (approximately 3:1) infected with the wt virus or with one of the mutant viruses. The ratios between genomic and antigenomic RNA in the purified virions from all of the viruses were also similar (approximately 20:1). The ration of the genomic RNA to antigenomic RNA measured was different from that (50:1) reported previously (Finke and Conzelmann, 1997). The discrepancy may be de to the methods and quantitation used in these two studies. The RNA was quantitated by densitometry in the present experiments, whereas the RNA was quantitated by phosphor-imagine in the previously reported study. Nevertheless, the data reported herein indicate that N phosphorylation does not affect the encapsidation of either the genomic or the antigenomic RNA.

Figure 8:
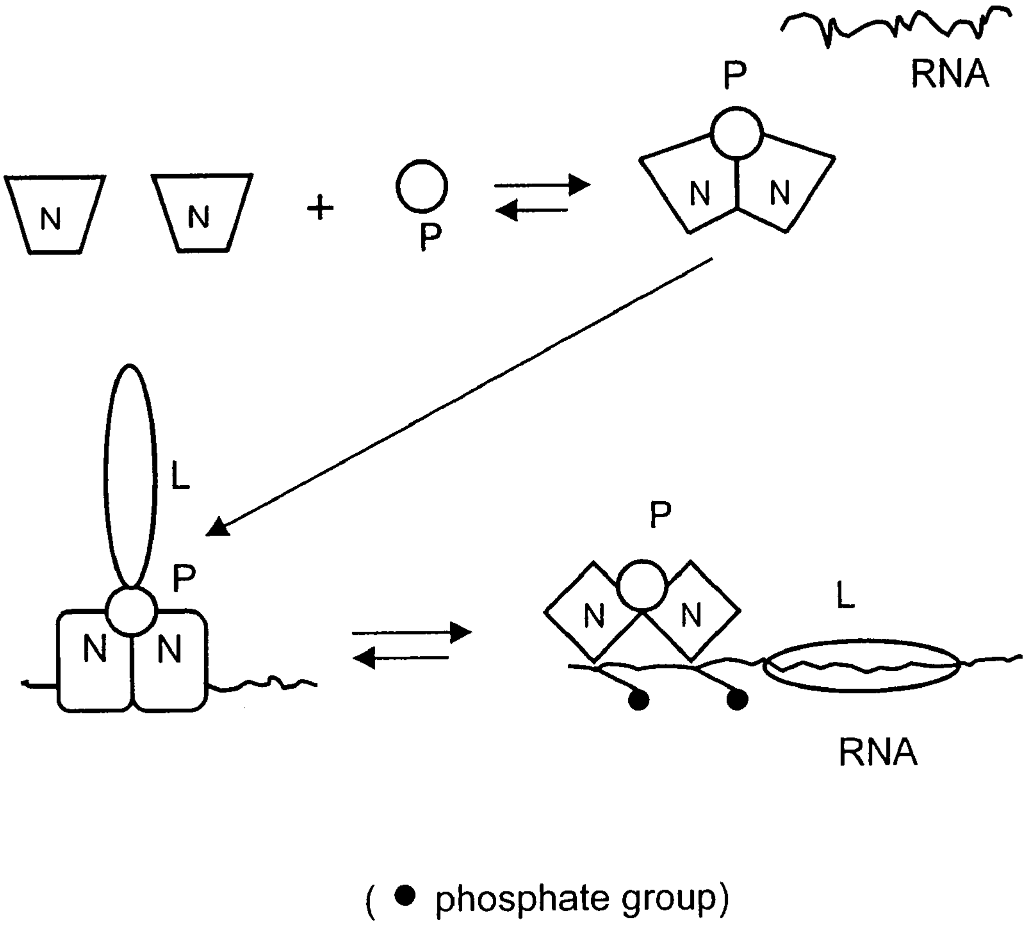
FIG. 8 shows a proposed model of N phosphorylation and its function in viral transcription and replication. N, once synthesized, interacts with P and/or L. At this stage, the N is not phosphorylated. It is possible that through the interaction of N with (encapsidation of) genomic RNA, the N goes through conformational changes, which expose the site for phosphorylation. Once the N is phosphorylated, the charge repulsion between the genomic RNA and N helps the L gain access to the genomic template for the initiation of viral RNA transcription and replication.

Recently, Kawai et al. (1999) reported that phosphorylated N is detected only in the nucleocapsid, whereas N in the free N pool (mostly in the N-P complex) is not phosphorylated. Based on that study and data presented herein, the following model is proposed to explain how rabies virus N is phosphorylated and how phosphorylation of rabies virus N modulates viral transcription and replication (FIG. 8). N is not phosphorylated in the free N or in the N-P heterocomplex, possibly because of the conformation. It is possible that the phosphorylation site is buried at this stage. It is advantageous for the N not to be phosphorylated before encapsidating genomic RNA because unphosphorylated N has higher affinity for genomic RNA than does phosphorylated N (Yang et al., 1999). The interaction (encapsidation) of genomic RNA with the N-P complex may induce conformational changes of the N, which enable N to interact with kinase, or expose serine 389 for phosphorylation, or both. Phosphorylation of N in turn may affect the interaction between the N and the genomic RNA. Following phosphorylation, the charge repulsion between the negatively charged phosphoserine and the negatively charged RNA may weaken the interaction between N and RNA. This could enable L to gain access and bind to genomic RNA, therefore initiating viral RNA transcription and replication. Evidence that supports this model comes from two studies. Unphosphorylated N binds to genomic RNA more strongly than does phosphorylated N (Yang et al., 1999), and the phosphorylation site (residue 389) is close to the putative RNA-binding domain (residues 289 to 352) (Kouznetzoff et al., 1992). Unphosphorylated N, because of tighter binding with RNA, could prevent the L from gaining access to the genome template. Consequently, the efficiency of viral RNA transcription and replication is reduced.

EXAMPLE 4

Construction of Avirulent Rabies Virus with Mutations on Both the N and G and Determination of Their Virulence and Immunogenicity Mutation of the phosphorylated serine, particularly to alanine, inhibited both viral transcription and replication in a rabies virus minigenome and with the infectious virus (Wu et al., 2001; Yang et al., 1999). The virus yield for this mutant virus (L16A) was at least 4 log units lower than the wt virus (Wu et al., 2001). All these data indicate that mutation on the N can inhibit viral replication and thus may attenuate the virus. Previously it has been reported that mutation on the G, particularly the amino acid arginine at position 333, resulted in attenuation of the rabies virus (Dietzschold et al., 1983). Attenuated rabies viruses with mutation in the arginine 333 of the G have reduced capacity to spread from the primarily infected neurons to secondary or tertiary neurons in the CNS (Coulon et al., 1989). However, the rate of replication of these mutant viruses in cell culture was not different from wt virus, indicating that mutation of G at position 333 does not result in reduced rate of viral replication (Lafay et al., 1994). This may explain why such mutant viruses can still cause rabies in neonatal animals via direct intracerebral inoculation (Schumacher et al., 1993; Lafay et al., 1994). Mutation of both the N and G will lead to further attenuation of rabies virus to an extent that the virus will no longer cause disease in animals at any age by any route of inoculation. This is because such mutant viruses will not only have a reduced ability to invade the nervous system but also have a reduced rate of replication. Therefore, avirulent rabies viruses may be selected by constructing mutations on both the N and the G proteins and to determine their virulence and immunogenicity.

Construct and select avirulent rabies viruses by mutating both the G and the N: Rabies viruses (L16A, L16D, and L16E) were constructed with mutation at the phosphorylation site of the N (Wu et al., 2001). Since the rate of replication of L16D and L16E is similar to the wt virus L16, a mutation of the G is introduced at 333 into L16 and L16A by site-directed mutagenesis as described previously (Wu et al., 2001) using two primers (SEQ ID NOS:16-17) (5'ATGCTCACTACAAGTGAAACTTGGAATCAG3' and 5'GGAGGATCTCATTCCAAGTTTCACTTGTAG3'). These primers result in mutation of the arginine residue (AGA) to glutamic acid (GAA). As has been reported previously for SAG2, two nucleotides are changed, which reduces the possibility for the G to revert to its virulent genotype (Schumacher et al., 1993; Lafay et al., 1994). A fragment (nucleotide sequences 3854-8273 of the rabies virus genome) (Conzelmann et al., 1990) containing the arginine codon of the G from the full infectious clone of the wt (pSAD-L16) (Schnell et al., 1994) is cut with XhoI and cloned into pGEM-3Z at the same site. The resulting plasmid is used as the template for construction of the mutation, using the method of Weiner et al. (Weiner et al., 1994) and the primers shown above. The arginine at position 333 is mutated to glutamic acid in the surrogate vector. After sequence analysis to confirm the mutation, the mutated XhoI fragments will be cloned back to pSAD-L16 and pSAD-L16A at the XhoI site. The mutant clones with the expected mutation and correct orientation are designated pSAD-L16G333 and pSAD-L16AG333, respectively.

To select mutant viruses with mutations on both the G and N, BSR T7/5 cells are transfected with 10 μg of pTIT-N, 2.5 μg of pTIT-P, 2.5 μg TIT-L, together with 10 μg of pSAD-L16G333 or pSAD-L16AG333, as described (Wu et al., 2001; Schnell et al., 2000). Cells are replenished with fresh medium and cultured for another three days before the supernatant is transferred to fresh BSR cells. Two days after infection, the virus are detected by using anti-rabies virus N antibodies conjugated with FITC. Positive staining of the cells will indicate successful rescuing of the infectious virus. The virus is propagated for further analysis. These two selected viruses will be designated L16G333 and L16AG333, respectively.

To further analyze the mutant viruses, growth curves are determined by infecting BSR cells with each of the viruses at a moi of 1. L16 and L16A are included for comparison. After 1 hr adsorption, the virus inoculum is removed and the cells washed three times with PBS. Fresh medium will then be added. Aliquots are removed from the culture medium at 6, 12, 18, 24, 36, 60, and 72 hr p.i. and used for virus titration as described (Wu et al., 2001). This experiment is repeated for three times and the average titer for each virus is used for comparison. To determine if these mutant viruses have reduced rate of viral replication, BSR cells are infected at a moi of 1 and harvested at 40 hr p.i. for total RNA isolation, using the method described (Wu et al., 2001). Viral genomic RNA and transcripts in the RNA preparations are analyzed by Northern blot hybridization using probes made from both the N (Fu et al., 1991) and the G cDNAs (Fu et al., 1993). Quantitation of the RNA is done by densitometry or phosphoimaging of the RNA bands. Alternatively, BSR cells infected with these viruses are labeled metabolically with [$^3$H]uridine (33 μCi/ml) for 4 hr in the presence of actinomycin D (5 μg/ml), as described for VSV (Wertz et al., 1998). Cells then are harvested for RNA extraction. The RNA is analyzed by gel electrophoresis and quantitated by densitometry. Molar ratios will be calculated from the density of each transcript and the genomic RNA.

Virus growth curves studies show that L16G333 grows in cell culture to the same high titers as L16 because previous studies showed that attenuated rabies virus with G mutation at 333 grew as well as the wt virus in cell culture (Lafay et al., 1994). Likewise, L16AG333 grows in cell culture to the same titers as the mutant virus L16A (Wu et al., 2001) and its yield will be at least 4 log units lower than that of wt virus. Northern blot hybridization and [$^3$H]uridine labeling indicates that the rate of viral replication is reduced at least five times for L16A and L16AG333 when compared with L16 and L16G333 as observed previously (Wu et al., 2001). This suggests that mutation of N at the phosphorylation site reduces the ability of the rabies virus to replicate.

EXAMPLE 5

Determination of the virulence of rabies viruses with mutations on both the G and the N. To determine the virulence of these mutant viruses, mice of two age groups (neonates and mice at 5 to 6 weeks of age) are selected. The attenuated SAD virus (L16) can induce disease in 5 to 6 week old mice (Winkler et al., 1976), and SAG-2 (with mutation on the G, similar to L16G333) can induce disease in neonatal mice (Schumacher et al., 1993) by intracerebral inoculation. There are 4 viruses to be tested including the wt L16 and mutant viruses L16A, L16G333, and L16AG333. Three doses ($10^5$, $10^6$ and $10^7$ ffu) are tested for each virus. A total of 12 groups of ICR mice (ten in each group, from Harlan) at the age of 5 to 6 weeks of age are needed for this experiment. An extra group is included as controls. Animals will be infected with 10 μl containing the desired dosage by i.c. inoculation. For the control group, mice will be injected with 10 μl of saline by the i.c. route. Animals will be observed twice daily for 20 days for signs of clinical rabies such as ruff fur, ataxia, and paralysis. Moribund mice and the mice at the end of the experiment will be euthanized by $CO_2$ inhalation. The mortality rate for each of the groups will be recorded and analyzed statistically using student T test or $X^2$ test.

To test the virulence of theses viruses in neonatal animals, a total of 12 litters of ICR mice (each pregnant mouse usually has 8 to 11 littermates, from Harlan) are needed for this experiment. Each litter is infected with one dosage of one virus. An extra litter is included as a control. Neonatal mice at one day of age are infected with 10 μl volume containing the desired doses of each virus by i.c. inoculation. For the control group, neonatal mice are injected with 10 μl of saline by the i.c. route. Animals are observed twice daily for 20 days for dead littermates. Surviving mice at the end of the experiment are euthanized by $CO_2$ inhalation. The mortality rate for each of the litters are recorded and analyzed statistically using student T test or $X^2$ test.

Wild-type (wt) virus L16 induces rabies in 5-6 week-old mice and in neonatal mice as has been shown previously (Winkler et al., 1976). Infected 5-6 week-old animals show clinical signs at day 5 to 6 p.i. and become moribund at day 6 to 8 p.i. Infected neonates show severe clinical signs or die at day 4 to 5 p.i. As described for SAG2 (Schumacher et al., 1993), L16G333, the virus that bears mutation at arginine 333 of the G, but not the mutation at the phosphorylation site of the N, will not induce any disease in the 5-6 week-old animals. However, it may induce clinical signs in neonates.

Brains of animal to which L16 is administered are removed from these animals for virus isolation and genotyping. Virus titers are determined in sick animals as described previously (Fu et al., 1996). For genotyping, total RNA is prepared from the brains and used for RT-PCR using primers (SEQ ID NOS: 13-14) 10 g (5'CTACAATGGATGCCGAC3') and 304 (5'TTGACGAAGATCTTGCTCAT3') as described (Smith et al., 1991). These primers can amplify the complete N coding sequence from the genomic RNA. The amplified fragment is directly sequenced using primer 113 (SEQ ID NO:15) (5'GTAGGATGCTATATGGG3') (Smith et al., 1991), which immediately precedes the area of the mutations on the N gene. If the titers for the mutant virus are similar to that of the wt virus and sequence analysis indicates the reversion of the mutated serine on the N, this indicates that the virus has reverted. In this case, the serine is mutated to glycine or glutamine, which changes two or all the three nucleotides of the serine codon, making it less likely to revert.

If rabies virus (L16A) with mutation at the phosphorylation site of the N does not induce any disease in either group of animals, this shows that reducing the rate of replication alone can also lead to attenuation of the rabies virus to the extent that they can no longer cause disease in neonatal animals. Such mutant viruses are sufficiently attenuated and are developed as live rabies virus vaccines.

Virus (L16AG333) that bears mutations at both the arginine 333 of the G and the phosphorylation site of the N, will not induce any disease by i.c. infection in any aged animals including the neonates. Thus, the mutation on both the G and the N renders the rabies virus avirulent because such mutated virus not only has the reduced ability to spread within the nervous system (Coulon et al., 1989) but also has a reduced rate of replication (Wu et al., 2002). If such viruses stimulate an active immune response in inoculated animals (see below), they are ideal candidates for developing avirulent live rabies virus vaccines.

EXAMPLE 6

Determination of the immunogenicity of mutant rabies viruses. To determine the immunogenicity of rabies virus (L16AG333) with mutation on both the G and the N, adult mice are selected. For comparison, L16, L16A, L16G333 are included. Three doses ($10^5$, $10^6$, and $10^7$ ffu) are tested for each virus and this will determine the minimal dose of a virus that can stimulate protective immunity. Each of the virus dosages are used for each of the three inoculation routes, that is intramuscular (i.m.), intradermal (i.d.), and subcutaneous (s.c.). A total of 36 groups of ICR mice (ten in each group) are needed for this experiment. An extra group is included as controls. Animals are immunized with 50 μL volume containing the desired virus at the desired dosage by i.m., i.d., or s.c. Mice in the control group are left unvaccinated. Mice are bled for measurement of VNA at 1, 2, 3, and 4 weeks after immunization. After the last bleeding, mice are challenged i.m. in the hind leg with 10 $MIMLD_{50}$ (50% mouse i.m. lethal dose) of CVS-24 virus as described (Fu et al., 1991). Animals are observed twice daily for development of neurological symptoms and deaths for 20 days. The mortality rates are recorded and analyzed statistically for each group of animals.

For measurement of anti-rabies virus neutralization antibodies, the rapid fluorescent focus inhibition test (RFFIT) is employed as described (Hable, 1996; Briggs et al., 1996). Briefly, serum is diluted and incubated with approximately 50 $TCID_{50}$ of the CVS-11 variant of rabies virus for 90 min. BHK cells are added and allowed to incubate for 24 hr. Cells are fixed and incubated with FITC-labeled antirabies antibody (Centocor). Virus infected cells are counted and the antibody titers are calculated using the method of Reed and Muench (Reed et al., 1938). The development of VNA is compared between all the groups of mice by statistical analysis using two-way analysis of variance with interactions (Littell et al., 1996).

WT virus L16 and all the mutant rabies viruses are capable of inducing immune responses by these parental routes of immunizations. None of these viruses will cause disease in adult mice by peripheral route of immunization, as has been demonstrated previously for the wt virus L16 (Finke et al., 2000). The VNA titers developed in mice by immunization with L16G333 may be higher than those with viruses with mutations on both the G and N because these viruses have a reduced rate of replication. Thus higher dosage may be required for L16A and L16AG333 that bear mutation on the phosphorylation site of N to induce protective immunity than the wt virus (L16) or viruses bearing only mutation on the arginine 333 of the G (L16G333). It is also possible that the VNA responses induced by these G and N mutant viruses are similar to those induced by L16G333 even though this virus may replicate better in vitro cell culture than the viruses with mutations on both the G and the N. Those viruses that grow better in cell culture may not have the advantage in the in vivo situation because these viruses have reduced ability to spread in vivo (Coulon et al., 1989). If the virus (L16AG333) with mutations on both the G and N induce comparable VNA titers as L16G333 and protect 100% of the immunized animals against challenge with virulent rabies virus, yet it will not induce any disease in neonatal animals by i.c. infection (see above), this virus is further tested as an avirulent rabies virus vaccine target animal species such as raccoons, dogs, or even humans by different routes of immunizations.

Because of the reduced rate of replication, mutant rabies virus L16A (bearing mutation from serine to alanine) grows very slowly and its yield is 4 log units lower than the wt virus L16 (Wu et al., 2002). Propagation of this virus at 31° C. increased virus production, but the virus yield is still lower than the wt virus. To overcome this difficulty, a cell line stably expressing the phosphorylated N is established for propagation of viruses with mutation on the phosphorylation site of the N. This is based on the previous observation that the unphosphorylated N is not a dominant-negative regulator and its inhibitory function on viral transcription and replication can be overcome by transcomplementing with the phosphorylated N (Yang et al., 1999). To establish a cell line stably expressing the phosphorylated N, rabies viral N coding sequence is digested from pRN with XbaI and PstI (Yang et al., 1998). The fragment is blunt-ended with Klenow and cloned into pcDNA3 (Invitrogen) at the EcoRV site. The resulting plasmid is sequenced for confirmation of orientation, and then the correct plasmid (pcDNA3-N) is transfected into BHK cells. At 48 hr after transfection, cells are harvested. Limited dilution coupled with detection of N expression are performed to select stably transfected cells. Harvested cells are diluted 10-fold serially in 96-well plate, and selective medium containing 50 μ/ml G-418 is added. The cells are further incubated for a week, and the cells expressing N are identified by FITC-conjugated anti-rabies virus N antibodies (Centoco). Cells that express N (BHK-N) are further cloned and used for propagation of N mutant rabies viruses. The level of N expression in these cells is monitored from time to time. Once the stable-N-expression cell line (BHK-N) is established, mutant rabies viruses including L16A, L16AG333, are propagated in the BHK-N cells. If a virus titer of $10^7$ ffu/ml or higher is obtainable, it will indicate that the BHK-N cells will supply sufficient phosphorylated N for the mutant virus to replicate to high titers.

Although the reduced rate of replication and the reduced ability to spread within the nervous system makes L16AG333 an ideal candidate for developing avirulent rabies virus vaccines, the mutation on N from serine (UCU) to alanine (GCU) on L16A and L16AG333 only changed one nucleotide of the serine codon. It is always possible that the alanine residue may mutate back to serine and the virus reverts to L16 genotype, particularly under the severe reduced rate of replication. Although L16A was passaged in cell culture for more than ten times, no reversion has occurred. To prevent eversion, the serine (TCT) is mutated to glycine (GGT) or glutamine (CAA), which changes either two or all the three nucleotides in the serine codon, making the reversion less likely. Glycine is a neutral amino acid and has a similar structure as alanine. Glutamine has the same structure as glutamic acid but without the negative charge. Mutation of the phosphorylated serine to either glycine or glutamine may have the same effect as the mutation from serine to alanine on viral transcription and replication (Wu et al., 2001). These mutations are easily carried out as described in Wu et al., 2001.

EXAMPLE 7

Construction of avirulent rabies virus by relocating rabies virus N gene along the virus genome and determination of their virulence and immunogenicity. Studies with a related virus, VSV, showed that rearrangement of the N within the VSV genome resulted in attenuation of VSV (Wertz et al., 1998). In that study, the N gene was relocated from the first position of the genome to the second, the third, or the fourth position along the VSV genome. The relocation of N resulted in a stepwise reduction in N expression, consequently in reduction in viral replication. Translocation of the N also resulted in stepwise attenuation of the virus in animals. Although all the mice infected intranasally with wt VSV at a dose of 300 pfu died, none of the mice infected with the same dose of N4 (the N gene is relocated to the fourth position along the genome) developed disease. Relocation of the N gene along the rabies virus genome may also lead to attenuation of the rabies virus. Thus, an avirulent rabies virus is constructed by relocating rabies virus N gene to the second, the third, or the fourth position within the rabies virus genome. The N-relocated rabies viruses, if sufficiently attenuated, have advantages over the N-mutant viruses at the phosphorylation site because the changes in the N-relocated viruses should be irreversible (Wertz et al., 1998). Although relocating the N gene resulted in attenuation of VSV, N4 still caused disease and death in mice when a higher dosage was inoculated (Wertz et al., 1998). The G mutation at arginine 333 is also incorporated into the N-relocated viruses to further attenuate the rabies virus.

Construct avirulent rabies virus by relocating the N gene. To relocate the N gene within the rabies virus genome, two plasmids are constructed. The plasmid pSAD-L16G333 is digested with XhoI, which will remove a fragment of about 4.5 kb (3854-8273 of the rabies virus genome) (Conzelmann et al., 1990) from the plasmid. pSAD-L16G333 is chosen because this plasmid already bears the mutation of arginine 333 on the G. Removing the XhoI fragment from pSAD-L16G333 aids subsequent mutagenesis because of the smaller sizes. After digestion and recovery of the two fragments (10.5 kb and 4.5 kb), the large fragment is self-ligated to form the plasmid pSAD-L16G333Xhol, which contains the N, P, M, and partial G and L genes. This plasmid also contains the intergenic sequences between N and P, between P and M and between M and G. Thus, it is used to relocate the N to the second and third position, which is between P and M and between M and G. The small fragments are cloned into pGEM-3Z vector at the XhoI site and designated pGEM-XhoI. This plasmid contains the G-L intergenic junction and is used to relocate the N to the fourth position between the G and L.

To construct recombinant viruses with rearranged N, the N at the first position is deleted from the plasmid pSAD-L16G333XhoI by using the PfuTurbo Hotstart DNA polymerase (Lundberg et al., 1991) (Stratagene). Two primers (SEQ ID NOS:18-19) are synthesized (5'ACACCCCTC-CTTTCGAACCATCCC3' and 5'CATTTTTGCTTTG-CAATTGACAATGTC3') and used in the PCR reaction. These two primers will amplify a 9 kb fragment, resulting in deletion of the N gene from the very beginning of the N transcript including the untranslated region at the 5 end, the coding region, the untranslated region at the 3 end, and the intergenic sequence between N and P. PfuTurbo Hotstart DNA polymerase creates blunt ends (Lundberg et al., 1991) in the amplified fragments and thus can be self-ligated. The ligated plasmids are sequenced at the mutation junction to make sure that there are no spurious mutations in the leader sequence and the starting sequence of the P mRNA. The resulting plasmid is designated pSAD-PMG and will be used for the construction of the rearranged N clones. Because PfuTurbo Hotstart DNA polymerase can amplify up to 15 kb sequence from vector DNA (Stratagene), there is no problem because the plasmid pSAD-L16G333XhoI is only about 10 kb in size.

Because every rabies virus transcript starts with AACA, a unique HpaI restriction site (GTTAAC) is created at each of the gene junctions for cloning of the N gene. To clone the N gene into the second position along the genome, a unique HpaI site is first created between the P and M genes, immediately after the intergenic sequence. This is accomplished by site-directed mutagenesis using the method of Weiner et al. (Weiner et al., 1994). Two primers (SEQ ID NOS:20-21) are synthesized (5'TCAACATGAAAAAAACAGTTAACAC-CACT3' and 5'AGGGGTGTTAACTGTTTTTTTCATGT-TGA3' and used to construct the unique HpaI site between the P and the M genes on pSAD-PMG. The mutation is confirmed by sequence analysis and the plasmid is designated pSAD-PHMG. Then the entire N gene from the beginning of the transcript to the intergenic sequence is amplified, using Pfu-Turbo Hotstart DNA polymerase with primers (SEQ ID NOS: 22-23) 5'ACACCCCTACAATGGATGCCG3' and 5"GTTTTTTTCATGATGGATATACAC3 and then cloned into the HpaI site of pSAD-PHMG. After confirmation by sequence analysis, the plasmid with the correct orientation is selected. The introduction of the HpaI site, although does not change the initiation of the inserted N transcript, alters the intergenic sequence. Thus, the intergenic sequence has to be restored. This is carried out by site-directed mutagenesis using primers (SEQ ID NOS:24-25) 5'ATGGAAAAAAA-CAGGCAACTG3' and 5'AGTTGCCTGTTTTTTTC-CATG3'. After confirmation by sequence analysis, the plasmid with the corrected intergenic sequence is selected and designated pSAD-PNMG. Finally, an XhoI fragment will be cut from pGEM-XhoI and cloned into the XhoI site of the pSAD-PNMG to create the full-length rabies virus clone with the N gene cloned into the second position. This plasmid is designated pSAD-N2, and contains the exact rabies virus full length sequence except the N gene is located between the P and M genes along the rabies virus genome.

To clone the N gene into the third position along the genome, a unique HpaI site is created between the M and G genes, immediately after the intergenic sequence. This is carried out by site-directed mutagenesis using primers (SEQ ID NOS:26-27) 5 'GATGTGAAAAAAACTGTTAACATC-CCTC3' and 5'AGGGATGTTAACAGTTTTTTTCA-CATCC3' which leads to the construction of a unique HpaI site between the M and the G genes on pSAD-PMG. The mutation is confirmed by sequence analysis, and the plasmid is designated pSAD-PMHG. Then the entire N gene amplified as described above will then be cloned into the HpaI site of pSAD-PMHG. After confirmation by sequence analysis, the plasmid with the correct orientation is selected. The introduction of the HpaI site alters one nucleotide in the intergenic sequence. Thus, the intergenic sequence is restored by site-directed mutagenesis using primers (SEQ ID NOS:28-29) 5'TGAAAAAAACTATTAACATCCCTC3' and 5'AGGGAT-GTTAATAGTTTTTTTCAC3'. After confirmation by sequence analysis, the plasmid with the corrected intergenic sequence is selected and designated pSAD-PMNG. Again, the XhoI fragment will be cloned into pSAD-PMNG to create the full-length rabies virus clone with the N gene cloned into the third position. This plasmid is designated pSAD-N3.

To clone the N gene into the fourth position along the genome, a unique HpaI site is created between the G and L genes, immediately after the intergenic sequence of the G+Y (Conzelmann et al., 1990). This mutation is introduced into the gene on plasmid pGEM-XhoI because this plasmid contains the intergenic sequence between the G and L genes. This is carried out by site-directed mutagenesis using primers (SEQ ID NOS:30-31) 5'CAGAAGAACAACTGTTAA-CACTTCTC3' and 5'AGAAGTGTTAACAGTTGTTCT-TCTG3' which will lead to the construction of a unique HpaI site between the G and L genes on pGEM-XhoI. The mutation is confirmed by sequence analysis and the plasmid is designated pGEM-GHL. Then the entire N gene amplified as described above is cloned into the HpaI site of pSAD-GHL. After confirmation by sequence analysis, the plasmid with the correct orientation is selected. The introduction of the HpaI site alters two nucleotides in the intergenic sequence. Thus, the intergenic sequence is restored by site-directed mutagenesis using the following primers (SEQ ID NOS:32-33) (5'AACAACTGGCAACACTTCTC3' and 5'AGAAGTGT-TGCCAGTTGTTC3'. After confirmation by sequence analysis, the plasmid with the corrected intergenic sequence is selected and designated pGEM-GNL. The XhoI fragment containing G, N, and L is cut and cloned into the XhoI sites of pSAD-PMG to create the full-length rabies virus clone with the N gene in the fourth position. This plasmid is designated pSAD-N4, and it will contain the exact rabies virus full-length sequence except the N gene is located between the G and L genes along the rabies virus genome.

To select these viruses with relocated N genes, these plasmids containing the full-length viral genome are individually transfected into BSR T7/5 cells, together with pTIT-N, pTIT-P, and TIT-L, as described (Wu et al., 2001; Schnell et al., 2000). Cells are replenished with fresh medium and cultured for another 3 days before the supernatant is transferred to fresh BSR cells. Two days after infection, virus is detected by using anti-rabies virus N antibodies conjugated with FITC. Positive staining of the cells will indicate successful rescuing of the infectious virus. These viruses are designated as L16N2G333, L16N3G333 and L16N4G333. The virus is propagated for further analysis in either BHK cells or BHK-N cells.

To further analyze these rearranged viruses, growth curves of these viruses are determined by infecting BSR cells with each of the viruses at a moi of 1. L16G333 is included for comparison. After 1 hr adsorption, virus inoculum is removed and cells washed three times with PBS. Fresh medium will then be added. Aliquots are removed from the culture medium at 6, 12, 18, 24, 36, 60, and 72 hr p.i. and used for virus titration as described (Wu et al., 2001). This experiment is repeated for three times and the average titer for each virus is used for comparison. To determine if these N-relocated viruses have reduced rate of viral replication, BSR cells are infected with L16G333 or each of the N-relocated viruses at a moi of 1 and harvested at 40 hr p.i. for total RNA isolation, using the method described (Wu et al., 2001). Viral genomic RNA and transcripts in the RNA preparations are analyzed by Northern blot hybridization using probes made from both the N (Fu et al., 1991) and the G cDNAs (Fu et al., 1993). Quantitation of the RNA is done by densitometry or phosphoimaging of the RNA bands. Alternatively, BSR cells infected with these viruses are labeled metabolically with [$^3$H]uridine (33 μCi/ml) for 4 hr in the presence of actinomycin D (5 μg/ml), as described for VSV (Wertz et al., 1998). Cells then are harvested for RNA extraction. The RNA is analyzed by gel electrophoresis and quantitated by densitometry. The molar ratio among the five transcripts and genomic RNA is determined and compared among these viruses.

Virus growth curves studies show that virus yield for these viruses is in the order of L16G333, L16N2G333, L16N3G333, and L16N4G333. In the study of VSV N relocation, it was found that the virus yield was reduced as much as 4 log units for the N4 virus when compared with the wt VSV (Wertz et al., 1998). The virus yield for L16N4G333 is reduced by as much as 4 log units when compared with that of L16G333. Northern blot hybridization and [$^3$H]uridine labeling indicates that the rate of viral replication (genomic RNA) is reduced for the N-relocated viruses when compared with L16G333, with the L16N4G333 the lowest. Furthermore, the molar ratio among the five viral transcripts is altered, depending on the relative position of the N along the viral genome. For L16G333, the amounts of the transcripts is in the order of N>P>M>G>L; L16N2G333, P>N>M>G>L; L16N3G333, P>M>N>G>L; and L16N4G333, P>M >G>N>L. These data together will indicate that by relocating the N along the rabies virus genome, the rate of rabies virus replication is reduced, which may result in attenuation of the N-relocated viruses. Because the mutation of G at arginine 333 is incorporated into these N-relocating viruses, these N-relocated viruses will not only have a reduced rate of replication but will also have a reduced capacity of invading the nervous system. The N-relocated rabies viruses, if sufficiently attenuated, have advantages over the N-mutant viruses at the phosphorylation site because the changes made in the N-relocated viruses should be irreversible (Wertz et al., 1998), whereas the point mutation at the phosphorylation site (Wu et al., 2002) may revert to its virulent genotype. If any of these N-relocated viruses no longer causes diseases in neonatal mice by i.c. inoculation (see below), it will have the potential to be developed as an avirulent rabies virus vaccine.

Determination of the virulence of the N-relocated rabies viruses. To determine the virulence of the N-relocated rabies viruses, mice of two age groups (neonates and mice at 5 to 6 weeks of age) are selected. For comparison, L16G333 is included. L16G333 can induce disease in neonatal mice, but not in older mice (Schumacher et al., 1993) by intracerebral inoculation. There are 4 viruses to be tested including L16G333, L16-N2G333, L16-N3G333, L16-N4G333. Three doses ($10^5$, $10^6$ and $10^7$ ffu) are tested for each virus. A total of 12 groups of ICR mice (ten in each group) at the age of 5 to 6 weeks of age are needed for this experiment. An extra group is included as controls. Animals are infected with 10 μl containing the desired dosage by i.c. inoculation. For the control group, mice are injected with 10 μl of saline by the i.c. route. Animals are observed twice daily for 20 days for signs of clinical rabies such as ruff fur, ataxia, and paralysis. Moribund mice and the mice at the end of the experiment are euthanized by $CO_2$ inhalation. The mortality rate for each of the groups is recorded and analyzed statistically using student T test or $X^2$ test.

To test the virulence of theses viruses in neonatal animals, a total of 12 litters of ICR mice is needed. Each litter is infected with one virus. An extra litter is included as a control. Neonatal mice at one day of age are infected with 10 μl volume containing the desired doses of mutant viruses by i.c. inoculation. For the control group, neonatal mice are injected with 10 μl of saline by the i.c. route. Animals are observed twice daily for 20 days for dead littermates. Surviving mice at the end of the experiment are euthanized by $CO_2$ inhalation. The mortality rate for each of the litters is recorded and analyzed statistically using student T test or $X^2$ test.

L16G333 does not induce disease in the 5 to 6-week-old animals. For the N-relocated viruses, the virulence is in the order of L16G333>L16N2G333>L16N3G333>L16N4G333. Because these viruses bear mutation on the arginine 333 of the G, they should not cause any diseases in the 5 to 6 week-old mice but may cause disease in the neonates. Because the studies with VSV indicate that the rate of replication for the N4 virus was severely reduced (Wertz et al., 1998), the rate of replication for L16N4G333 may also be reduced dramatically. Because L16-N4G333 also bears the mutation on the arginine 333 of the G, it will not only have a reduced rate of replication but will also have the reduced ability to spread in the CNS. Thus, it may not cause any disease in neonates. If this is the case, L16-N4G333 will have the potential to be developed as an avirulent rabies virus vaccine. L16N2G333 and L16N3G333 may also be avirulent in neonatal animals, thus they can also be developed as avirulent rabies virus vaccines.

Determination of the immunogenicity of the N-relocated rabies viruses. To determine the immunogenicity of these N-relocated viruses, adult mice are selected. There are 4 viruses to be tested including L16G333, L16N2G333, L16N3G333, and L16N4G333. Three doses ($10^5$, $10^6$, and $10^7$ ffu) are tested for each virus and this will determine the minimal dose of a virus that can stimulate protective immunity. Each of the virus dosages is used for each of the three inoculation routes, that is i.m., i.d., and s.c. A total of 36 groups of adult ICR mice (ten in each group) are needed for this experiment. An extra group will be included as controls. Animals are immunized with 50 μl volume containing the desired virus at the desired dosage by i.m., i.d., or s.c. Mice in the control group are left unvaccinated. Mice are bled for measurement of VNA (Hable, 1996; Briggs et al., 1996) at 1, 2, 3, and 4 weeks after immunization. After the last bleeding, mice are challenged i.m. in the hind leg with 10 $MIMLD_{50}$ (50% mouse i.m. lethal dose) of CVS-24 virus as described (Fu et al., 1991). Animals are observed twice daily for development of neurological symptoms and deaths for 20 days. The mortality rates are recorded and analyzed statistically for each group of animals.

All the N-relocated rabies viruses are capable of inducing immune responses by these parental routes of immunizations. None of these viruses cause disease in adult mice by peripheral routes of immunization. The VNA titers developed in mice by immunization with L16G333 may be higher than those immunized with the N-relocated viruses. Because of the differences in the rate of replication, the levels of VNA may be in the order of L16G333>L16N2G333>L16N3G333>L16N4G333. It is possible that the levels of VNA induced by these N-relocated viruses are similar. Immunization with any of these viruses leads to protection against a challenge. The virus that can induce comparable VNA as L16G333 and provide 100% protection, but does not induce disease in neonatal animals and grows the best in vitro cell culture, is selected for further testing in target animal species such as raccoons, dogs, or even humans.

As for the viruses with mutation on the phosphorylation site of the N, N-relocated viruses may not grow well in cell culture because of the reduced rate of replication as reported for VSV (Wertz et al., 1998). These viruses are grown in BHK-N cells that stably express the phosporylated N. Because the reduced rate of replication is due to the reduced level of N in the infected cells (Wertz et al., 1998), supplementing N in the BHK-N cells increases the virus yield for these N-relocated viruses.

Because of the sequence similarity between that spanning from the end of P, the intergenic region between P and M, to the beginning of the M transcript and that spanning from the end of M, the intergenic region between M and G, and the beginning of the G transcript, the insertion of the unique HpaI site may be difficult at the P-M and the M-G junctions on pSAD-PMG. Thus, the annealing temperature in the PCR reaction is varied, multiple clones are screened, and only the desired mutation is selected for further cloning.

As reported for VSV, N4, which is the mutant virus with the N in the fourth position along the VSV genome, still caused disease and death in mice when a higher dosage was inoculated (Wertz et al., 1998). If rabies virus with relocated N may still have residual virulence, the serine is mutated to alanine at the phosphorylation site of the N to further attenuate the N-relocated viruses. If the immune responses induced by the N-relocated viruses are low because the rate of replication of these viruses is severely decreased, viruses are constructed with increased expression of the G, which is the only antigen that induces protective viral neutralizing antibodies (Cox et al., 1977). This is accomplished by reshuffling the genes within the rabies virus genome.

EXAMPLE 8

Construction of avirulent rabies virus by shuffling the genes within the rabies virus genome and determination of the virulence and immunogenicity of these reshuffled rabies viruses. In addition to the relocation of the N gene along the VSV genome, reshuffling the genes within the VSV genome also led to phenotypic changes of VSV (Ball et al., 1999). Although some of the reshuffled VSV acquired more virulent characteristics when compared to the wt virus, other reshuffled VSV showed reduced rate of replication in cell culture and reduced virulence in animals (Ball et al., 1999). Most importantly, moving the G from the fourth position to the first position not only resulted in attenuation of the virus, but also led to accelerated and enhanced immune responses in animals (Flanagan et al., 2000). Thus, avirulent rabies virus is constructed by reshuffling rabies virus genes within the rabies virus genome, particularly by moving the G from the fourth position to the first position and reshuffling the P, M and G genes. In addition, the G mutation at arginine 333 is incorporated into each and every reshuffled virus to further attenuate the rabies virus.

Construction of avirulent rabies virus by reshuffling rabies virus genes within the viral genome. To reshuffle the genes within the rabies virus genome, the procedure used for relocating the N gene as described above is followed. To construct rabies viruses with the G in the first position, the plasmids pGEM-GHL and pSAD-L16G333XhoI is used. First, the N, P, and M genes are deleted from the plasmid pSAD-L16G333XhoI. Two primers (SEQ ID NOS:34 and 19) (5'ACATCCCTCAAAAGACTCAAGG3' and 5'CATTTTTGCTTTGCAATTGAC AATGTC3') are synthesized and used in the PCR reaction by using the PfuTurbo Hotstart DNA polymerase (Lundberg et al., 1991) (Stratagene). These two primers amplify a 7.3 kb fragment, resulting in the deletion of the N, P, and M genes from the very beginning of the N transcript to the intergenic sequence between M and G. PfuTurbo Hotstart DNA polymerase creates blunt ends (Lundberg et al., 1991) in the amplified fragments and thus are self-ligated. The ligated plasmids are sequenced at the mutation junction to make sure that there are no spurious mutations in leader sequence and the starting sequence for the G mRNA. The resulting plasmid is designed pSAD-L16G. Three rabies virus clones are constructed with the G in the first position in combination with the N in the second (G1N2), the third (G1N3), or the fourth position (G1N4). To construct the G1N2 clone, the N, P, and M genes from the beginning of the N transcript to the intergenic sequence of the M (3.2 .kb) are amplified from pSAD-L16G333XhoI by using PfuTurbo DNA polymerase with primers (SEQ ID NOS:22 and 35) 5'ACACCCCTACAATGGATGCCG3' and 5'ATAGTTTTTTTCACATCCAAGAGG3'. The amplified fragment is cloned into the HpaI site of pGEM-GHL. After confirmation by sequence analysis, the plasmid with the correct orientation is selected. Then the intergenic sequence is restored by site-directed mutagenesis using primers (SEQ ID NOS:36-37) (5'AGAAAGAACAACTGGCAACACCCCT3' and 5'GGGGTGTTGCCAGTTGTTCTTTCTG3'. After confirmation by sequence analysis, the plasmid with the corrected intergenic sequence is selected and designated pGEM-GNMPL. Finally, the XhoI fragment from pGEM-GNMPL is cloned into pSAD-G to create the full-length rabies virus clone with the G gene cloned in the first position. This plasmid is designated pSAD-L16G1N2G333.

To construct the G1N3 clone, the P, N, and M genes from the beginning of the P transcript to the intergenic sequence of the M (3.2 kb) are amplified from pSAD-PNMG, as constructed in specific aim 2, using Pfu DNA polymerase with primers (SEQ ID NOS:38-39) 5'ACACCCCTCCTTTCGAACCATCCC3' and 5'ATAGTTTTTTTCACATCCAAGAGG3'. The amplified fragment is cloned into the HpaI site of pGEM-GHL, also as constructed in specific aim 2. After confirmation by sequence analysis, the plasmid with the correct orientation is selected. Then, the intergenic sequence is restored by site-directed mutagenesis using primers (SEQ ID NOS:40 and 37) (5'AGAAAGAACAACTGGCAACAC-CCCT3' and 5'GGGGTGTTGCCAGTTGTTCTTTCTG3'. After confirmation by sequence analysis, the plasmid with the corrected intergenic sequence is selected and designated pGEM-GPNML. Finally, the XhoI fragment from pGEM-GPNML is cloned into pSAD-G to create the full-length rabies virus clone with the G gene cloned in the first position and the N in the third position. This plasmid is designated pSAD-L16G1N3G333.

To construct the G1N4 clone, the P, M, and N genes from the beginning of the P transcript to the intergenic sequence of the N (3.2 kb) is amplified from pSAD-PMNG by using PfuTurbo DNA polymerase with primers (SEQ ID NOS:38 and 23) 5'ACACCCCTCCTTTCGAACCATCCC3' and 5'GTTTTTTTCATGATGGATATACAC3' and cloned into the HpaI site of pGEM-GHL. After confirmation by sequence analysis, the plasmid with the correct orientation is selected. Then the intergenic sequence is restored by site-directed mutagenesis using primers (SEQ ID NOS:36-37) (5'AGAAAGAACAACTGGCAACACCCCT3' and 5'GGGGTGTTGCCAGTTGTTCTTTCTG3'). After confirmation by sequence analysis, the plasmid with the corrected intergenic sequence is selected and designated pGEM-GP-MNL. Finally, the XhoI fragment from pGEM-GPMNL is cloned into pSAD-G to create the full-length rabies virus clone with the G gene cloned in the first position and the N in the fourth position. This plasmid is designated pSAD-L16G1N4G333.

There are, in addition to the wt virus (P-M-G), five possible combinations (P-G-M, M-P-G, M-G-P, G-M-P, and G-P-M) for reshuffling the P, M, and G genes within the rabies virus genome. To construct M-P-G, M-G-P, and P-G-M, the plasmids pGEM-XhoI and pSAD-L16G333XhoI are used. First, the P gene will be deleted from the plasmid pSAD-L16G333XhoI. Two primers (SEQ ID NOS:41-42) (5'ACACCACTGATAAAATGAACCTCC3' and 5'GTTTTTTTCATGATGGATATAGAG3' are synthesized and used in the PCR reaction by using the PfuTurbo Hotstart DNA polymerase (Stratagene). These two primers amplify a 9.5 kb fragment, resulting in the deletion of the P gene from the very beginning of the P transcript to the intergenic sequence between P and M. PfuTurbo Hotstart DNA polymerase creates blunt ends (Lundberg et al., 1991) in the amplified fragments and thus can be self-ligated. The ligated plasmids are sequenced at the mutation junction to make sure that there are no spurious mutations in the 3 untranslated sequence of the N, the intergenic sequence of the N, and the starting sequence for the M mRNA. The resulting plasmid is designed pSAD-NMG.

To reshuffle the genes into the order of N-M-P-G-L, a unique HpaI restriction site (GTTAAC) is created on pSAD-NMG at the gene junction between M and G. This is carried out by site-directed mutagenesis using primers ((SEQ ID NOS:26-27) 5'GATGTGAAAAAAACTGTTAACATC-CCTC3' and 5'AGGGATGTTAACAGTTTTTTTCA-CATCC3' as described for the relocation of the N gene. The mutation is confirmed by sequence analysis and the plasmid is designated pSAD-NMHG. Finally, the entire P gene, from the beginning of the transcript to the intergenic sequence, is amplified by using PfuTurbo DNA polymerase with primers (SEQ ID NOS:18 and 43) 5'ACACCCCTCCTTTCGAAC-CATCCC3' and 5'CCTGTTTTTTTCATGT-TGACTTTGGG3' and cloned into the HpaI site of pSAD-PMHG. After confirmation by sequence analysis, the plasmid with the correct orientation is selected. Then the intergenic sequence is restored by site-directed mutagenesis using the following primers (SEQ ID NOS:24-25) (5'ATG-GAAAAAAACAGGCAACTG3' and 5'AGTTGCCT-GTTTTTTTCCATG3'). After confirmation by sequence analysis, the plasmid with the corrected intergenic sequence is selected and designated pSAD-NMPG. Finally, the XhoI fragment from pGEM-XhoI is cloned into pSAD-NMPG to create the full-length rabies virus clone with the P gene cloned between the M and G genes. This plasmid is designated pSAD-L16MPG.

To reshuffle the genes into the order of N-M-G-P-L, the entire P gene amplified as described above is cloned into the unique HpaI site of pGEM-GHL. After confirmation by sequence analysis, the plasmid with the correct orientation is selected. Then the intergenic sequence is restored by site-directed mutagenesis using the primers (SEQ ID NOS:32-33) 5'AACAACTGGCAACACTTCTC3' and 5'AGAAGTGT-TGCCAGTTGTTC3'. After confirmation by sequence analysis, the plasmid with the corrected intergenic sequence is selected and designated pGEM-GPL. The XhoI fragment from pGEM-GPL is cut and cloned into the XhoI sites of pSAD-NMG to create the full-length rabies virus clone with the P gene cloned between the G and the L genes. This plasmid is designated pSAD-L16MGP.

To reshuffle the genes into the order of N-P-G-M-L, the M gene is deleted from the clone pSAD-L16G333XhoI. Two primers (SEQ ID NOS:44 and 43) (5'ACATCCCTCAAA-GACTCAAGG3' and 5'CCTGTTTTTTTCATGT-TGACTTTGG3') are synthesized and used in the PCR reaction by using the PfuTurbo Hotstart DNA polymerase (Lundberg et al., 1991) (Stratagene). These two primers will amplify a 9.5 kb fragment, resulting in deletion of the M gene from the very beginning of the M transcript to the intergenic sequence between M and G. PfuTurbo Hotstart DNA polymerase creates blunt ends (Lundberg et al., 1991) in the amplified fragments and thus the PCR fragment can be self-ligated. The ligated plasmids are sequenced at the mutation junction to make sure that there are no spurious mutations in the 3 noncoding sequence of the P, the intergenic sequence, and the starting sequence for the G mRNA. The resulting plasmid is designated pSAD-NPG. The entire M gene is amplified using primers (SEQ ID NOS:45-46) 5'AACAC-CACTGATAAAATGAACCTCC3' and 5'AAT-AGTTTTTTTCACATCCAAGAGG3' and cloned into the unique HpaI site of pGEM-GHL. After confirmation by sequence analysis, the plasmid with the correct orientation is selected. Then the intergenic sequence is restored by site-directed mutagenesis using primers (SEQ ID NOS:32-33) 5'AACAACTGGCAACACTTCTC3' and 5'AGAAGTGT-TGCCAGTTGTTC3'. After confirmation by sequence analysis, the plasmid with the corrected intergenic sequence is selected and designated pGEM-GML. The XhoI fragment from pGEM-GML is cut and cloned into the XhoI sites of pSAD-NPG to create the full-length rabies virus clone with the M gene cloned between the G and L genes. This plasmid is designated pSAD-PGM.

To construct G-M-P and G-P-M, the plasmids pGEM-GML and pSAD-L16G333XhoI is used. First, the P and M genes are deleted from the clone pSAD-L16G333XhoI. Primers (SEQ ID NOS:34 and 42) 5'ACATCCCTCAAAA-GACTCAAGG3' and 5'GTTTTTTTCATGATGGATATA-GAG3' are synthesized and used in the PCR reaction by using the PfuTurbo Hotstart DNA polymerase (Lundberg et al., 1991) (Stratagene). These two primers will amplify a 8.5 kb fragment, resulting in deletion of the P and M genes from the very beginning of the P transcript to the intergenic sequence between M and G. PfuTurbo Hotstart DNA polymerase creates blunt ends (Lundberg et al., 1991), and the amplified fragments can be self-ligated. The ligated plasmids are sequenced at the mutation junction to make sure that there are no spurious mutations in the 3 end of the N sequence, the intergenic sequence, and the starting sequence for the G mRNA. The resulting plasmid is designed pSAD-NG.

To reshuffle the genes into the order of N-G-M-P-L, a unique HpaI site is created between the M and L genes on pGEM-GML. Two primers (SEQ ID NOS:47-48) are synthesized (5 'GATGTGAAAAAAACTGTTAACACTTCTC3' and 5'AGAAGTGTTAACAGTTTTTTTCACATCC3') and used for PCR using pfu DNA polymerase. The mutation is confirmed by sequence analysis, and the plasmid is designated pGEM-GMHL. Then the entire P gene amplified as described above is cloned into the HpaI site of pGEM-GMHL. After confirmation by sequence analysis, the plasmid with the correct orientation is selected. Then, the intergenic sequence is restored by with primers (SEQ ID NOS:49-50) 5'GATGTGAAAAAAACTATTAACACCC3' and 5'GGT-GTTAATAGTTTTTTTCACATCC3'. After confirmation by sequence analysis, the plasmid with the correct orientation is designated pGEM-GMPL. The XhoI fragment is cut from pGEM-GMPL and cloned into the XhoI site of pSAD-NG to create the full-length rabies virus clone with the genes in the order of N-G-M-P-L. This plasmid is designated pSAD-L16GMP.

To reshuffle the genes into the order of N-G-P-M-L, a unique HpaI site is created between the G and M genes on pGEM-GML. Two primers (SEQ ID NOS:51-52) are synthesized (5'AGAAGAACAACTGTTAACACCACTG3' and 5'AGTGGTGTTAACAGTTGTTCTTCTG3') and used for PCR. The mutation is confirmed by sequence analysis, and the plasmid is designated pGEM-GHML. Then the entire P gene amplified as described above is cloned into the HpaI site of pGEM-GHML. After confirmation by sequence analysis, the plasmid with the correct orientation is selected. Then the intergenic sequence has to be restored by site-directed mutagenesis, using primers (SEQ ID NOS:53-54): 5'AGAA-GAACAACTAAGAACACCACTG3' and 5'AGTGGTGT-TCTTAGTTGTTCTTCTG 3'. After confirmation by sequence analysis, the plasmid with the correct orientation is designated pGEM-GPML. The XhoI fragment is finally cut from pGEM-GPML and cloned into the XhoI site of pSAD-NG to create the full-length rabies virus clone with the genes in the order of N-G-P-M-L. This plasmid is designated pSAD-L16GPM.

To select the reshuffled rabies viruses, these plasmids with the reshuffled genes are individually transfected into BSR T7/5 cells, together with pTIT-N, pTIT-P, and TIT-L, as described (Schnell et al., 2000). Cells are replenished with fresh medium and cultured for another three days before the supernatant is transferred to fresh BSR cells. Two days after infection, virus is detected by using anti-rabies virus N antibodies conjugated with FITC. Positive staining of the cells indicates successful rescuing of the infectious virus. These viruses are designated as L16G1N2G333, L16G1N3G333, L16G1N4G333, L16GMPG333, L16MGPG333, L16PGMG333, L16GPMG333, and L16MPGG333, respectively. The virus is propagated for further analysis in either BHK cells or BHK-N cells.

To further analyze these reshuffled viruses, growth curves of these viruses are determined by infecting BSR cells with each of the viruses at a moi of 1. L16G333 are included for comparison. After 1 hr adsorption, virus inoculum is removed and cells washed three times with PBS. Fresh medium will then be added. Aliquots are removed from the culture medium at 6, 12, 18, 24, 36, 60, and 72 hr p.i. and used for virus titration as described (Wu et al., 2001). This experiment is repeated for three times and the average titer for each virus is used for comparison. To determine if these reshuffled viruses have a reduced rate of viral replication, BSR cells are infected at a moi of 1 ffu/cell and harvested at 40 hr p.i. for total RNA isolation, using the method described (Wu et al., 2001). Viral genomic RNA and transcripts in the RNA preparations are analyzed by Northern blot hybridization using probes made from both the N (Fu et al., 1991) and the G cDNAs (Fu et al., 1993). Quantitation of the RNA is done by densitometry or phosphoimaging of the RNA bands. Alternatively, BSR cells infected with these viruses are labeled metabolically with [$^3$H]uridine (33 μCi/ml) for 4 hr in the presence of actinomycin D (5 μg/ml), as described for VSV (Wertz et al., 1998). Cells then are harvested for RNA extraction. The RNA is analyzed by gel electrophoresis and quantitated by densitometry. The molar ratio among the five transcripts and genomic RNA is determined by densitometry and compared among these viruses.

Mutant rabies viruses with the G gene moved to the first position are constructed and selected. In addition, these viruses also bear the mutation at arginine 333 of the G. The gene order in these mutated viruses is confirmed by RT-PCR. Virus growth curves studies show that the virus yield is in the order of L16G333, L16G1N2G333, L16G1N3G333, and L16G1N4G333. Likewise, Northern blot hybridization and [$^3$H]uridine labeling indicates that the rate of viral replication (genomic RNA) is the highest for L16G333, followed by L16G1N2G333, L16G1N3G333, and L16G1N4G333. Furthermore, the molar ratio among the five viral transcripts are altered, depending on the relative position of these genes along the viral genome. For L16G333, the amounts of the transcripts are in the order of N>P>M>G>L; L16G1N2G333, G>N>P>M>L; L16G1N3G333, G>P>N>M>L; and L16G1N4G333, G>P>M>N>L. Because the mutation of G at arginine 333 is incorporated into these reshuffled viruses, these viruses not only have a reduced rate of replication but also have a reduced capacity of invading the nervous system.

Mutant rabies viruses with reshuffled P, M, and G genes within the rabies virus genome are also constructed and selected. In addition, these reshuffled viruses also bear the mutation of the G at arginine 333. The gene order in these mutated viruses is confirmed by RT-PCR. If the results for the reshuffled VSV are an indication (Ball et al., 1999), the virus growth curves studies shows that virus yield for some of these viruses (L16MPGG333, L16MGPG333, and L16PGMG333) is higher than that of L16G333. Virus yield for other reshuffled viruses (L16GPMG333 and L16GMPG333) is lower than that of L16G333. Likewise, Northern blot hybridization and [$^3$H]uridine labeling indicate that the rate of viral replication (genomic RNA) is increased for L16MPGG333, L16MGPG333, and L16PMGG333, whereas the rate of viral replication (genomic RNA) is decreased for L16GPMG333 and L16GMPG333 when compared with L16G333. Furthermore, the molar ratio among the five viral transcripts is altered, depending on the relative position of these genes along the viral genome. For L16G333, the amounts of the transcripts are in the order of N>P>M>G>L; L16MPGG333, N>M>P>G>L; L16MGPG333, N>M>G>P>L; L16PMGG333, N>P>M>G>L; L16GPMG333, N>G>P>M>L; and L16GMPG333, N>G>M>P>L. Because the mutation of G at arginine 333 is incorporated into these reshuffled viruses, these viruses not only have a reduced rate of replication but also have a reduced capacity of invading the nervous system.

Determination of the virulence of these reshuffled rabies viruses. To determine the virulence of these reshuffled viruses, mice of two age groups (neonates and mice at 5 to 6 weeks of age) are selected. There are 9 viruses to be tested including L16G333, L16G1N2333, L16G1N3G333, L16G1N4G333, L16PGMG333, L16-GPMG333, L16-GMPG333, L16-MGPG333, and L16-MPGG333. Three doses ($10^5$, $10^6$ and $10^7$ ffu) are tested for each virus. A total of 27 groups of ICR mice (ten in each group) at the age of 5 to 6 weeks of age are needed for this experiment. An extra group is included as controls. Animals are infected with 10 µl containing the desired dosage by i.c. inoculation. For the control group, mice are injected with 10 µl of saline by the i.c. route. Animals are observed twice daily for 20 days for signs of clinical rabies such as ruff fur, ataxia, and paralysis. Moribund mice and the mice at the end of the experiment are euthanized by $CO_2$ inhalation. The mortality rate for each of the groups is recorded and analyzed statistically using student T test or $X^2$ test.

To test the virulence of theses viruses in neonatal animals, a total of 27 litters of ICR mice are needed for this experiment. Each litter is infected with each dosage of one virus. An extra litter is included as a control. Neonatal mice at one day of age are infected with 10 µl volume containing the desired doses of mutant viruses by i.c. inoculation. For the control group, neonatal mice are injected with 10 µl of saline by the i.c. route. Animals are observed twice daily for 20 days for dead littermates. Surviving mice at the end of the experiment are euthanized by $CO_2$ inhalation. The mortality rate for each of the litters is recorded and analyzed statistically using student T test or $X^2$ test.

L16G333 does not induce any disease in the 5 to 6 week-old animals. However, it may induce clinical signs in neonates. Infection by viruses with the G moved into the first position, i.e., L16G1N2G333, L16G1N3G333 and L16G1N4G333, does not induce diseases in 5 to 6-week old mice because all these viruses have the arginine 333 mutated to glutamic acid. Ball et al. (Ball et al., 1999) reported that the pathogenicity of the P, M, and G reshuffled VSV did not correlate with the rate of replication in cell culture. Only those viruses that are less virulent than L16G333 are further tested for antigenicity and immunogenicity.

Determination of the immunogenicity of these reshuffled rabies viruses. To determine the immunogenicity of these reshuffled viruses, adult mice are selected. There are 9 viruses to be tested including L16G333, L16G1N2G333, L16G1N4G333L, L16-PGMG333, L16-GPMG333, L16-GMPG333, L16-MGPG333, and L16-MPGG333. Three doses ($10^5$, $10^6$, and $10^7$ ffu) are tested for each virus and this will determine the minimal dose of a virus that can stimulate protective immunity. Again three routes of inoculation are used, that is i.m., i.d., and s.c. A total of 81 groups of ICR mice (ten in each group) are needed for this experiment. An extra group is included as controls. Animals are immunized with 50 µl volume containing the desired virus at the desired dosage by i.m., i.d., or s.c. Mice in the control group are left unvaccinated. Mice are bled for measurement of VNA (Hable, 1996; Briggs et al., 1996) at 1, 2, 3, and 4 weeks after immunization. The development of VNA is compared between all the groups of mice by statistical analysis using two-way analysis of variance with interactions (Littell et al., 1996). At 4 weeks after immunization, mice are challenged i.m. in the hind leg with 10 $MIMLD_{50}$ (50% mouse i.m. lethal dose) of CVS-24 virus as described (Fu et al., 1991). Animals are observed twice daily for development of neurological symptoms and deaths for 20 days. Animals are observed twice daily and mortality rates are recorded and analyzed statistically for each group of animals.

All the mutant rabies viruses are capable of inducing immune responses by these parental routes of immunizations. None of these viruses cause disease in adult mice by peripheral route of immunization. Mice immunized with those viruses with the G in the first position may develop quicker and higher VNA responses than mice immunized with L16G333 and those reshuffled viruses with the G in other positions. This is very important for post-exposure treatment because quick immune response is necessary to neutralize incoming viruses to prevent CNS infection. Reshuffled viruses which induce comparable or higher VNA titers as L16G333 and protect 100% of the immunized animals against challenge with virulent rabies virus, yet it will not induce any disease in neonatal animals by i.c. infection (see above), are further tested as an avirulent rabies virus vaccine target animal species such as raccoons, dogs, or even humans by different routes of immunizations.

The effects on N mutants of mutating the phosphorylated serine (S) to alanine (A), glycine (G), aspartic acid (D), asparagine (N), glutamic acid (E), and glutamine (Q) were investigated by examining viral transcription and replication in the minigenome as well as the rescued virus. The results from these studies revealed that both viral transcription and replication were reduced when the N is not phosphorylated, and thus N phosphorylation plays an important role in modulating both transcription and replication of rabies virus. Furthermore, these results indicate that the effects of N phosphorylation on viral transcription and replication are due to a combination of the net negative charge of the phosphate moiety and the structure of the serine residue.

While the invention has been described and illustrated herein by references to various specific material, procedures and examples, it is understood that the invention is not restricted to the particular material combinations of material, and procedures selected for that purpose. Numerous variations of such details can be implied as will be appreciated by those skilled in the art.

The following is a list of documents related to the above disclosure and particularly to the experimental procedures and discussions. The documents should be considered as incorporated by reference in their entireties.

Aghomo, H. O., Oduye, O. O., Rupprecht, C. E. 1990. The serological response of young dogs to the Flury LEP strain of rabies virus vaccine. Vet. Res. Commun. 14:415-425.

Anderson, M. C., Baer, H., Frazier, D. J., Quinnan, G. V. 1987. The role of specific IgE and beta-propiolactone in reactions resulting from booster doses of human diploid cell rabies vaccine. J. Allergy Clin. Immunol. 80:861.

Anonymous 2000. Compendium of Animal Rabies Prevention and Control, 2000. MMWR 49:19-30.

Anonymous 1993. World survey of rabies 27. Veterinary Public Health Unit, WHO, Geneva, Switzerland.

Anonymous 1988. Rabies vaccine failures [editorial], Lancet 1:917.

Arvin, A. M. 2000. Measles vaccines—a positive step toward eradicating a negative strand. Nat Med. 6:744-745.

Baer, G. M. 1988. Oral rabies vaccination: an overview. Rev. Infect. Dis.10:S644-S647.

Ball, L. A., Pringle, C. R., Flanagan, B., Perepelitsa, V. P., Wertz, G. W. 1999. Phenotypic consequences of rearranging the P, M, and G genes of vesicular stomatitis virus. J. Virol. 73:4705-12.

Banerjee, A. K, and D. Chattopadhyay. 1990. Structure and function of the RNA polymerase of vesicular stomatitis virus. Adv Virus Res. 38:99-124.

Barr, J., C. R. Chambers, C. R. Pringle, and A. J. Easton. 1991. Sequence of the major nucleocapsid protein gene of pneumonia virus of mice: Sequence comparisons suggest structural homology between nucleocapsid proteins of pneumoviruses, paramyxoviruses, rhabdoviruses and filoviruses. J. Gen. Virol. 72:677-685.

Barth, R., Gruschkan, H., Bijok, U., Hilfenhaus, J., Hinz, J., Milcke, L., Moser, H., Jaeger, O., Ronneberger, H., Weinmann, E. 1984. A new inactivated tissue culture rabies vaccine for use in man. Evaluation of PCEC-vaccine by laboratory tests. J. Biol. Stand. 12:29-64.

Blancou, J., Kieny, M. P., Lathe, R., Lecocq, J. P., Pastoret, P. P., Soulebot, J. P., Desmettre, P. 1986. Oral vaccination of the fox against rabies using a live recombinant vaccinia virus. Nature. 322:373-375.

Boudinot, P., S. Salhi, M. Blanco and A. Benmansour. 2001. Viral haemorrhagic septicaemia virus induces vig-2, a new intereron-responsive gene in rainbow trout. Fish Shellfish Immunol. 11:383-397.

Briggs, D. J., Dreesen, D. W., Morgan, P., Chin, J. E., Seedle, C. D., Cryz, L., Gluck, R., Cryz, S. J. 1996. Safety and immunogenicity of Lyssavac Berna human diploid cell rabies vaccine in healthy adults. Vaccine 14,1361-1365.

Brochier, B., Kieny, M. P., Costy, F., Coppens, P., Bauduin, B., Lecocq, J. P., Languet, B., Chappuis, G., Desmettre, P., Afiademanyo, K., et al. 1991. Large-scale eradiation of rabies using recombinant vaccinia-rabies vaccine. Nature; 354: 520-522.

Brochier, B., Languet, B., Blancou, J., Languet, B., Artois, M., Kieny, M. P., Lecocq, J. P., Costy, F., Desmettre, P., Chappuis, G., et al.1989. Use of recombinant vaccinia-rabies virus for oral vaccination of wildlife against rabies: innocuity to several non-target bait consuming species. J Wildl Dis. 25:540-547.

Buchholz, U. J., Finke, S., Conzelmann, K. K. 1999. Generation of bovine respiratory syncytial virus (BRSV) from cDNA: BRSV NS2 is not essential for virus replication in tissue culture, and the human RSV leader region acts as a functional BRSV genome promoter. J Virol. 73:251-259.

Centers for Disease Control. 1984. Systemic allergic reactions following immunization with human diploid cell rabies vaccine. MMWR 33:12.

Charlton, K. M., Artois, M., Prevec, L., Campbell, J. B., Casey, G. A., Wandeler, A. I., Armstrong, J. 1992. Oral rabies vaccination of skunks and foxes with a recombinant human adenovirus vaccine. Arch. Virol. 123:169-179.

Clark, K. A., Wilson, P. J. 1996. Postexposure rabies prophylaxis and preexposure rabies vaccination failure in domestic animals. J. Am. Vet. Med. Assoc. 208:1827-1830.

Conzelmann, K. -L., Schnell, M. 1994. Rescue of synthetic genomic RNA analogs of rabies virus by plasmid-encoded proteins. J. Virol. 68:713-719.

Conzelmann, K. -L., Cox, J., Schneider, L. G., Theil, H -J. 1990. Molecular cloning and complete nucleotide sequence of the attenuated rabies virus SAD B19. J. Virol. 175:484-499.

Coulon, P., Derbin, C., Kucera, P., Lafay, F., Prehaud, C., Flamand, A. 1989. Invasion of the peripheral nervous systems of adult mice by the CVS strain of rabies virus and its avirulent derivative AvO1. J Virol. 63:3550-3554.

Cox, J. H., Dietzschold, B., Schneider, L. G. 1977. Rabies virus glycoprotein. II. Biological and serological characterization. Infect Immun. 16:754-759.

Dietzschold, B., Wunner, W. H., Wiktor, T. J., Lopes, A. D., Lafon, M., Smith, C. L., Koprowski, H. 1983. Characterization of an antigenic determinant of the glycoprotein that correlates with pathogenicity of rabies virus. Proc. Natl. Acad. Sci. USA. 80:70-74.

Dietzschold, B., Wiktor, T. J., Trojanowski, J. Q., Macfarlan, R. I., Wunner, W. H., Torres-Anjel, M. J., Koprowski, H. 1985. Differences in cell-to-cell spread of pathogenic and apathogenic rabies virus in vivo and in vitro. J Virol. 56:12-18.

Dietzschold, B., Lafon, M., Wang, H., Otvos, L., Celis, E., Wunner, W. H., Koprowski, H. 1987. Localization and immunological characterization of antigenic domains of rabies virus internal N and NS proteins. Virus Res. 8:103-125.

Duteil, X. 1986. New purified Vero-cell vaccine prevents rabies in patients bitten by rabid animals. Lancet. 2:129-31.

Emerson, S. U. 1982. Reconstitution studies detect a single polymerase entry site on the vesicular stomatitis virus genome. Cell. 31:635-642.

Enami, M., Luytjes, W., Krystal, M., Palese, P. 1990. Introduction of site-specific mutations into the genome of influenza virus. Proc. Natl. Acad. Sci. USA. 87:3802-3805.

Esh, J. B., Cunningham, J. G., Wiktor, T. J. 1982. Vaccine-induced rabies in four cats. J. Am. Vet. Med. Assoc. 180: 1336-1339.

Etessami, R., Conzelmann, K. K/, Fadai-Ghotbi, B., Natelson, B., Tsiang, H., Ceccaldi, P. E. 2000. Spread and pathogenic characteristics of a G-deficient rabies virus recombinant: an in vitro and in vivo study. J Gen Virol. 81:2147-53.

Fearneyhough, M. G., Wilson, P. J., Clark, K. A., Smith, D. R., Johnston, D. H., Hicks, B. N., Moore, G. M. 1998. Results of an oral rabies vaccination program for coyotes. J. Am. Vet. Med. Assoc. 212:498-502.

Finke, S., Conzelmann, K. -K. 1997. Ambisense gene expression from recombinant rabies virus: random packaging of positive- and negative-strand ribonucleoprotein complexes into rabies virions. J. Virol. 71:7281-7288.

Finke, S., Cox, J. H., Conzelmann, K. K. 2000. Differential transcription attenuation of rabies virus genes by intergenic regions: generation of recombinant viruses overexpressing the polymerase gene. J Virol. 74:7261-9.

Flamand, A., Coulon, P., Lafay, F., Tuffereau, C. 1993. Avirulent mutants of rabies virus and their use as live vaccine. Trends. Microbiol. 1:317-320.

Flamand, A., J. F. Delagneau, and F. Bussereau. 1978. An RNA polymerase activity in purified rabies virions. J. Gen. Virol. 40:233-238.

Flanagan, E. B., Ball, L. A., Wertz, G. W. 2000. Moving the glycoprotein gene of vesicular stomatitis virus to promoter-proximal positions accelerates and enhances the protective immune response. J. Virol. 74:7895-7902.

Fu, Z. F. 1997. Rabies and rabies research: past, present and future. Vaccine. 15: S20-S24.

Fu, Z. F., Dietzschold, B., Schumacher, C. L., Wunner, W. H., Ertl, H. C. J., Koprowski, H. 1991. Rabies virus nucleoprotein expressed in and purified from insect cells is efficacious as a vaccine. Proc. Natl. Acad. Sci. USA 88:2001-2005.

Fu, Z. F., Wickstrom, E., Jiang, M., Corisdeo, S., Yang, J., Dietzschold, B., Koprowski, H. 1996. Inhibition of rabies virus infection by an oligodeoxynucleotide complementary to rabies virus genomic RNA. Antisense and Nucleic Acid Drug Development. 6:87-93.

Fu, Z. F., R. Rupprecht, B. Dietzschold, P. Saikumar, H. S. Niu, I. Babka, W. H. Wunner, and H. Koprowski 1993. Oral vaccination of raccoons (Procyon lotor) with baculovirus-expressed rabies virus glycoprotein. Vaccine, 11:925-928.

Fu, Z. F., Y. M. Zheng, W. H. Wunner, H. Koprowski, and B. Dietzschold. 1994. Both the N- and C-terminal domains of the nominal phosphoprotein of rabies virus are involved in binding to the nucleoprotein. Virology , 200:590-597.

Fuenzalida, E. 1972. Human pre-exposure rabies immunization with suckling mouse brain vaccine. Bull World Health Organ. 46:561-563.

Fuerst, T. R., E. G. Niles, F. W. Studier, and B. Moss. 1986. Eukaryotic transient-expression system based on recombinant vaccinia virus that synthesizes bacteriophage T7 RNA polymerase. Proc. Natl. Acad. Sci. USA, 83:8122-8126.

Gosztonyi, G., Dietzschold, B., Kao, M., Rupprecht, C. E., Ludwig, H., Koprowski, H. 1993. Rabies and borna disease. A comparative pathogenetic study of two neurovirulent agents. Lab. Invest. 68:285-295.

Hable, K. 1996. Hable test for potency. In. Laboratory techniques in rabies. 4th edition. Meslin, F. X., Kaplan, M. M. and Koprowski, H (ed). World Health Organization. Geneva, pp. 369-72.

Hanlon, C. A., Niezgoda, M., Hamir, A. N., Schumacher, C., Koprowski, H., Rupprecht, C. E. 1998. First North American field release of a vaccinia-rabies glycoprotein recombinant virus. J. Wildl. Dis., 34:228-239.

Henderson, D. A. 1980. Smallpox eradication. Public Health Rep. 95:422-426.

Kawai, A. 1977. Transcriptase activity associated with rabies virion. J. Virol., 24:826-835.

Kawai, A., H. Toriumi, T. S. Tochikura, T. Takahashi, Y. Honda, and K. Morimoto. 1999. Nucleocapsid formation and/or subsequent conformational change of rabies virus nucleoprotein (N) is a prerequisite step for acquiring the phosphatase-sensitive epitope of monoclonal antibody 5-2-26. Virology, 263:395-407.

Khawplod, P., Glueck, R., Wilde, H., Tantawichien, T., Chomchey, P., Thipkong, P., Benjavongkulchai, M., Sumboonanondha, A., Prakongsri, S., Siakasem, A. et al. 1995 Immunogenicity of purified duck embryo rabies vaccine (Lyssavac-N) with use of the WHO-approved intradermal postexposure regimen. Clin. Infect. Dis., 20:646-651.

Kieny, M. P., Lathe, R., Drillen, R., Spehner, D., Skory, S., Schmitt, D., Wiktor, T., Koprowski, H., Lecocq, J. P. 1984. Expression of rabies virus glycoprotein from a recombinant vaccinia virus. Nature, 312:163-166.

Kouznetzoff, A., M. Buckle, and N. Tordo. 1998. Identification of a region of the rabies virus N protein involved in direct binding to the viral RNA. J. Gen. Virol., 79:1005-1013.

Krebs, J. W., Smith, J. S., Rupprecht, C. E., Childs, J. E. 2000. Mammalian reservoirs and epidemiology of rabies diagnosed in human beings in the United States, 1981-1998. Ann N Y Acad Sci., 916:345-53.

Krebs, J. W., Rupprecht, C. E., Childs, J. E. 2000. Rabies surveillance in the United States during 1999. J Am Vet Med Assoc., 217:1799-811.

Lafay, F., Benejean, J., Tuffereau, C., Flamand, A., Coulon, P. 1994. Vaccination against rabies: construction and characterization of SAG-2, a double avirulent derivative of SAD-Bern. Vaccine, 12:317-320.

Lawson, N. D., Stillman, E. A., Whitt, M. A., Rose, J. K. 1995. Recombinant vesicular stomatitis viruses from DNA. Proc. Natl. Sci. USA, 92:4477-4481.

Le Blois, H., Tuffereau, C., Blancou, J., Artois, M., Aubert, A., Flamand, A. 1990. Oral immunization of foxes with avirulent rabies virus mutants. Vet. Microbiol., 23:159-166.

Littell, R. C., Milliken, G. A., Stroud, W. W. and Wolfinger, R. D. 1996. SAS system for mixed models. SAS Institute Inc. Cary, N.C.

Lodmell, D. L., Ray, N. B., Parnell, M. J., Ewalt, L. C., Hanlon, C. A., Shaddock, J. H., Sanderlin, D. S., Rupprecht, C. E. 1998. DNA immunization protects nonhuman primates against rabies virus. Nat Med., 4:949-952.

Lumbiganon, P., Bunyahotra, V., Pairojkul, C. 1987. Human rabies despite treatment with rabies immune globulin and human diploid cell rabies vaccine-Thailand. MMWR 36:759-.

Lundberg, K. S., Shoemaker, D. D., Adams, M. W., Short, J. M., Sorge, J. A., Mathur, E. J. 1991. High-fidelity amplification using a thermostable DNA polymerase isolated from Pyrococcus furiosus. Gene, 108:1-6.

Masson, E., Cliquet, F., Aubert, M., Barrat, J., Aubert, A., Artois, M., Schumacher, C. L. 1996. Safety study of the SAG2 rabies virus mutant in several non-target species with a view to its future use for the immunization of foxes in Europe. Vaccine, 14:1506-1510.

Melter, M. I. 1996. Assessing the cost and benefits of an oral vaccine for raccoon rabies: a possible model. Emerging Infect. Dis., 2:343-349.

Meslin, F. X., Fishbein, D. B., Matter, H. C. 1994. Rationale and prospects for rabies elimination in developing countries. Curr. Top. Microbiol. Immunol., 187:1-26.

Mitmoonpitak, C., Tepsumethanon, V., Wilde, H. 1998. Rabies in Thailand. Epidemiol. Infect., 120:165-169.

Osorio, J. E., Tomlinson, C. C., Frank, R. S., Haanes, E. J., Rushlow, K., Haynes, J. R., Stinchcomb, D. T. 1999. Immunization of dogs and cats with a DNA vaccine against rabies virus. Vaccine, 17:1109-1116.

Pasteur L., Illo J.1996. Pasteur and rabies: an interview of 1882. Med Hist., 40:373-7.

Pattnaik, A. K., Wertz, G. W. 1990. Replication and amplification of defective interfering particle RNAs of vesicular stomatitis virus in cells expressing viral proteins from vectors containing cloned cDNAs. J. Virol., 64:2948-2957.

Pattnaik, A. K., Wertz, G. W. 1991. Cells that express all five proteins of vesicular stomatitis virus from cloned cDNAs support replication, assembly, and budding of defective interfering particles. Proc. Natl. Acad. Sci. USA, 88:1379-1383.

Prevec, L., Campbell, J. B., Christie, B. S., Belbeck, L., Graham, F. L. 1990. A recombinant human adenovirus vaccine against rabies. J. Infect. Dis., 161:27-30.

Ray, N. B., Ewalt, L. C., Lodmell, D. L. 1997. Nanogram quantities of plasmid DNA encoding the rabies virus glycoprotein protect mice against lethal rabies virus infection. Vaccine, 15:892-895.

Reed, E. J., Muench, H. 1938. A simple method of estimating fifty percent endpoints. Am. J. Hyg., 27:493-497.

Robbins, A. H., Borden, M. D., Windmiller, B. S., Niezgoda, M., Marcus, L. C., O'Brien, S. M., Kreindel, S. M., McGuill, M. W., DeMaria, A. Jr, Rupprecht, C. E., Rowell, S. 1998. Prevention of the spread of rabies to wildlife by oral vaccination of raccoons in Massachusetts. J. Am. Vet. Med. Assoc., 213:1407-1412.

Roscoe, D. E., Holste, W. C., Sorhage, F. E., Campbell, C., Niezgoda, M., Buchannan, R., Diehl, D., Niu, H. S., Rupprecht, C. E. 1998. Efficacy of an oral vaccinia-rabies glycoprotein recombinant vaccine in controlling epidemic raccoon rabies in New Jersey. J. Wildl. Dis., 34:752-763.

Rupprecht, C. E., Blass, L., Smith, K., Orciari, L. A., Niezgoda, M., Whitfield, S. G., Gibbons, R. V., Guerra, M., Hanlon, C. A. 2001. Human infection due to recombinant vaccinia-rabies glycoprotein virus. N Engl J Med. 345:582-6.

Rupprecht, C. E., Smith, J. S., Fekadu, M., Childs, J. E. 1995. The ascension of wildlife rabies: a cause for public health concern or intervention? Emerg Infect Dis. 1:107-14.

Rupprecht, C. E., Wiktor, T. J., Johnston, D. H., Hamir, A. N., Dietzschold, B., Wunner, W. H., Glickman, L. T., Koprowski, H. 1986. Oral immunization and protection of raccoons (*Procyon lotor*) with a vaccinia-rabies glycoprotein recombinant virus vaccine. Proc. Natl. Acad. Sci. USA, 83:7949-7950.

Rupprecht, C. E., Hanlon, A. N., Hamir, A., Koprowski, H. 1993. Oral wildlife rabies vaccination: development of a recombinant virus vaccine. Trans. 57th N.A. Wildl. Natl. Res. Conf., pp. 439-452.

Sabin, A. B., Boulger, L. R. 1973. History of the Sabin attenuated poliovirus oral live vaccine strain. J. Bio. Stand., 1:15-19.

Schneider, L. G., Cox, J. H., Muller, W. W. and Hohnsbeen, K -P. 1988. Current oral rabies vaccination in Europe: an interim balance. Rev. Infect. Dis., 10:S654-S659.

Schnell, M. J., H. D. Foley, C. A. Siler, J. P. McGettigan, B. Dietzschold, and R. J. Pomerantz. 2000. Recombinant rabies virus as potential live-viral vaccines for HIV-1. Proc Natl Acad Sci U S A., 97:3544-3549.

Schnell, M. J., T. Mebatsion, and K. -K. Conzelmann. 1994. Infectious rabies viruses from cloned cDNA. EMBO J., 13:4195-4203.

Schumacher, C. L., Coulon, P., Lafay, F., Benejean, J., Aubert, M. F., Barrat, J., Aubert, A., Flamand, A.1993. SAG-2 oral rabies vaccine. Onderstepoort J. Vet. Res., 60:459-462.

Sehgal, S., Bhattacharya, D., Bhardwaj, M. 1993. Ten year longitudinal study of efficacy and safety of purified chick embryo cell vaccine for pre- and post-exposure prophylaxis of rabies in Indian population. J Commun Dis., 27:36-43.

Seif, I., Coulon, P., Rollin, P. E., Flamand, A. 1985. Rabies virulence: effect on pathogenicity and sequence characterization of rabies virus mutations affecting antigenic site III of the glycoprotein. J. Virol., 53:926-934.

Shill, M., Baynes, R. S., Miller, S. D. 1987. Fatal rabies encephalitis despite appropriate post-exposure prophylaxis. N Engl J Med 1987, 316:1257-1258.

Smith, J. S., Orciari, L. A., Yager, P. A. 1995. Molecular epidemiology of rabies in the United States. Sem. Virol., 6:387-400.

Smith, J. S., Fishbein, D. B., Rupprecht, C. E., Clark, K. 1991. Unexplained rabies in three immigrants in the United States. A virologic investigation. N. Engl. J. Med., 324: 205-11.

Sokol, F., Clark, H. F. 1973. Phosphoproteins, structural components of rhabdoviruses. Virol., 52:246-263.

Spadafora, D., D. M. Canter, R. L. Jackson, and J. Perrault. 1996. Constitutive phosphorylation of the vesicular stomatitis virus P protein modulates polymerase complex formation but is not essential for transcription or replication. J. Virol., 70:4538-4548.

Suntharasamai, P., Warrell, M. J., Warrell, D. A., Viravan, C., Looareesuwan, S., Supanaranond, W., Chanthavanich, P., Supapochana, A., Tepsumethanon, W., Pouradier-Swanson, M. C., Rosanoff, E., Gurwith, M., Deitch, M., Schnurrenberger, P. O., Reed, C. E. 1987. IgE and IgG antibodies to beta-propiolactone and human serum albumin associated with urticarial reactions to rabies vaccine. J. Infet. Dis., 155:909.

Tims, T., Briggs, D. J., Davis, R. D., Moore, S. M., Xiang, Z., Ertl, H. C., Fu, Z. F. 2000. Adult dogs receiving a rabies booster dose with a recombinant adenovirus expressing rabies virus glycoprotein develop high titers of neutralizing antibodies. Vaccine, 18:2804-7.

Tordo, N., O. Poch, A. Ermine, and G. Keith. 1986. Primary structure of leader RNA and nucleoprotein genes of rabies genome: Segmented homology with VSV. Nucleic Acids Res., 14:2671-2683.

Trejos, A., Lewis, V., Fuenzalida, E., Larghi, O. P. 1974. Laboratory investigations of neuroparalytic accidents associated with suckling mouse brain rabies vaccine. I.—Encephalitogenicity and virological studies. Ann Immunol (Paris)., 125:917-24.

Wagner, R. R, and J. K. Rose. 1996. *Rhabdoviridae*: The viruses and their replication. In B. N. Fields, D. M. Knipe, P. M. Howley, R. M. Chanock, J. L. Melnick, T. P. Monath, B. Roizman, and S. E. Straus (ed.), Fields Virology, 3rd edition, pp. 1121-1136. Lippincott-Reven, Philadelphia, Pa.

Wandeler AI, Capt S, Kappeler A, Hauser R. 1998. Oral immunization of wildlife against rabies: concept and first field experiments. Rev. Infect. Dis., 10:S649-S653.

Wang, Y., Xiang, Z., Pasquini, S., Ertl, H. C. 1997. The use of an E1-deleted, replication-defective adenovirus recombinant expressing the rabies virus glycoprotein for early vaccination of mice against rabies virus. J Virol., 71:3677-3683.

Warrington, R. J., Martens, C. J., Rubin, M., Rutherford, W. J., Aoki, F. Y. 1987. Immunologic studies in subjects with a serum sickness-like illness after immunization with human diploid cell rabies vaccine. J. Allergy Clin. Immunol., 79:605.

Weiner, M. P., G. L. Costa, W. Schoettlin, J. Cline, E. Mathur, and J. C. Bauer 1994. Site-directed mutagenesis of double-stranded DNA by the polymerase chain reaction. Gene, 151:119-123.

Wertz, G. W., N. L. Davies, and J. Patton. 1987. The role of proteins in vesicular stomatitis virus RNA replication. In R. R. Wagner (ed.), The Rhabdoviruses, pp. 271-296. Plenum Press, New York.

Wertz, G. W., V. P. Perepelitsa, and L. A. Ball. 1998. Gene rearrangement attenuates expression and lethality of a non-segmented negative strand RNA virus. Proc. Natl. Acad. Sci. USA, 95:3501-3506.

Whelan, S. P. J., Ball, L. A., Barr, J. N., Wertz, G. T. 1995. Efficient recovery of infectious vesicular stomatitis virus entirely from cDNA clones. Proc. Natl. Acad. Sci. USA, 92:8388-8392.

Wiktor, T. J., Fernandes, M. V. and Koprowski, H. 1964. Cultivation of rabies virus in human diploid cell strain WI-38. *J. Immunol.,* 93:353-366.

Wilcock, B. P., Yager, J. A. 1986. Focal cutaneous vasculitis and alopecia at sites of rabies vaccination in dogs. J. Am. Vet. Med. Assoc., 188:1174-1177.

Winkler, W. G., Shaddock, J. H., Williams, L. W. 1976. Oral rabies vaccine: evaluation of its infectivity in three species of rodents. Am J Epidemiol., 104:294-298.

Wu, X., Gong, X., Foley, H. D., Schnell, M. J., Fu, Z. F. 2002. Both viral transcription and replication are reduced when the rabies virus nucleoprotein is not phosphorylated. J. Virol. 76:4153-4161.

Wunner, W. H. 1991. The chemical composition and molecular structure of rabies viruses. In: Natural History of Rabies, 2nd Ed., (G. M. Baer, ed.). CRC Press, Inc., Boca Raton, Fla., pp. 31-67.

Xiang, Z, Q., Spitalnik, S., Tran, M., Wunner, W. H., Cheng, J., Ertl, H. C. 1994. Vaccination with a plasmid vector carrying the rabies virus glycoprotein gene induces protective immunity against rabies virus. Virology, 199:132-140.

Xiang, Z. Q., Yang, Y., Wilson, J. M., Ertl, H. C. 1996. A replication-defective human adenovirus recombinant serves as a highly efficacious vaccine carrier. Virology, 219:220-227.

Yang, J.; Hooper, D. C.; Wunner, W. H.; Koprowski, H.; Dietzschold, B.; Fu, Z. F. 1998. The specificity of rabies virus RNA encapsidation by nucleoprotein. Virology, 242: 107-117.

Yang, J.; Koprowski, H.; Dietzschold, B.; Fu, Z. F. 1999. Phosphorylation of rabies virus nucleoprotein regulates viral RNA transcription and replication by modulating leader RNA encapsidation. J. Virol., 73:1661-1664.

What is claimed is:

1. A composition comprising an isolated nucleic acid encoding a mutant rabies virus comprising a rabies virus N protein, wherein said N protein comprises an amino acid other than serine at position 389.

2. The composition of claim 1, wherein the amino acid at position 389 is a neutral amino acid.

3. The composition of claim 1, wherein the amino acid at position 389 is alanine, glycine, glutamine, glutamic acid, aspartic acid, or asparagine.

4. The composition of claim 1, wherein said mutant rabies virus N protein is encoded by SEQ ID NO:62, SEQ ID NO:63, or SEQ ID NO:64.

5. The composition of claim 1, wherein said nucleic acid further encodes a mutant G glycoprotein.

6. The composition of claim 5, wherein said G glycoprotein comprises an amino acid other than arginine at position 333.

7. The composition of claim 6, wherein said G glycoprotein comprises a Glu at position 333.

8. The composition of claim 1, wherein the isolated nucleic acid is in a vector.

9. The composition of claim 2, wherein the isolated nucleic acid is in a vector.

10. The composition of claim 3, wherein the isolated nucleic acid is in a vector.

11. The composition of claim 4, wherein the isolated nucleic acid is in a vector.

12. The composition of claim 5, wherein the isolated nucleic acid is in a vector.

13. The composition of claim 6, wherein the isolated nucleic acid is in a vector.

14. The composition of claim 7, wherein the isolated nucleic acid is in a vector.

* * * * *